(12) United States Patent
Krywyj et al.

(10) Patent No.: US 11,566,957 B2
(45) Date of Patent: Jan. 31, 2023

(54) PIPE SENSORS

(71) Applicant: Orbis Intelligent Systems, Inc., San Diego, CA (US)

(72) Inventors: Daniel Milne Krywyj, La Jolla, CA (US); Jeffrey A. Prsha, San Diego, CA (US)

(73) Assignee: Orbis Intelligent Systems, Inc., San Diego, CA (US)

( * ) Notice: Subject to any disclaimer, the term of this patent is extended or adjusted under 35 U.S.C. 154(b) by 141 days.

(21) Appl. No.: 16/569,530

(22) Filed: Sep. 12, 2019

(65) Prior Publication Data

US 2020/0003646 A1 Jan. 2, 2020

Related U.S. Application Data

(63) Continuation of application No. 16/433,792, filed on Jun. 6, 2019, now Pat. No. 11,150,154.
(Continued)

(51) Int. Cl.
*G01L 9/04* (2006.01)
*G01F 1/66* (2022.01)
(Continued)

(52) U.S. Cl.
CPC ............. *G01L 9/04* (2013.01); *G01F 1/66* (2013.01); *G01F 1/667* (2013.01); *G01F 1/8413* (2013.01); *G01F 15/06* (2013.01); *G01K 7/22* (2013.01); *G01M 3/00* (2013.01); *G01N 29/041* (2013.01); *G01N 33/18* (2013.01); *G01P 15/18* (2013.01); *G01F 1/662* (2013.01); *G01F 1/6847* (2013.01);
(Continued)

(58) Field of Classification Search
CPC ..... G01L 9/04; G01L 9/0002; G01L 19/0023; G01L 19/0007; G01L 19/141; G01L 19/147; G01L 19/086; G01L 19/083; G01L 19/0092; G01F 1/667; G01F 1/8413; G01F 1/66; G01F 1/662; G01F 1/6847; G01F 15/06; G01F 15/063; G01K 7/22; G01M 3/00; G01M 3/243; G01M 3/2815; G01M 5/0025; G01M 5/0033; G01M 5/0066; G01N 29/041; G01N 33/18; G01N 2291/103; G01N 2291/2698; G01P 15/18
See application file for complete search history.

(56) References Cited

U.S. PATENT DOCUMENTS 3,612,922 A 10/1971 Furnival
5,228,329 A 7/1993 Dennison
(Continued)

FOREIGN PATENT DOCUMENTS

EP 2912416 9/2015
GB 1423569 A 2/1976
(Continued)

OTHER PUBLICATIONS

International Search Report and Written Opinion dated Aug. 20, 2019, issued in PCT/US2019/026169.
(Continued)

*Primary Examiner* — Jonathan M Dunlap
(74) *Attorney, Agent, or Firm* — Weaver Austin Villeneuve & Sampson LLP

(57) ABSTRACT

Methods, systems, and apparatuses are provided for detecting and determining conditions of and conditions within a fluid conduit.

20 Claims, 60 Drawing Sheets

Related U.S. Application Data

(60) Provisional application No. 62/823,539, filed on Mar. 25, 2019, provisional application No. 62/784,208, filed on Dec. 21, 2018, provisional application No. 62/683,566, filed on Jun. 11, 2018, provisional application No. 62/682,751, filed on Jun. 8, 2018.

(51) Int. Cl.

| | |
|---|---|
| *G01K 7/22* | (2006.01) |
| *G01M 3/00* | (2006.01) |
| *G01N 29/04* | (2006.01) |
| *G01N 33/18* | (2006.01) |
| *G01P 15/18* | (2013.01) |
| *G01F 1/667* | (2022.01) |
| *G01F 1/84* | (2006.01) |
| *G01F 15/06* | (2022.01) |
| *G01L 19/00* | (2006.01) |
| *G01L 9/00* | (2006.01) |
| *G01M 3/28* | (2006.01) |
| *G01L 19/08* | (2006.01) |
| *G01M 5/00* | (2006.01) |
| *G01L 19/14* | (2006.01) |
| *G01F 15/063* | (2022.01) |
| *G01M 3/24* | (2006.01) |
| *G01F 1/684* | (2006.01) |

(52) U.S. Cl.
CPC .......... *G01F 15/063* (2013.01); *G01L 9/0002* (2013.01); *G01L 19/0007* (2013.01); *G01L 19/0023* (2013.01); *G01L 19/0092* (2013.01); *G01L 19/083* (2013.01); *G01L 19/086* (2013.01); *G01L 19/141* (2013.01); *G01L 19/147* (2013.01); *G01M 3/243* (2013.01); *G01M 3/2815* (2013.01); *G01M 5/0025* (2013.01); *G01M 5/0033* (2013.01); *G01M 5/0066* (2013.01); *G01N 2291/103* (2013.01); *G01N 2291/2698* (2013.01)

(56) References Cited

U.S. PATENT DOCUMENTS

| | | | |
|---|---|---|---|
| 5,639,958 | A | 6/1997 | Lange |
| 5,970,434 | A | 10/1999 | Brophy et al. |
| 6,000,288 | A | 12/1999 | Kwun et al. |
| 6,289,723 | B1 | 9/2001 | Leon |
| 6,453,247 | B1 | 9/2002 | Hunaidi |
| 6,561,032 | B1 | 5/2003 | Hunaidi |
| 6,567,006 | B1 | 5/2003 | Lander et al. |
| 6,988,411 | B2 | 1/2006 | Gysling et al. |
| 7,434,473 | B1 | 10/2008 | Allen |
| 7,603,916 | B2 | 10/2009 | Gysling |
| 7,673,524 | B2 | 3/2010 | Bailey et al. |
| 7,882,750 | B2 | 2/2011 | Davis et al. |
| 8,402,841 | B2 | 3/2013 | Gysling et al. |
| 9,084,571 | B2 | 7/2015 | Belotserkovsky |
| 9,291,520 | B2 | 3/2016 | Fleury, Jr. et al. |
| 9,302,826 | B2 | 4/2016 | Brower |
| 9,410,833 | B1 | 8/2016 | Leaders et al. |
| 9,528,903 | B2 | 12/2016 | Zusman |
| 9,593,999 | B2 | 3/2017 | Fleury, Jr. et al. |
| 9,714,855 | B2 | 7/2017 | Bar-on |
| 9,772,250 | B2 | 9/2017 | Richarz et al. |
| 10,036,763 | B2 | 7/2018 | Hies et al. |
| 10,139,135 | B1 * | 11/2018 | Lesage ................ F24D 19/1051 |
| 10,175,135 | B2 | 1/2019 | Dintakurt et al. |
| 10,283,857 | B2 | 5/2019 | Ortiz et al. |
| 10,305,178 | B2 | 5/2019 | Gibson et al. |
| 10,309,813 | B2 | 6/2019 | Gestner |
| 10,378,940 | B2 | 8/2019 | Leaders et al. |
| 10,386,257 | B2 | 8/2019 | Fleury, Jr. et al. |
| 10,508,937 | B2 | 12/2019 | Dabak et al. |
| 10,557,731 | B2 | 2/2020 | Kippersund et al. |
| 10,564,016 | B2 | 2/2020 | Sai et al. |
| 10,881,888 | B2 | 1/2021 | Hyland et al. |
| 11,150,154 | B2 | 10/2021 | Krywyj et al. |
| 2003/0033870 | A1 | 2/2003 | Shah et al. |
| 2004/0226386 | A1 | 11/2004 | Gysling et al. |
| 2005/0011278 | A1 | 1/2005 | Brown et al. |
| 2006/0059999 | A1 | 3/2006 | Feller |
| 2006/0174707 | A1 | 8/2006 | Zhang |
| 2008/0143109 | A1 | 6/2008 | Pirchford et al. |
| 2008/0189056 | A1 | 8/2008 | Heidi et al. |
| 2009/0043530 | A1 | 2/2009 | Sittier et al. |
| 2009/0276167 | A1 | 11/2009 | Glaser et al. |
| 2010/0095782 | A1 | 4/2010 | Ferencz et al. |
| 2011/0219866 | A1 | 9/2011 | Brower |
| 2011/0308638 | A1 | 12/2011 | Hyland et al. |
| 2014/0056104 | A1 | 2/2014 | Buechler et al. |
| 2014/0238116 | A1 | 8/2014 | Kwan et al. |
| 2014/0312060 | A1 | 10/2014 | Heatherly et al. |
| 2014/0366612 | A1 | 12/2014 | Horne et al. |
| 2015/0000407 | A1 | 1/2015 | Seida et al. |
| 2016/0018283 | A1 | 1/2016 | Fleury et al. |
| 2016/0061640 | A1 | 3/2016 | Joshi et al. |
| 2016/0096717 | A1 | 4/2016 | Keating et al. |
| 2016/0208952 | A1 | 7/2016 | Howitt |
| 2017/0089047 | A1 | 3/2017 | Kovscek et al. |
| 2017/0153136 | A1 | 6/2017 | Shin |
| 2017/0176395 | A1 | 6/2017 | Burtea et al. |
| 2017/0254685 | A1 | 9/2017 | Wilt et al. |
| 2017/0261397 | A1 | 9/2017 | Horne et al. |
| 2017/0285665 | A1 | 10/2017 | Nunally et al. |
| 2017/0350100 | A1 | 12/2017 | Atkins et al. |
| 2018/0038722 | A1 | 2/2018 | Ozaki et al. |
| 2018/0052008 | A1 | 2/2018 | Maman et al. |
| 2018/0224349 | A1 | 8/2018 | Fleury, Jr. et al. |
| 2018/0354810 | A1 * | 12/2018 | Vielma .................. C02F 1/001 |
| 2019/0104890 | A1 | 4/2019 | Braddock |
| 2019/0135657 | A1 * | 5/2019 | Yates ...................... E03B 7/071 |
| 2019/0214717 | A1 | 7/2019 | Gibson et al. |
| 2019/0214718 | A1 | 7/2019 | Ortiz et al. |
| 2019/0390990 | A1 | 12/2019 | Krywyj et al. |
| 2021/0010681 | A1 * | 1/2021 | Deivasigamani ......... C02F 1/02 |
| 2022/0268654 | A1 | 8/2022 | Krywyj et al. |

FOREIGN PATENT DOCUMENTS

| | | | | |
|---|---|---|---|---|
| GB | 2375595 | A * | 11/2002 | ............. F24H 9/124 |
| GB | 2523402 | A * | 8/2015 | ............... H04Q 9/00 |
| GB | 2530004 | A * | 3/2016 | ......... F24D 17/0073 |
| WO | WO2016/094951 | A1 | 6/2016 | |
| WO | WO2016/13 9442 | A1 | 9/2016 | |
| WO | WO2017/149478 | A1 | 9/2017 | |
| WO | WO2019/195794 | | 10/2019 | |
| WO | WO2020/247982 | A1 | 12/2020 | |
| WO | WO-2020247984 | A1 | 12/2020 | |

OTHER PUBLICATIONS

Han et al., "Detection of pipe wall-thinning based on change of natural frequencies of shell vibration modes," 19th World Conference on Non-Destructive Testing 2016, Jun. 13-17, 2016 in Munich, Germany, 8 pp.
U.S. Appl. No. 16/433,792, filed Jun. 6, 2019, Krywyj et al.
U.S. Office Action dated Jul. 17, 2020 in U.S. Appl. No. 16/433,792.
U.S. Office Action dated Dec. 24, 2020 in U.S. Appl. No. 16/433,792.
International Preliminary Report on Patentability dated Oct. 15, 2020, issued in PCT/US2019/026169.
International Search Report and Written Opinion dated Oct. 18, 2019, issued in PCT/US2019/035857.
International Preliminary Report on Patentability dated Dec. 17, 2020, issued in PCT/US2019/035857.
International Search Report and Written Opinion (ISA/EP) dated Sep. 23, 2020, issued in PCT/US2020/070124.
International Search Report and Written Opinion (ISA/EP) dated Nov. 20, 2020, issued in PCT/US2020/070126.
U.S. Notice of Allowance dated May 28, 2021 in U.S. Appl. No. 16/433,792.

(56) References Cited

OTHER PUBLICATIONS

U.S. Corrected Notice of Allowability dated Sep. 15, 2021 in U.S. Appl. No. 16/433,792.
EP Office Action dated Mar. 29, 2022, in Application No. EP19718561.4.
International Preliminary Report on Patentability dated Dec. 16, 2021, for International Application No. PCT/US2020/070124.
International Preliminary Report on Patentability dated Dec. 16, 2021, for International Application No. PCT/US2020/070126.
U.S. Appl. No. 17/596,080, inventors Krywyj et al., filed Dec. 2, 2021.
U.S. Appl. No. 17/596,082, inventors Krywyj et al., filed Dec. 2, 2021.
U.S. Notice of Allowance dated Jul. 14, 2022 in U.S. Appl. No. 17/596,082.
U.S. Non-Final office Action dated Aug. 1, 2022 in U.S. Appl. No. 17/596,080.
U.S. Notice of Allowance dated Dec. 16, 2022 in U.S. Appl. No. 17/596,080.
U.S. Notice of Allowance dated Oct. 28, 2022 in U.S. Appl. No. 17/596,082.

* cited by examiner

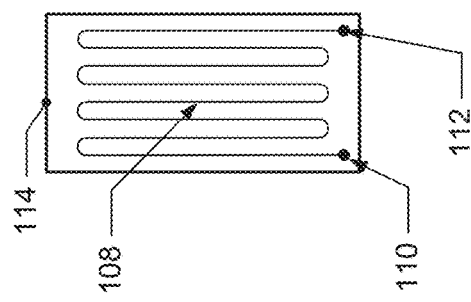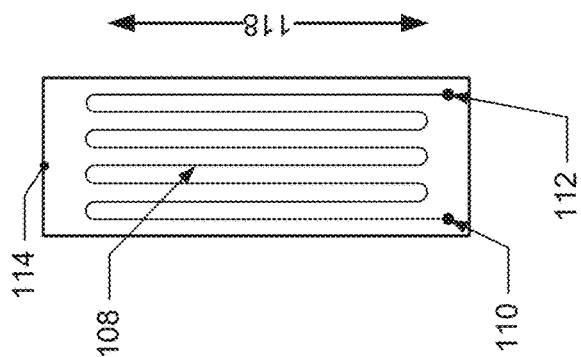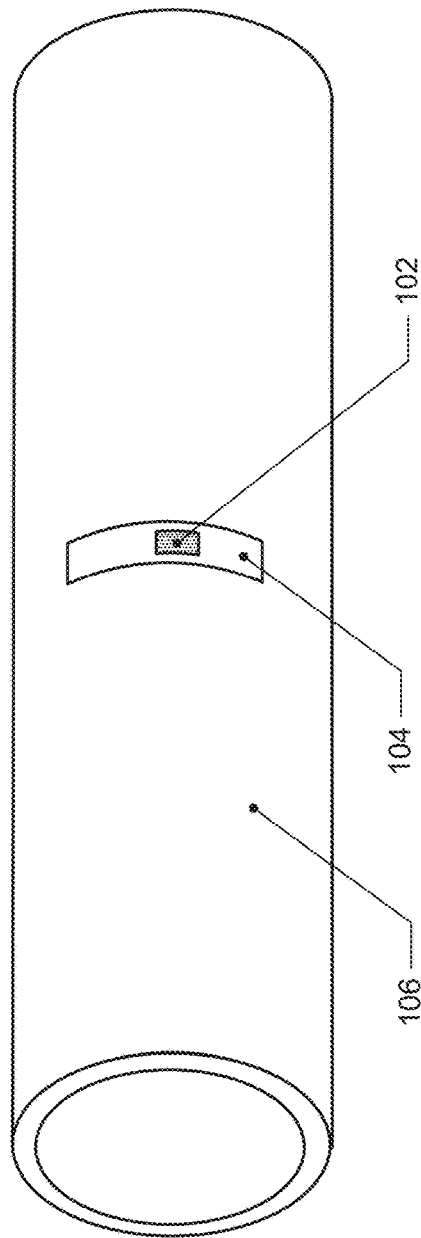
Figure 1A
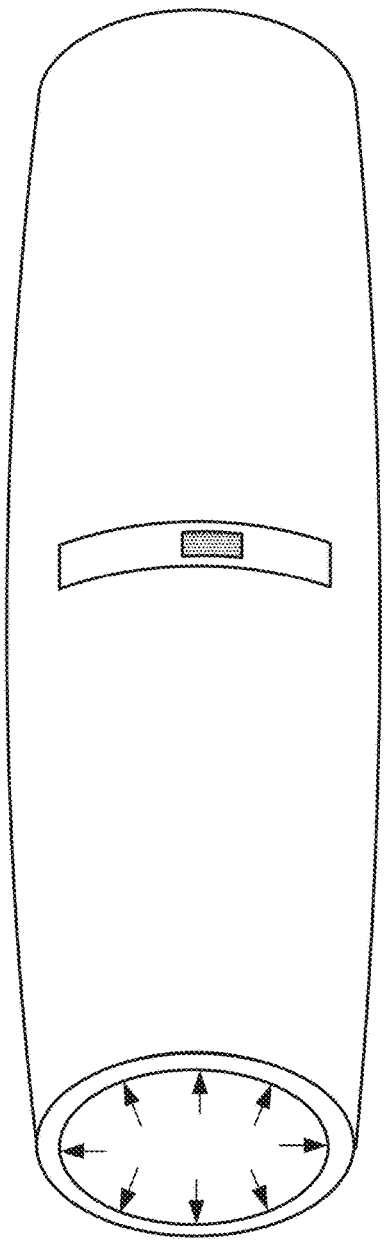
Figure 1B

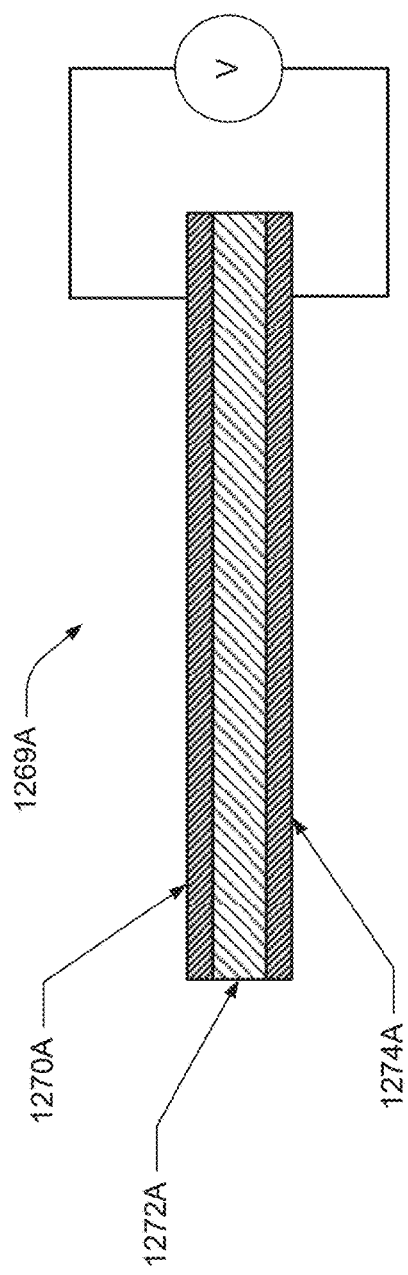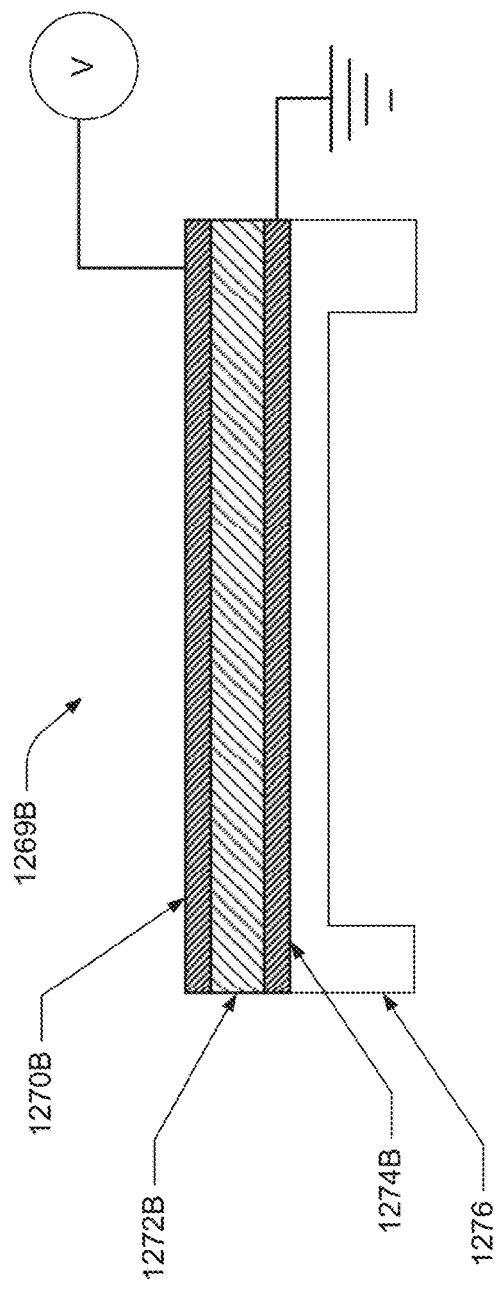
Figure 12A
Figure 12B

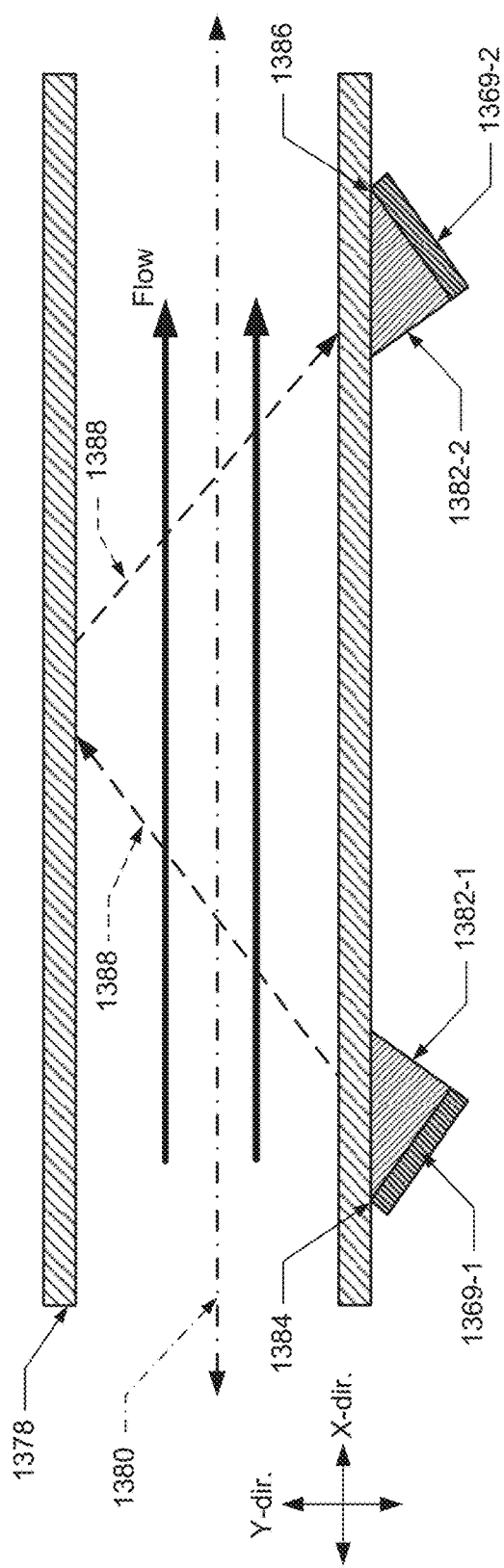
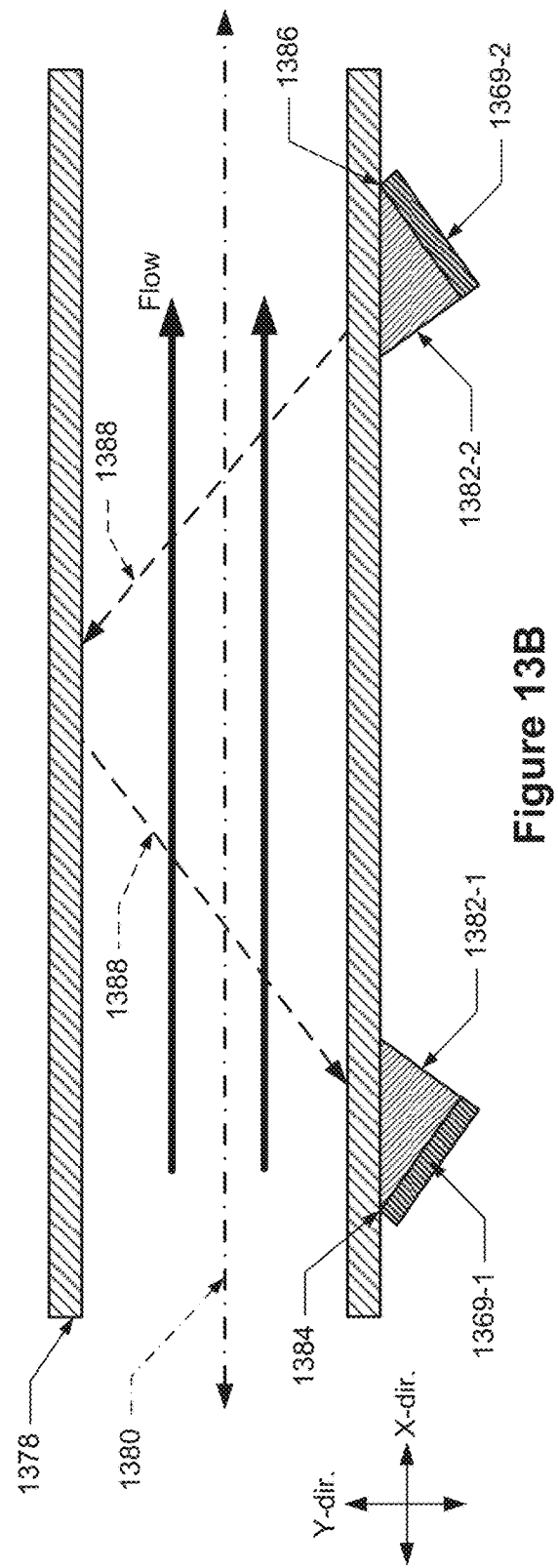
Figure 13A
Figure 13B

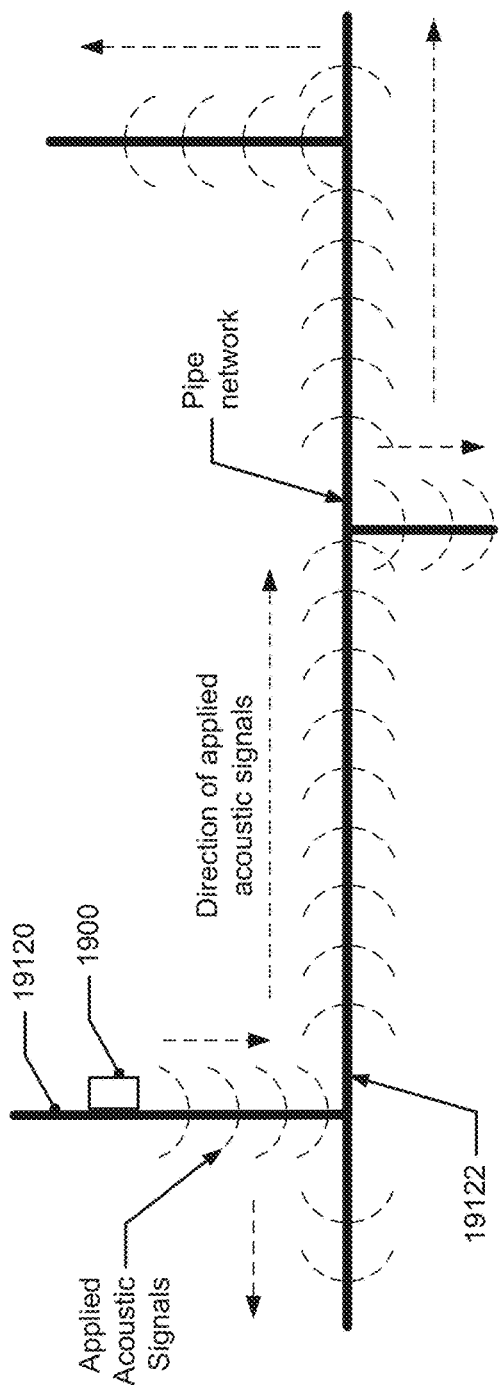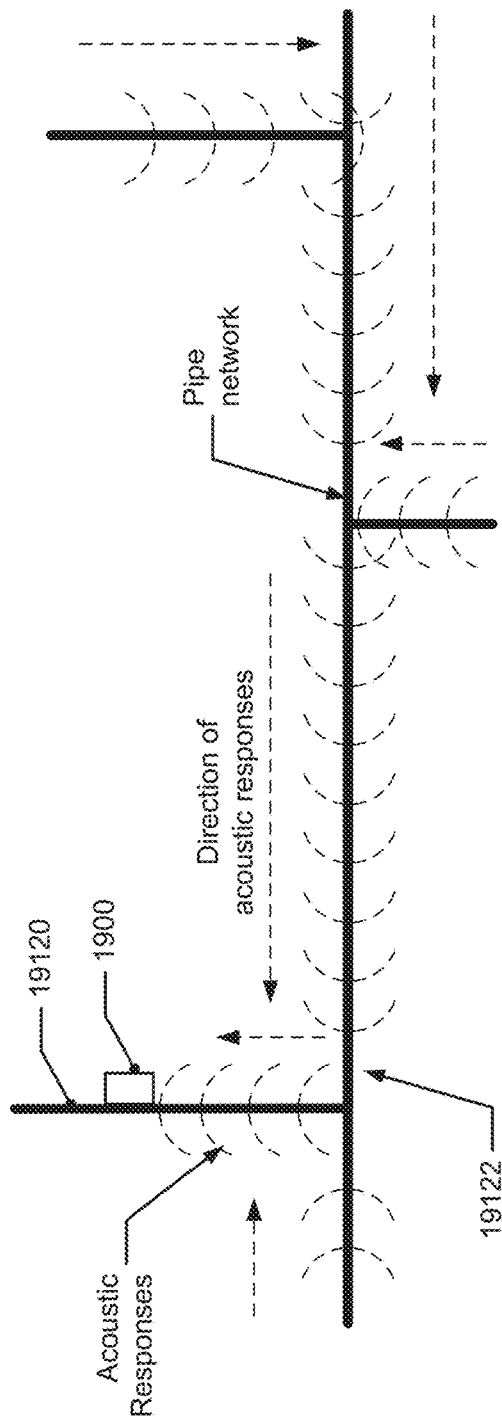

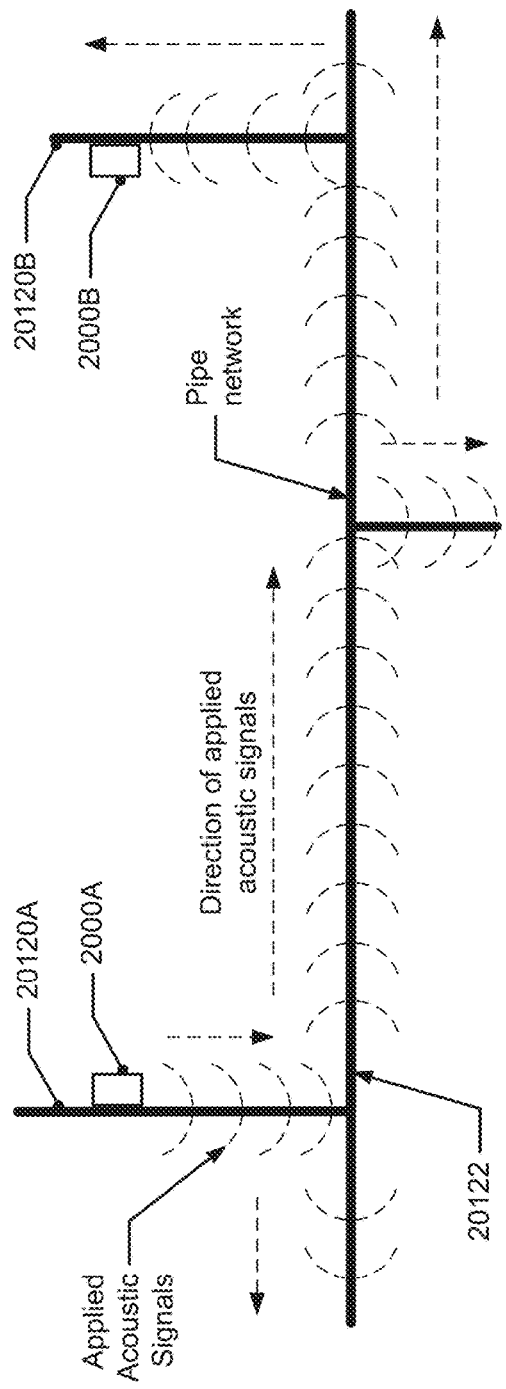
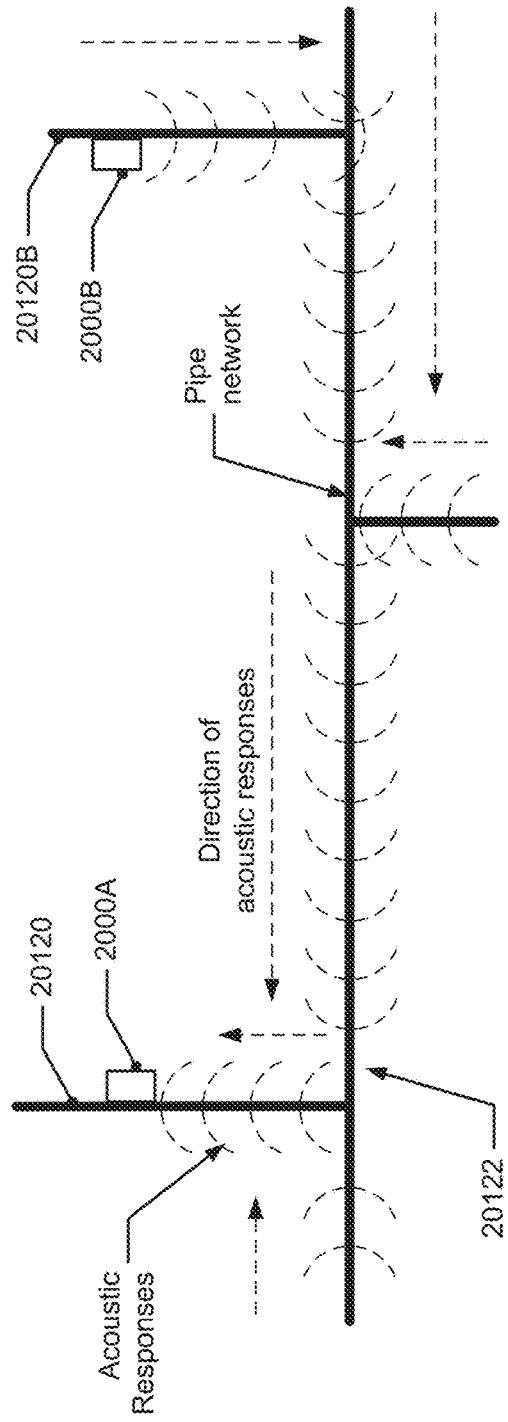
Figure 20A
Figure 20B

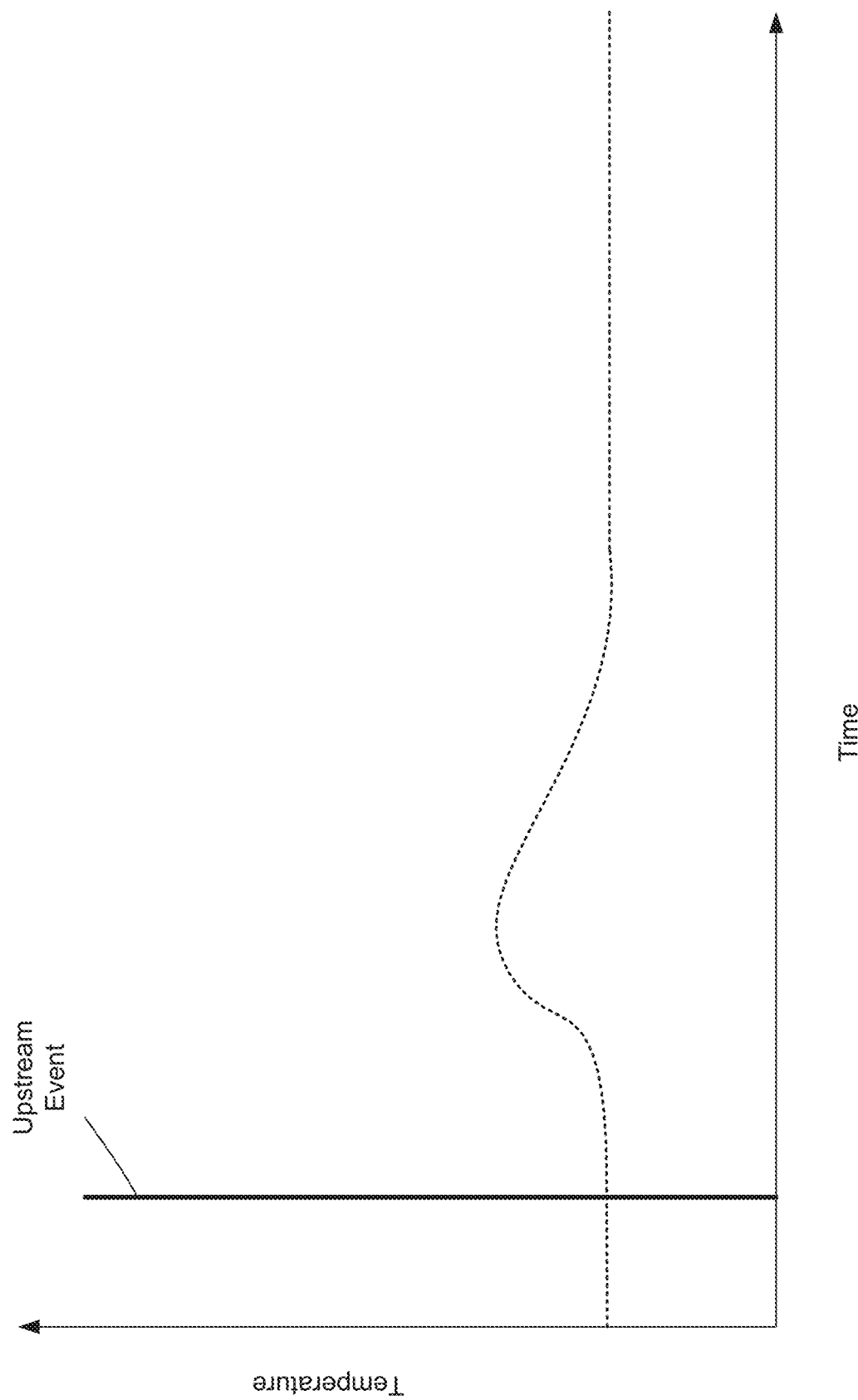

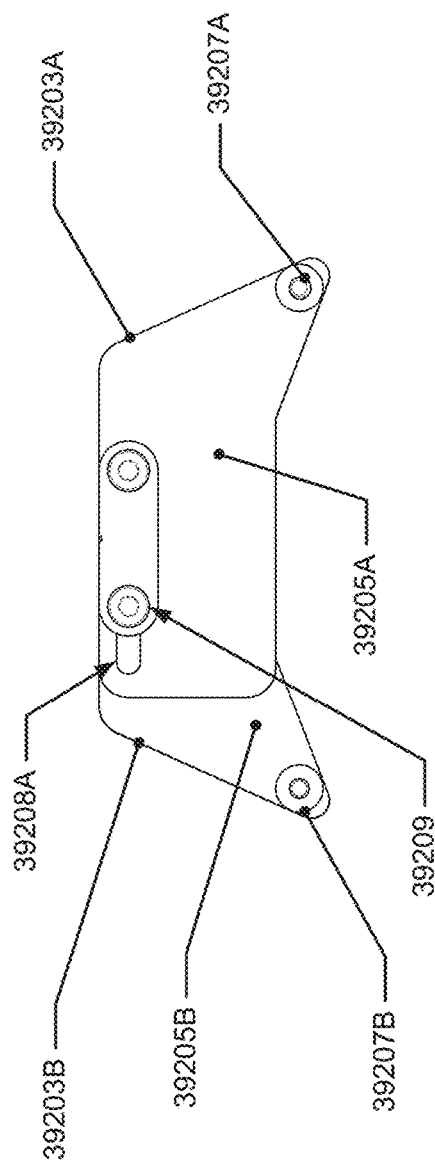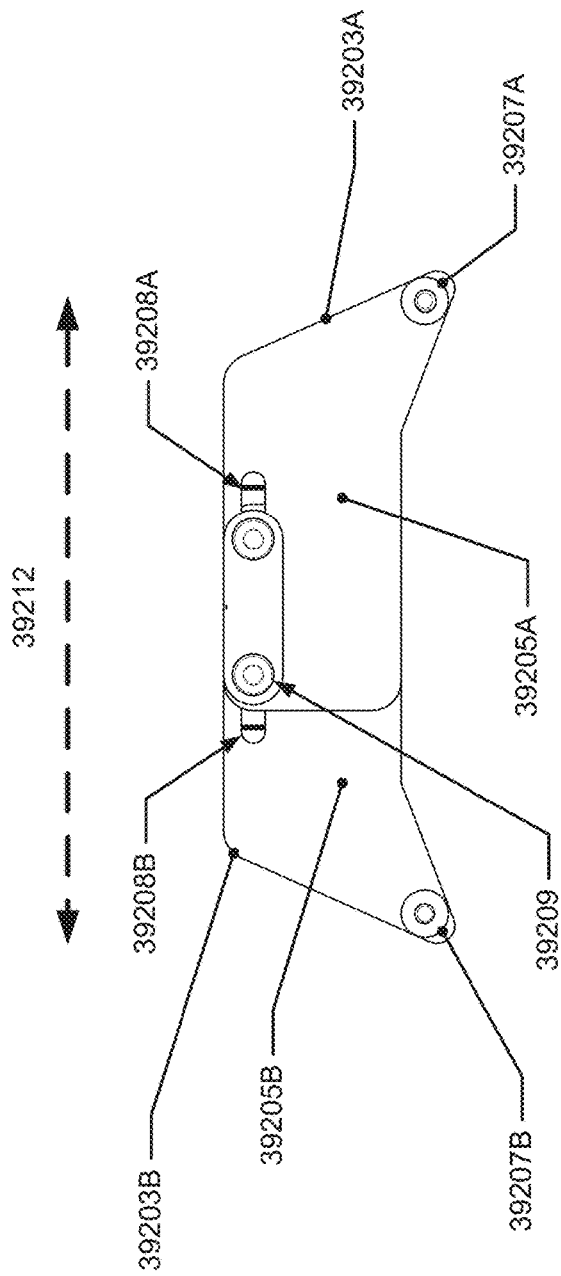

Alerts

| Asset # | Type | Customer | Location | Alert Details | Device Data |
|---|---|---|---|---|---|
| 61 | | | | Device Comms Alert: 23d 11h 29m | ⊙ |
| 21 | | | | Device Comms Alert: 23d 11h 29m | ⊙ |
| 49 | | | | Device Comms Alert: 23d 11h 29m | ⊙ |
| 57 | | | | Device Comms Alert: 23d 11h 29m | ⊙ |
| 55 | | | | Device Comms Alert: 23d 11h 29m | ⊙ |
| 58 | | | | Device Comms Alert: 23d 11h 29m | ⊙ |
| 16 | | | | Low Battery | ⊙ |
| NA | | | | Device Comms Alert: 23d 11h 29m | ⊙ |

PIPE SENSORS

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

Fluid is flowed through various conduits of a fluid delivery system and flowed out of the fluid delivery system at multiple geographical locations. Monitoring fluid flow within the conduits and monitoring events within a fluid delivery system can be difficult, particularly in real time and without invasive measures.

For example, fresh water distribution systems in municipalities have a network of water mains and other pipes that carry water to various customers and other destinations. It is difficult to monitor and control disposition of water throughout the network, particularly in real time.

SUMMARY

The systems, methods and devices of this disclosure each have several innovative aspects, no single one of which is solely responsible for the desirable attributes disclosed herein. Included among these aspects are at least the following implementations, although further implementations may be set forth in the detailed description or may be evident from the discussion provided herein.

In some embodiments, a method of detecting a pipe condition of a pipe using an acoustic sensor may be provided. The method may include receiving acoustic signals from the pipe using the acoustic sensor non-invasively, analyzing the acoustic signals received by the acoustic sensor to determine a pipe condition of a pipe, and reporting the pipe condition to an external device.

In some embodiments, the method may further include non-invasively measuring the acoustic signals received by the acoustic sensor.

In some embodiments, the receiving may include receiving acoustic signals from the pipe using a plurality of acoustic sensors, the measuring may include measuring the acoustic signals received by the plurality of acoustic sensors, and the analyzing may include analyzing the acoustic signals received by the plurality of acoustic sensors to determine the pipe condition.

In some such embodiments, the receiving may include receiving acoustic signals from the pipe using a plurality of ultrasonic transducers, and the pipe condition may include a flow of fluid within the pipe.

In some embodiments, the method may further include transmitting one or more acoustic signals to the pipe.

In some embodiments, the method may further include detecting a pipe condition trigger and transmitting one or more acoustic signals to the pipe in response to detecting the pipe condition trigger.

In some embodiments, the receiving acoustic signals from pipe may be performed continuously over a first time period.

In some embodiments, the method may further include determining a change in the one or more of the acoustic signals as compared to a first threshold, and the analyzing may further include analyzing the change in the one or more acoustic signals as compared to the first threshold.

In some embodiments, the pipe condition may be a leak in a pipe, crack in a pipe, bore loss, wall loss, flow in the pipe, detection of flow within the pipe, and a flow rate of flow within the pipe.

In some embodiments, the method may further include determining a pressure of the pipe using a hoop stress sensor.

In some embodiments, a detection device may be provided. The detection device may include a first acoustic sensor configured to receive acoustic signals, a power source, and a controller with a communications unit. The controller may be electrically connected to the first acoustic sensor and the power source, and configured to receive acoustic signals from a pipe using the first acoustic sensor, analyze the acoustic signals received by the first acoustic sensor to determine a pipe condition of the pipe, and transmit, using the communications unit, data representative of the pipe condition to an external device.

In some embodiments, the first acoustic sensor may be a microphone.

In some embodiments, the detection device may further include a plurality of acoustic sensors that include the first acoustic sensor. The controller may be further configured to receive acoustic signals from the pipe using the plurality of acoustic sensors, measure the acoustic signals received by the plurality of acoustic sensors, and analyze the acoustic signals received by the plurality of acoustic sensors to determine the pipe condition of the pipe.

In some such embodiments, the detection device may further include an acoustic exciter, and the plurality of acoustic sensors may include one or more microphones configured to apply the acoustic signals non-invasively.

In some further such embodiments, the detection device may further include a solenoid configured to apply an input acoustic signal to the pipe.

In some such embodiments, the plurality of acoustic sensors may include at least two ultrasonic transducers, and the pipe condition may include determining a flowrate of fluid within the pipe.

In some embodiments, the pipe condition may be a leak in a pipe, crack in a pipe, bore loss, wall loss, flow in the pipe, detection of flow within the pipe, and a flow rate of flow within the pipe.

In some embodiments, the detection device may further include an accelerometer. The controller may be further configured to detect a signal from the accelerometer, and measure, in response to the signal from the accelerometer, the acoustic signals in the pipe.

In some embodiments, the detection device may further include attachment features configured to enable the detection device to be connected with the pipe.

In some embodiments, a system may be provided. The system may include a plurality of detection devices, and each detection device may include a first acoustic sensor configured to receive acoustic signals, a power source, and a controller with a communications unit. The controller may be electrically connected to the first acoustic sensor and the power source, and configured to receive acoustic signals from a pipe using the first acoustic sensor, analyze the acoustic signals received by the first acoustic sensor to determine a pipe condition of the pipe, and transmit, using the communications unit, data representative of the pipe condition to a second controller. The system may also include the second controller with a second communications unit. The second controller may be configured to receive the data from each of the first communications unit from the plurality of detection devices.

In some embodiments, at least one of the controller and the second controller may be further configured to determine a pipe condition of a pipe between at least two detection devices.

In some embodiments, the pipe condition may be a pipe, crack in a pipe, bore loss, wall loss, flow in the pipe, detection of flow within the pipe, and a flow rate of flow within the pipe.

In some embodiments, the second controller may be further configured to cause a notification to be transmitted to an external device, and the notification may include information related to the pipe condition.

In some embodiments, a method of measuring pressure in a pipe using a hoop stress sensor may be provided. The method may include measuring a resistance or strain of the hoop stress sensor, analyzing the resistance or strain of the hoop stress sensor to determine an event of a pipe, and reporting the event to an external device.

In some embodiments, the measured resistance or strain may be a change in resistance or strain over time.

In some embodiments, the determined event may be a pressure of the pipe.

In some embodiments, the method may further include detecting a pipe condition trigger and applying a voltage across the hoop stress sensor.

In some embodiments, the measuring the resistance may be performed continuously over a first time period.

In some embodiments, the method may further include determining a change in the resistance or strain as compared to a first threshold resistance or stain, and the analyzing may further include analyzing the change in the resistance or strain as compared to the first threshold resistance or strain.

In some embodiments, the method may further include measuring a second resistance or strain of a second hoop stress sensor, and analyzing the resistance or strain of the hoop stress sensor and the second resistance or stain of the second hoop stress sensor to determine the event of the pipe.

In some embodiments, a processing module may be provided. The processing module may include a hoop stress sensor, a power source, and a controller with a communications unit. The controller may be electrically connected to the hoop stress sensor and the power source, and configured to apply a voltage across the hoop stress sensor, measure a voltage across the hoop stress sensor, and analyze the voltage across the hoop stress sensor to determine an event of a pipe, and transmit, using the communications unit, data representative of the event to an external device.

In some embodiments, the hoop stress sensor may be a strain gauge.

In some embodiments, the event may be a pressure of the pipe.

In some embodiments, the processing module may further include an accelerometer, and the controller may be further configured to detect a signal from the accelerometer, and measure, in response to the signal from the accelerometer, the voltage across the hoop stress sensor.

In some embodiments, a system may be provided. The system may include a plurality of detection devices, and each detection device may includes a hoop stress sensor, a power source, and a first controller with a first communications unit. The first controller may be electrically connected to the hoop stress sensor and the power source, and configured to apply a voltage across the hoop stress sensor, measure a voltage across the hoop stress sensor, analyze the voltage across the hoop stress sensor to determine an event of a pipe, and transmit, using the first communications unit, data representative of the event to a second controller. The system may also include the second controller with a second communications unit, and the second controller may be configured to receive the event from each of the first communications unit from the plurality of sensor units, and cause a notification to be transmitted to an external device, wherein the notification includes information related to the event.

In some embodiments, a method of assessing legionellosis risk in a water system may be provided. The method may include receiving sensed data from one or more sensors on pipes in the water system, and the data may include information about (i) temperature of a pipe or water in the water system, (ii) flow of water in the pipe or other component of the water system, (iii) a pressure change in the pipe or other component of the water system, and/or (iv) a vibration of the pipe or other component of the water system. The method may further include analyzing the received data to determine a risk of legionellosis resulting from water in the pipe or other component of the water system, and outputting a risk data containing data about the determined risk of legionellosis in the pipe or other component of the water system.

In some embodiments, the receiving the sensed data may include receiving the sensed data at multiple times over a period of time.

In some such embodiments, the period of time may be at least about 24 hours.

In some embodiments, the temperature of a pipe or water in the water system may be in a range between about 25 and 43° C.

In some embodiments, the one or more sensors may include a hoop stress sensor, a thermal flow condition sensor, and/or an acoustic pipe condition sensor.

In some embodiments, the method may further include issuing an alert based on the risk data.

In some embodiments, the method may further include adjusting operation of the water system based on the risk data.

In some embodiments, a detection device may be provided. The detection device may include a substrate, and a plurality of temperature sensing elements, each having an associated electrical connection and each disposed on the substrate. The detection device may be configured to attach to an exterior surface of a pipe and provide data on the electrical connections, and the data may represent temperatures of the pipe.

In some embodiments, a heating element may be disposed between at least two of the temperature sensing elements and disposed on the substrate.

In some embodiments, the detection device may further include logic for (i) receiving data representing temperature from one or more of the plurality of temperature sensing elements, and (ii) from the data, determining that an event has occurred on a pipe system comprising the pipe.

In some embodiments, the detection device may further include logic for causing (i) applying heat to the pipe via the heating element, (ii) receiving the data representing temperatures of the pipe from at least two of the temperature sensing elements, (iii) determining a temperature gradient on the pipe, and (iv) from the temperature gradient, determining a condition of fluid flowing in the pipe.

In some such embodiments, the condition may be a flow rate of the fluid flowing in the pipe.

In some embodiments an apparatus may be provided. The apparatus may include a hoop stress sensor configured to detect hoop stress of a pipe, and a mounting feature configured to engage with the pipe for the hoop stress sensor to it measure hoop stress of the pipe.

In some embodiments, the hoop stress sensor may be a strain gauge.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIGS. 1A and 1B depict an example hoop stress sensor indirectly affixed to a section of pipe.

FIGS. 12A and 12B depict examples of two ultrasonic transducers.

FIGS. 13A and 13B depict cross-sectional views of two transducers and associated lenses positioned on a fluid conduit.

FIGS. 19A and 19B depict a top view of an example pipe network with a tap connected to a pipe.

FIGS. 20A and 20B depict a top view of the example pipe network of FIGS. 19A and 19B with two detection devices having acoustic sensors.

FIG. 27 depicts a simple example of thermistor data evidencing a detectable pipe system event.

FIGS. 39A through 39D depict another example housing which also includes an adjustable positioning mechanism similar to that shown in FIGS. 35 through 38B.

FIG. 48 depicts an alerts section of a display.

FIG. 50 depicts an example display showing various details and data of numerous devices.

DETAILED DESCRIPTION

Figure 2A:
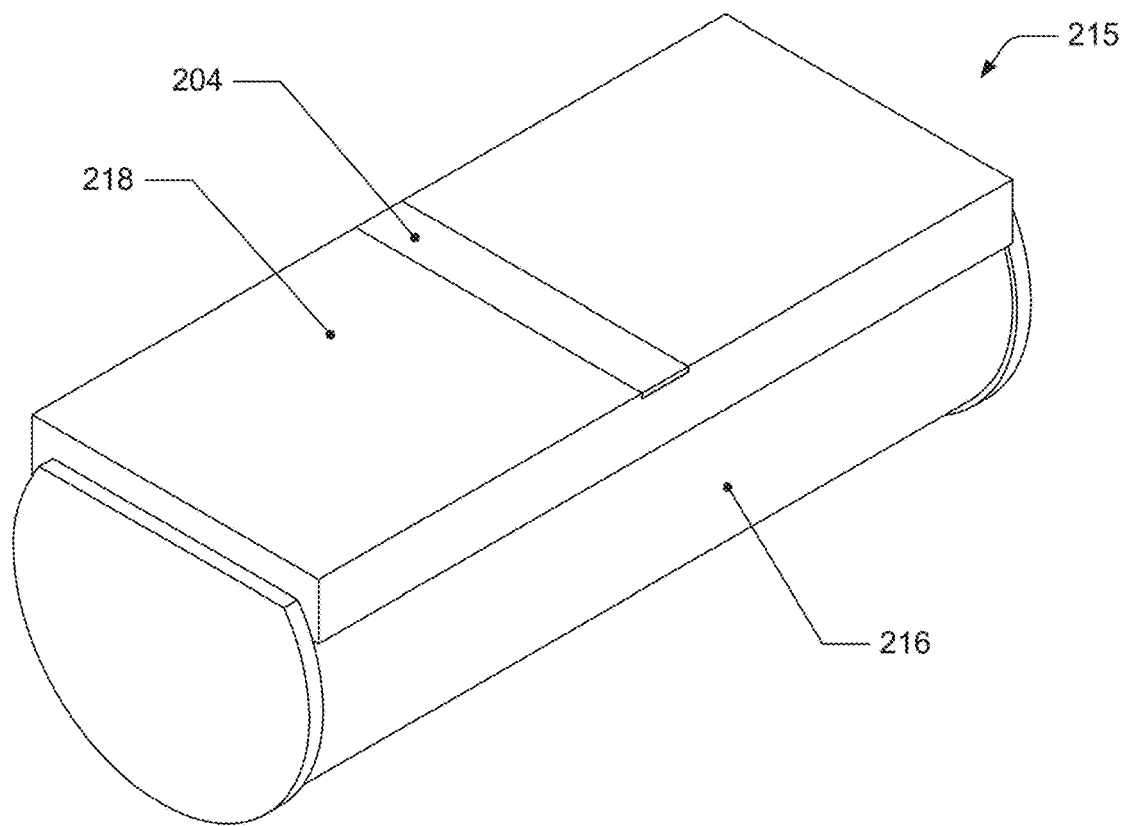
FIGS. 2A and 2B depict an example detection device that includes a hoop stress sensor, bridge, and housing.

In the following description, numerous specific details are set forth in order to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

I. Introduction and Context

Conventional fluid flow sensors typically use invasive techniques to determine flow and generally provided limited and incomplete information. For example, typical flow meters generally require the fluid being measured to flow through or contact an aspect of the flow mete; this may be considered "invasive" flow detection. In some instances, this includes the flow meter having a housing through which the fluid flows or a feature positioned within the fluid conduit that contacts the fluid in order to detect flow. This invasive flow detection has numerous drawbacks and disadvantages.

For example, some conventional flow meters have a housing through which fluid must flow in order for the flow meter to detect flow which requires that the flow meters are installed in-line with, and as a part of, the fluid flow delivery system being measured. This requires that the fluid conduits have a break, or are capable of having a break created, where the flow meter can be installed fluidically in-between at least two sections of fluid conduit; this may also require a pipe that is capable of being modified to connect with a flow meter, e.g., adding threaded connections to connect with threaded connections of a flow meter. Because of this, only those fluid conduits capable of these configurations may have a traditional flow meter.

Additionally, the nature and positioning of some fluid conduits prevent them from being separated or connected with a conventional flow meter. For instance, it may not be feasible to install a flow meter on a fluid conduit (e.g., it is positioned within a wall or concrete), and it may not be feasible to modify a fluid conduit to connect a flow meter because, for example, the positioning of the fluid conduit may prevent this or the type of fluid conduit may not allow this (e.g., it is a clay water pipe).

Even where conventional in-line flow meters are connected with fluid conduits, each connection point of the fluid conduit to a flow meter is a potential weak point and failure point for the fluid delivery system. Each additional connection point between the fluid conduit and the flow meter is a location where leakage, pressure fluctuations, splits, corrosion, rupture, contamination, and damage caused during the installation of the flow meter can occur. Furthermore, the conventional flow meters can also be a source of contamination (e.g., from aspects of the flow meter itself) and blockage within the fluid conduit.

Furthermore, the detection data provided by typical flow meters is limited. For some such flow meters, this includes only a real time detection of a flow rate that may only be displayed in a screen or display. Many conventional flow meters do not and cannot provide data other than a flow rate within the pipe.

Accordingly, provided herein are novel apparatuses and methods for detecting, monitoring, and determining fluid flow within a fluid conduit and a fluid delivery system, as well as for monitoring and determining various conditions within the fluid delivery system and conditions of the fluid delivery system itself. In some embodiments, the detections and determinations are done invasively such that they do not breach the fluid conduit on which they are positioned, or require contact with fluid within the fluid conduit.

II. Detection Devices

Described herein are detection devices that include one or more sensors configured to detect and/or determine one or more characteristics of a fluid conduit, fluid flow within that conduit, or both. As discussed in more detail below, these sensors may include a hoop stress sensor, one or more acoustic sensors, and a thermal flow condition sensor. The detection devices may be positioned onto fluid conduits so that the detection device's sensors are near, indirectly, or directly in contact with the fluid conduit which may enable, in some embodiments, these sensors to detect various conditions which in turn allows the detection device to perform the fluid flow and pipe conditions detections and determinations described herein. The sensors of a detection device may be used alone or in combination with other sensors in the detection device to detect and determine the one or more characteristics of the fluid conduit and fluid flow. Similarly, in some embodiments a single detection device may be used to determine the one or more characteristics of the fluid conduit and fluid flow, while in some other embodiments, the multiple detection devices may be used together to determine such characteristics.

In some embodiments, the detection device may include a leak detector that is configured to detect a leak in a pipe by detecting the presence of a liquid on and/or near the pipe. For example, the leak detector may be a cable with various regions of exposed, uninsulated wire that, when contacted by the liquid, are configured to create a signal, or cause the lack of a signal, which indicates the presence of a liquid which in turn may be used to detect the presence of a leak. The leak detection element (e.g., the exposed wires) of detector may be positioned on a pipe as well as on a location near the pipe, such as the ground, in order to detect the presence of the liquid that may be on or around the pipe. This leak detector may be the same as any other leak detector mentioned here.

A. Hoop Stress Sensor

In some embodiments, the detection device may include a hoop stress sensor for determining a pressure within a fluid conduit. The hoop stress sensor may be used to detect the pressure, pressure variations, and pressure transients within the pipe non-invasively. As used herein, non-invasively means that the inner wall of the pipe is not breached or otherwise compromised structurally. Further, no sensor element need be provided in the pipe interior. Examples of modes of attachment of the sensor to a pipe include pasting or welding a sensor on the outside of the pipe and strapping or clamping a detection device (described elsewhere herein) against the edge of the pipe.

For instance, the hoop stress sensor may be attached directly or indirectly to the outside of the pipe. For an indirect attachment, the hoop stress sensor may be affixed directly to another element, and that other element, not the hoop stress sensor, is directly attached to the pipe. Because of this, non-invasive also encompasses some alteration of the outer surface of the pipe, such as cleaning, polishing, milling, or drilling, but without breaching the inner wall of the pipe, in order to position the sensor directly or indirectly onto the outer surface of the pipe.

1. Mode of Detection

In some embodiments, a hoop stress sensor is used to determine the pressure within a fluid conduit by detecting the hoop stress of the pipe. Fluid flowing through fluid conduit, such as a pipe, exerts circumferential force (i.e., pressure) on the pipe wall, which is considered a hoop stress exerted on the pipe wall. Although a pipe is referred to herein, the concepts described herein are not limited to pipes; they are equally applicable to other fluid conduits. Pressure variations in the pipe correspondingly produce hoop stress variations which can be detected by the hoop stress sensor in order to measure and determine the pressure. For instance, the following equation may be used to determine a pressure within a pipe using hoop stress: $P=(t*\sigma_\theta)/r$ where P is fluid pressure, t is the wall thickness, r is the mean radius, and $\sigma_\theta$ is the hoop stress. In contrast, the longitudinal, or axial, stress of a pipe is the stress on the pipe in a direction parallel to the axis of cylindrical symmetry.

The hoop stress sensor may be a strain gauge that is directly or indirectly attached to the outside of a pipe. The strain gauge may have a metallic foil pattern connected to an insulated, flexible backing, and the electrical resistance of the metallic foil is configured to change as the shape of the metallic foil is deformed. For instance, as the metallic foil pattern becomes narrower and longer, its end-to-end electrical resistance may increase, and conversely, as the metallic foil becomes broader and shorter, its end-to-end electrical resistance may decrease. The strain gauge is connected to the pipe so that it detects hoop stress, not longitudinal stress, of the pipe.

In one example, a hoop stress sensor's strain gauge is a polymide resin strain gauge 0.05% FS accuracy transducer; in another example, the strain gauges may be wire resistance strain gauges construction of a non-magnetic 75/20 nickel chromium alloy modified with cobalt and aluminum, such as Moleculoy®. As examples, the strain gauge may have a nominal resistance of 120Ω, 350Ω, 650Ω, 1,000Ω, and 2,000Ω, a resistance tolerance to average resistance of ±0.1% and 0.15%, a gauge factor of between about 1.86 to 2.20, a dispersion of gauge factor of about ±1%, a fatigue limit of between about 2% and 1.5%, a fatigue life of about 10', and working temperature ranges of about −30° C. to about 250° C. The strain gauge may have foil grid dimensions that have a width of at least about 0.5 mm, 1.0 mm, 1.5 mm, and 2.0 mm, and a length of about 1.5 mm, 3.0 mm, 4.5, or 5.0 mm in length as well as, and a backing size that may have a width of at least about 2.0 mm, 2.5 mm, 3.5 mm, and 5.0 mm and a length of at least about 3.5 mm, 4.0 mm, and 7.0 mm, for example of about.

In some embodiments, the strain gauge may be affixed directly to, or a part of a patch that is affixed directly to, the outside of the pipe. In some other embodiments, the strain gauge may be attached to a bridge which is affixed to the outside of the pipe. The bridge may be an "I" shaped piece of material, such as aluminum or stainless steel, and may have ends that are thicker than the center of the bridge. The ends may be attached directly to the pipe, such as by an adhesive or welding, and the strain gauge may be positioned in the center, or middle, of the bridge. The bridge may have dimensions of about 10.00 mm by about 62.00 mm and may be comprised of aluminum, such as 6061-T6 aluminum. Examples of adhesives include ethyl-based cyanoacrylate or methyl-based cyanoacrylate. In other embodiments, the bridge may not be bent, but may remain straight and be attached to the pipe at other points closer to the center of bridge, such as points where the bridge is tangential to the pipe. This may allow the bridge to be easily removed from the pipe without damaging the strain gauge or bridge thus enabling reusability of the strain gauge and/or bridge.

2. Apparatus

FIGS. 1A and 1B depict an example hoop stress sensor indirectly affixed to a section of pipe. Here, the hoop stress sensor is a strain gauge 102, shown with shading, that is attached to a bridge 104 which is attached to a pipe 106. The bridge 104 is attached circumferentially to the pipe 106. On the right side of FIG. 1A is an example schematic of the strain gauge which has a metallic foil 108, a first terminal 110, a second terminal 112, and a backing 114. As mentioned above, the strain gauge 102 is indirectly connected to the pipe 106 so that the strain gauge 102 detects hoop stress, not longitudinal stress, of the pipe 106.

When the pipe 106 is subjected to changes in pressure, the pipe may be caused to expand or contract thereby deforming the strain gauge and causing a change in its resistance. This is illustrated in FIGS. 1A and 1B. In FIG. 1A, the pressure of pipe 106 is considered lower than the pressure of pipe 106 of FIG. 1B, as illustrated (albeit in an exaggerated manner) by the bulging, deformed pipe 106 in FIG. 1B. Here in FIG. 1B, the increased pressure within pipe 106, as indicated by the arrows, exerts a higher circumferential force against the inside of the pipe 106, thereby exerting a greater hoop stress on the pipe 106 and causing the pipe wall to expand and bulge. As illustrated in the right side of FIG. 1B, this hoop stress on the pipe 106 causes the strain gauge 102 to expand in the longitudinal direction, as indicated by the vertical arrow 118, which causes the metallic foil 108 to lengthen, narrow, and change its resistance. This change in resistance is used to determine the change in hoop stress of the pipe 106, which is used to determine pressure within the pipe 106.

In some embodiments, the strain of the strain gauge may be determined using the change in resistance and the gauge factor of the strain gauge. For example, the following equation may be used:

$$\varepsilon = \frac{\Delta R / R_G}{GF}$$

where ε is the strain, GF is the gauge factor of the strain gauge, ΔR is the change in resistance caused by the strain, and $R_G$ is the resistance of the undeformed strain gauge. In some embodiments, a Wheatstone bridge is used to determine the change in resistance of the strain gauge. In the Wheatstone bridge, the strain gauge may act as the resistor having unknown resistance while the remaining resistors are of known values. Based on a change in voltages across the Wheatstone bridge, the change in resistance of the strain gauge can be obtained.

In some embodiments, the determined strain may be correlated to a pressure within the pipe. In certain embodiments, a relationship between measured strain and pressure in the pipe is determined by calibrating the strain gauge. For example, a known pressure may be applied to the pipe while the strain of the pipe is measured using the hoop stress sensor and the resulting, measured strain may be associated with that known pressure. Additional calibration steps may be performed in order to associate multiple pressures with measured strain values. In one example, the calibration may include measuring the strain with zero pressure, storing that value, and correlating that measured strain with historically measured data of that of other pipes of similar diameter, material, condition, and other similar calibration steps. The resulting relationship may be stored in a memory of a controller of the hoop stress sensor. The memory may also contain instructions for measuring the change in resistance of the strain gauge, determining the strain of the pipe, and determining a pressure within the pipe based on these measurements and calculations, and in some embodiments, a correlation table.

In some embodiments, the determined strain may be converted to a hoop stress which is then used in the equation from above, $P=(t*\sigma_\theta)/r$, to determine the pressure in the pipe. Again, these calculations may be stored as instructions on a memory of a controller and performed by the processor. In some other embodiments, both this equation as well as pressure calibrations may be used to determine the pressure of the pipe.

Figure 2B:
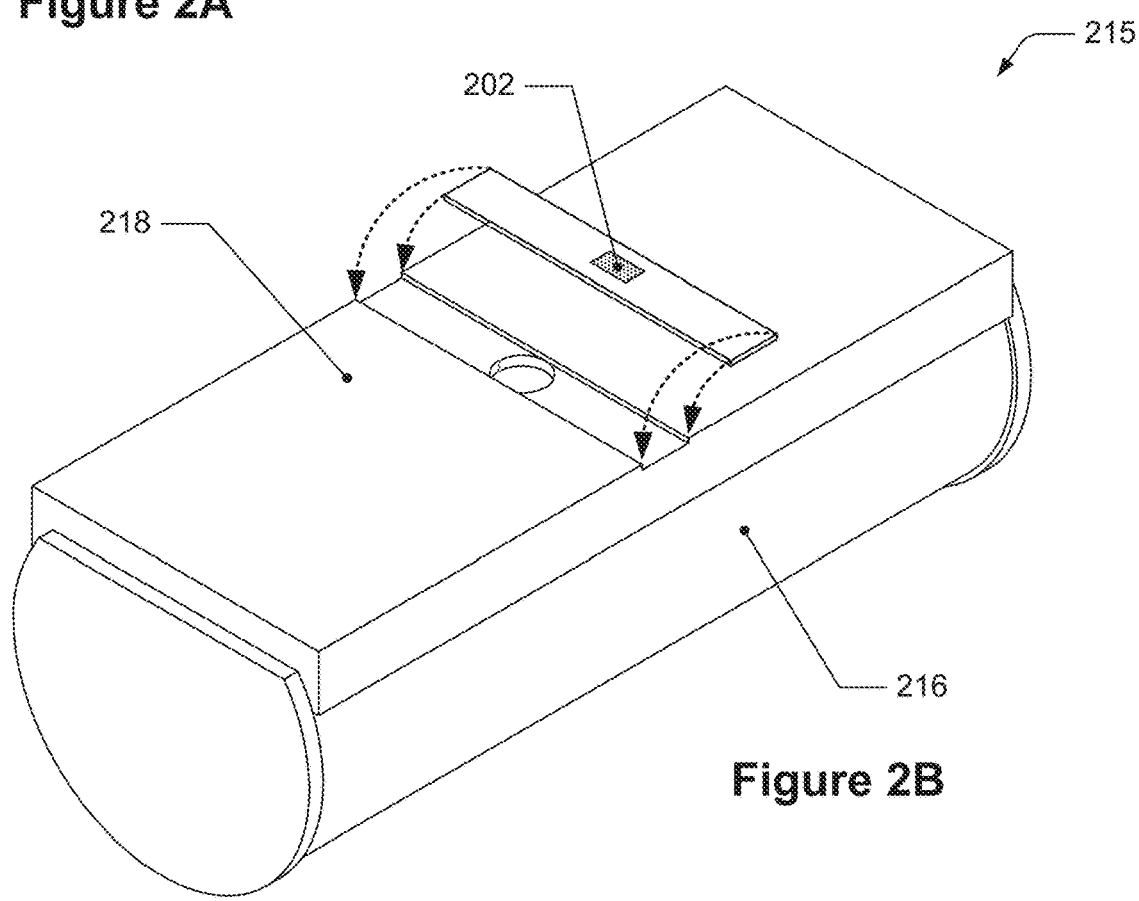

The hoop stress sensor may be a part of a detection device. FIGS. 2A and 2B depict an example detection device that includes a hoop stress sensor, bridge, and housing. In FIG. 2A, the detection device 215 includes a housing 216 along with a bridge 204 attached to the housing 216; the hoop stress sensor, not depicted in FIG. 2A, is attached to the surface of the bridge 204 facing the housing 216. The housing 216 includes a face 218 that may be configured to be positioned on or near the pipe or fluid conduit. The bridge 204 may be removable from the housing 216, as depicted in FIG. 2B, so that the bridge 204 may be attached directly to the pipe or fluid conduit, as described above, and then connected to the housing 216. The hoop stress sensor 202 is seen in FIG. 2B attached to the bridge 204. This detection device may also include a processing module described below.

3. Processing Logic for Hoop Stress Sensor

Figure 3:
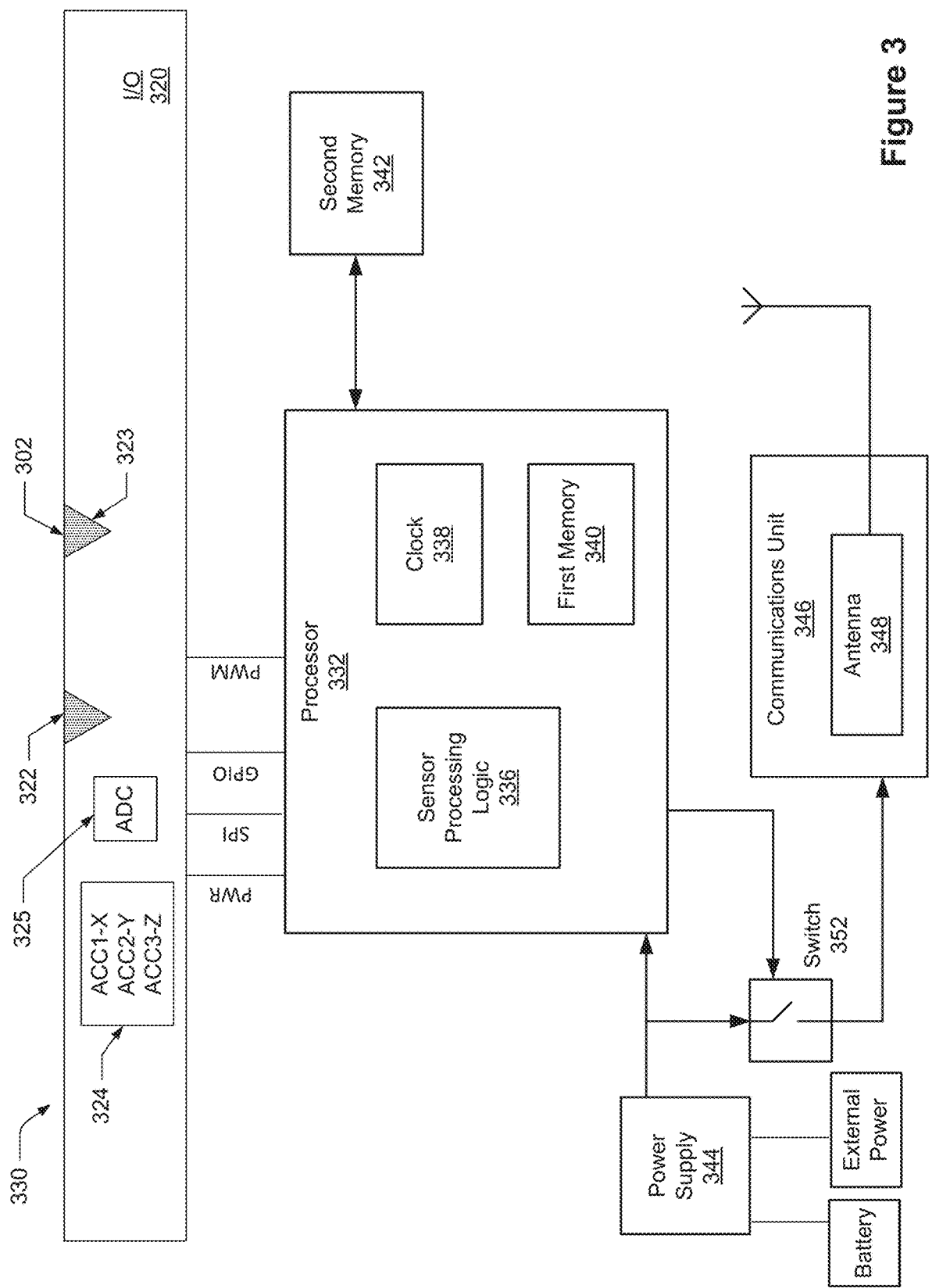
FIG. 3 schematically depicts an example processing module.

FIG. 3 schematically depicts an example processing module 330. The depicted processing module 330 includes an input/output unit 320 that includes a first input 321 for connection to a leak detector 322 and an accelerometer 324 that is depicted as a three-axis accelerometer. The input/output unit 320 may include an analog to digital converter 325, and the input/output unit 320 may be configured to receive power from the power supply 344 for various purposes including to power the hoop stress sensor 302. In some embodiments in which the hoop stress sensor 302 (or at least its strain gauge) is incorporated in a Wheatstone bridge, the input/output unit 320 may also electrically connect to the other resistors in the Wheatstone bridge and may be configured to apply voltages across the other legs of the Wheatstone bridge.

As depicted, input/output unit 320 includes various ports or electrical connectors for communicating with various sensors, including port 323 and the hoop stress sensor 302. For example, input/output unit 320 includes electrical connectors for receiving electrical signals corresponding to changes in resistance and voltage of the hoop stress sensor 302, including connecting to two terminals (e.g., terminals 110 and 112 of FIG. 1) of the hoop stress sensor 302. Input/output unit 320 may have ports for additional flow condition sensor components such as a light. In some cases, the input/output unit 320 has ports for components of other types of sensor that may share processing unit 330 with a thermal flow condition sensor. Examples of such other types of sensor include pipe condition sensors (e.g., acoustic sensors) and leak sensors. Ports for these additional types of sensor are not depicted in FIG. 3.

The processing module 330 also includes one or more processors (shown as processor 332) that include a clock 338, a first memory 340, and sensor processing logic 336. The first memory 340 may be a program memory that stores instructions to be executed by the processor 332 and buffers data for analysis and other processing. The sensor processing logic 336 (which may also or alternatively be instructions stored on the first memory 340) is configured to detect signals, including voltages, generated by any of the sensors, including the hoop stress sensor 302 and the leak detector 322. For example, as described above, sensor processing logic 336 may be configured to receive data from sensing elements, including from the hoop stress sensor. The data may be provided in many forms, including voltage levels. In some of the embodiments in which the hoop stress sensor 302 is incorporated in a Wheatstone bridge, the sensor processing logic 336 may also be configured to determine a voltage level across the Wheatstone bridge. The sensor processing logic 336 may also be configured to determine and store values of resistance and voltage to their corresponding values of strain, hoop stress, or pressure. In certain embodiments, sensor processing logic 336 may also be configured to determine and store strain values measured on the pipe, acoustic responses measured on the pipe, and/or calculated pressure values in the pipe.

The clock 338 may be a real time clock or a timer. The processing module 330 also includes a second memory 342 that may be a rewritable memory that is configured to store data generated by any of the sensors or other components described herein. A power supply 344, which may include a battery, is also a part of the depicted processing module 330 and is configured to provide power to the elements of the processing module 330, such as the processor 332, a communications unit 346, and any of the sensing elements, as described above.

The processor 332 may execute machine-readable system control instructions which may be cached locally on the first memory 340 and/or may be loaded into the first memory 340 from a second memory 342, and may include instructions for controlling any aspect of the processing module 330. The instructions may be configured in any suitable way and may by implemented in software, firmware, hard-coded as logic in an ASIC (application specific integrated circuit), or, in other suitable implementation. In some embodiments, the instructions are implemented as a combination of software and hardware.

The communications unit 346 may include an antenna 448. The communications unit 446 may be configured to acquire location data about the location of the detection device using the antenna 448 which is configured to connect with an external location device and receive location data from the external location device. The location data may include the latitude, longitude, and altitude, for example, of the processing module 330 which houses the first antenna 348.

The communications unit 346 may also be configured to wirelessly connect with, and transmit and receive data from, an external device, like a network or computer, using the antenna 348 that is configured to connect with the external device. The communications unit 346 and antenna 348 may be configured to communicate by an appropriate cellular protocol such as Code Division Multiple Access (CDMA), Global System for Mobile Communications (GSM), or Long-Term Evolution (LTE) high-speed data transmission, and LTE CAT M1 (which is a low-power wide-area (LPWA) air interface that is able to connect to the Internet of Things (IoT) and machine-to-machine (M2M) devices. Alternatively or in addition, the communications unit 346 and antenna 348 may be configured to communicate by a non-cellular wireless protocol such as a low power wide area network (LoRaWAN) protocol, which operates between 850 MHz and 1,900 MHz, or other sufficiently long range protocol. As an example, the communications unit 446 may be the SIM808 from SIMCom Wireless Solutions, Shanghai, China. The product may be packaged on a printed circuit assembly ("PCA") with support integrated circuits from Adafruit, Industries of New York, N.Y.

In some embodiments, the processing module 330 may also include a global positioning satellite ("GPS") antenna that can establish a connection with multiple GPS satellites. Using data from communications with such satellites, the communications unit 346 can determine the location of the detection device and thereafter send location data to the processor 332. The term "GPS" herein may mean the broader concept of a location system employing one or more satellites that transmit ephemeris (e.g., a table or data file that gives the calculated positions of a satellite at regular intervals throughout a period) and/or position fixing data to a GPS receiver or antenna on a device. The location of the device may be calculated from the position fixing data on the device itself—communications unit 346 in this case—on a secondary device. Multiple satellites may be used in the system with each one communicating ephemeris data and/or position fixing data. The same satellite may communicate both ephemeris data and position fixing data, or ephemeris data and position fixing data may be communicated through separate satellites. The satellites may be satellites in a GPS system, or it may be satellites in another satellite system such as the Russian Global Navigation Satellite System, the European Union Compass system, the Indian Regional Navigational Satellite System, or the Chinese Compass navigation system. Some GPS systems use a very slow data transfer speed of 50 bits per second, which means that a GPS receiver, in some cases, has to be on for as long as 12 minutes before a GPS positional fix may be obtained. Once a positional fix is obtained, subsequent positional fixes may take much less time to obtain (assuming that the subsequent positional fix occurs within a sufficiently close interval), but this initial lock-on period requires that the GPS receiver be powered for the entire initial lock-on, which can be taxing on devices with small battery capacities.

As further depicted in FIG. 3, the processor 332 is connected to a switch 352 that is interposed between the power source 444 and the communications unit 346. The processor 332 may cause the switch 352 to close, which causes power to be delivered to the communications unit 346, or to open which stops the power to the communications unit 346.

In certain embodiments, the second memory 342 is configured to store data received from the processor 332 and the antenna 348. Firmware updates, which may be received from the antenna 348, are stored at an appropriate location (e.g., second memory 342) accessible to the processor 332. The processor 332 is also configured to access and transmit data stored in the second memory 342 over the antenna 348. In some embodiments, the elements of the processor 332 may be communicatively connected with each other and the processor 332 is configured to control each such element, as well as any element of the processing module 330.

In some embodiments, sensor processing logic may also be configured to connect the accelerometer to the power supply 344 as well as receive signals, such as voltages, from the accelerometer 324. The accelerometer 324 may be continuously powered by the power supply 344 so that the accelerometer 324 can detect events that generate movement or vibrations, such as a seismic event, movement of the pipe to which the processing module 330 is connected, movement of the processing module (e.g., tampering or vandalism), fluid flow within the pipe, and events to the pipe or fluid conduit system upstream or downstream from the processing module (e.g., pipe burst).

In some embodiments, the processing module 330 may be in a sleep state in which power is on to the processor 332, the accelerometer 324, the leak detector 322, and/or the hoop stress sensor 302, but in a low power mode, with few if any operations being performed. In this state, the processor 332 can receive signals from the accelerometer 324, the leak detector 322, and/or the hoop stress sensor 302, and at the same time, the communications 346 module is not powered on. The processor 332 may exit the low power state, and "wake up", in response to detecting a signal of defined magnitude or other characteristic from any of the sensors, including the accelerometer 324, the leak detector 322, and/or the hoop stress sensor 302. Depending on the signal detected, the processor 332 may simultaneously or sequentially cause various functions to be performed, as described below.

4. Examples of Operation

Figure 4A:
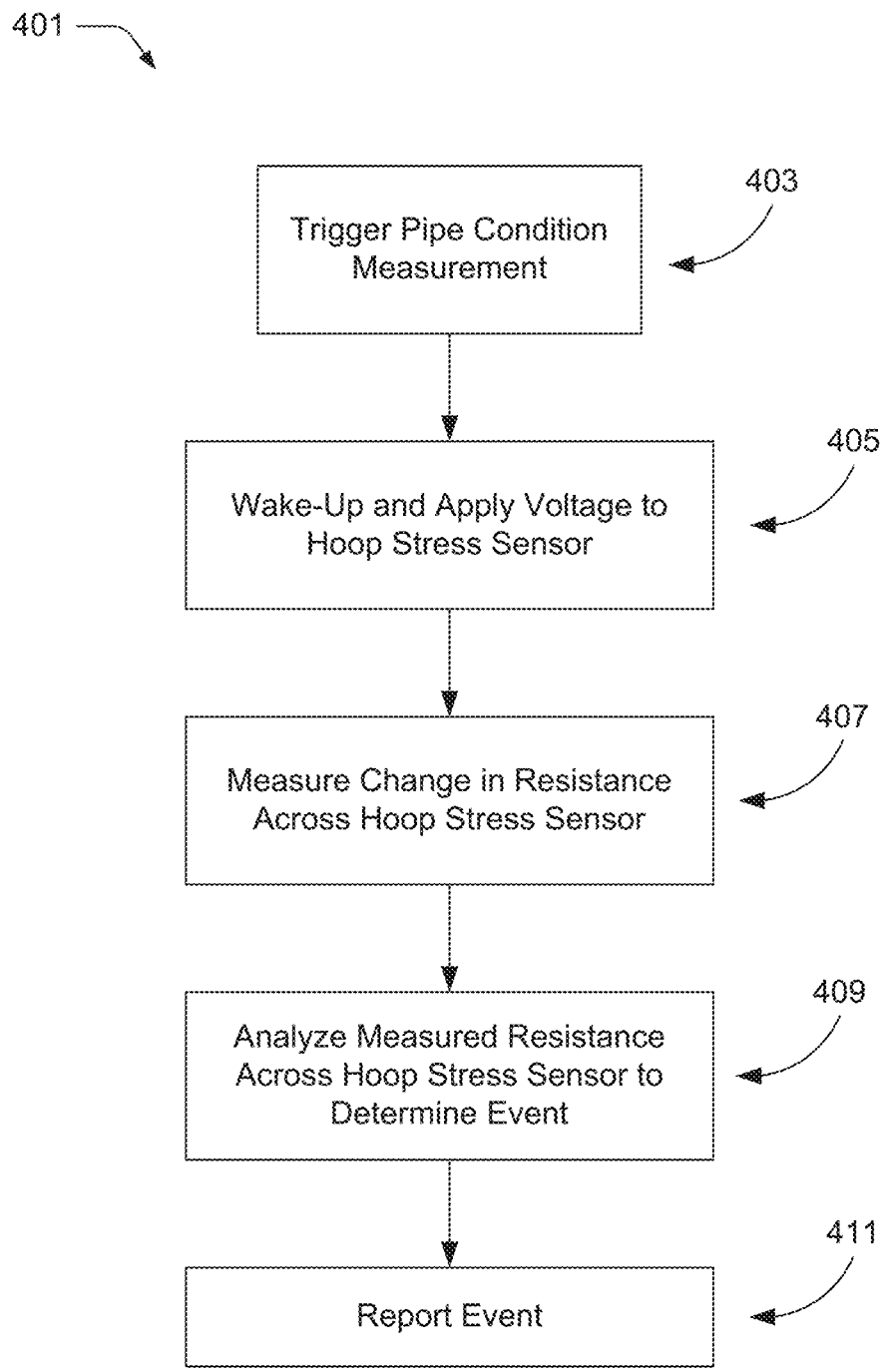
FIG. 4A depicts an example processing sequence for a processing module of a detection device with a hoop stress sensor.

FIG. 4A depicts an example processing sequence for a processing module of a detection device with a hoop stress sensor. The blocks shown in FIG. 4A may be implemented by the processor 332 and other components of processing module 330 of FIG. 3 executing instructions stored on, for example, the first or second memories 340 and 342.

The example technique 401 of FIG. 4A begins at block 403 in which a signal is detected. Similar to the above discussion, this signal may be from or generated by the accelerometer 324 and/or the leak detector 322; this signal may be an electrical voltage or a change in voltage from any of these sensors. Before receiving a signal at block 403 the processing module 330 may be in the sleep state discussed above; for instance, power is on to the processor 332, but in a low power mode, with few if any operations being performed, as well as to the accelerometer 324 and the leak detector 322 either continuously or intermittently. In technique 401, the hoop stress sensor 302 and the communications unit 346 are not powered on.

In block 405, the processor 332 exits the low power state, and "wakes up", in response to detecting the signal from sensors, including the accelerometer 324 and/or the leak detector 322. The signal is typically interpreted to indicate that an event has occurred and the processor 332 may then simultaneously or sequentially cause various functions to be performed, as described below. Also in block 405, the processor 332 causes a voltage to be applied to the hoop stress sensor and in some embodiments, may also cause a voltage to be applied across a Wheatstone bridge that incorporates the hoop stress sensor 302 (e.g., a strain gauge).

In block 407, the processor measures the resistance, a change in resistance, a voltage, and/or a change in voltage across the hoop stress sensor, like described above, in order to determine the hoop stress, or strain, in the pipe.

In block 409 the resistance across the hoop stress sensor, or across the Wheatstone bridge is analyzed in order to determine whether an event occurred. In some embodiments, this may include correlating a measured resistance, voltage, strain, or a measured change in these values, with an event, such as a pipe break, a pressure spike, leakage in the pipe, flow occurring in the pipe, freezing of the pipe, flow in the pipe, a pump being turned off, on, or having its speed hanged which may cause a pressure surge, and degradation of a pipe wall (e.g., corrosion or wall loss) that may occur overt time that may be determined by, for example, detecting higher stresses of the pipe, that is stored in a memory. For example, it may be known that a particular change in resistance across the hoop stress sensor corresponds with a break of the pipe, e.g., a large drop in pressure.

Additionally, in some implementations, the event determined in block 409 includes determining the pressure in the pipe. As described above, this pressure determination may include calculating the strain and the corresponding pressure, calculating the hoop stress and the corresponding pressure, and/or correlating the measure resistance and/or voltage with one or more measured pressures that are stored on the first or second memories 340 and 342.

In an optional step not included in FIG. 4A, the event, including a determined pressure, may be stored in the memory, such as the first memory 342.

In block 411, data associated with the event is reported. This data may include the measured values, the correlated data and other values, and the pressure within the pipe, for example. This data may be wirelessly transmitted over a network to an external device, such as a computer, server, cell phone, or mobile device, for instance. In certain embodiments, the processing module sends not only the most recent data (the one for the just determined event) but other records for other recent events (e.g., the ten or twenty most recent events). After this transmission, the communications unit 346 may be powered off. Further, the processing module 330 may be placed into a sleep state or low power mode as described above.

Figure 4B:
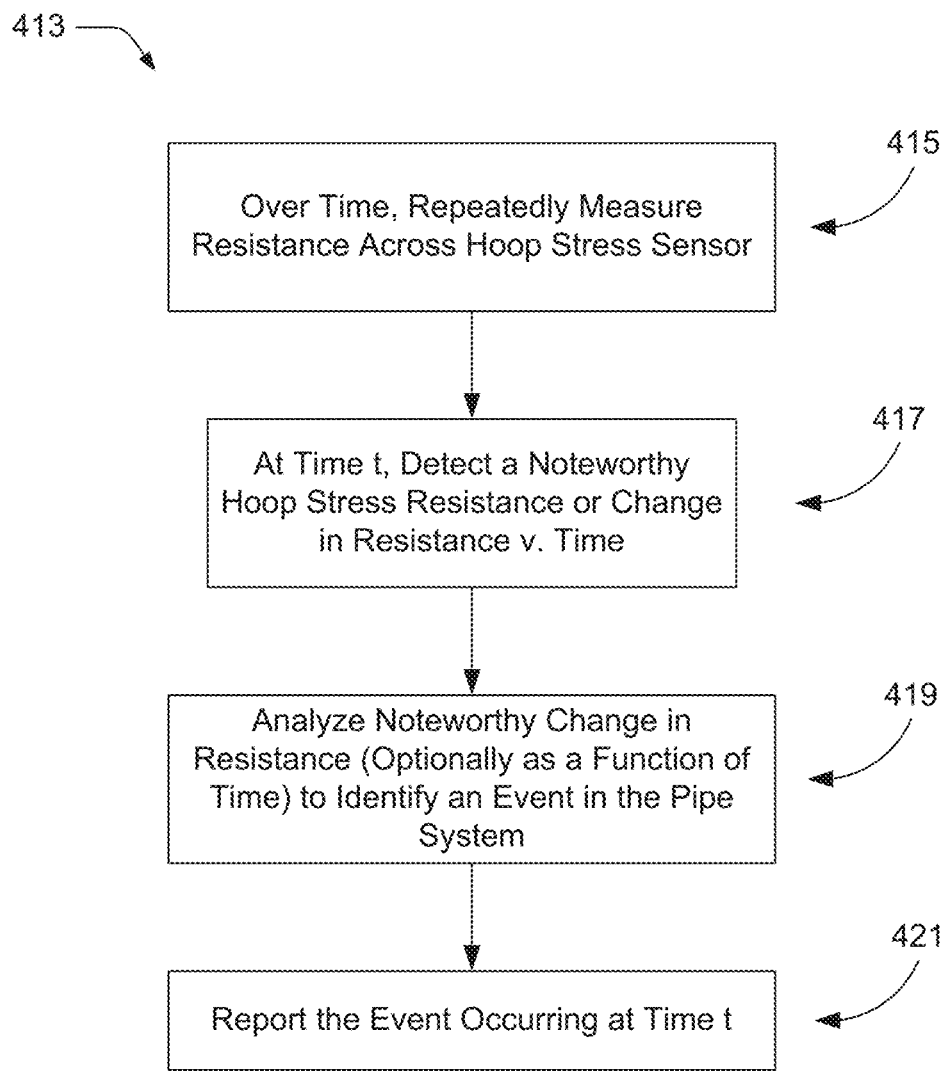
FIG. 4B depicts another example processing sequence for a processing module of a detection device with the hoop stress sensor.

FIG. 4B depicts another example processing sequence for a processing module of a detection device with the hoop stress sensor. The blocks shown in FIG. 4B, like with FIG. 4A, may be implemented by the processor 332 and other components of processing module 330 of FIG. 3 executing stored instructions.

The example technique 413 of FIG. 4B begins at block 415 in which over time, the hoop stress sensor is repeatedly or continuously measured. As discussed above, this can include measuring the resistance across the hoop stress sensor or a change in resistance across the hoop stress sensor, for example. If the measurement is a continuous measurement, then the hoop stress sensor may be continuously measured by the processing module 330, which may be in a low power state that is able to detect various changes in signals of the hoop stress sensor. If the measurement is an intermittent, repeated measurement, then the processing module 330 may be in a low power state in between measurements and in a powered state during the measurement.

In block 417, a noteworthy change in signal of the hoop stress signal is detected at time t. The change in signal may be an instantaneous change in resistance across the hoop stress sensor or a change in resistance over time. For example, the instantaneous change or measured resistance may be compared with one or more known values or thresholds and if the instantaneous change or measured resistance exceed or fall below such values or thresholds, then such change or measured resistance may be considered noteworthy. For instance, if the measured resistance is determined to indicate a pipe pressure higher than a safe operating pipe pressure, then this may be considered a noteworthy change. In another example, the change in resistance or measured resistance over a period of time may be noteworthy, such as a measured resistance over time indicating a decrease in pipe pressure or a lack of pressure over the time period. Additionally, pressure transients, as opposed to instantaneous change in pressure, may be determined in which the change in pressure over time is measured.

In block 419, the noteworthy change in signal is analyzed to determine an event. This may include interpreting, determining, and correlating the hoop stress signal, at least in part, with events, such as a pipe break, leakage in the pipe, a pressure spike, flow occurring in the pipe, freezing of the pipe, flow in the pipe, or degradation of the pipe wall (e.g., pipe wall loss caused by corrosion. Like described above, this may include correlating the detected hoop stress signals with data stored on a memory, such as data indicating that a measured resistance indicates a pressure spike, a leak in the pipe, or a pressure drop.

Additionally, the event determined in block 419 may include determining the pressure in the pipe. As described above, this pressure determination may include calculating the strain and the corresponding pressure, calculating the hoop stress and the corresponding pressure, and/or correlating the measure resistance and/or voltage with one or more measured pressures that are stored on the first or second memories 340 and 342.

In an optional step not included in FIG. 4B, the event, including a determined pressure, may be stored in the memory, such as the first memory 342.

In block 421, like block 411, data associated with the event is reported, including the time t when the event occurred. This data may include the measured values, the time t, the time period over which the measurements were taken, and one or more pressures of the pipe, for example. This data may be wirelessly transmitted over a network to an external device, such as a computer, server, cell phone, or mobile device, for instance. In certain embodiments, the processing module sends not only the most recent data (the one for the just determined event) but other records for other recent events (e.g., the ten or twenty most recent events). After this transmission, the communications unit 346 may be powered off. Further, the processing module 330 may be placed into a sleep state or low power mode as described above.

5. Example Applications

In some implementations, the flow condition processing module that includes a hoop stress sensor may monitor water pressure, and water usage, in a room, building, or geographic region. For example, the system may monitor water consumption and where it occurs and/or in what type of appliance (toilet v. shower v. faucet v. landscaping, etc.) it occurs. Such monitoring may be used for conservation, auditing, etc. In certain embodiments, the system flags a water usage sequence that indicates a problem or need for corrective action; e.g., toilet flush not followed by faucet indicates a hygiene issue for restaurant employees.

The condition to be detected, including pipe pressure, may be present in various contexts such as utilities, municipalities, plants, large buildings, compounds, complexes, and residences. In other words, the sensors used to detect the condition are present on pipes employed in any such location. Of course, the software or other logic used to determine that a potentially hazardous condition exists need not be present at the location of the sensors, although it may be. The logic simply needs to receive input from the sensors and then analyze the sensor data to determine whether condition exists or should be flagged.

Figure 5:
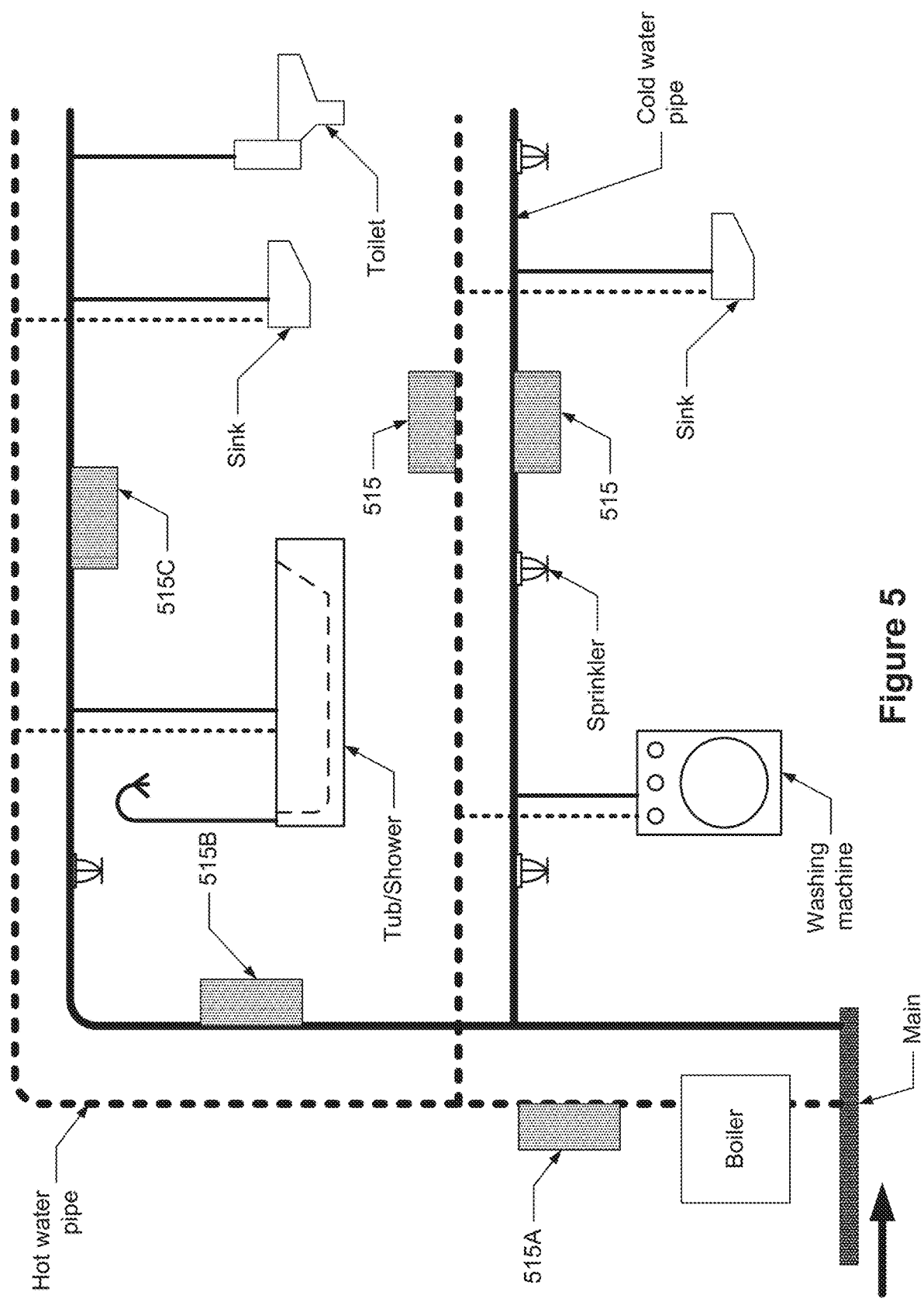
FIG. 5 depicts an example water system that includes multiple water pipes and appliances that use water, such as toilets, sinks, and sprinklers.

FIG. 5 depicts an example water system that includes multiple water pipes and appliances that use water, such as toilets, sinks, and sprinklers. In this example water system, a main water line is connected to various hot water pipes (dotted lines) and various cold water pipes (solid lines) and numerous sprinklers, two sinks, one toilet, one tub/shower, and one washing machine. The detection device 515, which includes a hoop stress sensor described above, is positioned on various pipes of this example water system in order to determine, among other things, pressure in the pipes at its location as well as upstream and downstream from the module. For example, the detection device 515A is positioned so that in can detect water pressure in the hot water pipe close to the boiler which can be used to determine, for instance, whether hot water is being flowed out of the boiler, whether there is a pressure spike or pressure drop in this hot water pipe, and whether there has been damage, or other impulsive event, to this water pipe. These types of conditions and events may be determined at any specific location where the detection device 515 is positioned, as well as to the whole pipe to which the detection device is connected and the pipe system to which that pipe is connected.

Multiple detection devices may also be used together in order to determine events along a single pipe or within a pipe system. For instance, detection devices 515B and 515C are positioned along the same cold water pipe with detection device 515C positioned downstream from detection device 515B and in between the tub/shower and the sink. By measuring the pressure at these different locations, and in some implementations comparing them together, various information can be determined about the pipe and pipe systems, such as flow within the pipe, the presence and location of leaks within the pipe, and the usage of various aspects connected to the pipe, such as the sprinkler in between the detection devices 515B and 5150C.

Furthermore, pressures detected by detection devices on different pipes may also be used to determine various events within the system. For example, two detection devices positioned on different pipes, such as detection devices 530A and 530B, may be used to determine flow, lack of flow, freezing, leaks, and usage of, for instance, the hot water pipe/system versus the cold water pipe/system.

Conditions to be detected need not occur in water or piping for water. More generally, certain conditions may be detected in pipes of portions of a pipe system for any type of liquid (e.g., petroleum, chemical feedstocks in chemical plants). In certain embodiments, the conditions being detected may even apply to gases (e.g., gas pipelines in residences, chemical plants, etc.) or other fluids such as supercritical fluids. Such conditions may relate to overheating, explosive conditions, toxic chemical generation or release conditions, and the like.

In some cases, the conditions to be detected are not limited to systems that contain only fluid carrying pipes. Other conduits such as channels and reservoirs may be monitored. These may be monitored in municipal, residential, or industrial settings; and possibly even human body arteries (e.g. capillary bed).

6. Illustration of Data

Figure 6:
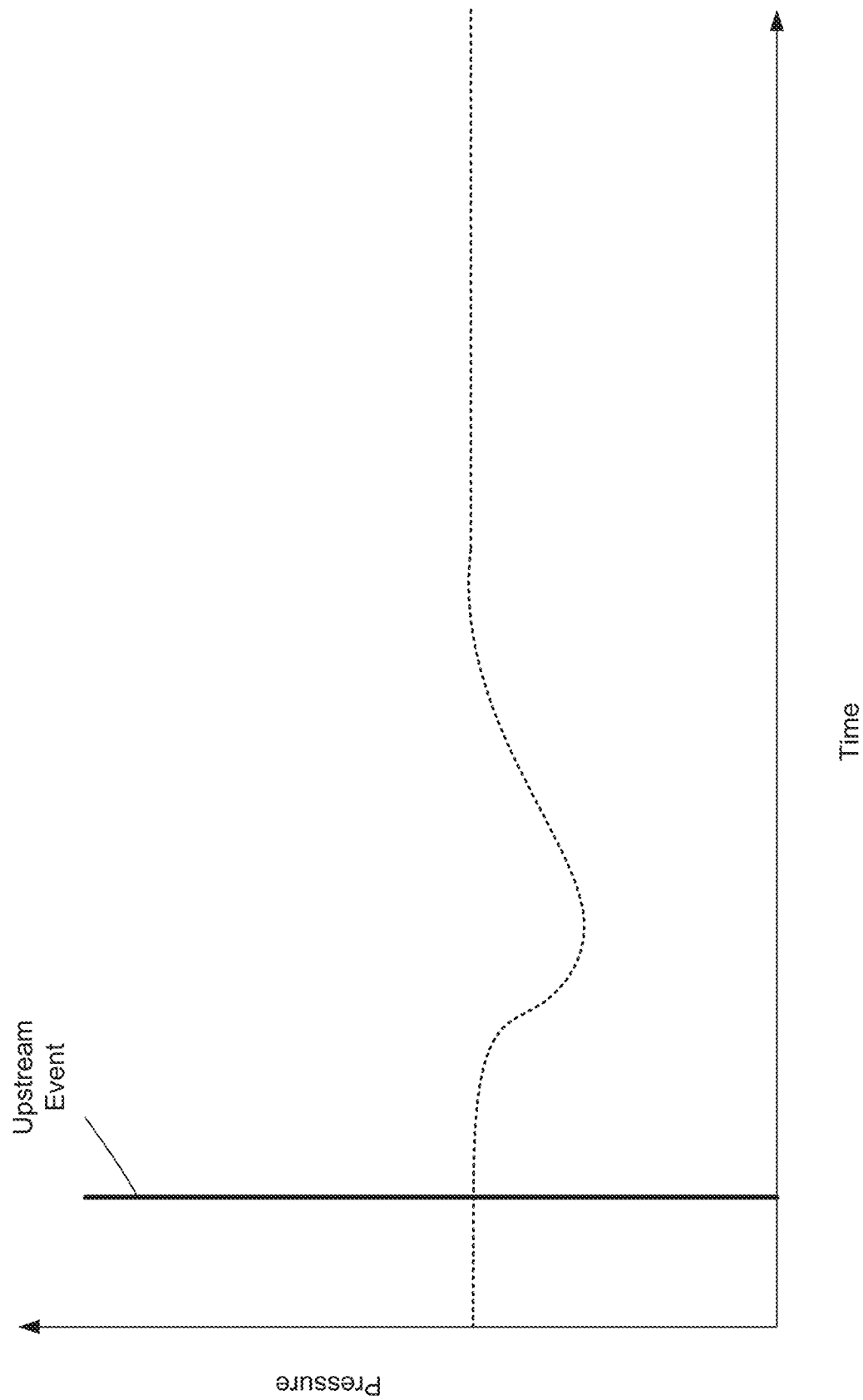
FIG. 6 depicts example pressure data detected by a hoop stress sensor.

FIG. 6 depicts example pressure data detected by a hoop stress sensor. Here, the x-axis is time, the y-axis is pressure, and the dotted line is measured pressure. As can be seen, an upstream event, such as a leak or increase in flow, causes a decrease in pipe pressure that is measured by the hoop stress sensor and also delayed in reaching the hoop stress sensor. For instance, if an increase in flow occurs for a first time period that causes a pipe pressure decrease, then that pressure decrease may propagate downstream in the pipe to the location where the hoop stress sensor is located which is measured by the hoop stress sensor. In another example, a change in pressure over time may be observed which can be categorized as various events, such as a pressure increase caused by a pump being turned on or a pressure drop that may indicate a leak (e.g., a decrease in pressure over time; the decrease may get larger over time if the leak also becomes larger).

B. Acoustic Sensors

In some embodiments, a detection device includes one or more acoustic sensors that can be used to detect various conditions that exist within a pipe, including wall loss, bore loss, other conditions of the pipe wall (e.g., fractures, holes, pits, cracks, etc.) and pipe-related events elsewhere in the pipe system. Wall loss may be generally described as a reduction of the pipe wall material, such as by corrosion and metal loss of the pipe wall. Bore loss may include the reduction of a pipe's nominal pipe size, bore, or internal diameter, which may include buildup of material, such as biological sludge, grease, oxidation products (including corrosion products), tuberculation, and blockages from material originating upstream. In addition to pipe conditions, an acoustic sensor may be able to detect certain properties of a fluid flowing within a pipe. For example, the sensor may be able to determine, at least roughly, whether fluid is flowing, flow rate, and/or flow state (e.g., whether the flow is laminar, turbulent, or transitional). Flow noise has been found to correlate with flow rate in various ranges. Determining whether a flow is laminar, turbulent, or transitional can be assisted by knowing, at least roughly, the fluid's flow rate, which may be derivable from another readings by another sensor such as a thermal flow condition sensor.

1. Example Acoustic Sensors

Figure 7:
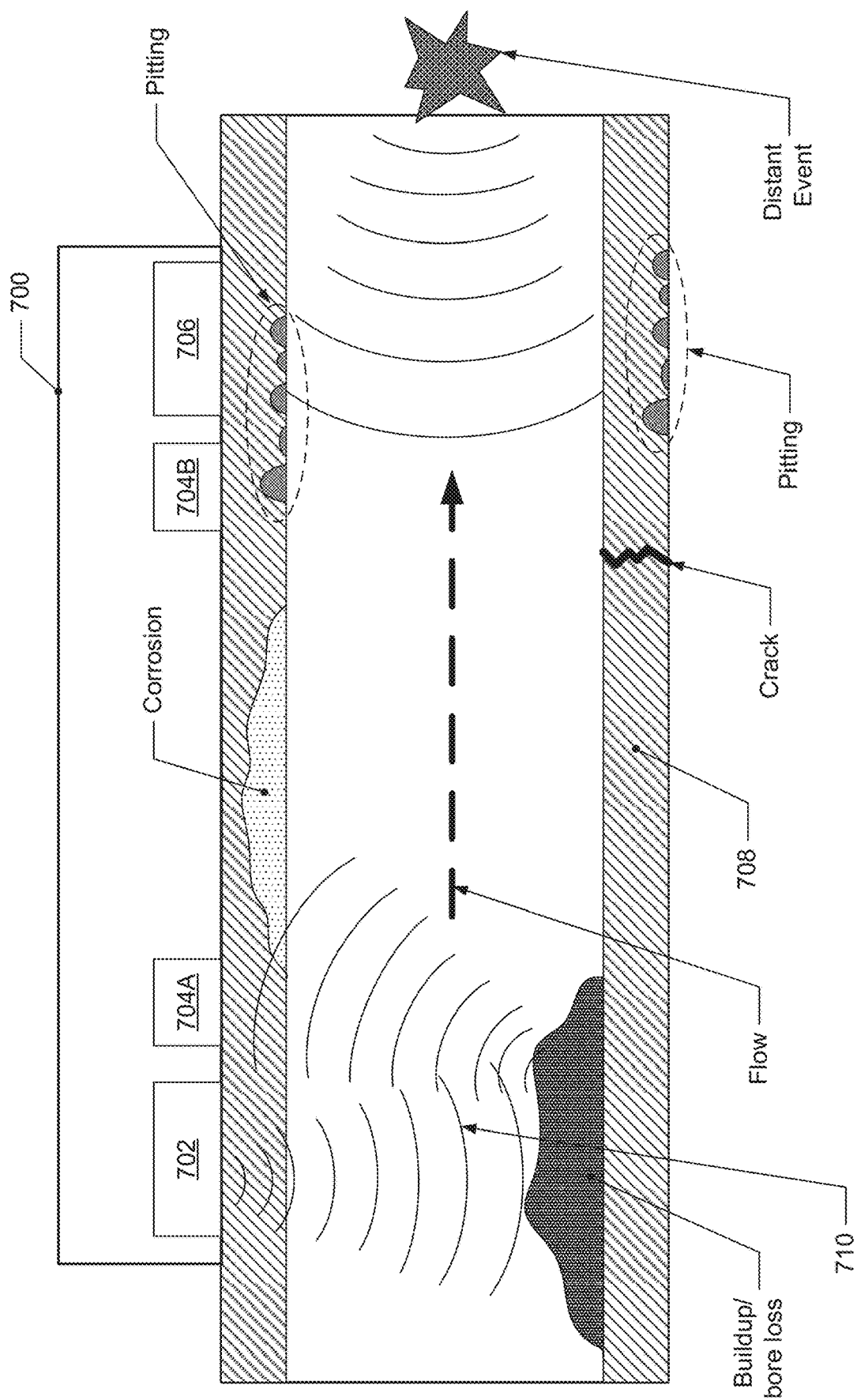
FIG. 7 depicts an axial cross-section of a pipe with numerous pipe conditions.

FIG. 7 depicts an axial cross-section of a pipe with numerous pipe conditions. The figure also shows one example of a an example detection device 700 having multiple acoustic transducers including a speaker 702, two small microphones 704A and 704B, and a large microphone 706 that is larger than the other two microphones 704A and 704B. These acoustic sensors are located adjacent to the pipe to facilitate detection of various conditions of the pipe. In FIG. 7, bore loss is illustrated as a buildup within the pipe interior represented while wall material loss is illustrated as corrosion of the pipe wall. A crack in the pipe 708 wall, as well as pitting on the interior and exterior wall surfaces, are also illustrated. The figure also illustrates that the microphones can pick up a distant event (e.g., a pipe burst, a pipe leak, a frozen pipe, a blockage, a tap opening or closing, etc.).

The microphones 704A, 704B, and 706 are configured to detect acoustic signals of the pipe which can be measured and analyzed in order to determine the presence of any of these pipe conditions. For instance, microphone 706 may be configured detect the signal produced by the distant event, such as a burst pipe, while microphones 704A and 704B may detect the signals produced by more local events such as pipe defects or fluid flow close to the pipe condition sensor. The speaker 702 may be configured to generate one or more acoustic signals that can be transmitted onto and into the pipe. These signals can travel to, contact, and reflect against the pipe 708, and any defects or buildups in the pipe (e.g., cracks, corrosion, or scum within the pipe 708) The generated acoustic signals, as modified by the pipe or material within it, can be detected by one or more of the microphones. For example, speaker 702 may generate an acoustic signal 710 that contacts the buildup and reflects back to, and is detected by, the microphone 704A.

In some embodiments, as noted above, the large microphone 706 may be used to listen for abnormalities at distant locations within the pipe, such as a single distant event, which may be represented as a signal spike. If such an event is detected, then a notification or alert may be generated and sent to an external device (e.g., a controller with a memory, described herein, may include instructions for detecting this event, and generating and transmitting the notification). One or more of the microphones, e.g., large microphone 706, may also be used to detect a deviation of acoustic signals over one or more periods of time. For instance, a microphone may receive acoustic signals over a particular time period (such as days, weeks, or even months), which may be recorded and compared against currently collected signals. If the current and historical signals deviate by more than a threshold amount or are otherwise sufficiently different, the sensor or logic configured to interpret the sensor signals can determine that a particular event has occurred. Alternatively or in addition, a deviation may indicate wall loss, bore loss, or other deleterious pipe condition. In certain embodiments, one or more of the microphones, e.g., large microphone 706, may also be configured to determine the presence of flow within the pipe 708.

In certain embodiments, an acoustic sensor determines the resonant or ringing frequency of the pipe. In certain embodiments, the acoustic sensor determines when (and optionally by how much) the resonant or ringing frequency changes from a prior value. To measure the resonant frequency, the pipe may be excited by an impulse or by a swept frequency. The amplitude and decay rate of the pipe's response may be repeatedly assessed over time (during similar conditions such as noise level) and the change in the response indicates the change in the pipe's wall.

In certain embodiments, the large microphone 706 (which is larger than the small microphone, e.g., 706 in FIG. 7), used in the in the detection device is able to reliably detect acoustic signals over a wide frequency range, that may roughly correspond to the frequency range of human hearing. In one embodiment, the lower end of the microphones detectable range is about 5 Hz to about 20 Hz. In one embodiment, the upper end of the detectable frequency range is about 20 kHz, to about 25 kHz. In certain embodiments, the sensitivity of the microphone is at least about −10, decibels (dB), or at least about −30 dB, or at least about −40 dB, which may be frequency dependent. In certain embodiments, the large microphone used in the in the detection device can interpret acoustic signals over a dynamic range of at least about 70 dB, which may be frequency dependent. Examples of suitable microphones include piezoelectric microphones or transducers that capture or sense vibrations and acoustic signals, microphones with high sensitives (e.g., up to about −30 dB), and those microphones used in musical applications. The size of the large microphone may be selected based on the pipe diameter. In certain embodiments, the size of its largest dimension is between about 0.3 to 2 inches. In one example, the microphone's size is at most 0.8 inches for a pipe having a diameter of about 12 inches or less, for instance.

In certain embodiments, one or both of the small microphones 704A or B used in the in the detection device is able to reliably detect acoustic signals down to at least about 10 Hz to about 20 Hz. In certain embodiments, one or both of the small microphones are able to reliably detect acoustic signals at frequencies up to at least about 20 or at least about 25 kHz. In certain embodiments, one or both of the small microphones has a sensitivity of at least about −10 dB, or at least about −30 dB, or at least about −40 dB, for example, which may be frequency dependent. In certain embodiments, one or both of the small microphones can interpret acoustic signals over a dynamic range of at least about 90 dB, which may be frequency dependent. Examples of suitable microphones include condenser microphones that may include a buffer. The small microphones may be selected based on the pipe diameter and, in certain embodiments, are at least 0.2 inches in diameter for a pipe having a diameter of about 12 inches or less, for instance. One example of a microphone suitable for use as the small microphone is the PUI Audio, product number POM-2730L-HD-R.

In certain embodiments, the speaker 702 used in the detection device is an acoustic exciter such as a voice coil or a device capable of delivering a mechanical ping or strike, such as a solenoid. In certain embodiments, speaker 702 is configured to produce an excitation signal with a fast rise time than can excite harmonics in the pipe or fluid conduit. In certain embodiments, the speaker 702 used in the detection device has a dynamic range of at least about 100 dB. In certain embodiments, the speaker used in the in the detection device can produce low frequency acoustic signals of about 30 Hz or lower. In certain embodiments, the speaker used in the in the detection device can produce high frequency acoustic signals of about 20 kHz or higher. Examples of suitable speakers include those having a relative small size (appropriate for the pipe), are mechanically coupled (as opposed to air coupled) to the pipe, consume low power, and are energy efficient. One example of a suitable speaker is the DAEX-13-4SM Skinny Mini Exciter Audio and Haptic Feedback 13 mm 3 W 4 Ohm by Dayton Audio. In some embodiments, similar to above, the size of the acoustic exciter may scale with the pipe diameter, such that larger acoustic exciters may be used for larger and/or thicker pipes. For instance, an exciter that is about 1.5 in by 0.5 in (pipe facing surface) may be used on a pipe having a diameter of about 12 in or less. When two microphones, such as the small microphones 704A and 704B, are configured to be used in concert, they may be used to determine the relative location of a pipe condition with respect to the pipe condition sensor. These two microphones are spaced apart along the length of the pipe, they can be used to determine whether an event or pipe condition is upstream or downstream from the detection device. Determining the direction of the event with respect to the sensor may employ signal processing such as described elsewhere herein. Generally, the process involves determining which of the two microphones received the signal first. For instance, upstream may be to the right of FIG. 7 and the acoustic signals caused by the distant event in FIG. 7 may reach microphone 704B before reaching microphone 704A, which is used to determine that the distant event occurred closer to microphone 704B, i.e., it occurred upstream of the detection device 700.

Similarly, in some implementations, the two microphones (e.g., small microphones 704A and 704B) may also be used to determine the presence and, optionally, the direction of flow within the pipe 708. In some embodiments, only one microphone is needed to determine the presence of flow within the pipe 708.

In some embodiments, as described above, the small microphones 704A and 704B may be used in conjunction with the speaker 702 to determine the presence and location (e.g., upstream or downstream with respect to the sensor) of various pipe conditions, such as bore loss, wall loss, leaks, and cracks. A controller may include instructions to cause the speaker to emit signals of a defined type (e.g., having a defined frequency and intensity). The controller may also be configured to interpret and process the signals received by one or more of the microphones. In particular, the controller may be configured to determine whether pipe conditions exist, which conditions exist, and the upstream/downstream direction of such conditions. An example of a controller is described with reference to FIG. 3 discussed below.

Figure 8A:
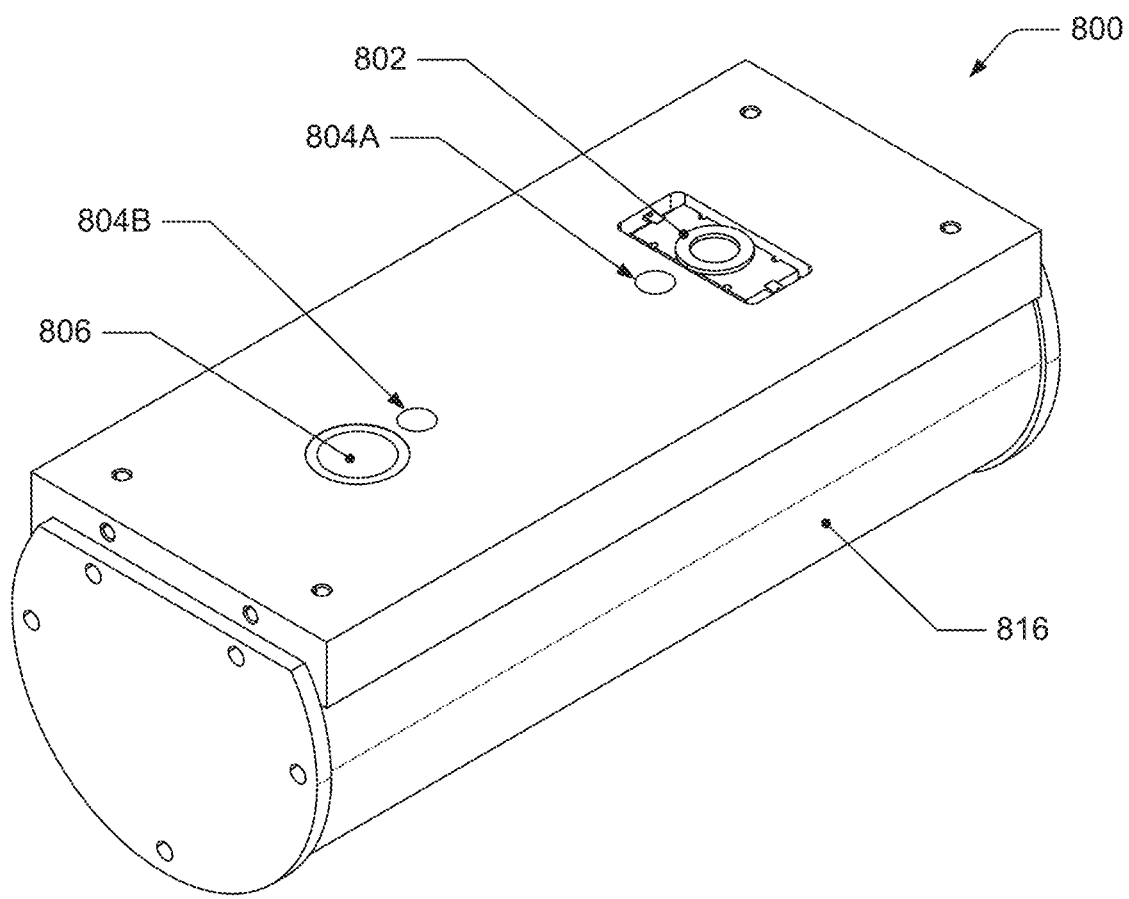
FIGS. 8A and 8B depict an example detection device.
Figure 8B:
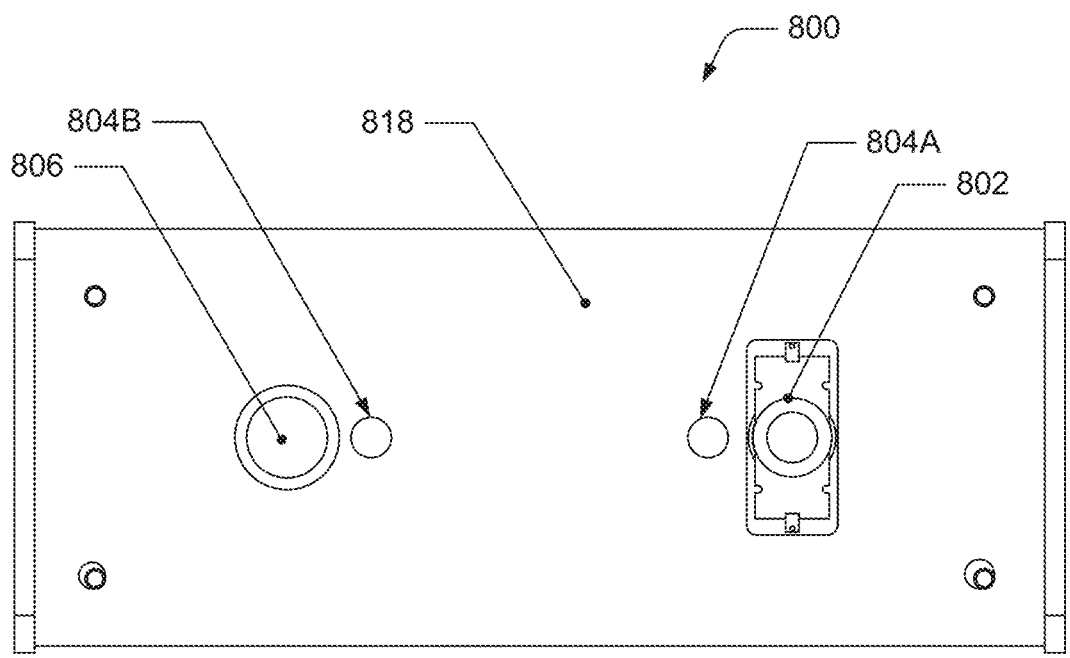

FIGS. 8A and 8B depict an example detection device. In FIG. 8A, the detection device 800 includes a housing 816 and a face 818 with ports in which the acoustic sensors 802 (speaker), 804A and 804B (small microphones), and 806 (large microphone) may be positioned. In some embodiments, the small microphones 804A and 804B are flush with the face 818 while the large microphone 806 and the speaker 802 may be recessed and offset from the face 818 such that they are within the housing 816. This detection device 800 may also include a processing module described below.

In some implementations, a sound conductor may be positioned between the large microphone 806 and the pipe wall, such as a petroleum jelly or grease, in order to facilitate the transmission of acoustic signals from the pipe to the large microphone 806. In certain embodiments, the large microphone is in acoustic contact with the pipe through a coupling agent (grease, etc.) but the two small microphones are coupled through the air. In some cases, even one or both of the small microphones employs a coupling agent. In some implementations, using two axially separated, air-coupled microphones allows good phase response, which can be useful in determining the direction of an event (with respect to the sensor), etc.

Figure 11A:
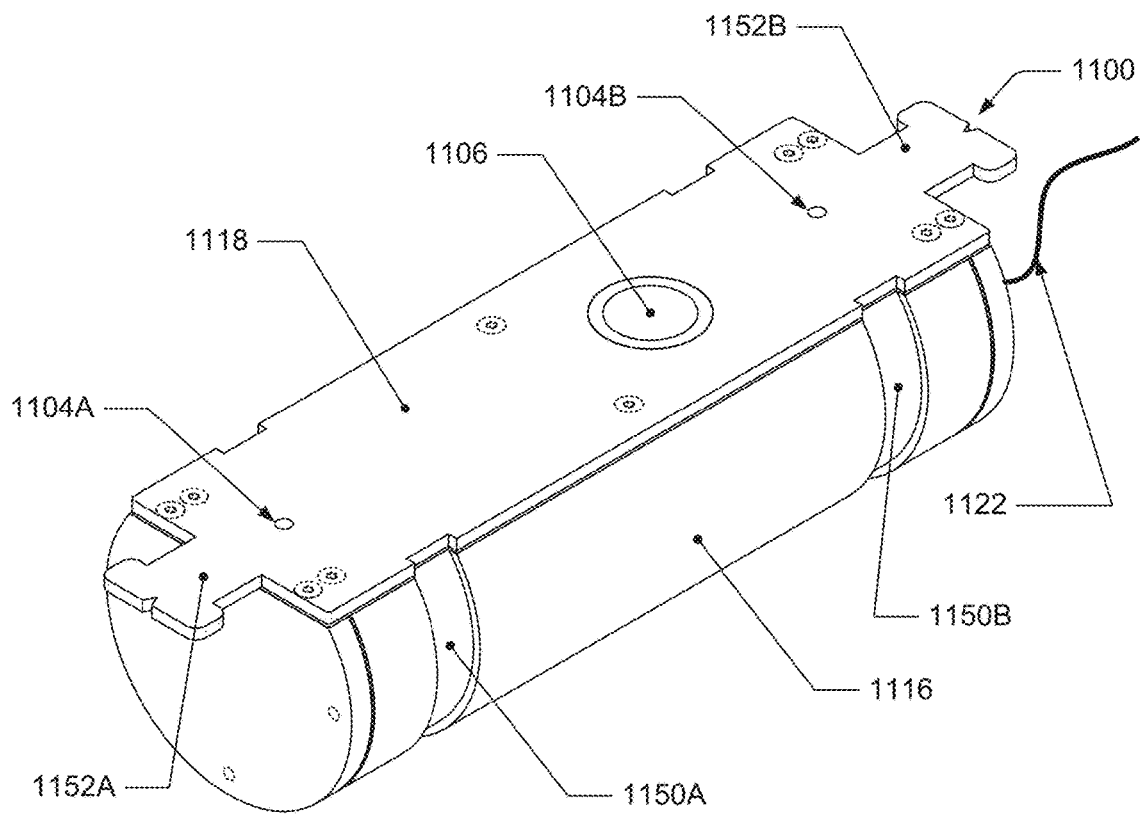
FIGS. 11A and 11B depict another example detection device.
Figure 11B:
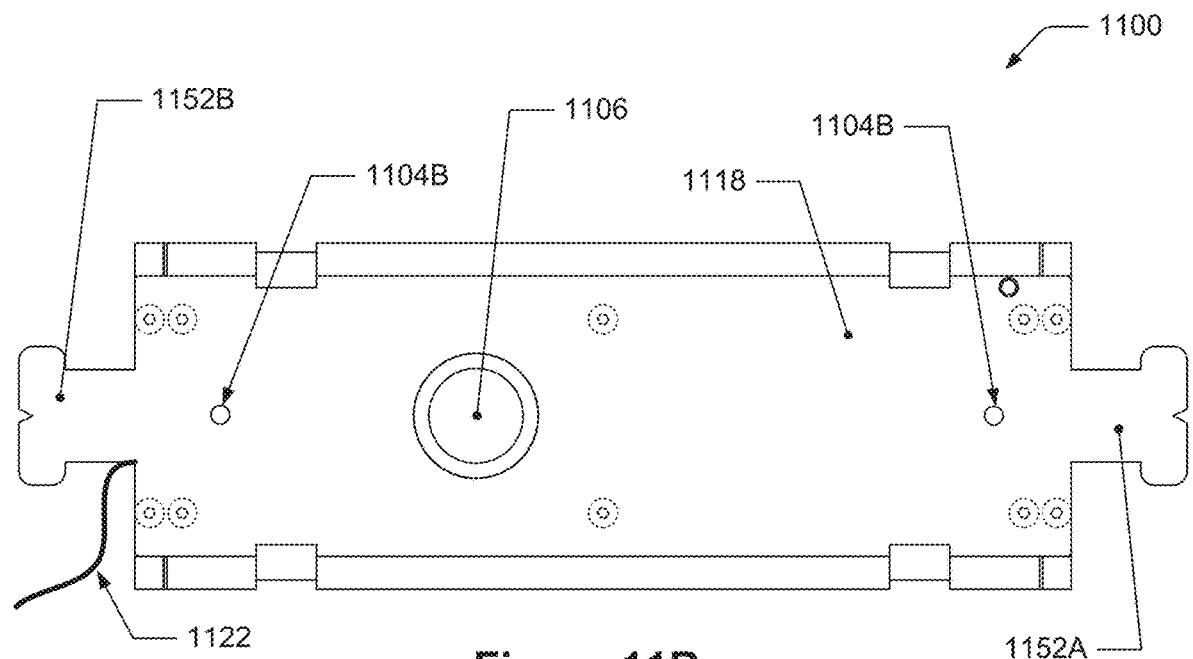

FIGS. 11A and 11B depict another example detection device. In FIG. 11A, the detection device 1100 includes a housing 1116 and a face 1118 with ports in which the acoustic sensors 1104A and 1104B (small microphones), and 1106 (large microphone) may be positioned. In some embodiments, the small microphones 1104A and 1104B are flush with the face 1118 while the large microphone 1106 may be recessed and offset from the face 1118 such that they are within the housing 1116. The speaker may be positioned completely within the housing 1116. In some embodiments, the second example detection device depicted in FIGS. 11A and 11B is configured to detect the condition of a pipe using a solenoid (not depicted; instead of a speaker, a solenoid is used) and the microphone 1106 by using the solenoid to deliver a mechanical ping or strike to the pipe. It may accomplish this by producing an excitation signal with a fast rise time than can excite harmonics in the pipe or fluid conduit. In certain embodiments, the solenoid 1102 used in the detection device has a dynamic range of at least about 100 dB. In certain embodiments, the solenoid 1102 used in the in the detection device can produce low frequency acoustic signals of about 30 Hz or lower. This detection device 1100 may also include a processing module described below.

In some implementations, a sound conductor may be positioned between the large microphone 1106 and the pipe wall, such as a petroleum jelly or grease, in order to facilitate the transmission of acoustic signals from the pipe to the large microphone 1106. In certain embodiments, the large microphone is in acoustic contact with the pipe through a coupling agent (grease, etc.) but the two small microphones are coupled through the air. In some cases, even one or both of the small microphones employs a coupling agent. In some implementations, using two axially separated, air-coupled microphones allows good phase response, which can be useful in determining the direction of an event (with respect to the sensor), etc.

The detection device depicted in FIGS. 11A and 11B may also include a leak detector 1122 as described herein. In some implementations, this leak detector 1122 is configured to detect a leak in a pipe by detecting the presence of a liquid on and/or near the pipe. For example, the leak detector 1122 may be a cable with various regions of exposed, uninsulated wire that, when contacted by the liquid, are configured to create a signal, or cause the lack of a signal, which indicates the presence of a liquid which in turn may be used to detect the presence of a leak. The leak detection element (e.g., the exposed wires) of detector 1122 may be positioned on the pipe as well as on a location near the pipe, such as the ground, in order to detect the presence of the liquid that may be on or around the pipe.

2. Additional Example Acoustic Sensors—Ultrasonic Transducers

As stated herein, the detection device may take many forms. In some embodiments, the components used for detecting flow and/or quantitating flow may include a pair of discrete and separated acoustic sensors, such as ultrasonic transducers. This pair of acoustic sensors may, in some embodiments, be positioned within a housing of the detection device, and in some other embodiments, they may be external to the housing of the detection device. This pair of discrete and separated ultrasonic transducers may be employed to determine a flow rate or other flow condition in a fluid conduit, such as a pipe, to which the pair of transducers are attached. Certain embodiments employ such transducers and associated data analysis to supplement, or to use as an alternative to, a thermal flow condition assessment methodology as described herein.

In a typical case, an ultrasonic flow condition system, applies an ultrasonic signal at each of two locations where flow condition is to be measured. A first ultrasonic transducer is attached at a first location and a second ultrasonic transducer is attached at a second location that is offset in the axial direction of the fluid conduit (e.g., along the center axis of the pipe), and during data collection, the two transducers measure time of flight of ultrasonic signal propagation in each direction (upstream to downstream, and downstream to upstream). An example is shown in FIGS. 13A and 13B which are discussed below.

The flow condition assessment logic then determines a time of flight difference between the upstream and downstream directions. Depending on the fluid flow rate, the separation distance between the sensors, etc., the time of flight difference may be quite small, e.g., on the order of microseconds or less. Regardless of magnitude, the flow condition assessment processing logic may use the time of flight difference to determine fluid flow rate in fluid conduit.

An ultrasonic transducer used for time of flight measurements may be disposed in a casing or other enclosure of a detection device or housing as described below. As examples, the two ultrasonic transducers may be provided in a single detection device that houses the pair or they may be provided as discrete sensors, with or without their own housings or casings. While the design and operation of ultrasonic transducers is well known, a few features of a typical ultrasonic transducer will now be provided.

FIGS. 12A and 12B depict examples of two ultrasonic transducers. FIG. 12A depicts an example of a one suitable design for a transducer 1269A which includes a piezoelectric element 1272A straddled by two electrodes, first electrode 1270A and second electrode 1274A. In certain embodiments, the piezoelectric element 1272A of the device is powder pressed in the desired shape and sintered. Electrodes may be screened or painted on. "PZT" refers to lead zirconate titanate which is a frequently used ultrasonic transducer material. Applying an electric field as shown mechanically distorts the material and reflexively, distorting the material generates an electric charge between the electrodes. FIG. 12B depicts an alternative ultrasonic transducer 1269B that includes the elements as FIG. 12A, but further includes a supportive membrane 1276 that is attached to the second electrode 1274A. In some embodiments, the ultrasonic transducer employs an alternative design, such as one employing a capacitive transducer. An example of a suitable ultrasonic transducer is the JIAKANG, Water Flow Meter External Piezo 1 Mhz Ultrasonic Transducer.

Various embodiments employ two ultrasonic transducers, each operating a particular ultrasonic frequency (e.g., 1 Mhz) to measure the time of flight differential through a pipe (including a pipe) and the flowing fluid. The time of flight difference varies depending upon the flow velocity. The difference in time of flights from one transducer to the other (both directions) increases with fluid increasing flow rate.

FIGS. 13A and 13B depict cross-sectional views of two transducers and associated lenses positioned on a fluid conduit, which is depicted, and referred to, as a pipe. The outer walls of the pipe 1378 are seen and the pipe has a center axis 1380. A first transducer 1369-1 and its associated lens 1382-1 is positioned at a first location 1384 and a second transducer 1369-2 and its associate lens 1382-2 is positioned at a second location 1386; these transducers are offset from each other by a first distance along the center axis 1380 of the pipe, e.g., in the axial direction. In some embodiments, this first distance may be at least about 1.3 inches, 1.6 inches, 1.9 inches, 2.2 inches, 2.5 inches, 3.25 inches, 4 inches, 5.25 inches, 6.5 inches, and 7.25 inches (+/−0.25 inches). The transducers 1369-1 and 1369-2 may be adhered (using acrylic or other suitable bonding agent) to couple the ultrasonic wave into the pipe wall at an off axis angle (e.g., approximately 35 degrees in this example). Because of the impedance change between the acrylic (or other bonding agent) and the metal pipe wall, the ultrasound bends inward to about 45 degrees in this example. The ultrasound waves, dashed lines 1388, propagate across the pipe (through the water) reflects off the other side and excites the complimentary transducer. In FIG. 13A, for instance, transducer 1369-1 generates the ultrasound waves which propagate left to right in the Figure towards transducer 1369-2 which receives these waves. The transducers then switch such that the transmitter becomes the receiver and the receiver the transmitter, so that the process can repeat in the opposite direction. For example, in FIG. 13B, for example, transducer 1369-2 generates the ultrasound waves which propagate right to left in the Figure towards transducer 1369-1 which receives these waves. Depending on the transceiver capabilities of the two transducers, the upstream and downstream measurements may be performed concurrently or sequentially.

Note that only the "X" direction component (parallel to the pipe axis 1380) of time of flight is affected by the fluid flow. The "Y" direction component (along the transverse axis perpendicular to the pipe axis 1380) of time of flight is not substantially affected by the flow. So in the illustrated case, at 45 degrees, only the "X" component (or about 0.7 of the total length) is affected by the flow velocity.

Figure 14A:
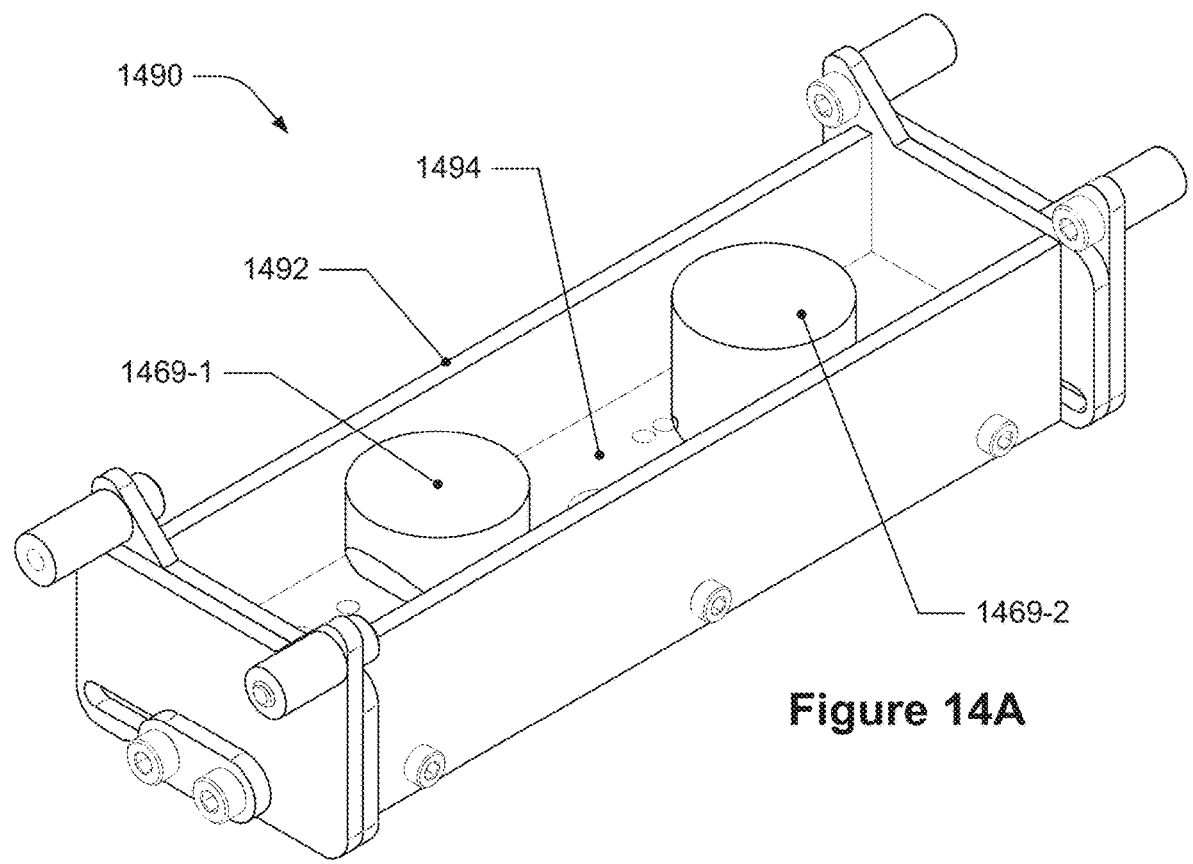
FIG. 14A depicts an off-angle view of the underside of an example housing with two transducers.
Figure 14B:
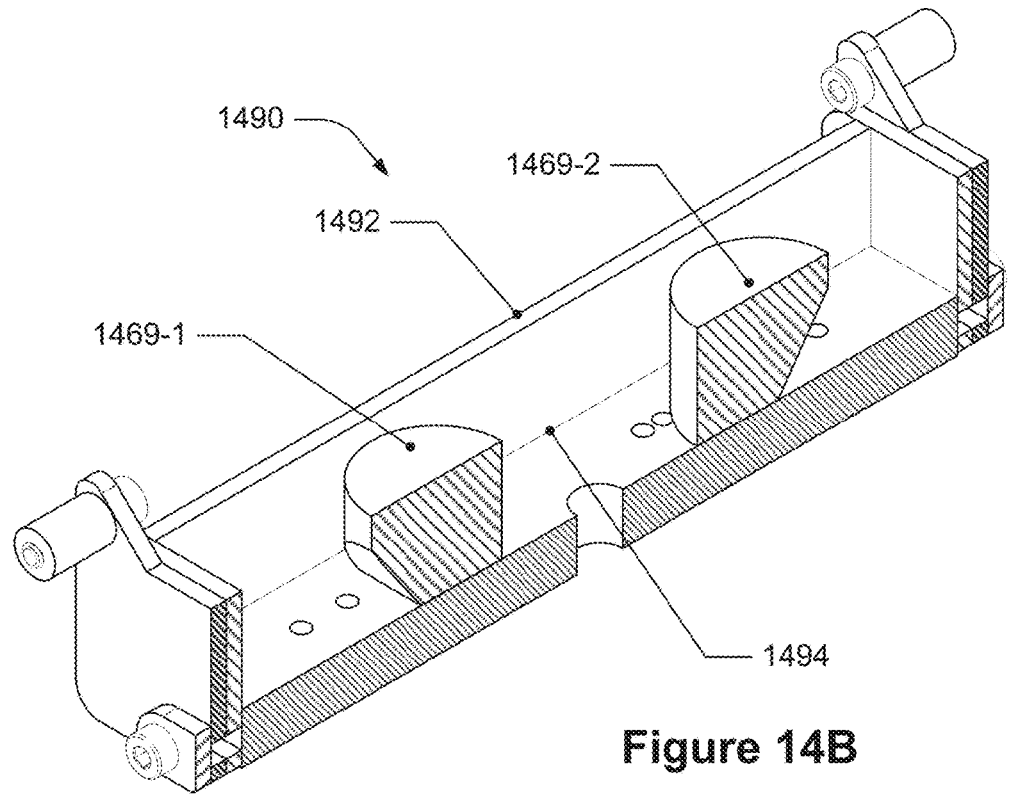
FIG. 14B depicts a cross-sectional view of the example housing of FIG. 14A.

As stated above, these acoustic sensors may be positioned directly to the fluid conduit, or pipe, and may also be a part of a housing. FIG. 14A depicts an off-angle view of the underside of an example housing with two transducers and FIG. 14B depicts a cross-sectional view of the example housing of FIG. 14A. As can be seen, this example housing 1490 has a body 1492 with a cavity 1494 in which two transducers 1469-1 and 1469-2 are positioned.

Figure 15A:
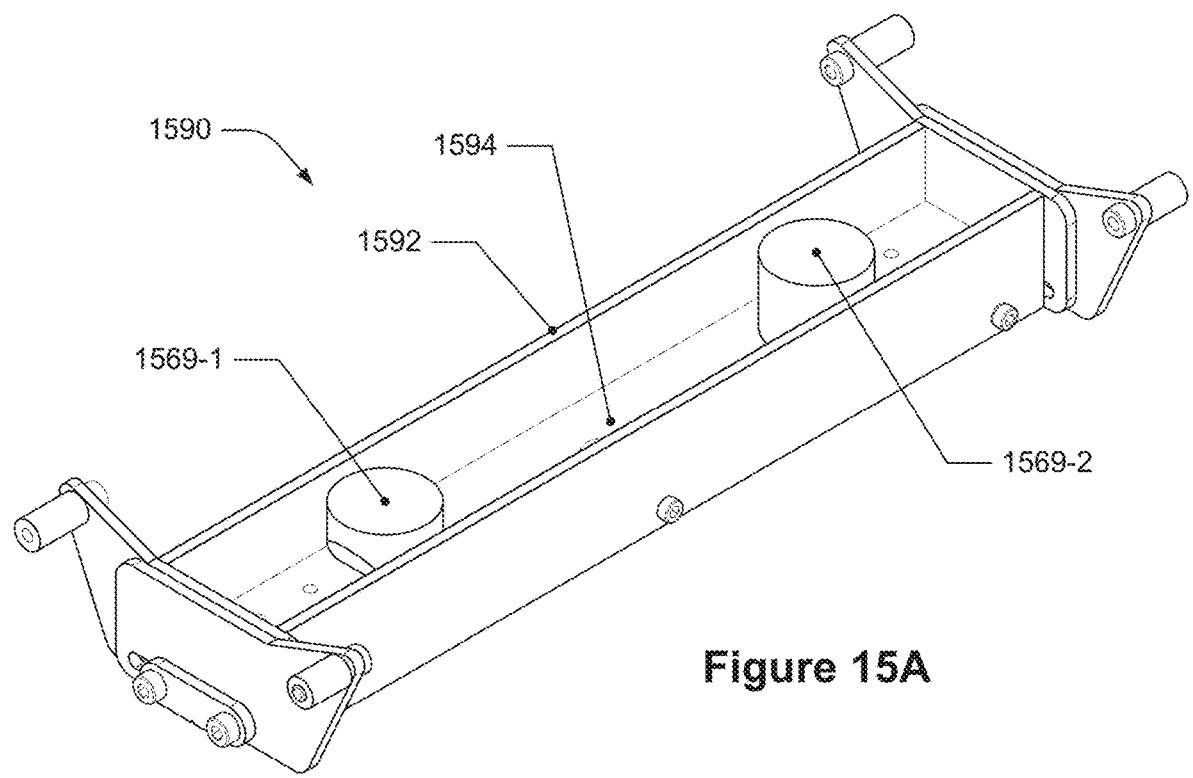
FIG. 15A depicts an off-angle view of the underside of a second example housing with two transducers.
Figure 15B:
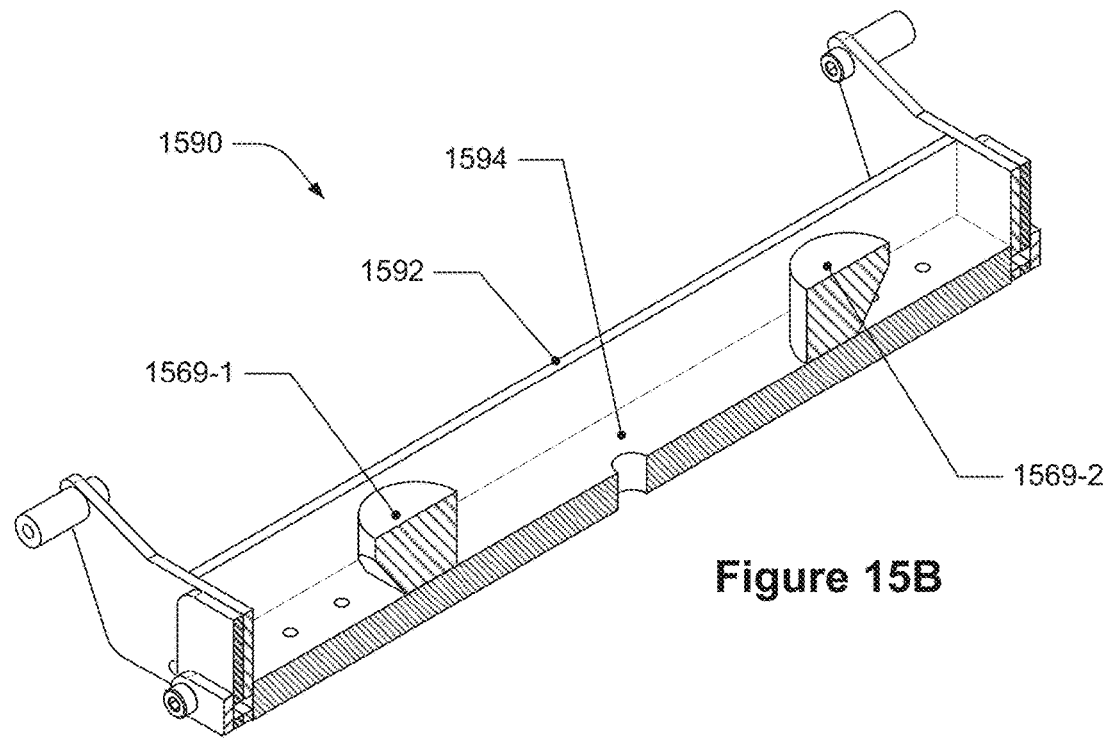
FIG. 15B depicts a cross-sectional view of the second example housing of FIG. 15A.

Similarly, a second example in depicted in FIGS. 15A and 15B. Here, FIG. 15A depicts an off-angle view of the underside of a second example housing with two transducers and FIG. 15B depicts a cross-sectional view of the second example housing of FIG. 15A. This second example housing 1590 also has a body 1592 with a cavity 1594 in which two transducers 1569-1 and 1569-2 are positioned. In some embodiments, these transducers may be attached to the body 1592 or 1592 and in some embodiments, these transducers may be positioned and attached to the pipe after which the housing is positioned around the transducers.

3. Example Processing Logic for Acoustic Sensors

Figure 9:
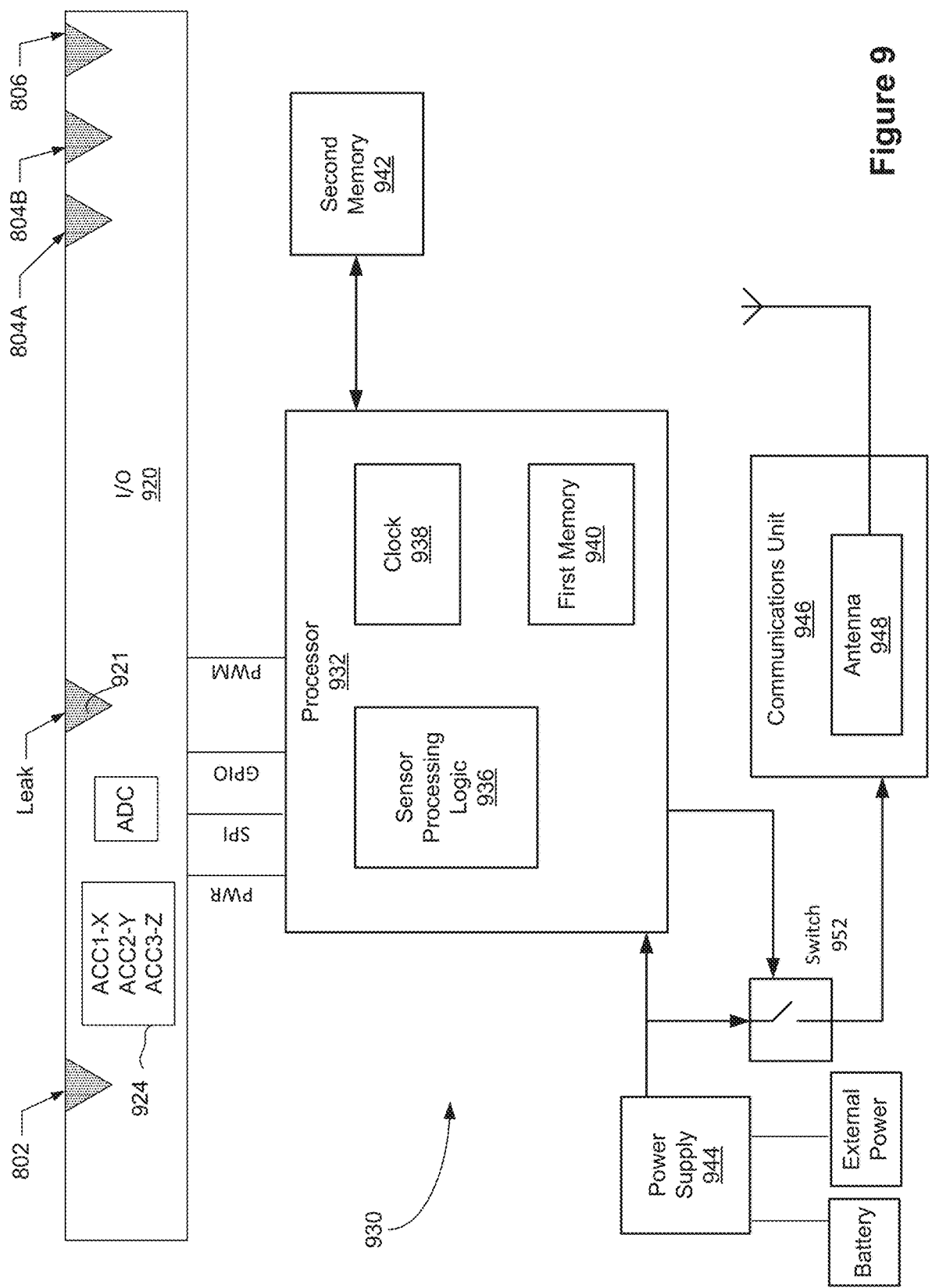
FIG. 9 schematically depicts an example of a pipe condition processing module.

FIG. 9 schematically depicts an example of a pipe condition processing module 930. The depicted processing module 930 includes an input/output unit 920 that includes a first input 921 for connection to a leak detector and an accelerometer 924 that is depicted as a three-axis accelerometer. The input/output unit 920 may include an analog to digital converter 925, and the input/output unit 920 may be configured to receive power from the power supply 944 for various purposes including to power one or more peripherals such as one more speakers and/or microphones of a detection device.

As depicted, input/output unit 920 includes various ports or electrical connectors for communicating with one or more acoustic sensing elements (e.g., microphones or ultrasonic transducers) and one or more sound producing elements (e.g., speakers) on a detection device. For example, input/output unit 920 includes electrical connectors for receiving electrical signals corresponding to acoustic signals detected by microphones. These may correspond to the microphones shown in FIG. 7, as well as FIGS. 10-15B, and described above. Additionally, input/output unit 920 includes one or more electrical connectors for providing power to one or more speakers (e.g., the speakers shown in FIG. 7) of a detection device. Still further, input/output unit 920 includes electrical connectors for receiving electrical signals corresponding to acoustic signals detected by the microphones. The electrical signals provide information about, at least, the frequency and intensity of the acoustic signals received by each microphone. Input/output unit 920 may have ports for additional pipe condition sensor components such as a status light. In some cases, the input/output unit 920 has ports for components of other types of sensor that may share processing unit 930 with a detection device. Examples of such other types of sensor include flow condition sensors (e.g., thermal flow condition sensors) and pressure sensors (e.g., hoop stress sensors). Ports for these additional types of sensor are not depicted in FIG. 9.

The pipe condition processing module 930 also includes one or more processors (shown as processor 932) that include a clock 938, a first memory 940, and sensor processing logic 936. The first memory 940 may be a program memory that stores instructions to be executed by the processor 932 and buffers data for analysis and other processing. The sensor processing logic 936 (which may also or alternatively be instructions stored on the first memory 940) is configured to detect signals, such as current, impedance, or voltage values, generated by any of the sensors, including the microphones of the detection device and the leak detector 922. For example, as described above, sensor processing logic 936 may be configured to receive data representing acoustic frequency and/or intensity from sensing elements including microphones of a detection device. The sensor processing logic 936 may also be configured to determine and store values of resistance and voltage or their corresponding values of acoustic frequency and/or intensity or relative to a baseline values measured during calibration or normal operation. In certain embodiments, sensor processing logic 936 may also be configured to determine and store strain values measured on the pipe, temperature values measured on the pipe, and/or calculated pressure or flow rate values in the pipe.

The clock 938 may be a real time clock or a timer. The depicted pipe condition processing module 930 also includes a second memory 942 that may be a rewritable memory that is configured to store data generated by any of the sensors or other components described herein. A power supply 944, which may include a battery, is also a part of the depicted pipe condition processing module 930 and is configured to provide power to the elements of the pipe condition processing module 930, such as the processor 932, a communications unit 946, and any of the acoustic signal sensing and generating elements, as described above.

The processor 932 may execute machine-readable system control instructions which may be cached locally on the first memory 940 and/or may be loaded into the first memory 940 from a second memory 942, and may include instructions for controlling any aspect of the pipe condition processing module 930. The instructions may be configured in any suitable way and may by implemented in software, firmware, hard-coded as logic in an ASIC (application specific integrated circuit), or, in other suitable implementation. In some embodiments, the instructions are implemented as a combination of software and hardware.

The communications unit 946 may include an antenna 948. The communications unit 946 may be configured to acquire location data about the location of the detection device using the antenna 948 which is configured to connect with an external location device and receive location data from the external location device. The location data may include the latitude, longitude, and altitude, for example, of the pipe condition processing module 930 which houses the first antenna 948.

The communications unit 946 may also be configured to wirelessly connect with, and transmit and receive data from, an external device, such as a network or computer, using the antenna 948 that is configured to connect with the external device. The communications unit 946 and antenna 948 may be configured to communicate by an appropriate cellular protocol such as Code Division Multiple Access (CDMA), Global System for Mobile Communications (GSM), or Long-Term Evolution (LTE) high-speed data transmission, and LTE CAT M1 (which is a low-power wide-area (LPWA) air interface that is able to connect to the Internet of Things (IoT) and machine-to-machine (M2M) devices. Alternatively or in addition, the communications unit 946 and antenna 948 may be configured to communicate by a non-cellular wireless protocol such as a low power wide area network (LoRaWAN) protocol, which operates between 850 MHz and 1,900 MHz, or other sufficiently long range protocol. As an example, the communications unit 946 may be a 2G cellular device such as the SIM808 from SIMCom Wireless Solutions, Shanghai, China. The product may be packaged on a printed circuit assembly ("PCA") with support integrated circuits from Adafruit, Industries of New York, N.Y. The communications module may also use an 'Internet of Things' (IOT) friendly protocol such as LTE Cat M1.

In some embodiments, the processing module 930 also includes a global positioning satellite ("GPS") antenna that can establish a connection with multiple GPS satellites. Using data from communications with such satellites, the communications unit 946 can determine the location of the detection device and thereafter send location data to the processor 932. The term "GPS" herein may mean the broader concept of a location system employing one or more satellites that transmit ephemeris (e.g., a table or data file that gives the calculated positions of a satellite at regular intervals throughout a period) and/or position fixing data to a GPS receiver or antenna on a device. The location of the device may be calculated from the position fixing data on the device itself—communications unit 946 in this case—on a secondary device. Multiple satellites may be used in the system with each one communicating ephemeris data and/or position fixing data. The same satellite may communicate both ephemeris data and position fixing data, or ephemeris data and position fixing data may be communicated through separate satellites. The satellites may be satellites in a GPS system, or it may be satellites in another satellite system such as the Russian Global Navigation Satellite System, the European Union Compass system, the Indian Regional Navigational Satellite System, or the Chinese Compass navigation system. Some GPS systems use a very slow data transfer speed of 50 bits per second, which means that a GPS receiver, in some cases, has to be on for as long as 12 minutes before a GPS positional fix may be obtained. Once a positional fix is obtained, subsequent positional fixes may take much less time to obtain (assuming that the subsequent positional fix occurs within a sufficiently close interval), but this initial lock-on period requires that the GPS receiver be powered for the entire initial lock-on, which can be taxing on devices with small battery capacities.

As further depicted in FIG. 9, the processor 932 is connected to a switch 952 that is interposed between the power source 944 and the communications unit 946. The processor 932 may cause the switch 952 to close, which causes power to be delivered to the communications unit 946, or to open which stops the power to the communications unit 946.

In certain embodiments, the second memory 942 is configured to store data received from the processor 932 and the antenna 948. Firmware updates, which may be received from the antenna 948, are stored at an appropriate location (e.g., second memory 942) accessible to the processor 932. The processor 932 is also configured to access and transmit data stored in the second memory 942 over the antenna 948. In some embodiments, the elements of the processor 932 may be communicatively connected with each other and the processor 932 is configured to control each such element, as well as any element of the pipe condition processing module 930.

In some embodiments, pipe condition processing module is also configured to connect the accelerometer to the power supply 944 as well as receive signals, such as voltages, from the accelerometer 924. The accelerometer 924 may be continuously powered by the power supply 944 so that the accelerometer 924 can detect events that generate movement or vibrations, such as a seismic event, movement of the pipe to which the processing module 930 is connected, movement of the detection device (e.g., tampering or vandalism), and events to the pipe or fluid conduit system upstream or downstream from the detection device (e.g., pipe burst).

In some embodiments, the pipe condition processing module 930 may be configured to reside in a sleep state in which only limited power is available to the processor 932, the accelerometer 924, the leak detector, etc., and few if any operations are performed. In this state, the processor 932 can receive signals from the accelerometer 924, the leak detector, and/or the detection device, and at the same time, the communications 946 module is not powered on. The processor 392 may exit the low power state, and "wake up", in response to detecting a signal of defined magnitude or other characteristic from any of the sensors, including the accelerometer 924, the leak detector, and/or the detection device. Depending on the signal detected, the processor 932 may simultaneously or sequentially cause various functions to be performed, as described below.

4. Examples of Operation

Figures 10A, 10B:
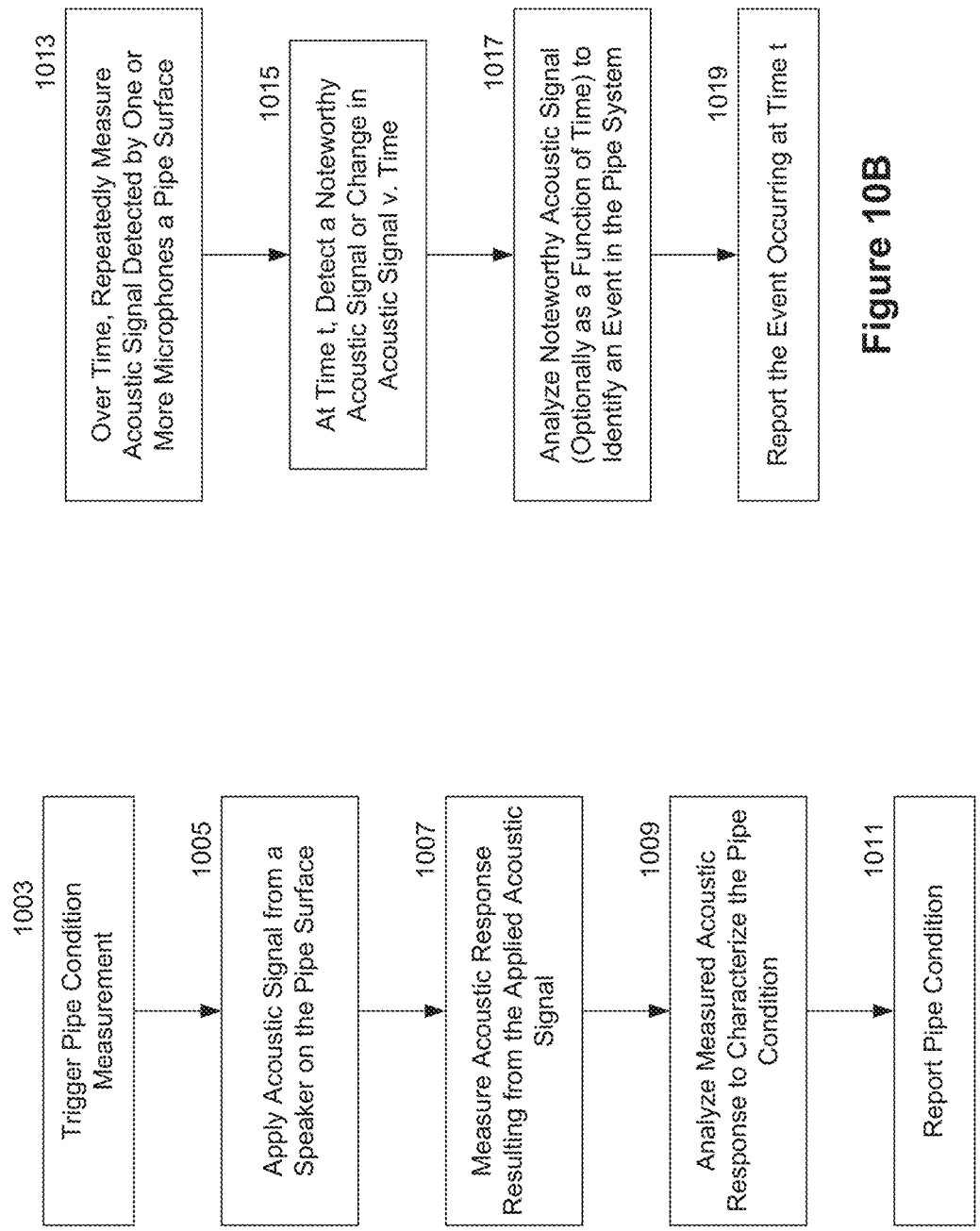
FIGS. 10A and 10B present flow charts for treating acoustic measurements made by detection devices.

FIGS. 10A and 10B present flow charts for treating acoustic measurements made by detection devices such as those described herein. As indicated, in certain embodiments, operations using detection devices may follow this sequence: (a) determine that a triggering event has occurred (block 1003), (b) in response, producing an acoustic signal to the pipe (block 1005), (c) measure a resulting acoustic response (after applying producing the acoustic signal and optionally various microphone positions and/or time steps; block 1007), (d) determine a pipe condition based on the measured acoustic response (block 1009), and (e) optionally report the determined pipe condition (block 1011). Also, as indicated, in certain embodiments, operations using a detection device may follow the following sequence: (a) repeatedly measure an acoustic signal using one or more microphones of the detection device (block 1013), (b) in one of the measurements (associated with a time t), detect a noteworthy acoustic signal and/or a noteworthy change in acoustic signal (block 1015), (c) based on noteworthy signal or change in signal, determine an event or a new pipe condition occurring at time t (block 1017), and (d) optionally reporting the event or new pipe condition (block 1019).

In certain embodiments, operation of a detection device and associated logic includes: (a) applying acoustic stimulus at time 1, (b) measuring an acoustic response at time 1, (c) applying an acoustic stimulus at later time 2, (d) measuring an acoustic response at time 2, and (e) determining whether difference in acoustic response at times 1 and 2 indicates a pipe condition issue.

In certain embodiments, operation of a detection device and associated logic includes: (a) monitoring steady state acoustics from the pipe, (b) detecting a change (e.g., an unexpected pulse) in the acoustics, (c) optionally using upstream and downstream microphones to determine a direction from which the change emanated, and (d) based on the acoustic change, determining a type of event that caused the acoustic change and optionally location or direction. In certain embodiments, monitoring acoustics from a pipe may be performed in a manner that consumes relatively little power (particularly if a battery is used to power the sensor). For example, a microphone such as the large microphone shown and described with respect to FIG. 7 may remain on to monitor acoustics but without providing signals to the processing logic. This allows monitoring without performing analog to digital conversion, which is an energy intensive procedure. In some implementations, the monitoring microphone or associated circuitry compares acoustic signals picked up by the microphone against a threshold, and only when the microphone or associated circuitry determines that an acoustic signal is greater than the threshold does the system begin to acquire data from other sources (e.g., other microphones and/or flow sensor(s)) and/or convert analog data to digital data for triggering further analysis of the pipe or flow condition. In some cases, detecting large acoustic signals triggers the system to issue pulses or stimuli from a speaker so that the detection device can assess pipe condition. In some embodiments, in lieu of or in addition to monitoring acoustics with a microphone, the system uses an accelerometer to trigger the analog to digital conversion and/or operation of other sensors in the system. Again, these techniques may be used when the detection devices are installed at a location over a period of time, such as hours, days, weeks, months, or years.

5. Example Processing of Acoustic Signals

Various characteristic features of an acoustic signal are useful for determining a fluid flow or pipe condition. Examples of such features include an oscillating acoustic signal's wave envelopes and frequency spectrum.

Figure 16:
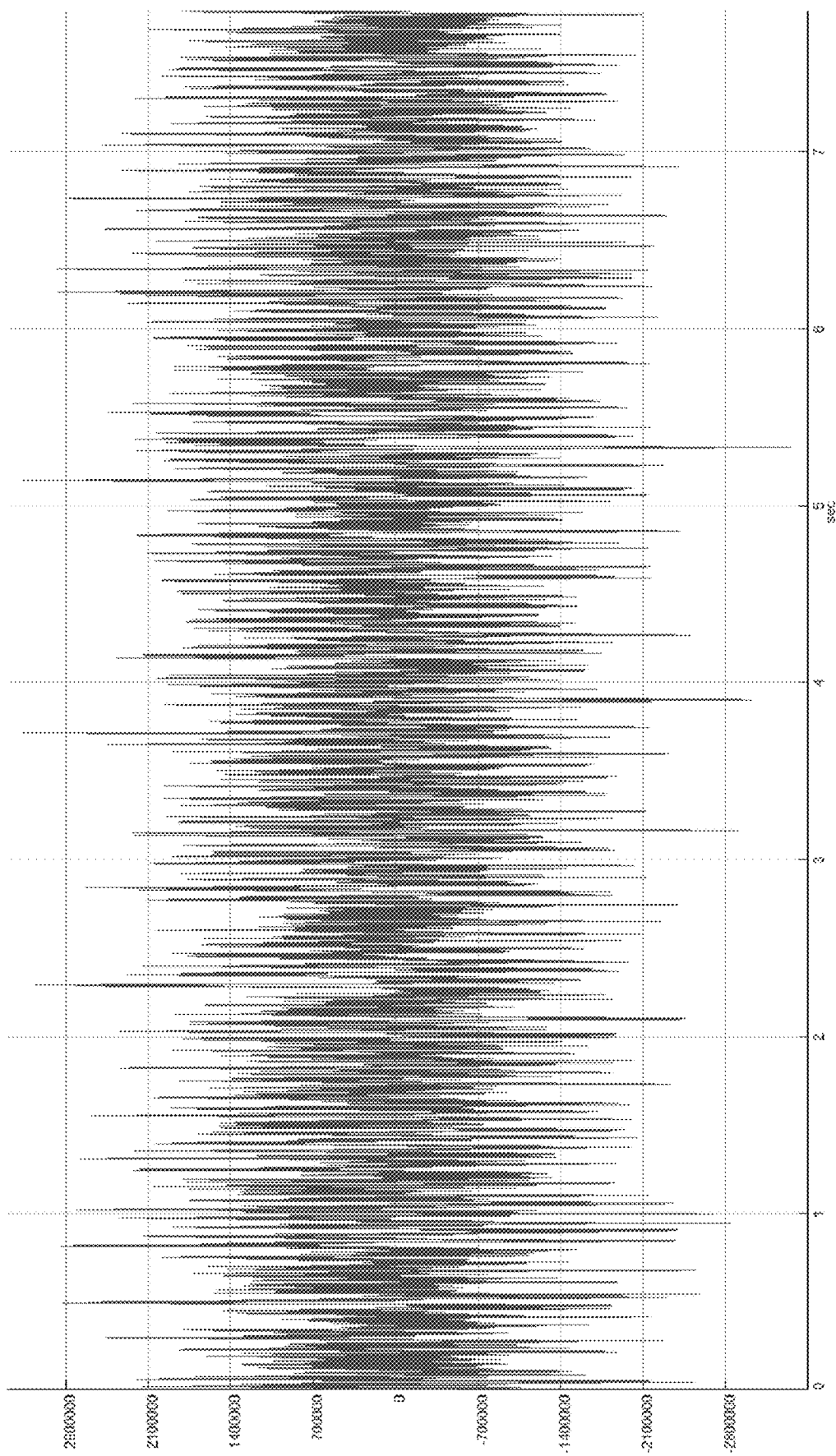
FIG. 16 depicts an example of a signal received from a microphone of a detection device.

Data from a detection device may be processed in various ways to improve the usefulness of the readings. Frequently, the signals from microphones on detection devices are noisy and/or have many frequency components. As such, they sometime require significant signal processing. FIG. 16 depicts an example of a signal received from a microphone of a detection device.

Appropriate signal processing may take various forms. With a complex signal (e.g., multiple tones with noise), cross correlation can help identify the delay between two signals that is not easily perceived from simple observation and provide a mathematical tool to measure delay. This is useful for a variety of analysis but is particularly valuable in determining which direction a particular sound came from. If for example a microphone picks up leaks at 1 kHz, the signal processing may apply a 1 kHz bandpass filter (e.g., one that does not induce significant phase shift) around the signal from two microphones separated by a known distance "x". Then using a cross correlation function, the processing logic can determine the speed of signal propagation between the microphones (by the delay time) and the direction the sound is coming from (by the sign of the delay). In typical systems, the cross correlation is not clean and typically the logic sees multiple points where signals align for better or worse. Harmonics and sampling artifacts can produce interference. Accounting for the speed of sound, at least approximately, the processing logic can narrow the possibilities by considering options at approximately the correct delay time.

In some embodiments, where the acoustic signals are particularly noisy or have apparently multiple frequency components, a Fourier transform may be employed to convert time domain temperature measurements to frequency domain temperature measurements.

Figure 17:
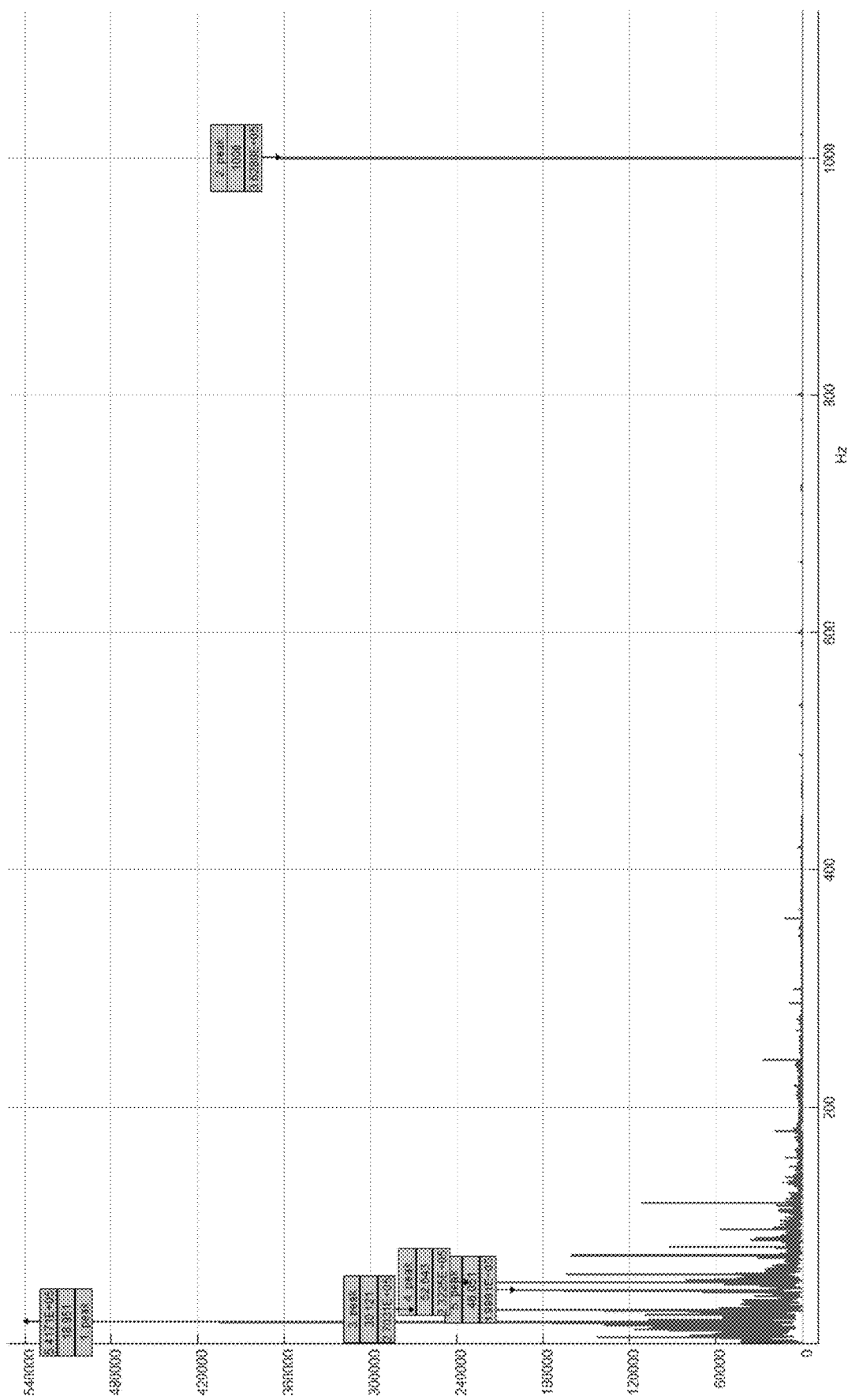
FIG. 17 depicts a spectrum (frequency domain) of 1 kHz noise.

The signal in FIG. 16 shows the time domain plot of a 1 kHz signal (simulating a leak) in the presence of flow noise. Signal amplitude is on the vertical axis and time in seconds is along the horizontal axis (amplitude vs time). FIG. 17 depicts a spectrum (frequency domain) of 1 kHz noise with amplitude again on the vertical axis and frequency on the horizontal axis. A Fast Fourier Transform separates out the flow noise (low frequency peaks) from the leak noise (here the 1 kHz peak).

In some embodiments, as described herein, wall loss or other wall condition assessment is based on observing changes in the natural frequency of the pipe and/or the damping of ringing in the pipe. As noted, the response signal frequency(ies) may be determined by analyzing data collected by a microphone, accelerometer, etc.

In one example, a solenoid or other stimulus applicator is used as a striker to excite the pipe wall with an impulse. A microphone or other acoustic transducer picks up frequency signals in a way that can discriminate between frequencies. As an example, the processing logic identifies the natural frequencies (e.g., through a Fast Fourier Transform (FFT) or some other means) and identifies any changes in the natural frequencies from a baseline frequency signature or other baseline characteristic(s) indicating wall loss.

As an alternative, or in addition, to considering natural frequencies of the pipe response to a ping or other stimulus, the processing logic may consider damping of the stimulus. For example, the processing logic may consider an envelope of a ring down signal and from it, determine a time constant of that envelope which can determine if the pipe is full of liquid or dry, and, in some cases, whether there is something creating additional damping such as bacterial mats, large amounts of sediment, or tuberculation within the pipe being assessed.

In certain embodiments, the processing logic is configured to determine whether a pipe's or a pipe network's natural frequency decreases from a baseline. The occurrence and/or magnitude of such decrease is used to assess the presence or degree of wall thinning. See for example, the discussion in S. Han et al., "Detection of pipe wall-thinning based on change of natural frequencies of shell vibration modes,"19thWorld Conference on Non-Destructive Testing 2016, (available on the World Wide Web at //www.ndt.net/article/wcndt2016/papers/th3c2.pdf), which is incorporated herein by reference in its entirety.

In certain embodiments, the processing logic is configured to determine the average radius of a pipe (or a change in the average radius) acoustically. See for example, the discussion in U.S. Pat. No. 6,000,288 to Kwun, which is incorporated herein by reference in its entirety. Such assessment employs, in certain embodiments, information about the pipe wall material. While Kwun identifies magnetostrictive sensors, a similar analysis may be accomplished using microphones, accelerometers, and/or strain gauges.

The same hardware may be employed for assessing various wall conditions including average pipe inner radius, specific instances of pipe wall thinning, and the presence of deposits, sediments, etc. Collecting data using various types of sensors (e.g., strain gauges, accelerometers, and/or microphones) and/or analyzing collected information using multiple algorithms, such as those for identifying wall thinning and average pipe radius, may provide a higher confidence in an ultimate assessment of pipe wall condition.

In certain embodiments, a pipe condition assessment is made in the context of current conditions, which may different from previous or future conditions. Thus, a pipe condition assessment may account for current temperature, fluid pressure, fluid flow, and/or other ambient factor that impacts signal propagation in the pipe. In some embodiments, the system includes one or more sensors, and associated logic, for measuring and/or determining temperature, fluid flow rate, hoop stress, etc. to appropriate adjust pipe condition assessment.

6. Example Applications

As indicated, a detection device may measure the acoustics of a pipe and/or a fluid flowing in the pipe. It may do this in response to an acoustic stimulus applied to a pipe surface as part of the measurement process. By measuring and/or monitoring the intensity, frequency, and/or delay of an acoustic signal received on the pipe surface, a detection device may be used to determine various properties of the pipe and/or a fluid flowing in a pipe. As indicated, one such pipe condition is the presence of a crack or other weakness in the pipe wall. Another such pipe condition is the presence of a material buildup on a pipe wall. Characteristics of an acoustic signal can help determine not only whether the pipe has a weakness or buildup up, but also the nature of any such weakness or buildup. For example, the acoustic signal may indicate how much material has been removed from the pipe by corrosion, how much material has built up on the pipe interior, the size of a crack, etc. The acoustic signal may also indicate a condition of the flow within a pipe such as the flow rate of the fluid, whether the fluid is leaking, whether the flow is laminar or turbulent, etc. Eddies, mixing, etc. caused by vortices in turbulence can create detectable features in temperature gradients or changes in acoustic signatures.

In some implementations, an acoustic detection device may monitor flow, water usage, pipe conditions, or any combination thereof in a room, building, or geographic region. For example, the sensor may monitor water consumption and where it occurs and/or in what type of appliance (toilet v. shower v. faucet v. landscaping, etc.) it occurs. Such monitoring may be used for conservation, auditing, etc. In certain embodiments, the sensor flags a water usage sequence that indicates a problem or need for corrective action; e.g., a pipe blockage, a pipe crack, or toilet flush not followed by faucet indicates a hygiene issue for restaurant employees.

The conditions to be detected may be present in various contexts such as municipal utilities, factories, large buildings such as office buildings or apartment buildings, compounds, complexes, and residences. The sensors used to detect the conditions are present on pipes employed in any such location. Of course, the software or other logic used to determine that a condition exists or potentially exists may be located remotely, i.e., it need not be present at the location of the sensors. The logic simply needs to receive input from the sensors and then analyze the sensor data to determine whether a condition exists or should be flagged.

Figure 18:
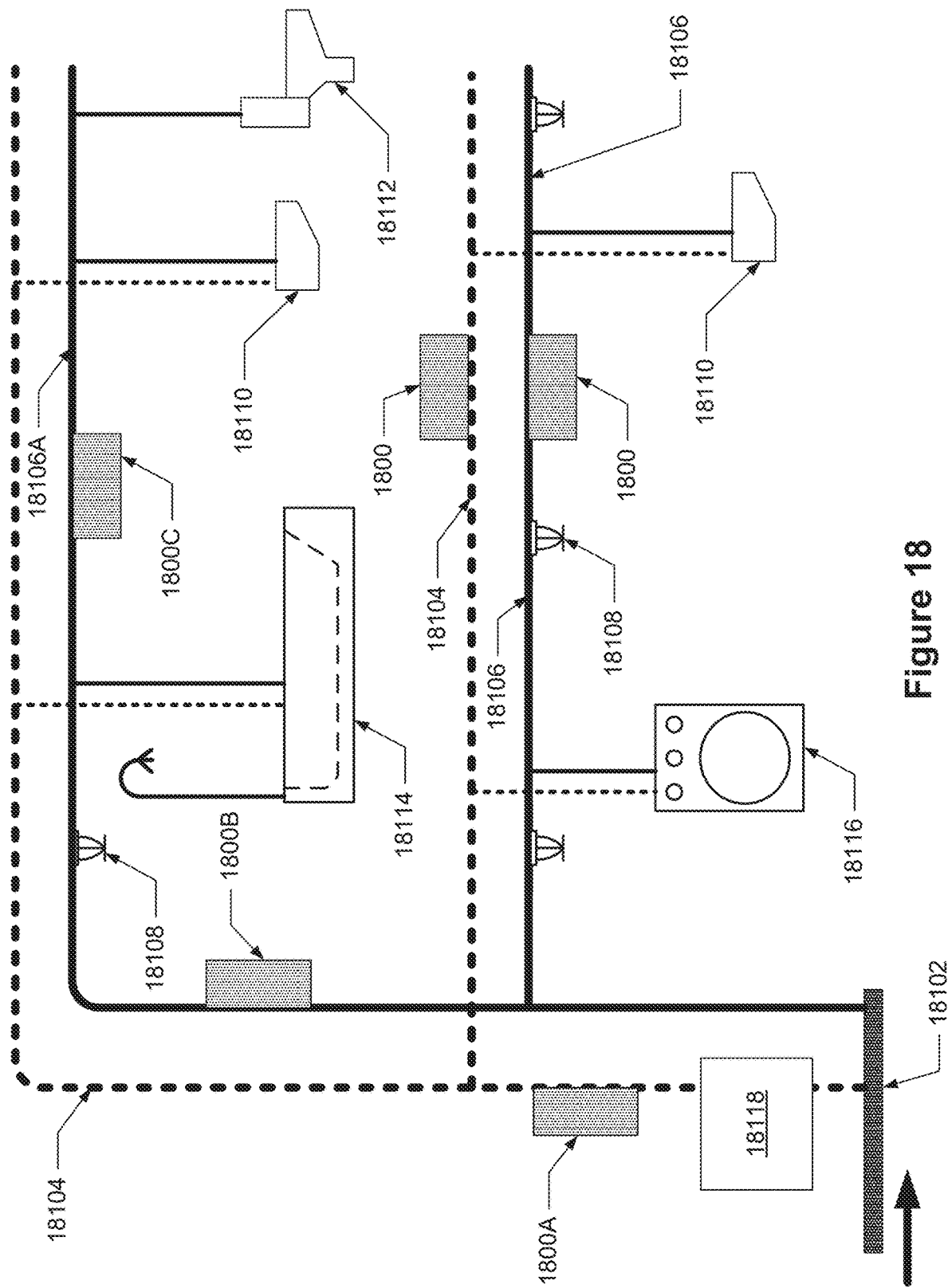
FIG. 18 depicts an example water system that includes multiple water pipes and appliances that use water, such as toilets, sinks, and sprinklers.

FIG. 18 depicts an example water system that includes multiple water pipes and water using appliances, such as toilets, sinks, and sprinklers. In this example water system, a main water line 18102 is connected to various hot water pipes 18104 (dotted lines) and various cold water pipes 18106 (solid lines) and numerous sprinklers 18108, two sinks 18110, one toilet 18112, one tub/shower 18114, and one washing machine 18116. The detection device 1800, which includes one or more acoustic sensors described above, such as one including microphones and a speaker, is positioned on various pipes of this water system in order to determine, among other things, flow within the pipes and pipe conditions of the pipes at or near its location as well as upstream and downstream from the detection devices 1800. For example, the detection device 1800A is positioned so that in can detect water flow and pipe conditions in the hot water pipe 18104 close to the boiler 18118 and can therefore be used to determine, for instance, whether hot water is flowing out of the boiler 18118, whether there is an event within the boiler 18118 or hot water pipes 18104, whether there has been degradation, wall loss, damage to, or bore loss of the hot water pipes. In some systems, detection device 1800A is configured to assess pipe conditions or events at more remote locations such as locations well upstream and/or downstream of the device. These types of conditions and events may be determined at any specific location where the detection device 1800 is positioned, as well as to the whole pipe or pipe system to which the detection device 1800 is connected.

Multiple detection devices may also be used together in order to determine events along a single pipe or within a pipe system. For instance, as depicted, detection devices 1800B and 1800C are positioned along cold water pipe 18106A, while detection device 1300C is positioned downstream from detection device 1300B and in-between the tub/shower 18114 and the sink 18110. By measuring the pipe conditions at these different locations, and in some implementations comparing them, various types of information can be determined about the pipe and pipe systems, such as flow within the pipe 18106A, the presence and location of leaks within the pipe 18106A, and the usage of various aspects connected to the pipe 18106A, such as the sprinkler 18108 in-between the detection device 1300B and 1300C.

Furthermore, pipe conditions detected by detection devices on different pipes may be used to determine various events within the system. For example, two detection devices positioned on different pipes, such as detection device 1300A and 1300B may be used to determine flow, lack of flow, freezing, leaks, and usage of, for instance, the hot water pipe/system versus the cold water pipe/system.

As further explained herein, various acoustic devices or other components (pipe stimulation elements and sensors) may be employed to assess pipe condition. And various measurement triggering and/or data analysis procedures may be employed: e.g., a process flow that involves uploading measured data to the cloud. Further, various data collection and analysis methods may be employed.

In some cases, pipe condition assessment includes pinging a pipe with a stimulation element such as a solenoid and measuring the frequency, amplitude, or other response characteristic with sensors affixed to the pipe. The frequency response of the pipe can interpreted in various ways to assess pipe condition.

As indicated, a detection device may measure the acoustics of pipes to which it is directly or indirectly connected, including directly measuring a response to an acoustic stimulus applied to a pipe surface which propagates into the pipes to which the pipe is connected. By measuring and/or monitoring the intensity, frequency, and/or delay of an acoustic signal received, a fluid flow processing module may be used to determine various properties of the pipes and pipe system. As stated, examples of such pipe conditions include the presence of a crack or other weakness in the pipe wall, and the presence of a material buildup on a pipe wall. Characteristics of an acoustic signal can help determine not only whether the pipe has a weakness or buildup up, but also the nature of any such weakness or buildup. For example, the acoustic signal may indicate how much material has been removed from the pipe by corrosion, how much material has built up on the pipe interior, the size of a crack, etc. The acoustic signal may also indicate a condition of the flow within a pipe such as the flow rate of the fluid, whether the fluid is leaking, whether the flow is laminar or turbulent, etc. Eddies, mixing, etc. caused by vortices in turbulence can create detectable features in temperature gradients or changes in acoustic signatures.

As explained, a pipe condition assessment system may employ both an acoustic stimulus issuing device and an acoustic detection element. In certain embodiments, the stimulus issuing device is the solenoid or other element (such as a loud speaker or electromechanical driver) capable of acoustically exciting the pipe. It is mounted to or otherwise associated with the pipe, whose condition is to be assessed, as part of a detection device such as one of those illustrated herein. In some implementations, multiple stimulus issuing devices are employed, and in some cases, they are provided at various locations.

And as explained, the system may include one or more detectors or other transducers for collecting signal associated with the pipe condition assessment, particularly signal generated by the stimulus issuing device. One or more of these detectors is used for collecting data used to determine the frequency response of the pipe. For example, a microphone and/or an accelerometer may be used for this purpose. The collected information provides information about the magnitude of the stimulator-originated signal at various frequencies. For example, the detectors may pick up or provide a spectrum of the pipe's response to the stimulus.

In some cases, as described below, one or more non-acoustic sensors or detections, such as a strain gauge, may be used in conjunction with an acoustic sensor. Further, parameters other than frequency/magnitude of the pipe's response to the stimulus may be collected. For example, pressure may be measured using a strain gauge, temperature may be measured using a thermistor, fluid flow rate may be measured using a thermal element as described herein and/or an ultrasonic transducer, also as described herein. The one or more one or more detectors or other transducers for collecting signal associated with the pipe condition assessment may be mounted to a pipe as part of a detection device such as one of those illustrated herein. Alternatively, at least some of these detectors or transducers may be mounted at separate locations, or at least not in a single detection device.

The stimulus issuing device(s) and the one or more stimulus response detecting sensors may be placed at any of various locations in a pipe or pipe network. For example, one or both of the device and sensor(s) may be located proximate an area of a pipe that requires assessment. In another example, the stimulus issuing device and at least one sensor are widely separated, in which case the pipe assessment may be conducted for the region between the device and sensor, whether for identifying any particular isolated pipe condition or determining an average condition between the device and the sensor.

In the context of a hydrant or municipal water system, the system may be configured to assess a pipe condition between one hydrant and another hydrant. In such cases, the system is installed so that a ping can be issued at a first hydrant and the hydrant/pipe response can be detected at a second hydrant. In some cases, the system is attached to only a single hydrant, in which case both the ping and response detection is performed at a single hydrant. The resulting pipe or hydrant condition assessment may be focused on the hydrant and/or the local pipe attached to the hydrant.

Using two sensors or other devices, attached to two different hydrants, allows assessment of a greater range of pipe in a network, but any results may be adjusted to account for material changes, repairs etc. along the route of the pipe.

FIGS. 19A and 19B depict a top view of an example pipe network with a tap connected to a pipe. As can be seen, a detection device 1900 including acoustic sensors configured to detect pipe conditions like described above is attached to a pipe 19120 of a pipe network 19122. In some embodiments, like shown in FIG. 19A and illustrated in FIG. 10A, the detection device 2230 may apply an acoustic signal to the pipe 19120, as indicated in block 1005 of FIG. 10A, which propagates into the pipe network 12122 to which the detection device is connected. As illustrated in FIG. 19B, like in block 1007 of FIG. 10A, the acoustic response or responses may propagate back to the detection device 1900 where the acoustic sensors, such as the large and/or small microphones, detect and measure these responses.

In some embodiments, multiple detection devices, each with acoustic sensors, may be used together in order to determine events along a single pipe or within a pipe system. FIGS. 20A and 20B depict a top view of the example pipe network of FIGS. 19A and 19B with two detection devices 12000A and 2000B having acoustic sensors like described above, positioned on pipes 20120A and 20120B, respectively. By measuring the pipe conditions at these different locations of the pipe network, and in some implementations comparing them together, various information can be determined about the pipe and pipe systems, such as flow within the pipe, the presence and location of leaks within the pipe, and the usage of various aspects connected to the pipe.

Like depicted in FIGS. 20A and 20B, the stimulus issuing device(s) of one detection device and the one or more stimulus response detecting sensors of another detection device may be placed at any of various locations in a pipe or pipe network. For example, the stimulus issuing device (e.g., a solenoid) of one detection device and at least one sensor of another detection device are widely separated, in which case the pipe assessment may be conducted for the region between the device and sensor, whether for identifying any particular isolated pipe condition or determining an average condition between the device and the sensor.

In the context of a tap or municipal water system, the system can assess a pipe condition between one location and another location. In such cases, the system is installed so that a ping can be issued at a first location to which one detection device is connected and the pipe response can be detected at a second location. In some cases, like described above with FIGS. 19A and 19B, the detection device is attached to only a single tap, in which case both the ping and response detection is performed at a single location. The resulting pipe condition assessment may be focused on the local pipe attached to the detection device.

When using two sensors or other devices, attached to two different locations, allows assessment of a greater range of pipe in a network, but any results may be adjusted to account for material changes, repairs etc. along the route of the pipe. Referring back to FIG. 20A, the detection devices 2000A on pipe 20120A is seen generating one or more acoustic signals into the pipe 20120A which travels within the pipe network, including to the second detection device 2000B, as shown with the labelled acoustic signals (dashed semi-circles) and dashed arrows. Detection device 2000B is configured to receive and detect these acoustic signals, and also to interpret these signals, as described herein. Additionally, the detection device 2000B may also be configured to generate the acoustic signals and the detection device 2000A is configured to receive these acoustic signals.

Furthermore, pipe conditions detected by acoustic sensors at different locations in a pipe network as depicted in FIGS. 19A-B and/or 20A-B may also be used to determine various events within the pipe network. For example, two detection device positioned on the two pipes may be used to determine flow, lack of flow, freezing, leaks, and usage of, for instance, the water in the pipe network.

7. Illustration of Data

Figure 21:
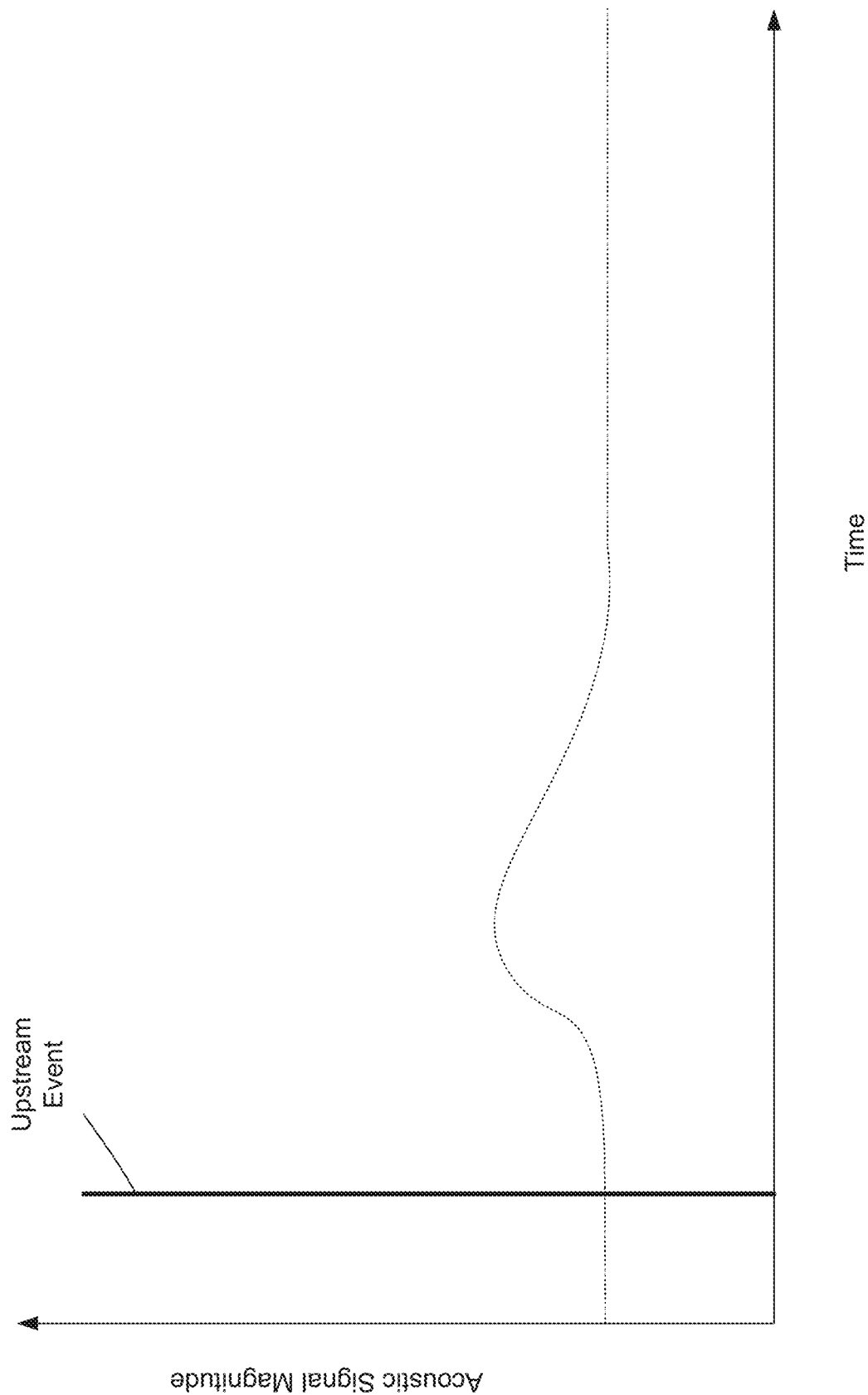
FIG. 21 depicts example acoustic signal magnitude data detected by an acoustic sensor of the detection device.

FIG. 21 represents example acoustic signal magnitude data detected by an acoustic sensor of the detection device. Here, the x-axis is time and the y-axis is the acoustic signal magnitude. As suggested by the data, an upstream event, such as a leak or increase in flow, causes an increase in acoustic signal magnitude that is measured by the acoustic sensor and also delayed in reaching the acoustic sensor. For instance, a pipe bursting may create an acoustic signal with a large amplitude that may propagate in the pipe to the location where the acoustic is located which can be detected and measured by the detection device.

C. Thermal Flow Condition Sensor

In certain embodiments, a detection device may include thermal flow condition sensors, such as multiple temperature sensing elements (e.g., thermistors) in a relatively small area. It may also contain a heating element such as a resistive heater disposed in the same area. The temperature sensing elements and the heating element are arranged on substrate so that, when installed, they contact a surface of a pipe where measurements are to be made. In various embodiments, these elements contact only on the outside of the pipe; i.e., they may operate alone to sense a flow condition within the pipe.

A thermal flow condition sensor may have one or more of various functions. One example of a function is detection of the temperature of a fluid within the pipe. The sensor may be designed to provide multiple measurements of fluid temperature over time. When installed, the sensor can measure fluid temperature at an axial position of the pipe where the sensor is attached. Another example of a function is detection of volumetric or mass flow rate of a fluid flowing within pipe. The sensor may be designed to provide multiple measurements of fluid flow rate over time. The sensor can measure fluid flow rate at the axial position of the pipe where the sensor is attached. In some instances, the thermal flow condition sensor may also detect the ambient temperature of the environment in which the detection device is positioned.

In many cases, thermal flow condition sensors make fluid temperature and/or fluid flow rate measurements non-invasively; i.e., sensors are installed on a pipe and make measurements without breaching the wall of the pipe. Further, no sensor element need be provided in the pipe interior. Examples of modes of attachment of the sensor to a pipe include pasting a sensor on the outside of the pipe and strapping or clamping a multi-sensor unit (described elsewhere herein) against the edge of the pipe.

1. Example Modes of Detection

Single value measurement—To detect the temperature of a fluid in a pipe, one or more sensors directly measure temperature (or a sensed quantity correlating with temperature) on the pipe external wall. A function relates the sensed quantity (e.g., temperature on the pipe exterior wall) with the temperature of the fluid in the pipe. The function may be obtained by calibration, a model, etc. By making multiple temperature measurements over a period of time, a temperature variation in flowing fluid may be detected. Depending on the construction of the water system or other pipe network, such temperature variation can be associated with a transient event in the network. In cases, the transient event occurs upstream from the thermal sensor.

Differential value measurement—A temperature gradient across two locations on a pipe (disposed in upstream-downstream relation) may provide an indication of a flow characteristic of water or other fluid within the pipe. In some embodiments, the temperature gradient is produced by heating the pipe by using a heating element in the thermal flow condition sensor. The heat produced by the heating element is dissipated by thermal conduction in the pipe and the flowing fluid. A temperature gradient proximate the heating element is produced by this conduction. Measuring temperature at two defined locations proximate the heating element allows direct calculation of the temperature gradient; by making temperature readings around the heating element, a thermal flow condition sensor can provide data to determine the temperature gradient. The size of the temperature gradient is a function of the fluid flow rate within the pipe (as well as other factors including the thermal conductivity of the pipe, the thermal conductivity of the fluid, the specific heat of the fluid, etc.). By measuring a differential temperature at two more locations on the sensor (and controlling for or accounting for other variables), the system can assess a flow rate of fluid. In some embodiments, to allow for the necessary measurements, the sensor includes two or more thermistors other temperature sensing elements provided at different locations on the sensor. The differential temperature measurement is correlated with fluid flow rate using a relationship may account for other parameters such as absolute temperature (as opposed to differential temperature). The function may be obtained by calibration, a model, etc. Note that by using a heating element on the sensor, the flowing water itself need not be heated or cooled to assess flow rate. As with single value (or single location) temperature measurements, multiple differential temperature measurements may be made over a period of time. Such measurements may provide an indication of changes in flow rate over time.

2. Example Apparatuses

In certain embodiments, a detection device may include includes two or more temperature sensing elements (e.g., thermistors) and optionally a heating element. In some cases, the detection device includes an array of temperature sensing elements. The individual sensing elements may be arranged in various patterns such as rectangular, triangular, other polygonal, circular, and the like. In certain embodiments, a heating element is disposed at an interior location with respect to the temperature sensing elements; e.g., the heating element is straddled by at least two temperature sensing elements.

In certain embodiments, adjacent temperature sensing elements are spaced apart from one another by at least about 5 mm or at most about 15 mm. In certain embodiments, the pipe-facing side of a temperature sensing element has a largest dimension of at about 1 mm or at most about 2 mm (i.e., the long dimension of each thermistor). In certain embodiments, the temperature sensing elements and, if present, the heating element are disposed on a relatively small area. In some cases, the area on which the elements reside is no greater than about 2.5 mm$^2$ or no greater than about 7 mm$^2$.

As mentioned, the temperature sensing elements may be thermistors. In certain embodiments, a suitable thermistor has one or more of the following properties: a nominal resistance in the thousands of Ohms, a negative temperature coefficient, and uses surface mount technology. One example of a suitable thermistor is available from Murata Electronics North America part number: NCP15Xh103D03RC). It is a negative temperature coefficient device with a nominal resistance at 25 C of 10,000 Ohms. It has resistive tolerance at 25 C of 0.5% and dimensions of 1 mm long, 0.5 mm wide, and 0.5 mm high. It uses surface mount technology to electrically connect to the circuit board. Many other thermistors exist at other nominal resistances and temperature-resistance curves, with positive or negative temperature coefficients in a variety of physical packages. Other devices such as resistance temperature detectors (RTDs), thermal sensing junctions (such as diodes and transistors), thermocouples, infrared sensors, semiconductor thermal sensors, etc. are used in some implementations.

In certain embodiments, the heating element is a resistive heater. One example of a suitable heating element is Rohm Semiconductor part number ESR01MZPJ510. It is a thick film resistor with a tolerance of 5% and power dissipation rating of 1/5 Watt. It is packaged in a 1 mm long, by 0.5 mm wide by 0.35 mm high, laser trimmed, ceramic substrate. It has a nominal resistance of 51 Ohms. Many other resistors exist at other nominal resistances, accuracies, and power levels including resistors fashioned from wire or foil. Other devices such as transistors, diodes, or integrated circuits could be used and configured to sink constant current or constant power. In certain embodiments, radiating devices such as masers, lasers, or radio wave generating devices are used as the heating element. These may be aimed at the pipe to provide heating at a desired location.

Depending on the required functions of the detection device, the detection device will have at least one or at least two temperature sensing elements. A single temperature sensing element is all that is required if the sensor need only provide a temperature magnitude reading (not a differential temperature value). Two temperature sensing elements are required if the sensor must provide a different temperature measurement across two locations. However, in some embodiments, a thermal flow condition sensor contains more temperature sensing elements than are strictly required for the function. The extra temperature sensing elements may be provided for various purposes. For example, the thermal flow condition sensor may include multiple redundant temperature sensing elements to account for the possibility that one will fail or not be in intimate contact with the pipe and therefore unable to provide reliable temperature readings. Note that in some cases the thermal flow condition sensor is applied to a pipe by an adhesive or pressed against the pipe by a normal force. In any case, it is possible that any given temperature sensing element may not achieve intimate thermal contact with the pipe surface due to irregularities on pipe surface or other reasons. However, if the sensor includes multiple temperature sensing elements, there is a better chance that at least one or two of them will achieve thermal contact sufficient for reliable temperature sensing. After installation, the temperature sensing elements can be individually tested to determine which ones are in thermal contact with the pipe. Only those that are determined to be in good contact of used for temperature readings during operation.

When a thermal flow condition sensor is used for measuring a temperature gradient, at least one pair of temperature sensing elements is normally needed, one upstream from the other. To allow for alternative gradient measurements across different pipe segments or over different distances of a pipe segment, additional temperature sensing elements may be provided to provide different combinations of upstream-downstream sensing elements to allow different measurements of temperature gradient. The different values can be compared, averaged, etc. Multiple sensors arrayed along the direction of fluid flow can be used to indicate the flow velocity.

In various embodiments, the detection device has associated logic configured to interpret temperature values (possibly with the aid of calibration). The logic may include software or firmware programmed or configured to receive data taken from one or more thermal flow condition sensors and analyze such data to determine fluid temperature, flow rate, and/or events on the pipe network. The logic for interpreting data from such sensors may be located on a server or other computing system associated with the pipe network (located either at the network or remote therefrom) or the logic may be located on a leased or shared computational system such as a cloud-based system available over the internet or other network.

Figure 22A:
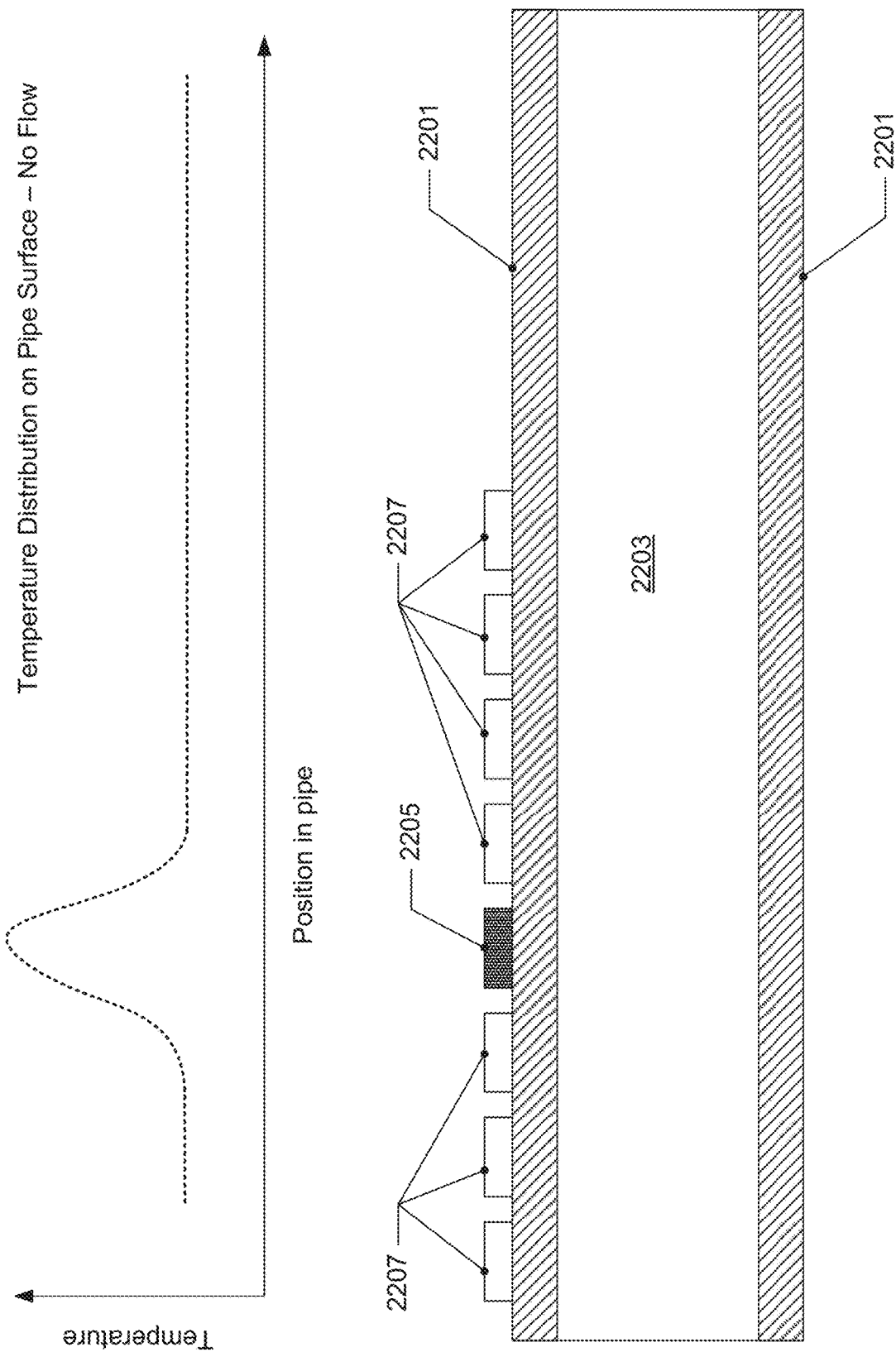
FIG. 22A depicts an axial cross-section of a pipe with a thermal flow condition sensor of a detection device attached to it.

FIG. 22A shows an axial cross-section of a pipe 2201 with a thermal flow condition sensor of a detection device attached to it. The sensor includes temperature sensing elements 2207 and a heating element 2205. An interior 2203 of pipe 2201 has a quiescent fluid. When heating element 2205 is turned on and generates heat energy, the temperature on the pipe wall decreases roughly uniformly in all directions away from heating element 2205. This is reflected in the roughly symmetric temperature versus axial pipe position plot shown above the pipe in FIG. 22A. The temperature sensing elements (or at least two of them optionally on opposite sides heating element 2205) are able to detect this roughly uniform distribution and associated logic is able to determine that the fluid in pipe interior 2203 is quiescent.

Figure 22B:
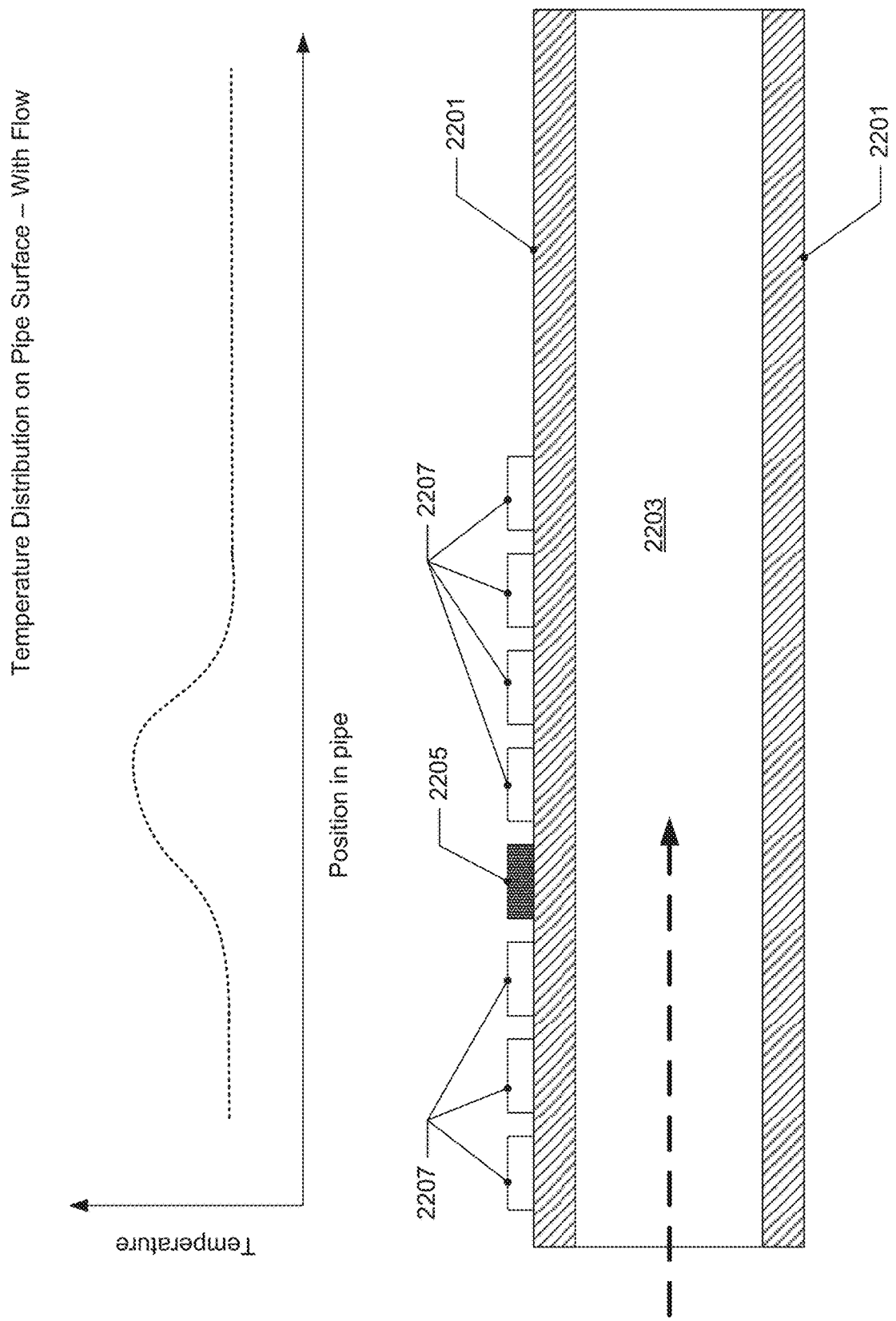
FIG. 22B again depicts the axial cross-section of the pipe of FIG. 22A with a thermal flow condition sensor attached to it.

FIG. 22B again shows the axial cross-section of pipe 2201 with a thermal flow condition sensor attached to it. As in FIG. 22A, the sensor includes temperature sensing elements 2207 and heating element 2205. Unlike in FIG. 22A, the interior 2203 of pipe 2201 contains a fluid from left to right. When heating element 2205 is turned on and generates heat energy, the temperature on the pipe wall decreases more abruptly in the upstream direction than in the downstream direction. This is reflected in the skewed temperature versus axial pipe position plot shown above the pipe in FIG. 22A. The temperature sensing elements (or at least two of them optionally on opposite sides heating element 2205) are able to detect this skewed distribution and associated logic is able to determine that the fluid in pipe interior 2203 is flowing left to right. The logic may also be able to determine a flow rate of the fluid.

Figure 23A:
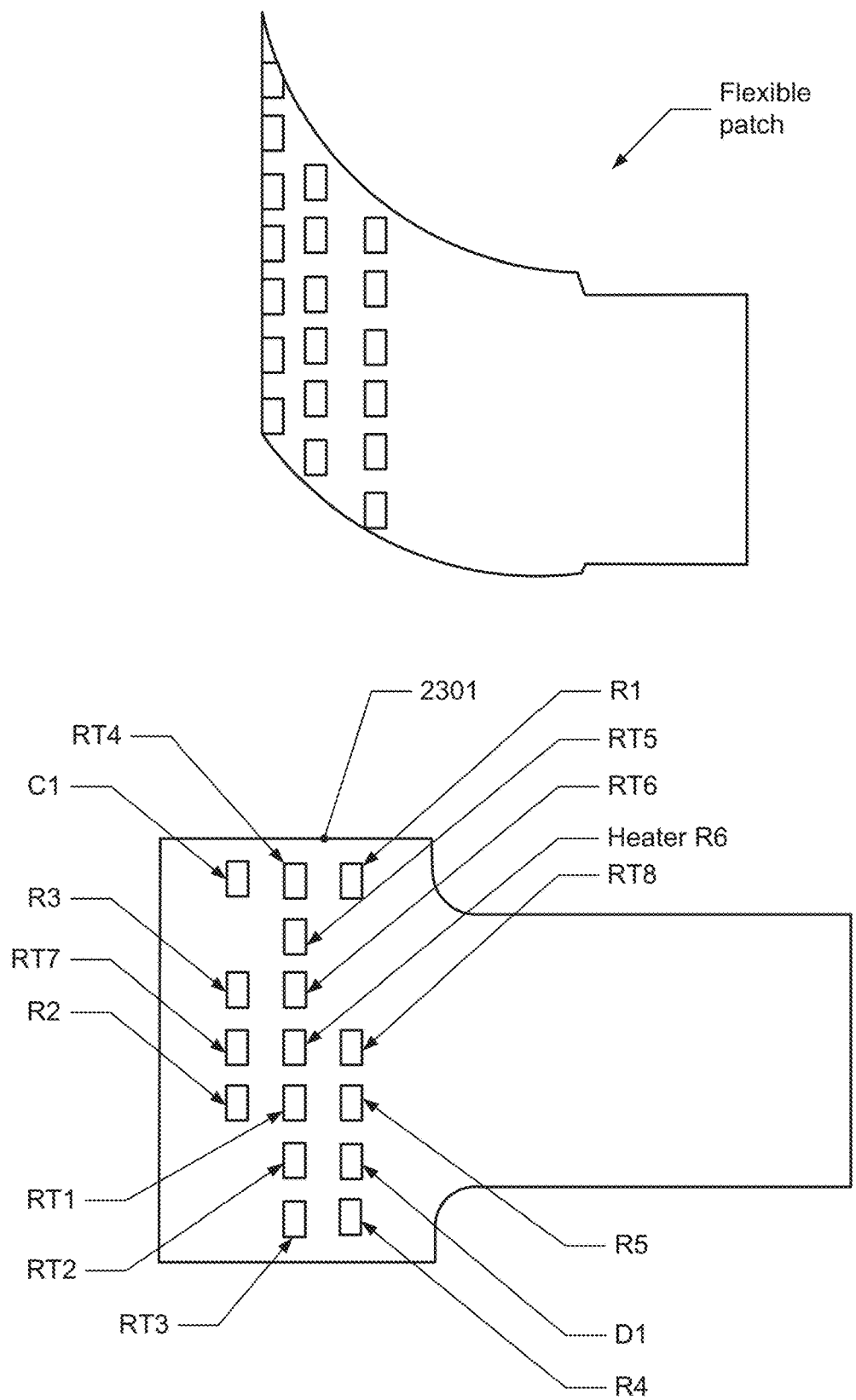
FIG. 23A depicts two views of an example array of heating and sensing elements for a thermal flow condition sensor.

FIG. 23A shows two views of an example array of heating and sensing elements for a thermal flow condition sensor. The sensor has a backing or substrate 2301 on which are provided a plurality of temperature sensing elements, an optional heating element, and one or more optional circuit elements. The substrate 2301 may made from any of various materials. In some cases, it is flexible as depicted in the upper representation shown in FIG. 23A. It may also be adhesive to promote good contact between the pipe surface and the temperature sensing elements (and the heating element if present).

In certain embodiments, the thermistor support substrate is somewhat flexible to allow it to conform to the pipe exterior. In various cases, it is sufficiently rigid however to support the ceramic substrates of the components mounted to it. In various embodiments, it has limited thermal conductivity so it does not dominate the thermal profile of the pipe. In some designs, the temperature sensing elements are arrayed along the pipe's axis of curvature to facilitate flexing along the axis of the pipe. The support may also provide selective electrical conductivity to allow the thermal-electric properties of the devices to be read by the host. One example of a suitable substrate material is a polyimide (e.g., Kapton™) laminate with etched copper foil traces and gold plated connector fingers.

In the example, elements labled "RT" are temperature sensing elements such as thermistors, and elements labeled "R" are resistors (not necessarily temperature sensing).

In one example, any of temperature sensing elements RT1, RT2, and RT3 can be used interchangeably for one temperature measurement in a differential temperature measurement. Similarly, any of temperature sensing elements RT4, RT5, and RT6 may be used for a second temperature measurement in the differential temperature measurement. The thermal flow condition sensor would be installed on a pipe such that sensing elements RT1/2/3 and sensing elements RT4/5/6 are positioned in an upstream-downstream orientation. Different combinations of the sensing elements may be employed for providing the differential temperature reading. For example, RT1-RT6 may be used as a pair, or RT3-RT4 may be used as a pair, or RT1-RT5 may be used as a pair, etc. In some cases, such as a pipe with a non-uniform exterior that compromises thermal contact, one combination performs better than others. This fact can be discovered and utilized after installation of the thermal flow condition sensor on a pipe. Further, in some cases, one or more of sensing elements RT1/2/3 and/or or more of sensing elements RT4/5/6 fail to establish suitable thermal contact with the pipe and therefore cannot be used in a differential temperature reading. Having alternative sensing elements available provides a needed redundancy.

Figure 24:
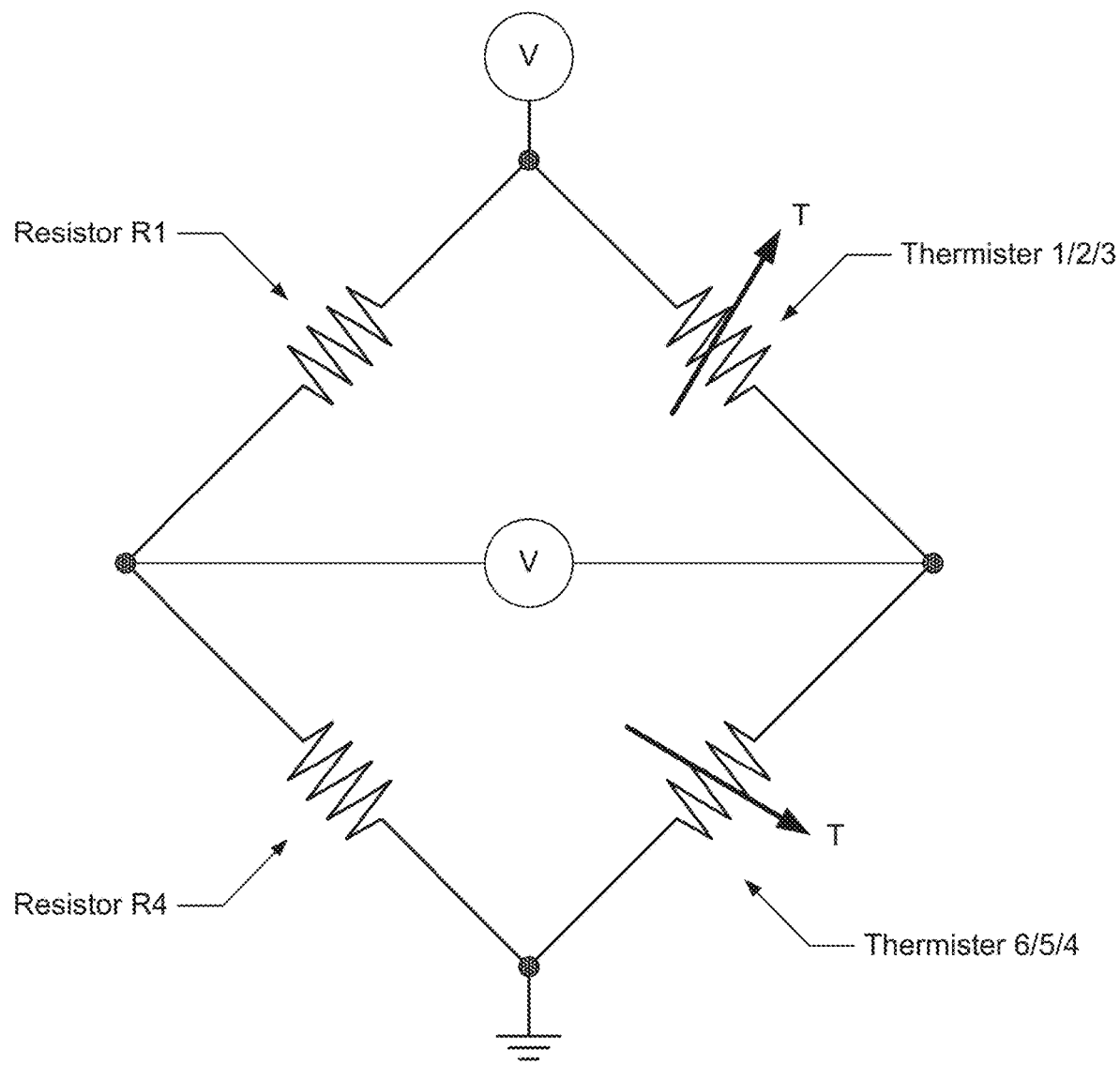
FIG. 24 depicts an example Wheatstone bridge.

In certain embodiments, a differential temperature measurement is made using a Wheatstone bridge as shown in FIG. 24. In the illustrated example, one leg of the bridge contains one of temperature sensing resistors RT1/2/3, another leg of the bridge contains one of temperature sensing elements RT4/5/6, and the other two legs have reference resistors R1 and R4. In some implementations, a capacitor such as C1 shown in FIG. 23A is employed to reduce noise in the bridge sensing.

As mentioned, to allow for measuring temperature gradients, a thermal flow condition sensor may have a heating (or cooling) element. As shown in the example of FIG. 23A, a heater is provided as a resistive element R6, which is strategically located between sensing elements RT1/2/3 and sensing elements RT4/5/6.

In one example, any of temperature sensing elements RT7 and RT8 are used to measure an absolute temperature value (rather than a differential measure). As such elements RT7 and RT8 and not included in a circuit that produces a ratio or difference of temperature values. In certain embodiments, circuits including RT7 and RT8 include a reference resistor to facilitate accurate measurement of the thermistor values output by RT7 and RT8. In one example, R2 and R3 are used as reference resistors in circuits containing RT7 and RT8.

Finally, in some embodiments, the thermal flow condition sensors includes a light (e.g., and LED) or other visual or auditory signaling element to signal a particular operating state of the sensor such as "heater on." In the depicted embodiment, a light D1 and associated ballast resistor are provided to indicate heating or other state of the sensor.

Figure 23B:
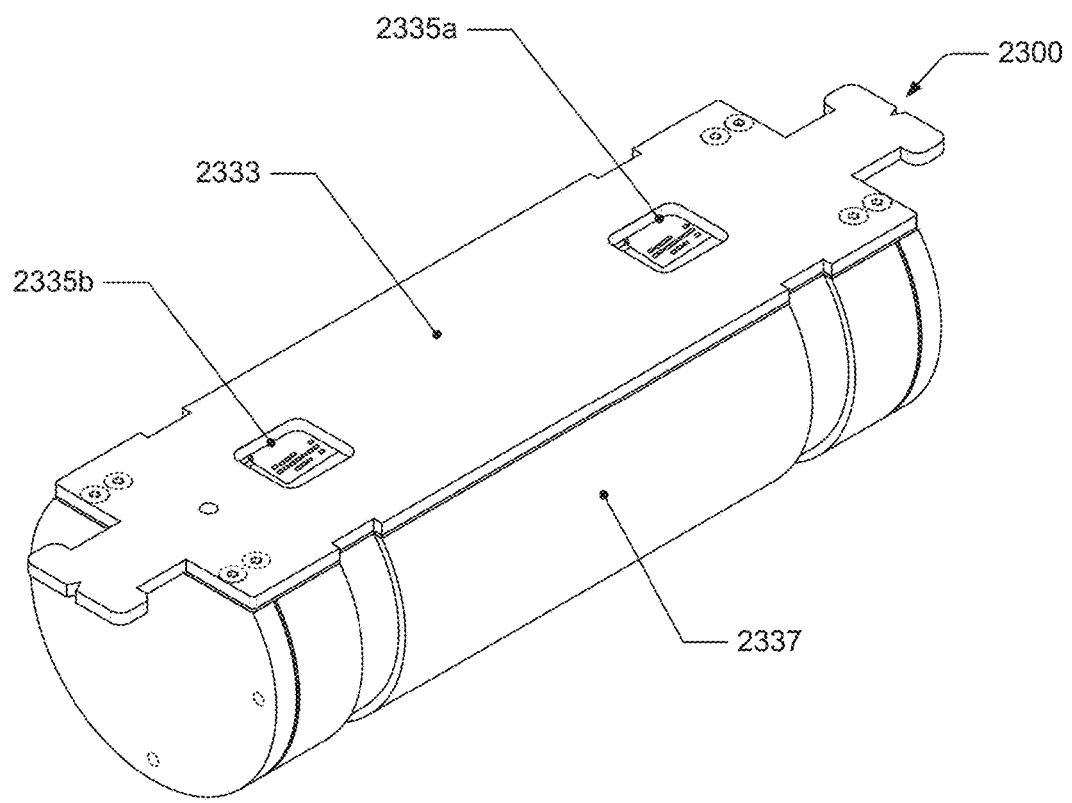
FIG. 23B depicts a perspective view and FIG. 23C depicts a top view of a detection device having a face that is designed to engage with an exterior surface of a pipe.
Figure 23C:
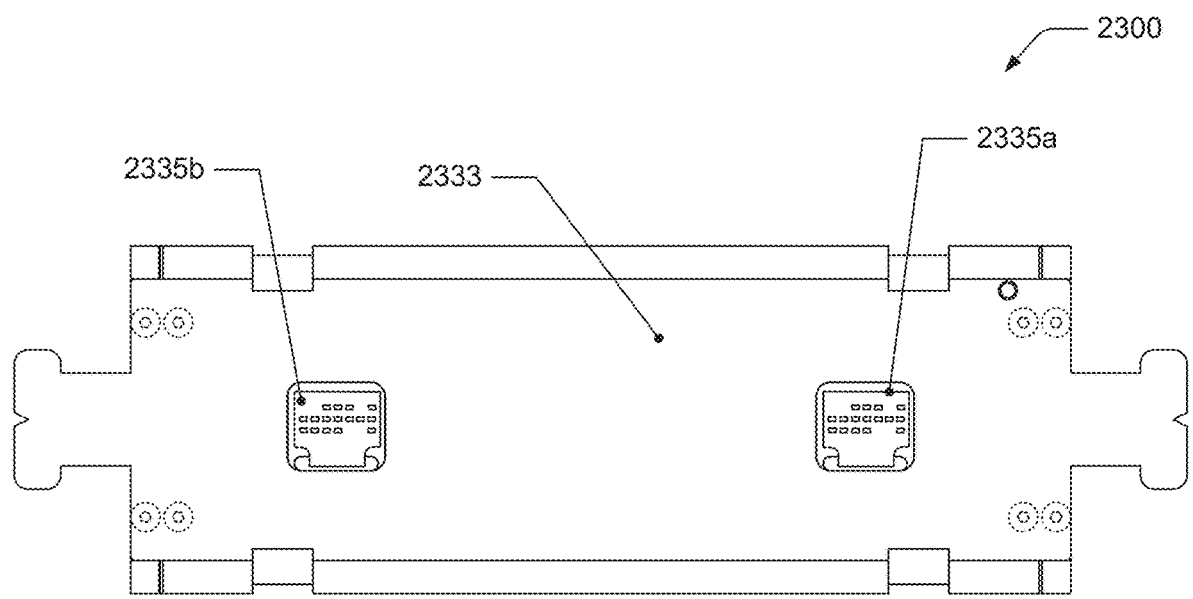

FIG. 23B shows a perspective view and FIG. 23C shows a top view of a detection device 2300 having a face 2333 that is designed to engage with an exterior surface of a pipe. When installed, as described below, detection device 2300 is clamped or otherwise attached to the pipe such that face 2333 presses against a pipe and brings one or both of thermal flow condition sensors 2335a and 2335b into thermal contact with the pipe surface. In certain embodiments, one or both of thermal flow condition sensors 2335a and 2335b are implemented with temperature sensing elements as described above, for example as shown in FIG. 23A, and optionally with a heating element. In certain embodiments, the face 2333 of detection device 2300 has recesses sized and shaped to accommodate thermal flow condition sensors 2335a and 2335b. Detection device 2300 has a body 2237 that encloses a volume in which sensor data processing logic, communications logic, an inertial sensor, and/or other component(s) supporting thermal flow condition sensors 2335a and 2335b. Such components may include a processor, memory, electrical wiring, etc. In some cases, these components are provided on printed circuit board. A thermal flow condition sensor may be electrically connected to processing logic by, for example, electrically connected terminals.

The differential temperature between upstream and downstream locations on a pipe can be determined using various circuit designs that include the upstream and downstream thermistors. For example a Wheatstone bridge as shown in FIG. 24 may be used for this purpose. In alternative embodiments, an absolute temperature is measured at a upstream position and an absolute temperature is measured at a downstream position and comparison logic receives both the upstream and downstream readings and provides a differential reading.

3. Processing Logic for Thermal Flow Condition Sensor

Figure 25:
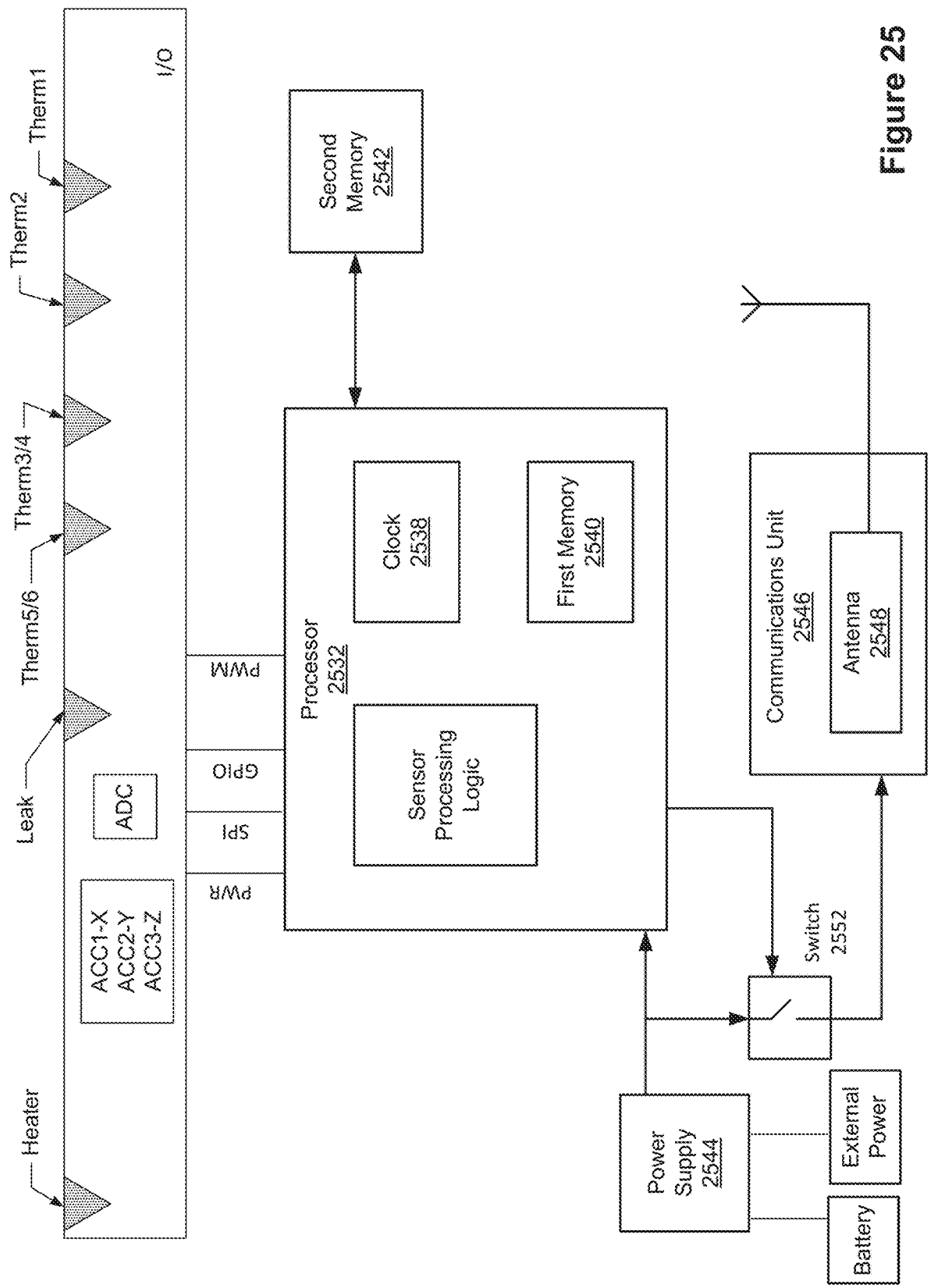
FIG. 25 schematically depicts an example of a processing module.

FIG. 25 schematically depicts an example of a processing module 2530 that is similar to FIGS. 3 and 9 herein. The depicted processing module 2530 includes an input/output unit 2520 that includes a first input 2521 for connection to a leak detector (like described herein above) and an accelerometer 2524 that is depicted as a three-axis accelerometer. The input/output unit 2520 may include an analog to digital converter 2525, and the input/output unit 2520 may be configured to receive power from the power supply 2544 for various purposes including to power the sensing and heating elements of a thermal flow condition sensor. In some embodiments in which temperature sensing elements of the thermal flow condition sensor 2502 are incorporated in a Wheatstone bridge, the input/output unit 2520 may also electrically connect the other resistors in the Wheatstone bridge and may be configured to apply voltages across the other legs of the Wheatstone bridge.

As depicted, input/output unit 2520 includes various ports or electrical connectors for communicating with temperature sensing elements and a heating element on a thermal flow condition sensor. For example, input/output unit 2520 includes electrical connectors for receiving electrical signals corresponding to temperature detected by temperature sensing units for providing differential temperature measurements; thermistors 1/2/3 and thermistors 4/5/6. These may correspond to temperature sensing elements RT1/2/3 and RT4/5/6 shown in FIG. 23A and described above. Additionally, input/output unit 2520 includes one or more electrical connectors for providing power to a heating element (e.g., Heater R6) of a thermal flow condition sensor. Still further, input/output unit 2520 includes electrical connectors for receiving electrical signals corresponding to temperature detected by temperature sensing units for providing absolute temperature measurements; thermistors 7 and 8. These may correspond to temperature sensing elements RT7 and RT8 shown in FIG. 23A and described above. Input/output unit 2320 may have ports for additional flow condition sensor components such as a light. In some cases, the input/output unit 2320 has ports for components of other types of sensor that may share processing unit 2330 with a thermal flow condition sensor. Examples of such other types of sensor include pipe condition sensors (e.g., acoustic pipe condition sensors) and pressure sensors (e.g., hoop stress sensors). Ports for these additional types of sensor are not depicted in FIG. 25.

The fluid flow processing module 2530 also includes one or more processors (shown as processor 432) that include a clock 2538, a first memory 2540, and sensor processing logic 2536. The first memory 2540 may be a program memory that stores instructions to be executed by the processor 2532 and buffers data for analysis and other processing. The sensor processing logic 2536 (which may also or alternatively be instructions stored on the first memory 2540) is configured to detect signals, including voltages, generated by any of the sensors, including the thermal flow condition sensor 2502 and the leak detector 2522. For example, as described above, sensor processing logic 2536 may be configured to receive data from sensing elements including temperature sensing elements of a thermal flow condition sensor. The data may be provided in many forms, including voltage levels. In some of the embodiments in which the thermal flow condition elements are incorporated in a Wheatstone bridge, the sensor processing logic 2536 may also be configured to determine a voltage level across the Wheatstone bridge. The sensor processing logic 2536 may also be configured to determine and store values of resistance and voltage or their corresponding values of temperature or relative temperature measured via the various temperature sensing elements. In certain embodiments, sensor processing logic 2536 may also be configured to determine and store strain values measured on the pipe, acoustic responses measured on the pipe, and/or calculated pressure values in the pipe.

The clock 2538 may be a real time clock or a timer. The fluid flow processing module 2530 also includes a second memory 2542 that may be a rewritable memory that is configured to store data generated by any of the sensors or other components described herein. A power supply 2544, which may include a battery, is also a part of the depicted fluid flow processing module 2530 and is configured to provide power to the elements of the fluid flow processing module 2530, such as the processor 2532, a communications unit 2546, and any of the sensing elements, as described above.

The processor 2532 may execute machine-readable system control instructions which may be cached locally on the first memory 2540 and/or may be loaded into the first memory 2540 from a second memory 2542, and may include instructions for controlling any aspect of the fluid flow processing module 2530. The instructions may be configured in any suitable way and may by implemented in software, firmware, hard-coded as logic in an ASIC (application specific integrated circuit), or, in other suitable implementation. In some embodiments, the instructions are implemented as a combination of software and hardware.

The communications unit 2546 may include an antenna 2548. The communications unit 2546 may be configured to acquire location data about the location of the detection device using the antenna 2548 which is configured to connect with an external location device and receive location data from the external location device. The location data may include the latitude, longitude, and altitude, for example, of the fluid flow processing module 2530 which houses the first antenna 2548.

The communications unit 2546 may also be configured to wirelessly connect with, and transmit and receive data from, an external device, like a network or computer, using the antenna 2548 that is configured to connect with the external device. The communications unit 2546 and antenna 2548 may be configured to communicate by an appropriate cellular protocol such as Code Division Multiple Access (CDMA) or Global System for Mobile Communications (GSM). Alternatively or in addition, the communications unit 2546 and antenna 2548 may be configured to communicate by a non-cellular wireless protocol such as a low power wide area network (LoRaWAN) protocol, which operates between 850 MHz and 1,900 MHz, or other sufficiently long range protocol. The communications module may also use an 'Internet of Things' (IOT) friendly protocol such as LTE Cat M1. In one example, the communications unit 2546 may be the SIM808 from SIMCom Wireless Solutions, Shanghai, China. The product may be packaged on a printed circuit assembly ("PCA") with support integrated circuits from Adafruit, Industries of New York, N.Y.

In some embodiments, the fluid flow processing module 2530 also includes a global positioning satellite ("GPS") antenna that can establish a connection with multiple GPS satellites. Using data from communications with such satellites, the communications unit 2546 can determine the location of the water release assembly and thereafter send location data to the processor 2532. The term "GPS" herein may mean the broader concept of a location system employing one or more satellites that transmit ephemeris (e.g., a table or data file that gives the calculated positions of a satellite at regular intervals throughout a period) and/or position fixing data to a GPS receiver or antenna on a device. The location of the device may be calculated from the position fixing data on the device itself—communications unit 2546 in this case—on a secondary device. Multiple satellites may be used in the system with each one communicating ephemeris data and/or position fixing data. The same satellite may communicate both ephemeris data and position fixing data, or ephemeris data and position fixing data may be communicated through separate satellites. The satellites may be satellites in a GPS system, or it may be satellites in another satellite system such as the Russian Global Navigation Satellite System, the European Union Compass system, the Indian Regional Navigational Satellite System, or the Chinese Compass navigation system. Some GPS systems use a very slow data transfer speed of 50 bits per second, which means that a GPS receiver, in some cases, has to be on for as long as 12 minutes before a GPS positional fix may be obtained. Once a positional fix is obtained, subsequent positional fixes may take much less time to obtain (assuming that the subsequent positional fix occurs within a sufficiently close interval), but this initial lock-on period requires that the GPS receiver be powered for the entire initial lock-on, which can be taxing on devices with small battery capacities.

As further depicted in FIG. 25, the processor 2532 is connected to a switch 2552 that is interposed between the power source 2544 and the communications unit 2546. The processor 2532 may cause the switch 2552 to close, which causes power to be delivered to the communications unit 2546, or to open which stops the power to the communications unit 2546.

In certain embodiments, the second memory 2542 is configured to store data received from the processor 2532 and the antenna 2548. Firmware updates, which may be received from the antenna 2548, are stored at an appropriate location (e.g., second memory 2542) accessible to the processor 2532. The processor 2532 is also configured to access and transmit data stored in the second memory 2542 over the antenna 2548. In some embodiments, the elements of the processor 2532 may be communicatively connected with each other and the processor 2532 is configured to control each such element, as well as any element of the fluid flow processing module 2530.

In some embodiments, sensor processing logic may also be configured to connect the accelerometer to the power supply 2544 as well as receive signals, such as voltages, from the accelerometer 2524. The accelerometer 2524 may be continuously powered by the power supply 2544 so that the accelerometer 2524 can detect events that generate movement or vibrations, such as a seismic event, movement of the pipe to which the fluid flow processing module 2530 is connected, movement of the fluid flow processing module (e.g., tampering or vandalism), and events to the pipe or fluid conduit system upstream or downstream from the fluid flow processing module (e.g., pipe burst).

In some embodiments, the fluid flow processing module 2530 may be in a sleep state in which power is on to the processor 2532, the accelerometer 2524, the leak detector, and/or the thermal flow condition sensor, but in a low power mode, with few if any operations being performed. In this state, the processor 2532 can receive signals from the accelerometer 2524, the leak detector, and/or the thermal flow condition sensor, and at the same time, the communications 2546 module is not powered on. The processor 2532 may exit the low power state, and "wake up", in response to detecting a signal of defined magnitude or other characteristic from any of the sensors, including the accelerometer 2524, the leak detector, and/or the thermal flow condition sensor. Depending on the signal detected, the processor 2532 may simultaneously or sequentially cause various functions to be performed, as described below.

4. Example Operation of Thermal Flow Conditions Sensors

Figure 26B:
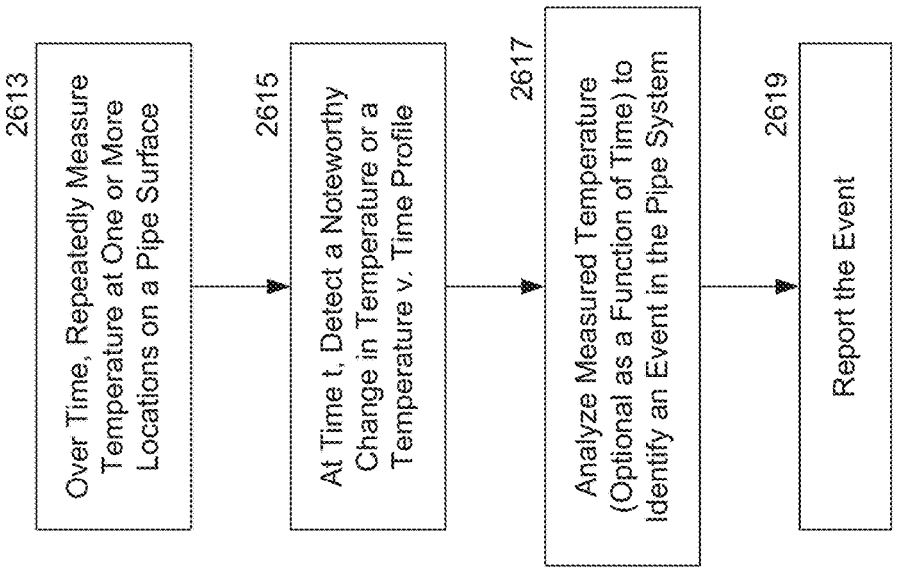
FIGS. 26A and 26B depict flow charts for treating temperature measurements made by thermal flow condition sensors such as those described herein.
Figure 26A:
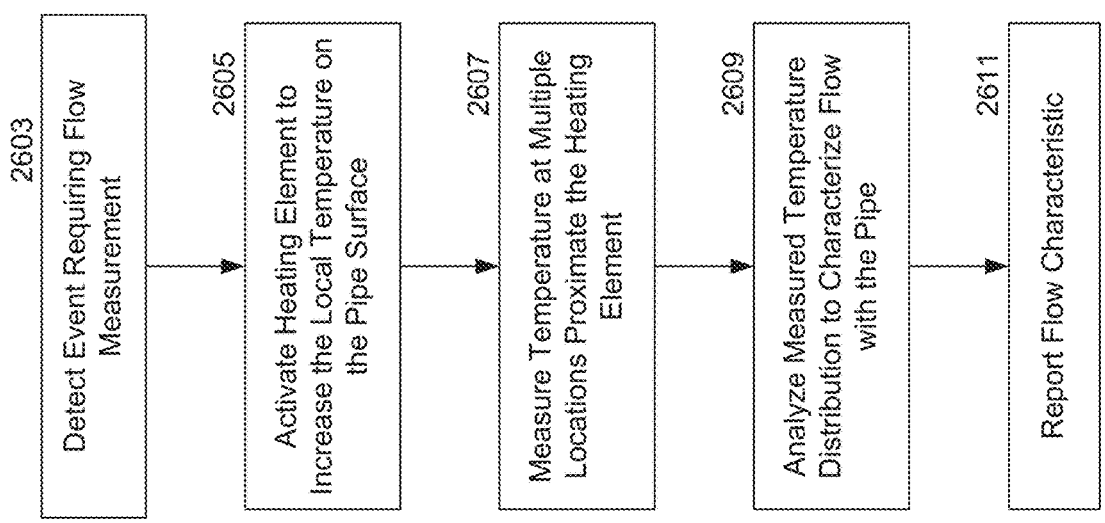

FIGS. 26A and 26B show flow charts for treating temperature measurements made by thermal flow condition sensors such as those described herein. As indicated, in certain embodiments, operations using thermal flow condition sensors may follow this sequence: (a) measure temperature with heater off, (b) turn on heater, (c) measure temperature change (before and after heater turned on) at various thermistor positions, and (d) determine flow rate based on measured temperature change. Also, as indicated, in certain embodiments, operations using thermal flow condition sensors may follow this sequence: (a) monitor steady state temperature, (b) detect a temperature change, and (c) based on temperature change, determine a type of event that caused the temperature change.

Calibration may be conducted at the factory using a predetermined set of conditions or it could be done in the field by setting a no flow condition and a known flow rate condition. Alternatively, calibration may be conducted in the field, at or after the time of installation.

5. Example Applications of Thermal Flow Conditions Sensors

As indicated, a detection device with a thermal flow condition sensor may directly measure the temperature of pipe surface and/or indirectly measure the temperature of a fluid in the pipe. Also, a thermal flow condition sensor may directly measure a temperature difference across two positions on a pipe surface. By measuring and/or monitoring the size, stability, and/or direction of a temperature gradient on the pipe surface, a thermal flow condition sensor may be used to determine various properties of the fluid flowing in a pipe to which the sensor is attached. As indicated, one such property is the flow rate of fluid in the pipe at the location of the temperature sensing elements in the sensor. Another such property is fluid's state, i.e., laminar or turbulent. Further, a thermal flow condition sensor may detect a transition between laminar and turbulent in fluid flowing in the pipe. Eddies, mixing, etc. caused by vortices in turbulence can create detectable features in temperature gradients or changes in temperature gradients.

In certain embodiments, the temperature measurements are used in building energy efficiency monitoring or auditing. In certain embodiments, variations in temperature not caused by a heating element in the sensor can be used to identify an event in a water system. Examples of such events include turning on tap, flushing a toilet, turning on an irrigation system, turning on a fire extinguishing sprinkler system, etc.

Referring back to FIG. 18, each of the detection devices 1800 of FIG. 18 may have one or more thermal flow condition sensors as described herein. An event produced at one location in the system can be detected at a remote location, where the thermal flow condition sensor is located. In this example water system, the detection device 1800 which includes one or more thermal flow condition sensors described above, is positioned on various pipes of this example water system in order to determine, among other things, flow in the pipes of this system. For example, the detection device 1800A is positioned so that in can detect water flow in the hot water pipe close to the boiler which can be used to determine, for instance, whether hot water is being flowed out of the boiler and the water flow rate in this hot water pipe, among other things. These types of conditions and events may be determined at any specific location where the detection device 1800 is positioned, as well as to the whole pipe to which the detection device is connected and the pipe system to which that pipe is connected.

Similar to above, multiple detection devices 1800 may also be used together in order to determine events along a single pipe or within a pipe system. For instance, detection devices 1800B and 1900C are positioned along the same cold water pipe and by measuring the temperature at these different locations, and in some implementations comparing them together, various information can be determined about the pipe and pipe systems, such as flow within the pipe and flow rates of the water, and the usage of various aspects connected to the pipe, such as the sprinkler in between the detection devices 1800B and 1800C.

Furthermore, flows detected by detection devices on different pipes may also be used to determine various events within the system. For example, two detection devices positioned on different pipes, such as detection devices 1800A and 1800B, may be used to determine flow, lack of flow, freezing, leaks, and usage of, for instance, the hot water pipe/system versus the cold water pipe/system.

Conditions to be detected need not occur in water or piping for water. More generally, certain conditions may be detected in pipes of portions of a pipe system for any type of liquid (e.g., petroleum, chemical feedstocks in chemical plants). In certain embodiments, the conditions being detected may even apply to gases (e.g., gas pipelines in residences, chemical plants, etc.) or other fluids such as supercritical fluids. Such conditions may relate to overheating, explosive conditions, toxic chemical generation or release conditions, and the like.

In some cases, the conditions to be detected are not limited to systems that contain only fluid carrying pipes. Other conduits such as channels and reservoirs may be monitored. These may be monitored in municipal, residential, or industrial settings; and possibly even human body arteries (e.g. capillary bed).

FIG. 27 presents a simple example of thermistor data evidencing a detectable pipe system event (e.g., turning on faucet, a laminar to turbulent transition, etc.). The measured data is simply temperature versus time as measured by a thermal flow condition sensor. It has been found that many common events on a pipe network produce a temperature variation such as shown in FIG. 27. Further, by knowing the direction of flow, which is a property that can be determined by a flow condition sensor, the temperature data also indicate where, relatively speaking, the event occurred. Typically, a detectable event will have occurred upstream of a thermal flow condition sensor. Still further, if the time of the event and the fluid flow rate are also known, the temperature data can also indicate the actual location of the event.

Data from a thermal flow condition sensor may be processed in various ways to improve the usefulness of the readings. However, the temperature readings from thermal flow condition sensors are frequently provided as slow time varying, DC values and require relatively little signal processing. For example, the temperature differential measured between upstream and downstream thermistors may be translated directly to a flow rate of the water in the pipe based on a simple proportionality constant or an expression containing the differential temperature. In some cases noting the change in absolute temperature and the change in differential temperature is useful However, in some cases the temperature readings will be relatively noisy and may benefit from some processing before they can be used to provide either the absolute local temperature of the pipe or a differential temperature reading. Such processing may take various forms. In one case, where multiple readings are made at physically separated locations, e.g., at least one meter apart, cross-correlation may be employed to identify the direction of an event that is detected by the temperature sensors.

In other embodiments, such as where in the temperature signals are particularly noisy or have apparently multiple frequency components, a Fourier transform may be employed to convert time domain temperature measurements to frequency domain temperature measurements. In some examples, a Fast Fourier Transform is used in providing data on the temperature's rate of change rather than strict frequency content.

III. Multi-Sensor Detection Devices

In some embodiments, a detection device may include more than one of the sensors described herein, including more than one of a hoop stress sensor, an acoustic sensor, an ultrasonic transducer sensor, and a thermal flow condition sensor. This may also include a combination or subsets of any of the above-described detection devices, components thereof, and/or corresponding processing modules. For example, a detection device may include both a hoop stress sensor and an acoustic sensor (such as one employing an ultrasonic transducer), including some or all of the components from each, as described above. In another example, a detection device may include both a hoop stress sensor and a thermal flow condition sensor, including some or all of the components from each, as described above. In yet another example, a detection device may include both an acoustic sensor (such as one employing an ultrasonic transducer) and a thermal flow condition sensor, including some or all of the components from each, as described above. Of course, in any of these combinations, some of the processing logic may be shared across the two or more sensor types.

In such embodiments, the detection device is configured to detect any one or more of the conditions and events described above, as well as perform additional assessments described herein. In some embodiments the detection device may include the hoop stress sensor, one or more microphones, an acoustic exciter (e.g., a solenoid or a speaker), and ultrasonic transducers which may therefore be able to detect all of the conditions associated with these sensors, such as the pressure in the pipe, the occurrence of flow, the direction of flow, and pipe conditions of the pipe to which the device is connected, as well as information gathered from multiple detected conditions as described herein. In some additional embodiments, the detection device may include one or more microphones, an acoustic exciter (e.g., a solenoid or a speaker), and a thermal flow condition sensor which may enable the detection device to detect and determine, for example, the occurrence of flow, the direction of flow, temperature of the pipe and environment of the detection device, and pipe conditions of the pipe to which the device is connected. In some such embodiments the ultrasonic transducers may be positioned within the same housing as the other sensors, while in other embodiments the ultrasonic transducers may be positioned in a separate housing, such as those shown in FIGS. 14A through 15B.

Figure 28:
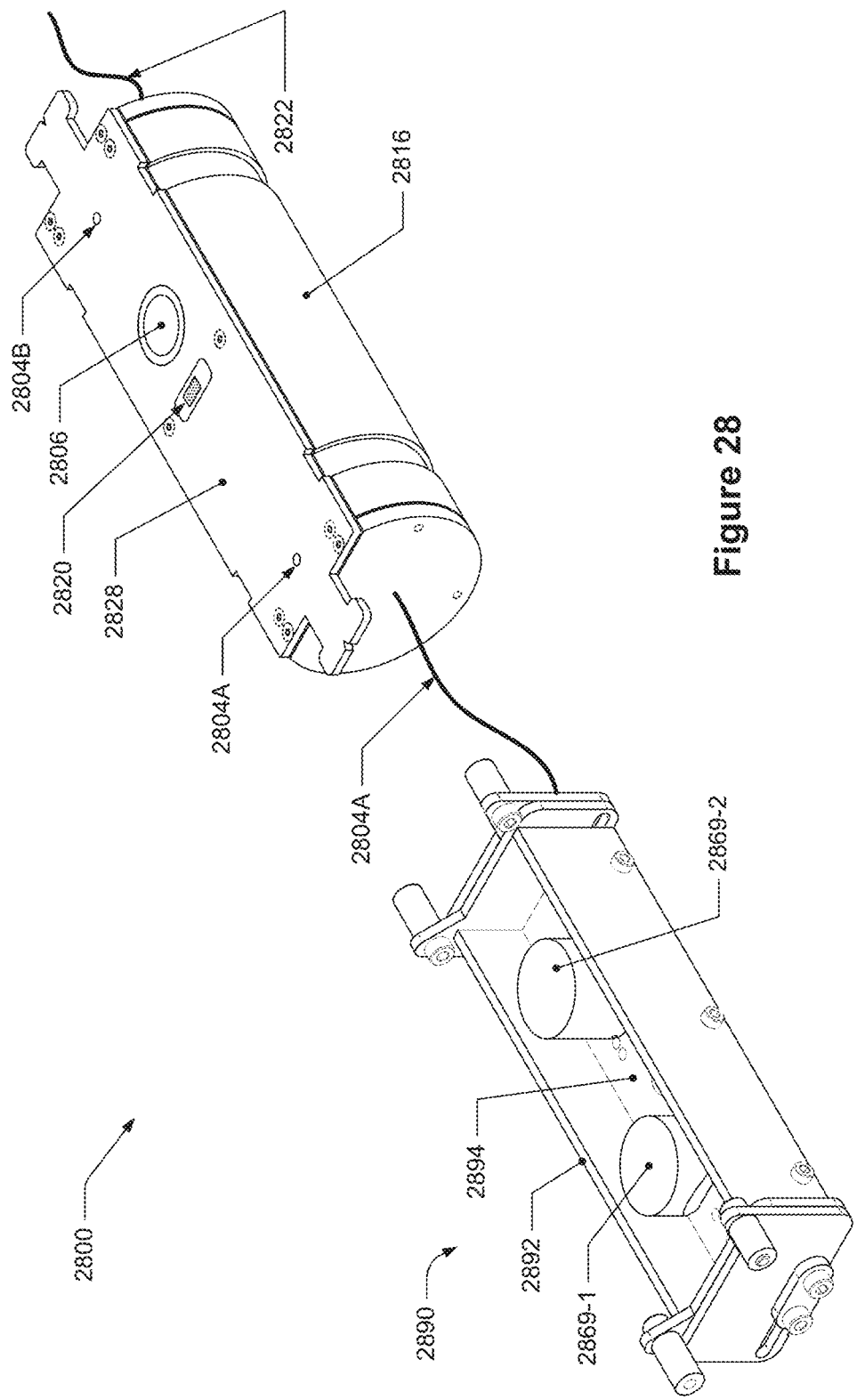
FIG. 28 depicts an example detection device having multiple sensors.

FIG. 28 depicts an example detection device having multiple sensors. As can be seen, detection device 2800 includes a hoop stress sensor 2820, three microphones 2804A, 2804B, and 2806, an acoustic exciter (e.g., a solenoid or a speaker; not depicted), a leak detector 2822, and two ultrasonic transducers 2869-1 and 2869-2 in a separate body 2892 but electrically connected (e.g., by wireless or wired connection 2888). The detection device 2800 includes a housing 2818 that includes the processing module described herein. In some other embodiments, the ultrasonic transducers may be in the same body 2816 as the other sensors.

Figure 29:
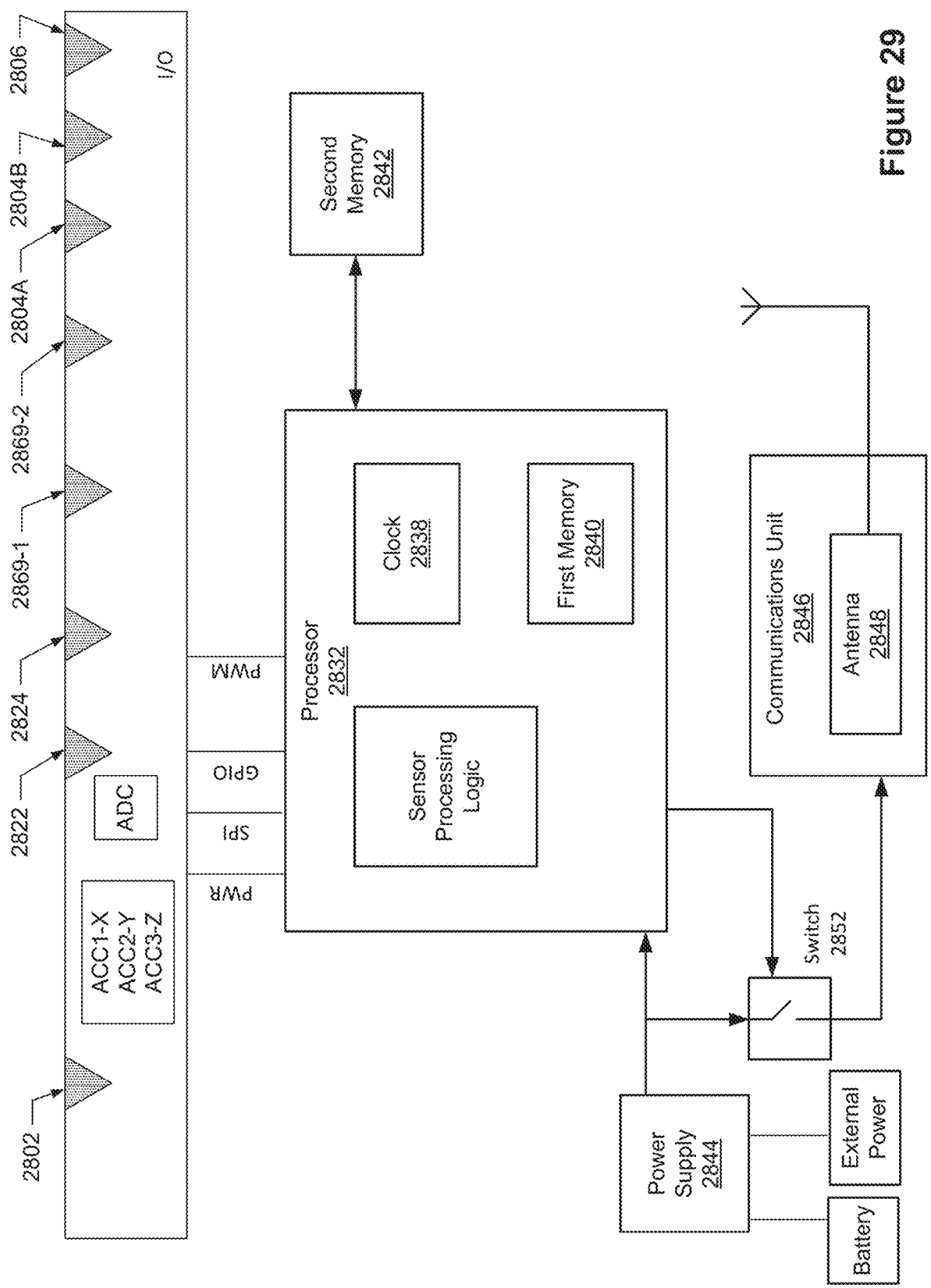
FIG. 29 depicts an example processing module for a detection device having the hoop stress sensor, one or more microphones, an acoustic exciter, and ultrasonic transducers.

FIG. 29 depicts an example processing module for a detection device having the hoop stress sensor, one or more microphones, an acoustic exciter (e.g., a solenoid or a speaker), and ultrasonic transducers, such as that depicted in FIG. 28. This Figure depicts a module having a combination of some components of the other processing modules shown and described herein, such as in FIGS. 3 and 9. For instance, the processing module of FIG. 28 has an input/output unit that is configured to connect with all of the sensors described herein, such as solenoid 2802, leak detector 2822, hoop stress sensor 2824, ultrasonic transducers 2869-1 and 2869-2, and microphones 2804A, 2804B, and 2806. The processor and sensor processing logic also includes any and all the instructions described herein. For instance, this module is configured to detect and determine any and all of the conditions associated with these sensors, such as pipe conditions, flow, presence of flow, pressure, events within the pipe and pipe system.

Figure 30A:
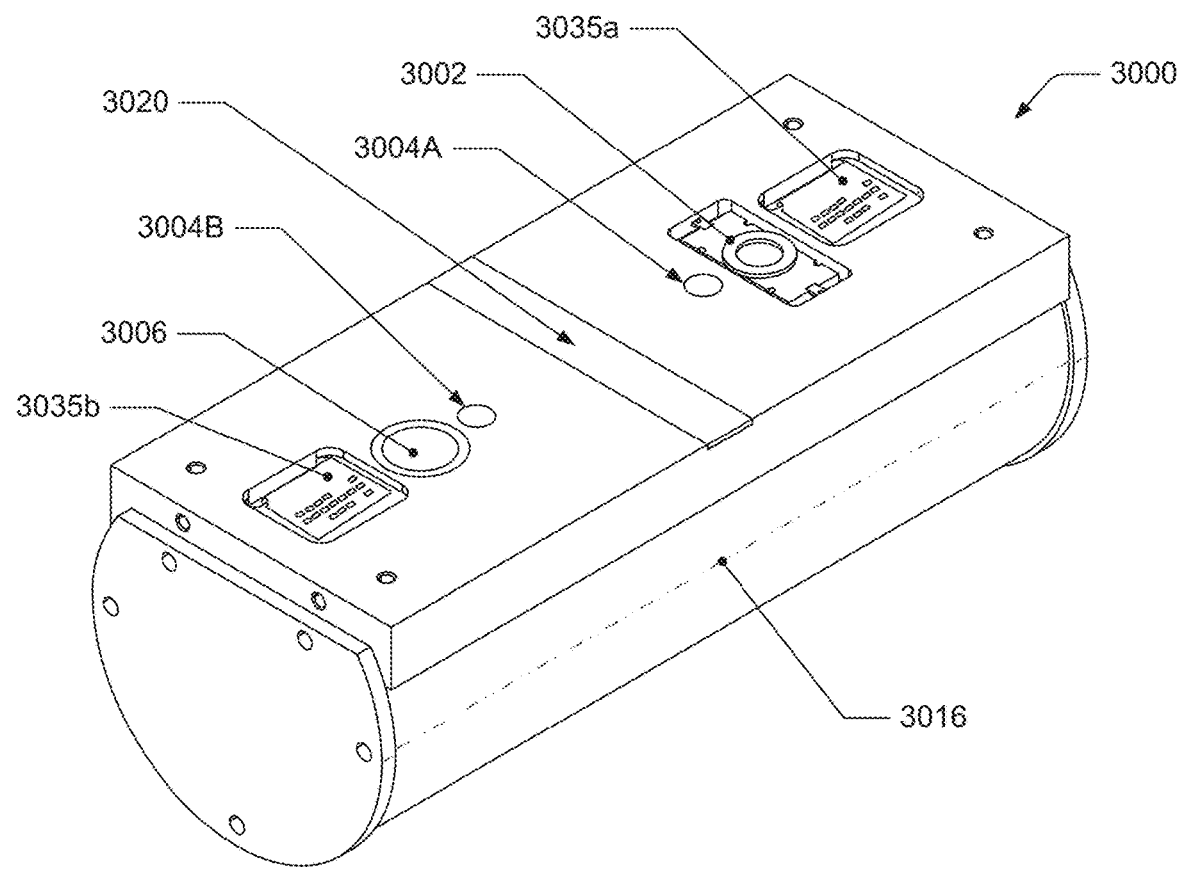
FIGS. 30A and 30B depict another example of a multi-sensor detection unit.
Figure 30B:
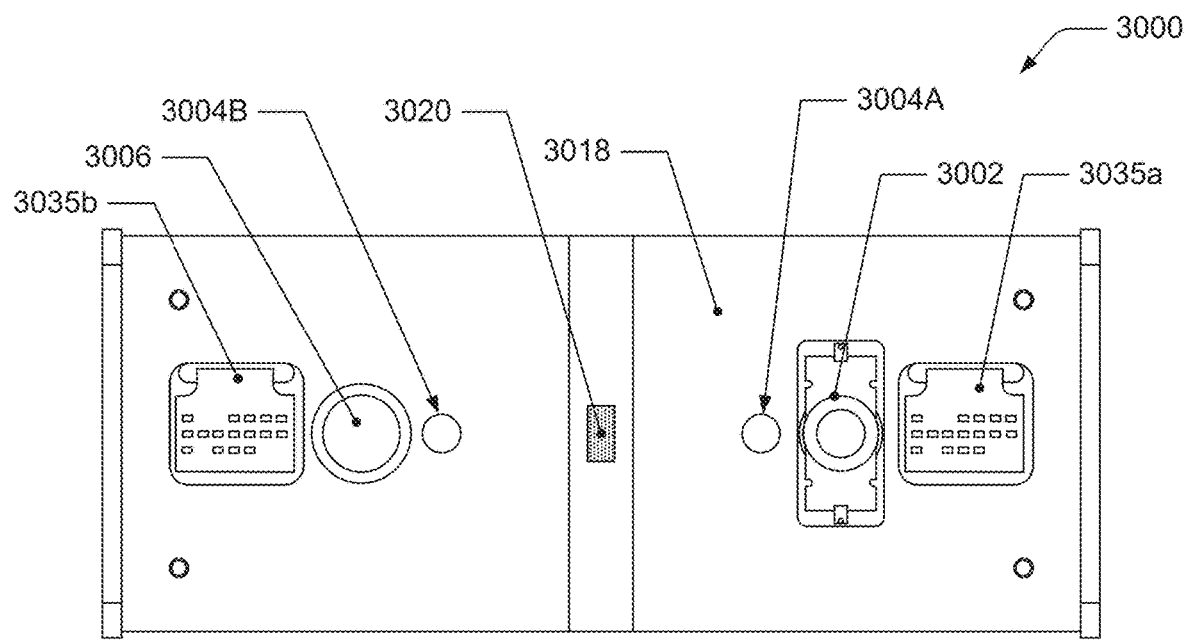

FIGS. 30A and 30B depict another example of a multi-sensor detection unit. Here, a detection device 3000 includes two temperature condition sensors, a hoop stress sensor, and some of the acoustic sensors described herein. Here, the detection device 3000 includes a housing 3016, a face 3018, thermal flow condition sensors 3035$a$ and 3035$b$, a hoop stress sensor 3020, and acoustic sensors 3006 (a large microphone or solenoid), 3004A and 3004B (small microphones), and 3002 (a speaker). The detection device 3000 is configured to detect and measure any of the items described herein using any of the sensors described herein.

Figure 31:
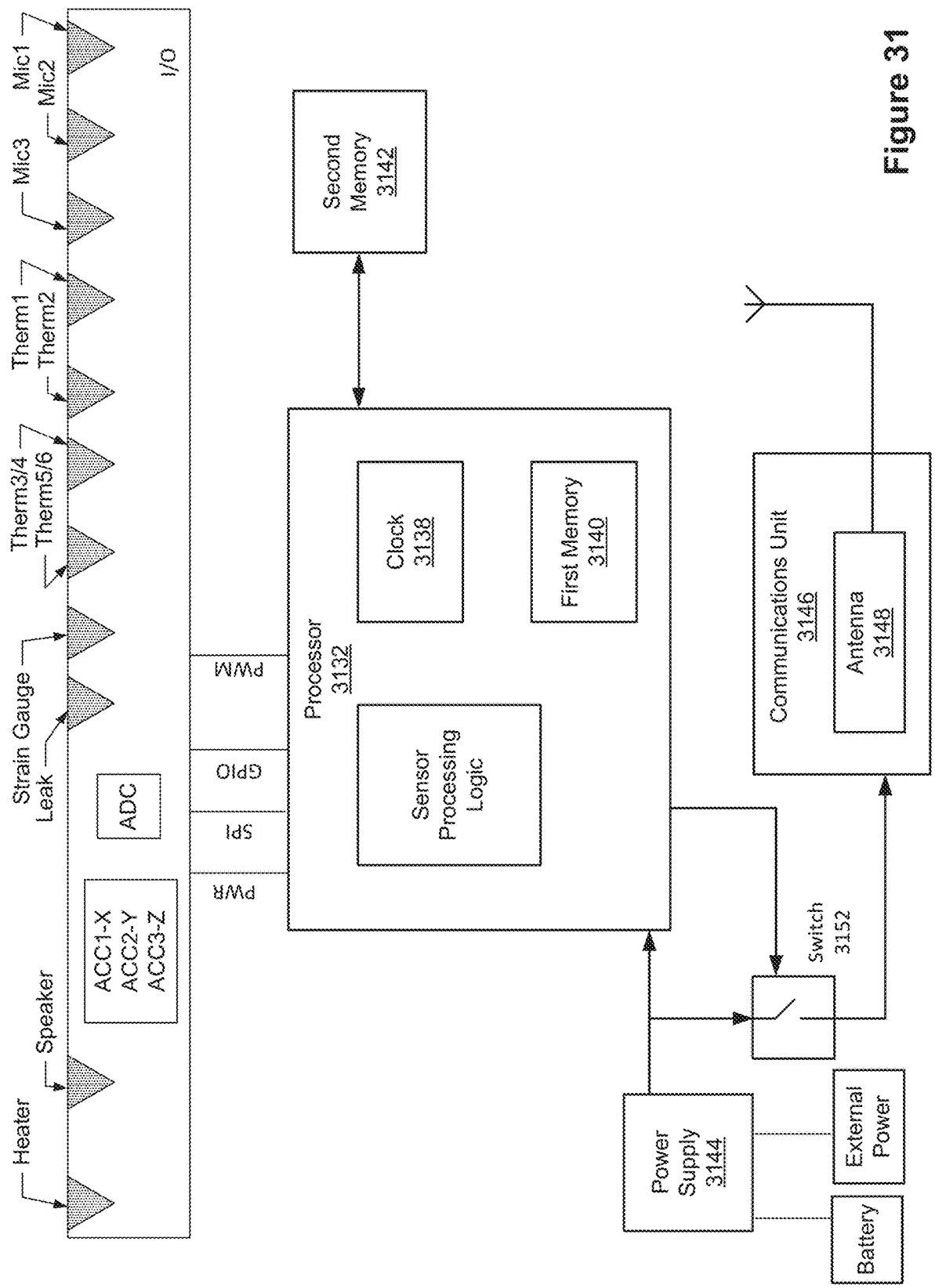
FIG. 31 depicts another example processing module.

Additionally, the detection device 3000 may also include a processing module shown in FIG. 31 which is a different combination of some of the other processing modules shown and described herein. For instance, the processing module of FIG. 31 has an input/output unit that is configured to connect with all of the sensors described herein that are included in the detection device 3000, such as the speaker and microphones of the acoustic sensors, the heater and thermistors of the thermal condition sensor, and the hoop stress sensor. The processor and sensor processing logic also includes any and all the instructions described herein.

Figure 32A:
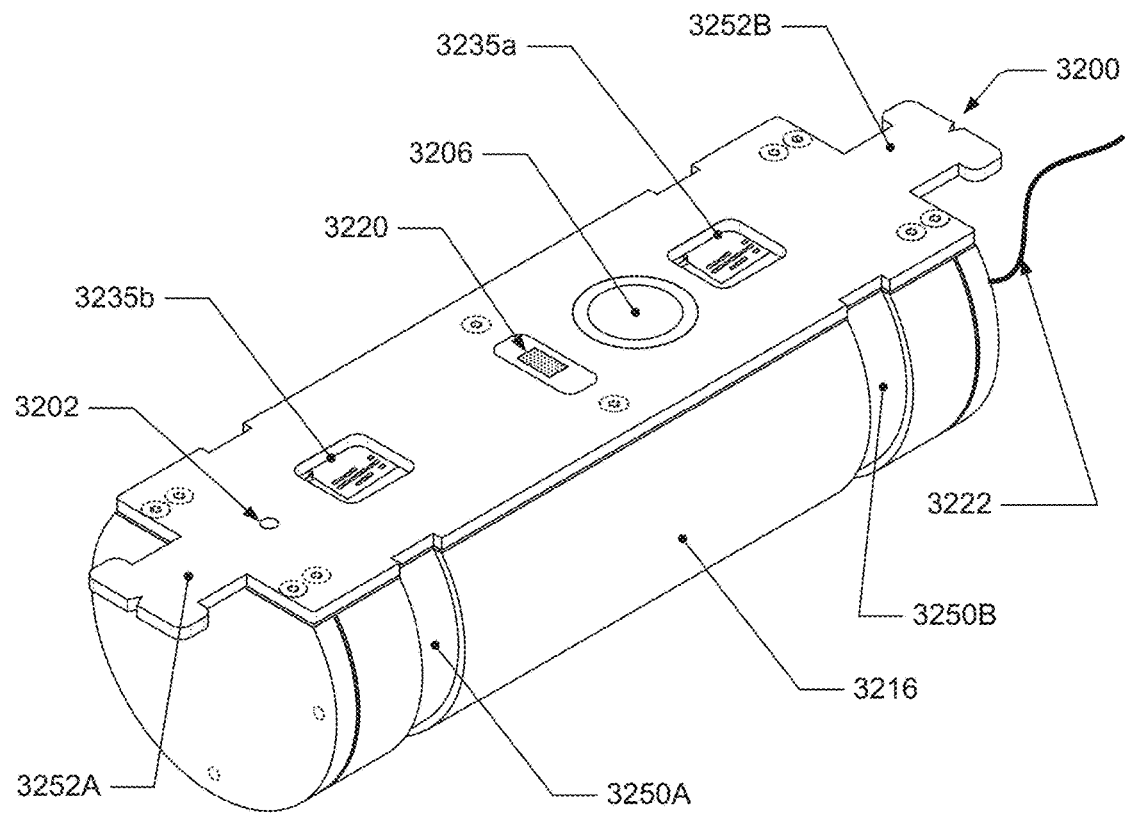
FIGS. 32A and 32B depict yet another detection device which includes multiple sensors.
Figure 32B:
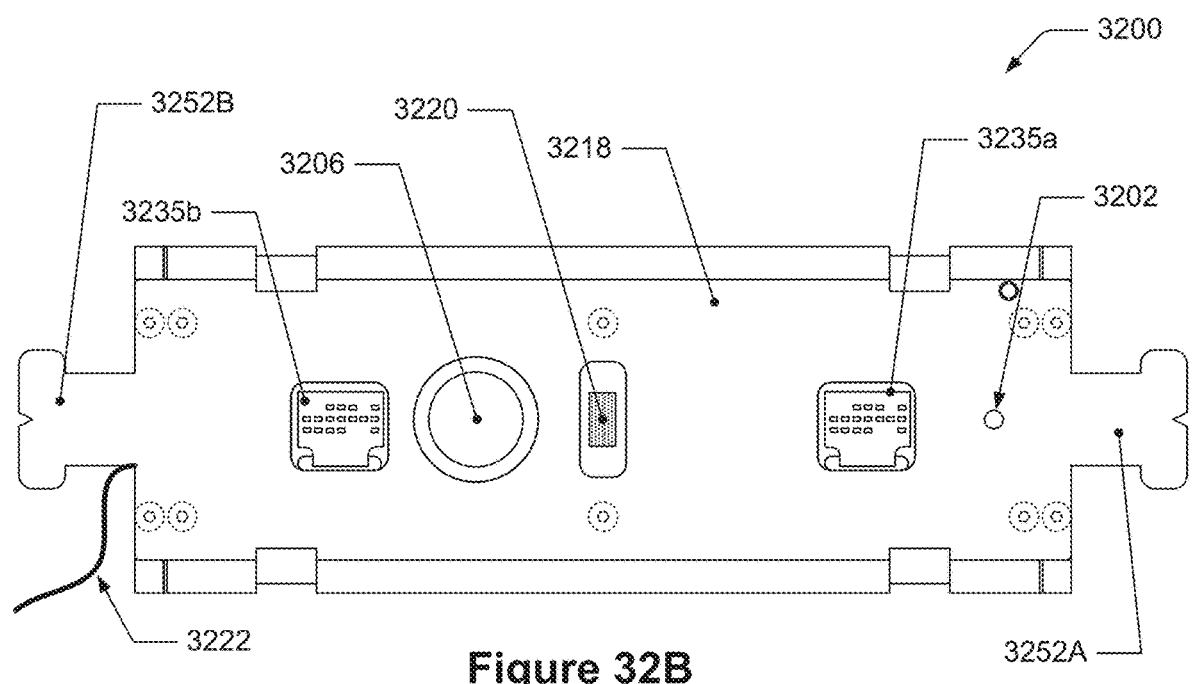

FIGS. 32A and 32B depict yet another detection device which includes multiple sensors. Here, the detection device 3200 includes a housing 3216, a face 3218, thermal flow condition sensors 3235$a$ and 3235$b$, a hoop stress sensor 3220, a single acoustic sensor 3206 (a large microphone), and a solenoid 3202. In some embodiments, the locations of the acoustic sensor 3206 and the solenoid 3202 may be moved from their positions in FIGS. 32A and 32B or they may be interchanged. The detection device 3200 is configured to detect and measure any one or more of the flow or pipe conditions. To do so, it may employ data from any of the sensors described herein. For instance, the second example detection device 3200 depicted in FIGS. 32A and 32B may be configured to detect the presence of flow in a pipe using one or more of the thermal flow condition sensors 3235$a$ and 3235$b$, the acoustic sensor 3206, and the hoop stress sensor 3220. In some implementations, the thermal flow condition sensors 3235$a$ and 3235$b$ and the hoop stress sensor 3220 may be used to detect flow events and/or measure flow conditions within a pipe.

Additionally, the example detection device depicted in FIGS. 32A and 32B is configured, in some implementations, to detect the condition of a pipe using the solenoid 3202 and the microphone 3206 by using the solenoid 3202 to deliver a mechanical ping or strike to a pipe. It may accomplish this by producing an excitation signal with a fast rise time than can excite harmonics in the pipe or fluid conduit. In certain embodiments, the solenoid 3202 used in the detection device has a dynamic range of at least about 100 dB. In certain embodiments, the solenoid 3202 used in the in the detection device can produce low frequency acoustic signals of about 30 Hz or lower. As described above, the signals received by the microphone 3206 may be used to detect and/or characterize various pipe conditions, such as leaks, bore loss (which may be caused by a buildup within the pipe interior), a crack in the pipe wall, pitting on the interior and exterior wall surfaces, as well as a pipe burst, a pipe leak, a frozen pipe, a blockage, and a tap opening or closing.

The second example detection device depicted in FIGS. 32A and 32B also includes a leak detector 3222 as described herein. In some implementations, this leak detector 3222 is configured to detect a leak in a pipe by detecting the presence of a liquid on and/or near the pipe. For example, the leak detector 3222 may be a cable with various regions of exposed, uninsulated wire that, when contacted by the liquid, are configured to create a signal, or cause the lack of a signal, which indicates the presence of a liquid which in turn may be used to detect the presence of a leak. The leak detection element (e.g., the exposed wires) of detector 3222 may be positioned on a pipe as well as on a location near the pipe, such as the ground, in order to detect the presence of the liquid that may be on or around the pipe. This leak detector 3222 may be the same as any other leak detector mentioned here.

While the disclosed embodiments have focused on detection devices, other types of sensor may also collect data useful in assessing pipe condition. Examples of such non-detection devices include sensors for measuring electrical inductance and/or magnetic permittivity of a sensor.

The condition to be detected, including flow and temperature of the pipe and environment of the detection device, may be present in various contexts such as utilities, municipalities, plants, large buildings, compounds, complexes, and residences. In other words, the sensors used to detect the condition are present on pipes employed in any such location. Of course, the software or other logic used to determine that a potentially hazardous condition exists need not be present at the location of the sensors, although it may be. The logic simply needs to receive input from the sensors and then analyze the sensor data to determine whether condition exists or should be flagged.

Figure 33:
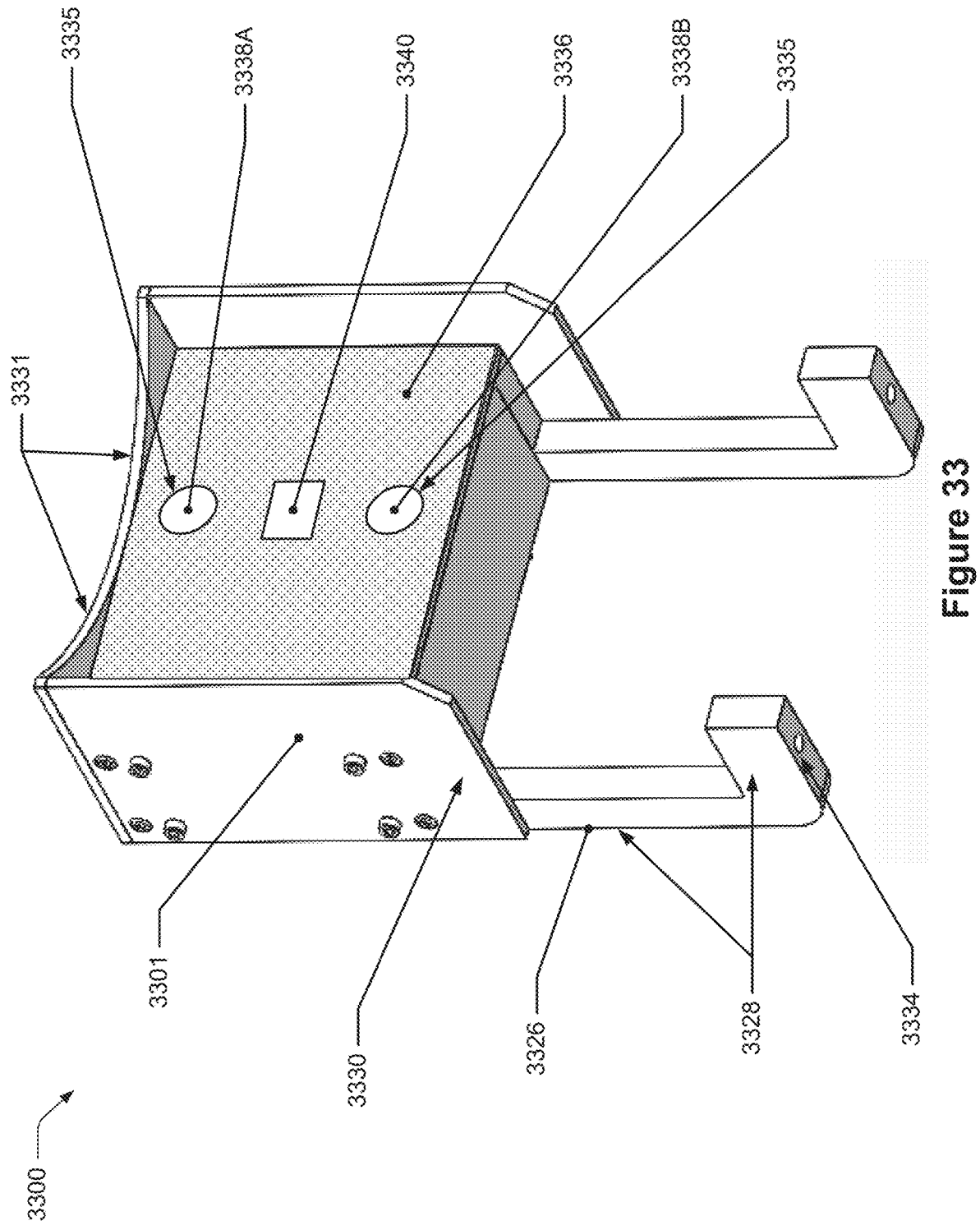
FIG. 33 depicts another example detection device having multiple sensors.

FIG. 33 depicts another example detection device having multiple sensors. As can be seen, detection device 3300 includes the hoop stress sensor 3340, two acoustic sensors 3338A and 333B (e.g., microphones like 2804A and 2804B, and an acoustic exciter (e.g., a solenoid or a speaker; not depicted). In another embodiment, the detection device 3300 may also include the two ultrasonic transducers 2869-1 and 2869-2 in a separate body 2892 but electrically connected (e.g., by a wireless or wired connection) like in FIG. 28. The detection device 3300 includes a housing 3301 that includes the processing module described herein. In some other embodiments, the ultrasonic transducers may be in the same body 3301 as the other sensors. The processing module for detection device 33 includes the input/output unit that is configured to connect with all of the sensors described herein, such as the solenoid, microphones, and hoop stress sensor 2824, and the ultrasonic transducers in those embodiments which include them. The processor and sensor processing logic also includes any and all the instructions described herein for such sensors. For instance, this module is configured to detect and determine any and all of the conditions associated with these sensors, such as pipe conditions, flow, presence of flow, pressure, events within the pipe and pipe system. In some other embodiments, the detection device 3300 may not have the hoop stress sensor and may only include the acoustic sensors, and in some instances, may also include the accelerometer.

The detection device of FIG. 33 may be configured to connect with, and detect flow, flow conditions, and pipe conditions associated with a fire hydrant or other similar cylindrical fluid conduits. With regard to fire hydrants, some fire hydrants are considered a dry barrel in which the hydrant barrel generally does not contain water until a main valve (typically at the bottom or below the hydrant) is opened to flow water into the barrel from a water source. In other words, when water is not being drawn out of these dry barrel hydrants, the hydrant barrel does not contain water. Water exits these dry barrel hydrants by thorough its nozzles on the barrel, such as the hose nozzle or pumper nozzle.

In contrast, some other hydrants are considered a wet barrel in which the hydrant barrel generally does contain water regardless of whether water is being flowed out of the hydrant through a nozzle. Water may remain within the barrel until a horizontally positioned valve positioned between the hydrant barrel and an outlet nozzle, such as a hose outlet or a pumper outlet, is opened to allow water to flow from the barrel to the outlet, and out of the hydrant through these outlet nozzles.

As stated above, the detection device of FIG. 33 may be positioned on various fluid conduits, including a fire hydrant, such as a dry or wet barrel hydrant. Regardless of whether the hydrant is a wet or dry barrel type, the detection device may be able to detect and determine conditions and characteristics of the hydrant itself and pipes to which the hydrant is directly and indirectly connected. These detections and determinations may be made in any way described above, including using acoustic sensors. Once water is flowing inside the hydrant, the detection device may be able to detect and determine any flow characteristic or pipe condition described herein, including flow rate, flow quantity, and the presence of flow for instance; the detection device may use any sensor described herein to perform these detections and determinations, such as the hoop stress sensor, accelerometer, and acoustic sensors. For example, referring back to FIGS. 20A and 20B, the detection devices 2000A and 2000B may be detection devices 3300 of FIG. 33. Again, the solenoid or acoustic exciter within the housing 3301 is configured to send an acoustic signal into the pipe system which can be detected by acoustic sensors in the same detection device or other detection devices positioned on other hydrants within the pipe system. In some instances, the ultrasonic transducers described above may also be positioned on the hydrant, similar to described above, in order to determine flow through the fire hydrant.

For some wet barrel hydrants, the detection device may also be able to detect pressure within the hydrant, which may be performed using, e.g., a hoop stress sensor. This pressure detection may be employed in hydrants containing water within the barrel.

Conditions to be detected need not occur in water or piping for water. More generally, pipe or flow conditions may be detected in pipes of portions of a pipe system for any type of liquid (e.g., petroleum, chemical feedstocks in chemical plants, and particularly toxic or corrosive fluids that would damage or destroy sensors). In certain embodiments, the flow conditions being detected may even apply to gases (e.g., gas pipelines in residences, chemical plants, etc.) or other fluids such as supercritical fluids.

In some cases, the pipe or flow conditions to be detected are not limited to systems that contain only fluid carrying pipes. Other conduits such as channels and reservoirs may be monitored. These may be monitored in municipal, residential, or industrial settings; and possibly even human body arteries (e.g. a capillary bed).

IV. Example Attachment Mechanisms to Fluid Conduits

A. Introduction

Detection devices may be positioned onto fluid conduits so that the detection device's sensors are near, indirectly, or directly in contact with the fluid conduit. As described herein, a "detection device" refers to a device having any sensor described herein, and that is configured to detect and/or determine one or more characteristics of a fluid conduit, fluid flow within that conduit, or both. In some embodiments, this positioning of some of the detection device's sensors enables these sensors to detect various conditions, which in turn allows the detection device to perform the fluid flow and pipe conditions detections and determinations described herein.

Examples of a direct connection include some acoustic sensors or the hoop-stress sensor that may be adhered directly to a fluid conduit; the detection device housing may be positioned around such sensors. An example of an indirect connection is an accelerometer (or other sensor) that may be positioned within the detection device housing such that once the detection device is positioned directly on the fluid conduit the accelerometer (or other sensor) is near the fluid conduit and is indirectly connected to the fluid conduit through the direct connection of the detection device with the fluid conduit.

Some of the detection devices may therefore have positioning features that are configured to allow the detection device to be positioned on and connected to the fluid conduit.

B. Examples of Attachment Mechanisms for Pipes

The detection devices described herein may include features that enable it to engage with a pipe or other type of fluid conduit without damaging or penetrating the pipe. As described, the pipe condition sensors described herein enable noninvasive sensing and detection of conditions within a pipe (e.g., fluid flow and flow characteristics, wall loss, bore loss and pipe-related events elsewhere in the pipe system) and these features further enable the pipe condition sensor to provide noninvasive sensing and detection. These features, which may be considered positioning or mounting features, may include structural elements on one or more aspects of the detection devices described herein. For example, FIGS. 11A and 11B includes examples of such features (the same features are also seen in FIGS. 23A, 23B, 32A, and 32B. A first example of these features is the two grooves 1150A and 1150B located on the exterior of the housing, or cover, of the pipe condition sensor. Straps, bands, zip ties, rope, cable, or other securement element may be wrapped around the pipe and the pipe condition sensor, positioned within the grooves 1150A and 1150B, and then tightened in order to position and secure the pipe condition sensor onto the pipe.

A second example of these features is the two tabs 1152A and 1152B which extend from the detection device 1100 in FIGS. 11A and 11B. Similar to the grooves 1150A and 1150B, straps, bands, zip ties, cable, or other securement items may be wrapped around the pipe and the tabs 1152A and 1152B, and then tightened in order to position and secure the detection device 1100 onto the pipe. Use of the tabs 1152A and 1152B for securing the detection device 1100 may provide certain advantages. For instance, using the tabs allows for the remainder of the detection device 1100 to be unencumbered and therefore accessible for setup and maintenance activities, such as connecting wires, checking and fixing components, and placing fresh batteries in the detection device. In some embodiments, the detection device 1100 may have a multi-part housing that is comprised of one or more plates and a cover. The one or more plates or a separate structure may include the processing module, one or more of the sensors, and the tabs 1152A and 1152B. These embodiments allow the one or more plates to be positioned onto and secure to the pipe with the tabs while the cover is not attached which may allow for more accurate and precise positioning of the sensors and plates onto the pipe as well as access to the internal elements of the pipe condition sensor for setup and maintenance of the pipe condition sensor.

Figure 34:
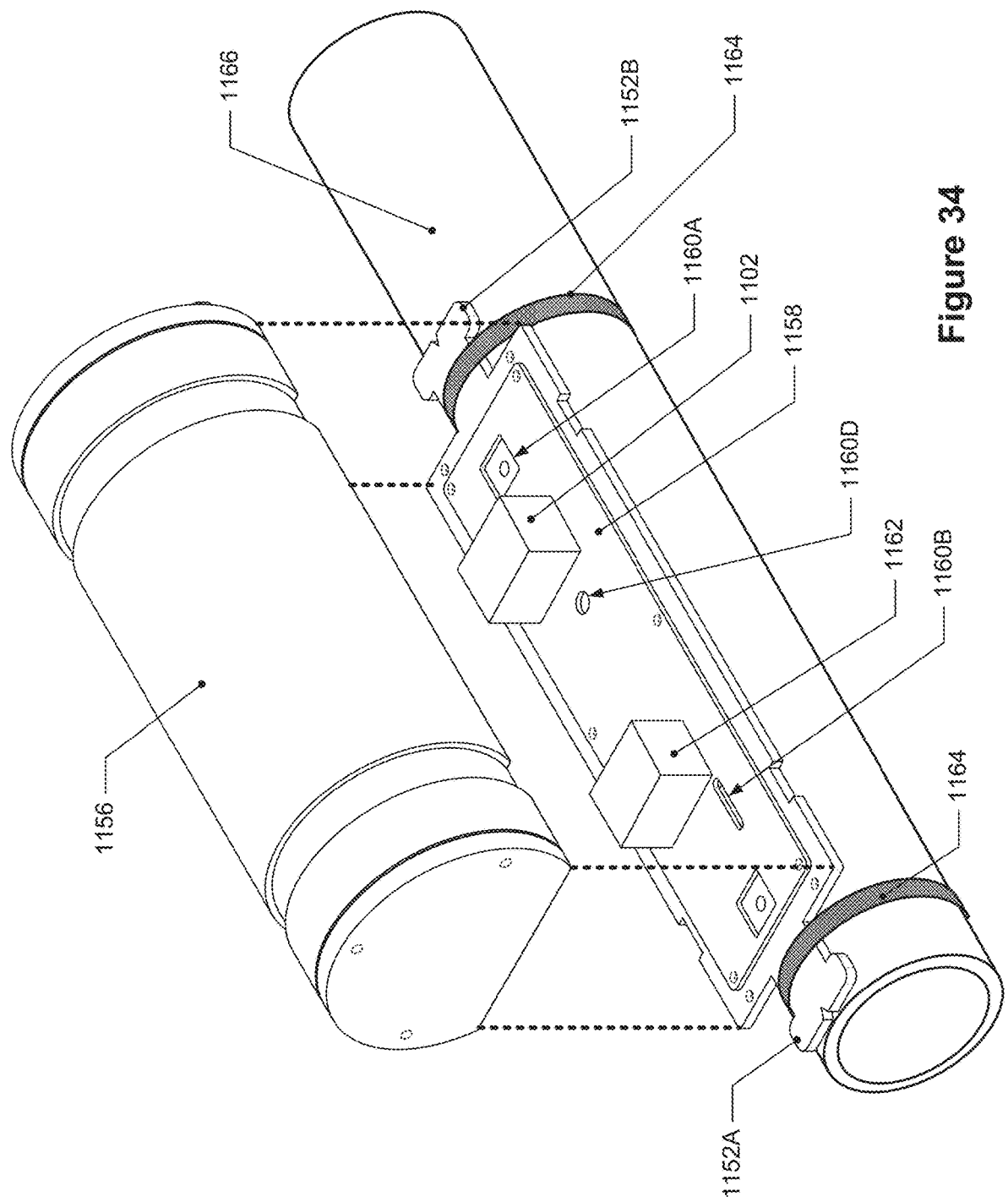
FIG. 34 depicts a partially exploded view of an example positioning of the second example pipe condition sensor to a pipe.

FIG. 34 depicts a partially exploded view of an example positioning of the second example pipe condition sensor to a pipe. Here, the detection device 1100 includes a cover 1156 that is separated from plate 1158 (which includes the face 1118); the plate 1158 includes ports 1160A through 1160E, or holes, through which sensors and wires for sensors may run between the processing module, represented as box 1162, and the various sensors. For instance, thermal sensors 1135a and 1125b may extend through, or have electrical connections that extend through, ports 1160B and 1160E, the hoop stress sensor 1120 may have electrical connections that extend through port 1160C, the microphone 1106 may have electrical connections that extend through port 1160D, and the solenoid 1102 may have electrical connections that extend through port 1160A. The plate 1158, in some embodiments, may also include multiple other plates. The plate 1158 also includes tabs 1152A and 1152B; fasteners 1164, such as zip ties or straps for example, may be wrapped around these tabs 1152A and 1152B and the pipe 1166, as shown, in order to secure the plate 1158 to the pipe 1166. Positioning and securing the plate to the pipe may therefore position the sensors onto and against the pipe thus allowing them to sense conditions of and within the pipe; doing so while the cover 1156 is removed allows for access to the sensors, their electrical connections, and the processing module which may be advantageous during installation and maintenance because, for example, the internal elements of the pipe condition sensor are accessible for connecting elements together, performing calibration steps, checking elements of the unit, and replacing parts, such as a battery. Afterwards, the cover 1156 may be attached to the plate 1158.

Although the detection device 1100 includes both tabs and grooves, some implementations of the pipe condition sensor may only have one of these features, such as only the tabs 1152A and 1152B. Referring back to FIG. 12, the detection device 1100 may only be connected to the pipe 1166 using the tabs 1152A and 1152B.

C. Examples of Adjustable Attachment Mechanisms

The housings of the detection devices may be positioned onto fluid conduits, e.g., pipes, so that the sensors are near, indirectly, or directly in contact with the pipe. In some embodiments, this positioning of some of the sensors enables these sensors to detect various conditions, which in turn allows the housing and flow detection module to perform the fluid flow and pipe conditions detections and determinations described herein.

Examples of a direct connection include some acoustic sensors that may be adhered directly to a fluid conduit, such as the pipe; the housing may be positioned around such sensors. An example of an indirect connection is an accelerometer (or other sensor) that may be positioned within the housing such that once the housing is positioned directly on the pipe the accelerometer (or other sensor) is near the pipe and is indirectly connected to the pipe through the direct connection of the housing with the pipe.

Some of the housings and flow detection modules may therefore have positioning features that are configured to allow the housings and flow detection modules to be positioned on and connected to the pipe. In some embodiments, the housings and flow detection modules may have an adjustable positioning mechanism that is configured to be positioned on and connected to a pipe. The adjustability of this mechanism enables it to be moved and repositioned so that it can be placed on and connected to pipes of different sizes and/or cross-sectional shapes (e.g., circular, rectangular, obround, oval, elliptical, etc.). The adjustable positioning mechanism may have one or more contact portions that are configured to contact the pipe, and one or more body portions that connect at least one of the contact portions with the housings and flow detection modules. The one or more body portions, and thus the one or more contact portions, are configured to be movable with respect to the housings and flow detection modules. In some instances, the housings and flow detection modules may not contact the pipe while one of the contact portions directly contacts the pipe. Once the contact portion is secured to the pipe, the body portion and the housing, are therefore also secured to the pipe.

Figure 35:
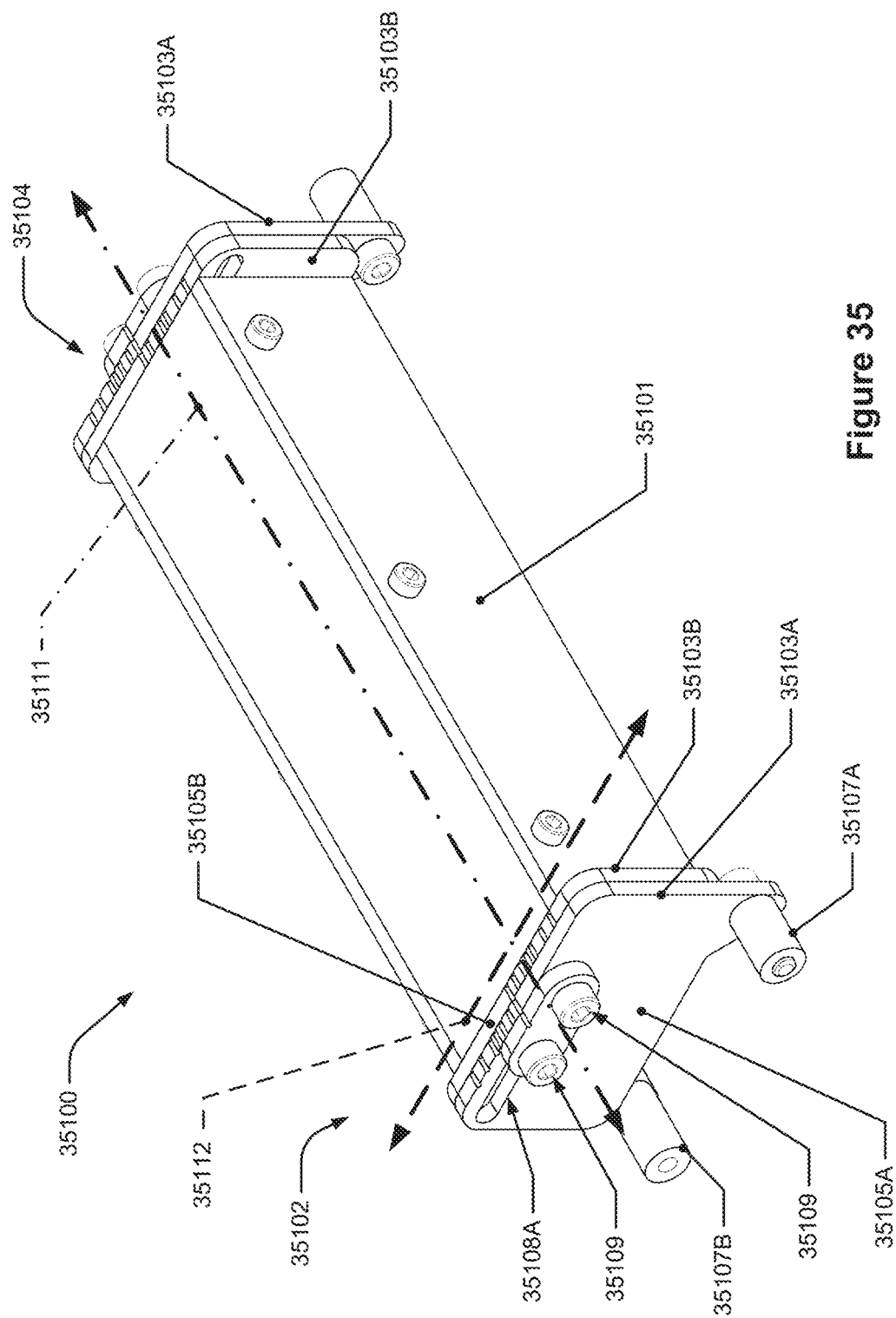
FIG. 35 depicts an example housing with an adjustable positioning mechanism having two brackets.

In some embodiments, the adjustable positioning mechanism may have two or more adjustable brackets, with each bracket including one contact portion and one body portion that is adjustably connected to the housing (or flow detection module). FIG. 35 depicts an example housing with an adjustable positioning mechanism having two brackets. This housing 35100 is the same as depicted in FIGS. 14A and 14B, and has a body 35101 and two brackets at each end (first 35102 and second 35104) of the body 35101; these brackets are part of the adjustable positioning mechanism. At the first end 35102, each bracket 3503A and 3503B has a bracket body portion 35105A and 35105B, respectively and a contact portion 35107A and 35107B, respectively. The contact portions 35107A and 35107B are cylinders that can be positioned onto a fluid conduit, such as a pipe. Each bracket body portion 35105A and 35105B also includes a slot 35108A and 35108B through which a screw 35109 (or bolt, pin, etc.) passes; the screws 35109 connect with the body 35101 and can secure the bracket body portions 35105A and 35105B directly or indirectly to the body 35101. Bracket body portion 35105B is connected directly to the body 35101 while bracket body portion 35105A is directly connected to bracket body portion 35105B and therefore indirectly connected to the body 35101; these two bracket body portions are connected by the screws 35109 to the body 35101.

The slots 35108A and 35108B allow the bracket body portions 35105A and 35105B to move with respect to the housing 35101. As illustrated in FIG. 35 with the double-sided dashed arrow 35112, the bracket body portions 35105A and 35105B are moveable in a direction perpendicular to a longitudinal axis 35111 of the body 35101. In some embodiments, the body 35101, and thus the housing, may be positioned such that the longitudinal axis 35111 is parallel to a center axis of the pipe.

Figure 36:
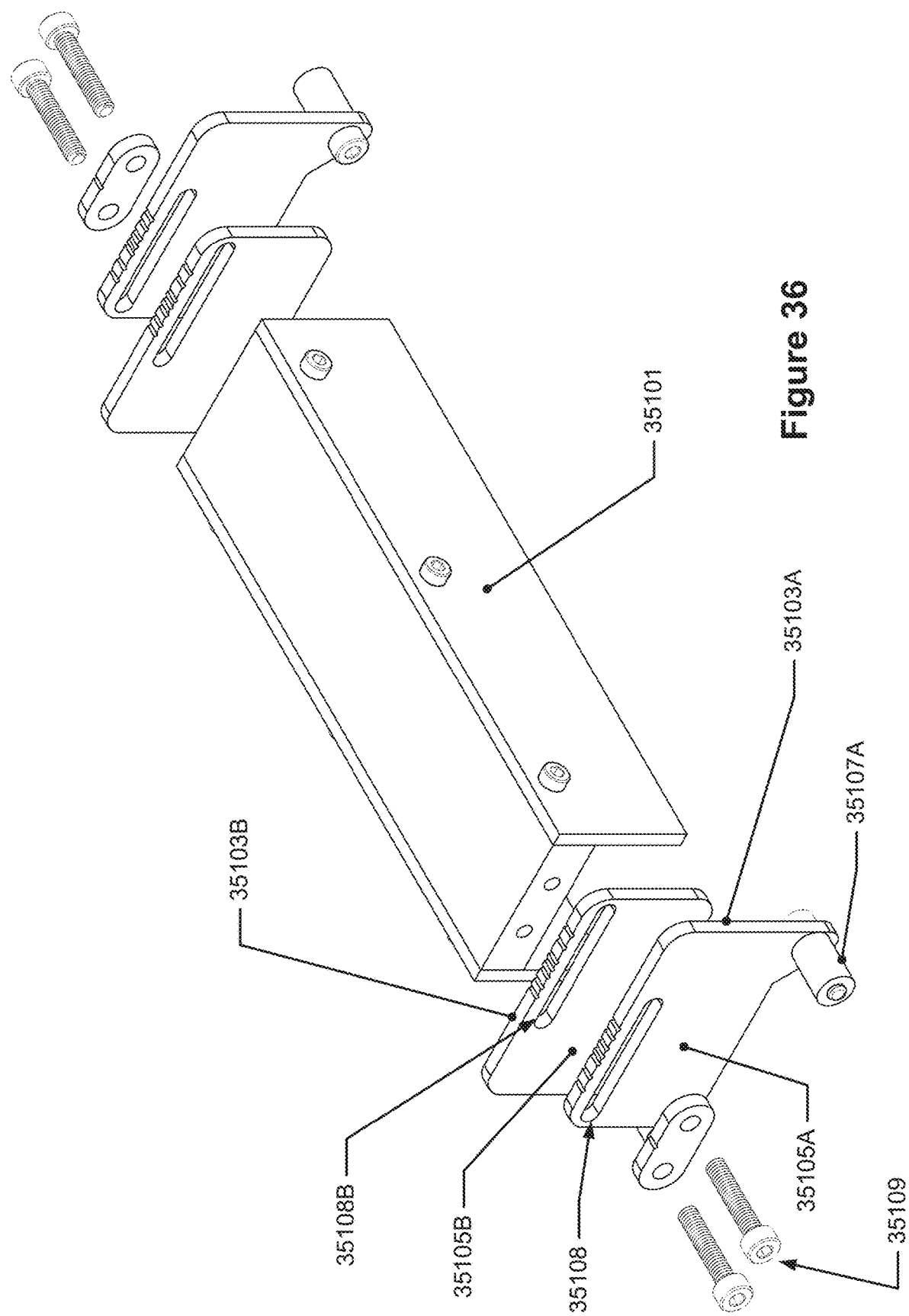
FIG. 36 depicts an exploded view of the housing of FIG. 35.

FIG. 36 depicts an exploded view of the housing of FIG. 35. The slots 35108A and 35108B can be more clearly seen here, along with the screws 35109.

Figure 37:
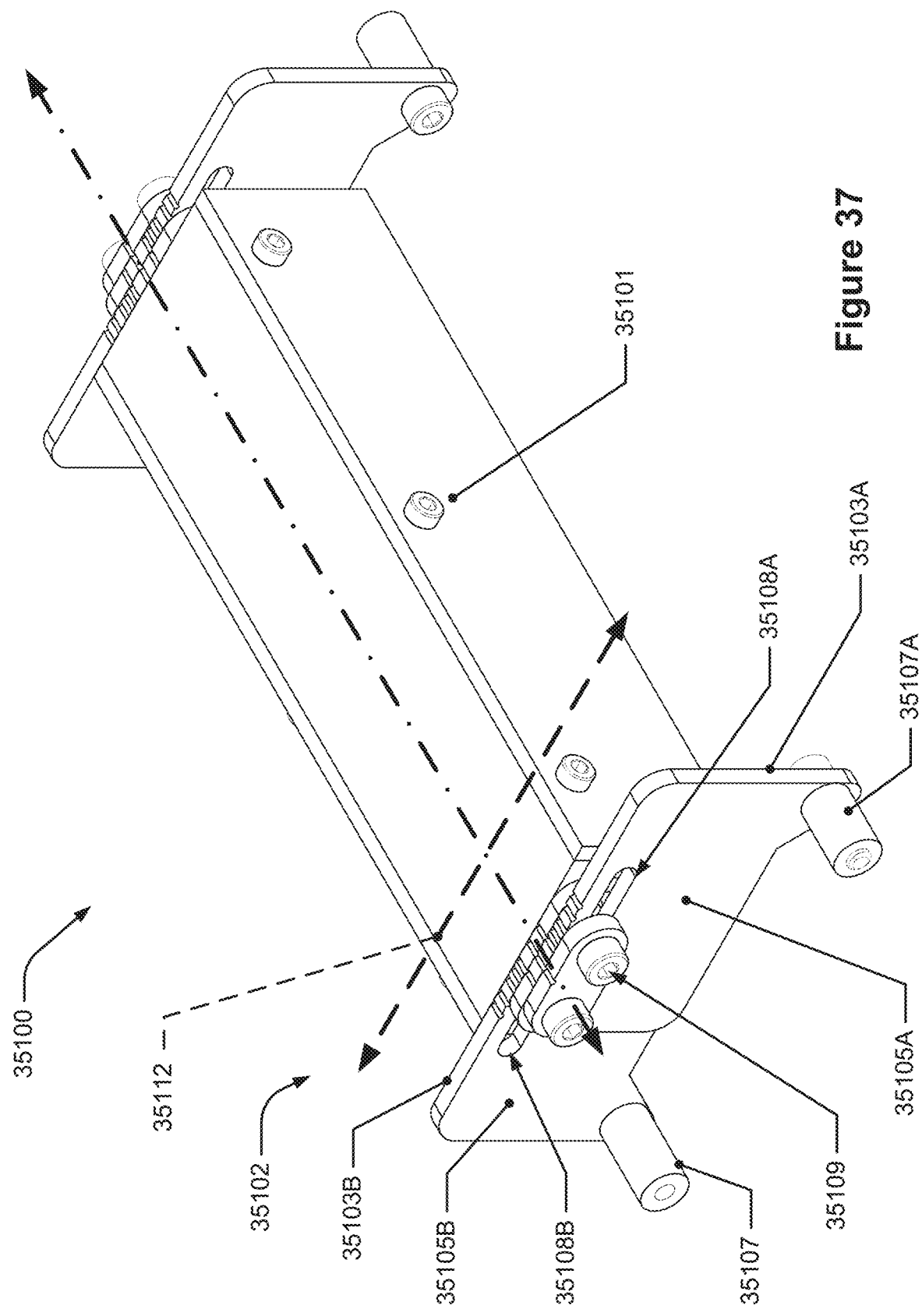
FIG. 37 depicts the housing of FIG. 35 in a second configuration.

FIG. 37 depicts the housing of FIG. 35 in a second configuration; here, the bracket body portions of the adjustable positioning mechanism are moved in the direction perpendicular to the longitudinal axis 35111 and of the center axis of the pipe. As stated above, this adjustability and movability of the positioning mechanism allows the housing to be positioned on pipes or pipes of different sizes and shapes.

Figure 38B:
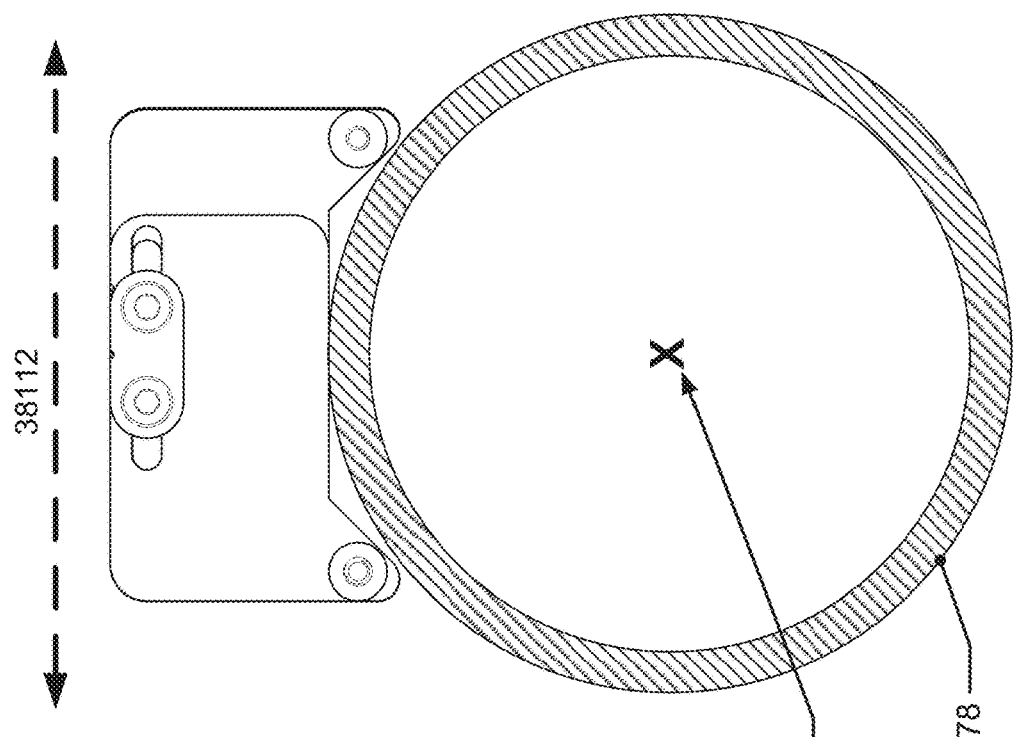
FIGS. 38A and 38B depict front views of the housing of FIG. 35 positioned on different sized pipes.
Figure 38A:
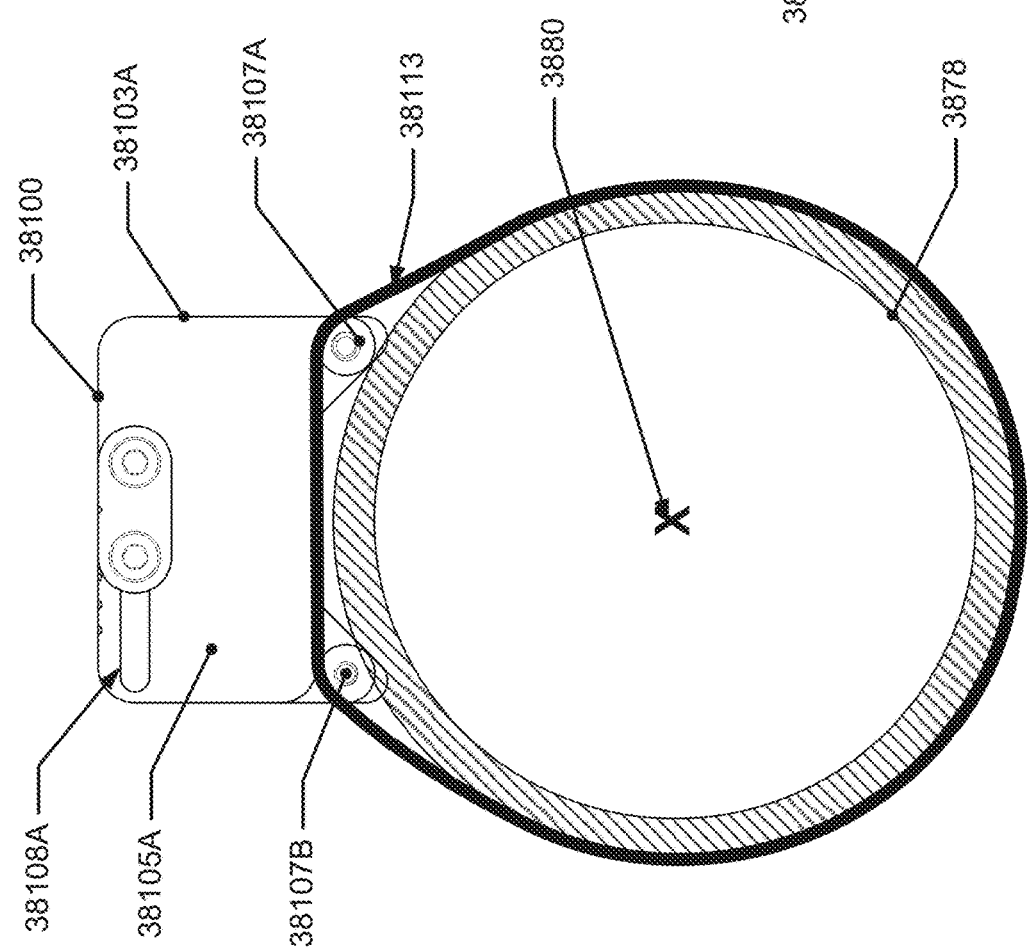
Figure 39A:
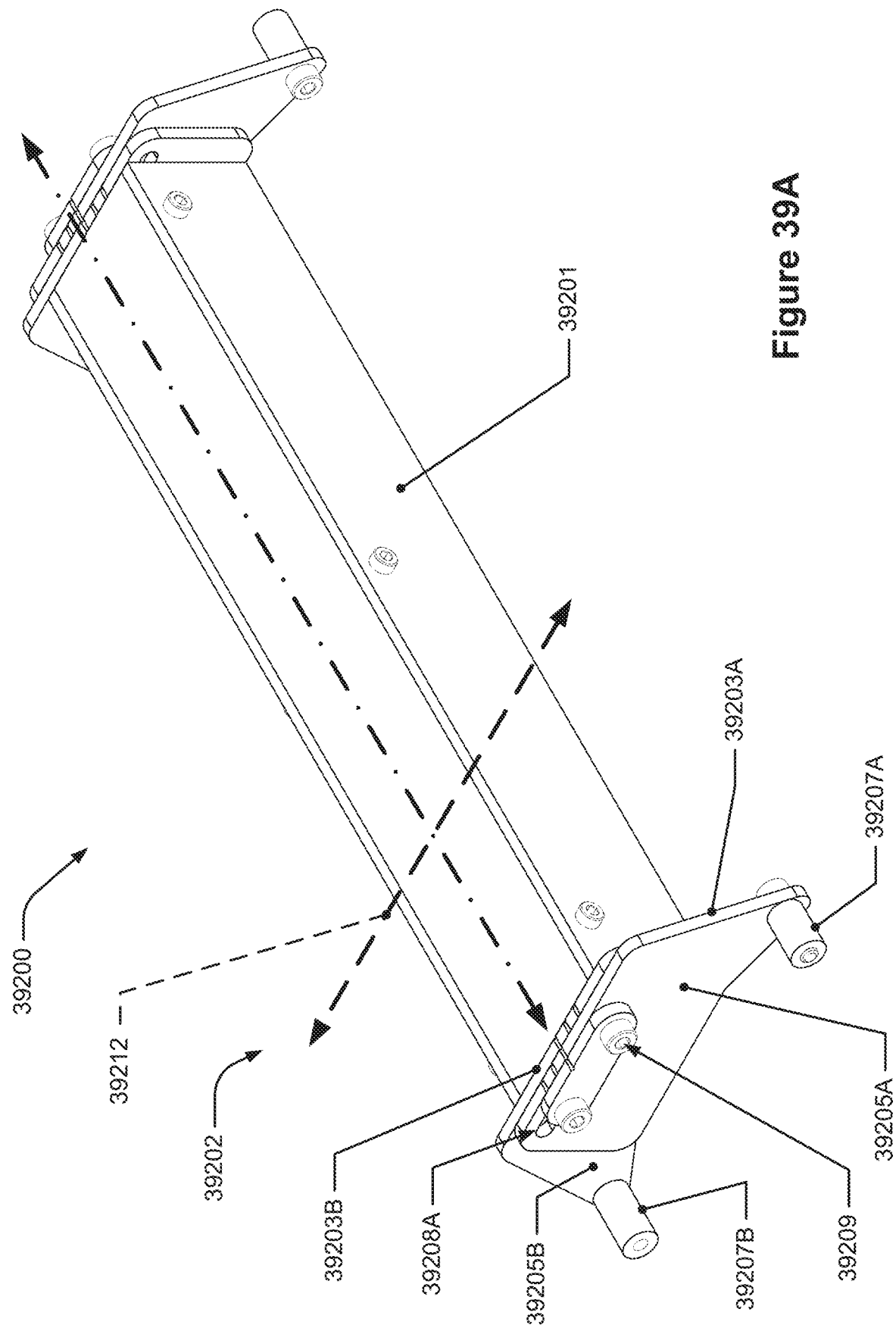
Figure 39D:
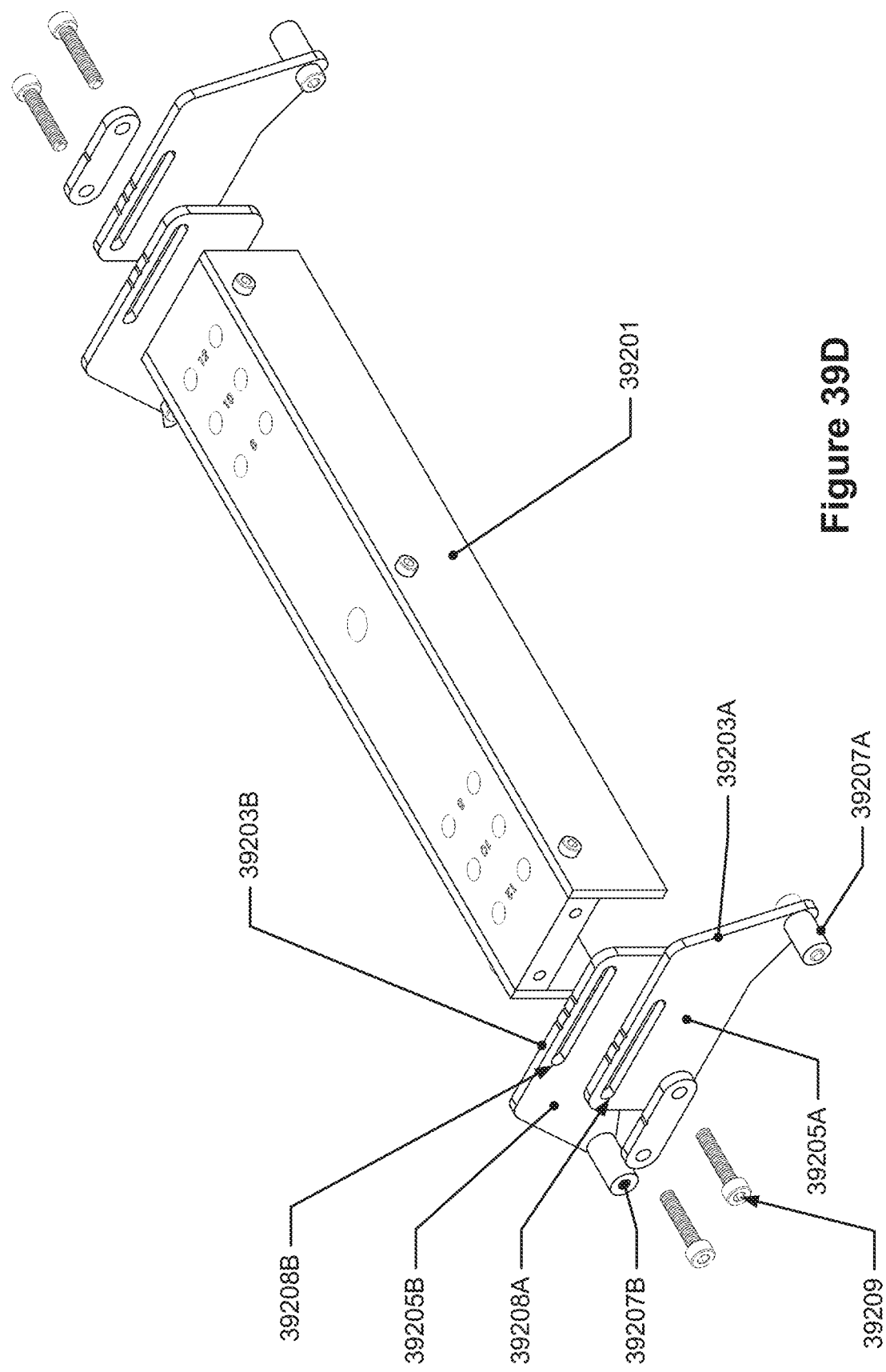

The adjustability of the adjustable positioning mechanism is illustrated in FIGS. 38A and 38B which depict front views of the housing of FIG. 35 positioned on different sized pipes. As can be seen in FIG. 38A, the adjustable positioning mechanism is in a position to allow just the contact potions to contact the pipe 3878, while in FIG. 38B, the adjustable positioning mechanism has been adjusted, e.g., moved in the direction of arrow 3812 in a direction perpendicular to the center axis of the pipe (marked with an "X" and 3880), so that the housing and the contact portions are in contact with the same pipe 3878.

FIGS. 39A through 39D depict another example housing which also includes an adjustable positioning mechanism similar to that shown in FIGS. 35 through 38B; this housing is the same as in FIGS. 15A and 15B. This housing 39200 includes similar some similarly labeled features as in FIGS. 35 through 38B, including the bracket body portions 39205 which are also movably connected to the body 39201 like described above using slots and screws as seen in these Figures.

The contact portions may provide an attachment surface for an attachment mechanism to contact the contact portions in order to connect the contact portion to the pipe (e.g., pipe). These contact portions may be connected to the pipe in various ways. In some embodiments, this may include adhering the contact portions to the pipe using an adhesive material or a weld. In some other embodiments, the attachment mechanism may be configured to enable the housing to be removably attached without damaging the pipe. This may include using a strap, band, pipe band, or the like that is positioned around one or more of the contact portions and the pipe; this may also include a magnetic attachment mechanism. Referring back to FIG. 15A, an example pipe band is depicted extending around both contact portions and the pipe which causes the housing to be connected to the pipe. An example connection mechanism, e.g. a band 38113 is depicted in FIG. 38A and extends around the contact portions and the pipe in order to secure the housing to the pipe.

D. Examples of Connection Mechanisms to Flanges, Flanged Joints, or Protrusions

In another example, the detection device may be configured to connect with a flange or other protrusion of a fluid conduit. For example, pipes and other piping elements (e.g., valves, pumps, joints, taps, hydrants, pipes, etc.) may be connected to each other using flanges.

Generally speaking, a pipe flange is a disc, collar, or ring that is attached to, or a part of, a pipe in order to provide increased support for strength, block off a pipeline, and attach to other piping items. Some flanges are welded or screwed to a pipe end, while other flanges are a part of the pipe, such as with a fire hydrant, for example. Some flanges include a welding neck flange, a slip on flange, a socket weld flange, a lap joint flange, a threaded flange, and a blind flange.

Figure 40:
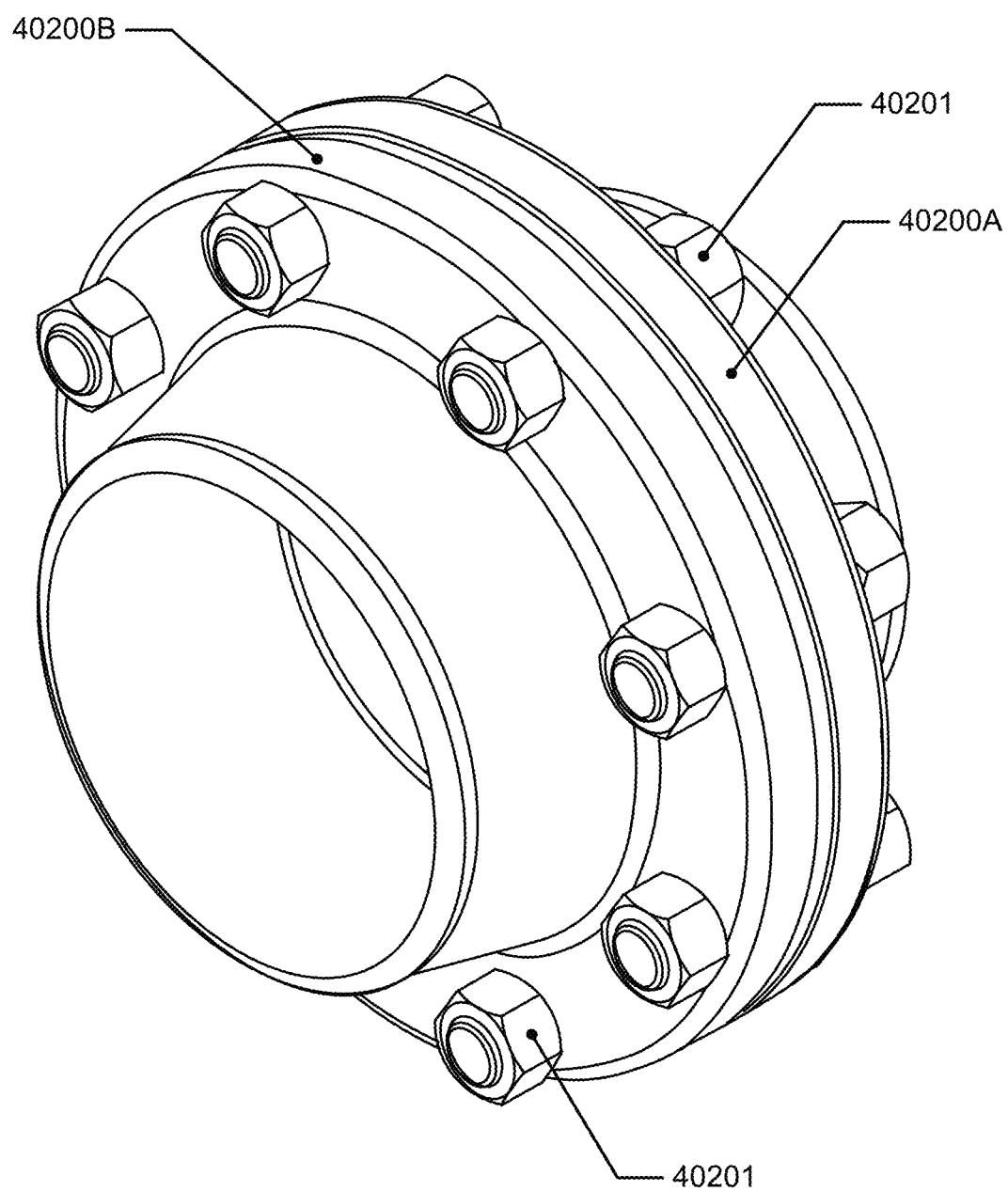
FIG. 40 depicts an example of a bolted flange joint.

In order to join two pipes together, the flanges of these pipes are connected together with a gasket between them to provide a seal. This may be considered a flanged joint. The connection of a flanged joint may be made using welds or bolts, for instance. An example of a bolted flange joint is seen in FIG. 40 in which the two flanges 40200A and 40200B are connected and joined with numerous bolts 40201.

In some embodiments, the detection device is configured to connect with and attach to a flanged joint between two fluid conduits, such as pipes. The detection device may include a second adjustable connection mechanism that is configured to connect to the flanged joint in various ways.

In some embodiments, the second adjustable connection mechanism includes a first structure that extends around two or more surfaces of the flanged joints. The first structure may have a curved or linear shape, including in a "D", "C", "L", or "U" shape, for instance. The second adjustable connection mechanism may also include more than one first structure in order to provide at least two connection points to the flanged joint. In some embodiments, the second adjustable connection mechanism may include features configured to connect with one or more bolts or connection means of the flanged joint; this may include, for instance, a plate with a hole that can be positioned around a bolt of the flanged joint.

The second adjustable connection mechanism is also adjustable so that it can connect to flanged joints of different shapes and sizes. This adjustability allows the housing of the detection device to be positioned at different locations on the pipe so that the housing is not positioned on undesirable locations, such as locations on the pipe that are damaged or have obstructions on them. This adjustability may be in a direction parallel and/or perpendicular to the center axis of the pipe.

In some embodiments, the housing itself may have features that are configured to position it in a desirable position against the fluid conduit. As described above, it may be advantageous and desirable to position a baseplate (i.e. back plate, face plate) in direct contact with the fluid conduit. The housing may have positioning features that are configured to be positioned against the pipe in order to place the baseplate at a desired position. These positioning features may be a curved surface that has a radius greater than or substantially equal to (within +/−10%), the radius of the pipe on which it is positioned (see positioning feature 3331 in FIG. 33).

Figure 41:
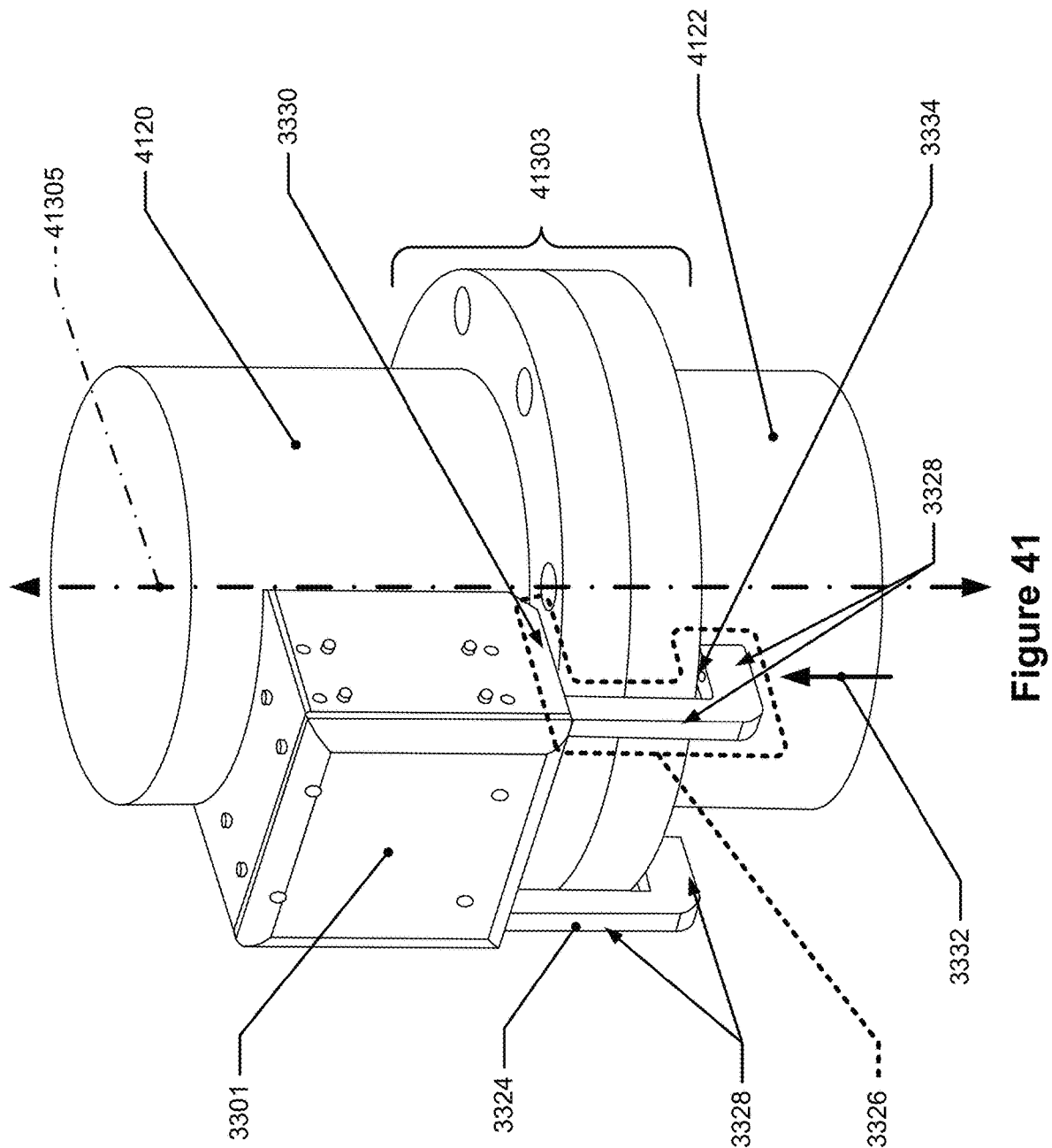
FIG. 41 depicts the example detection device of FIG. 33 connected to a flanged joint.

FIG. 41 depicts the example detection device of FIG. 33 connected to a flanged joint. The flanged joint 41303 is made from a first pipe 4120 and a second pipe 4122. Although these pipes are illustrated as straight pipes, they may be any fluid conduits, such as a fire hydrant and a pipe.

The housing 3301 includes a second adjustable connection mechanism that includes a first structure 3324 and a second structure 3326 (encompassed by a dotted shape) that are identical to each other (in some embodiments). These structures include a section 3328 that extends around two surfaces of the flanged joint using two linear portions. The second adjustable connection mechanism also includes a third structure that extends along another surface of the flanged joint; this third structure is formed by a part of the housing 3301 and is identified as section 3330. The first structure and third structure may be considered to make a "C" or a "U" shape.

Figure 42:
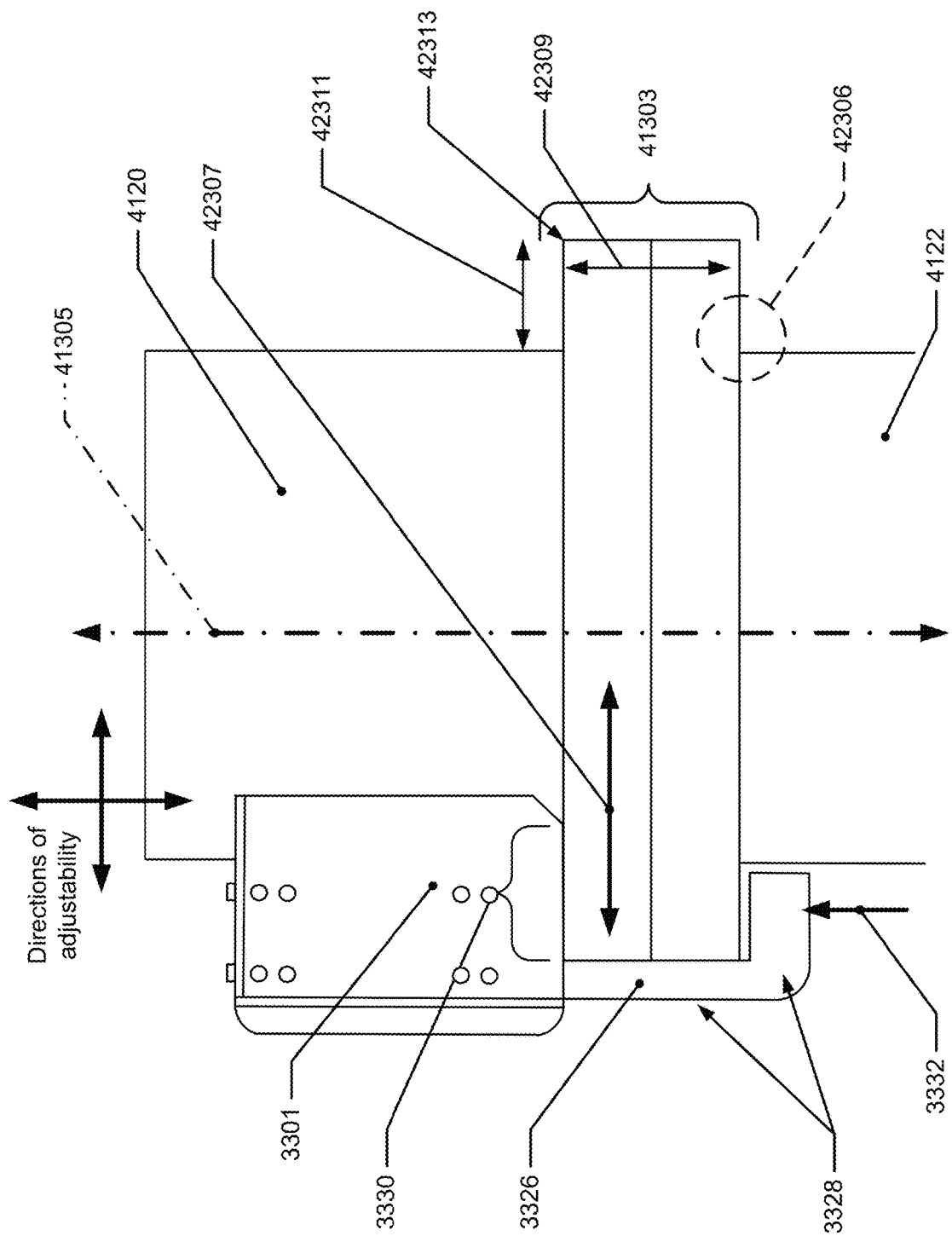
FIG. 42 depicts a side view of FIG. 41.

In some embodiments, the second adjustable connection mechanism uses an additional connection means, such as a bolt or screw, to connect with the flanged joint. This additional connection means may pass through the second adjustable connection mechanism, contact the flanged joint, and cause the flanged joint to be clamped between the additional connection means and a portion of the second adjustable connection mechanism. For example, in FIG. 41 the additional connection means may be a screw that passes through a threaded hole 3334 in the direction of arrow 3332 which causes the third section to contact the flanged joint, and causes the flanged joint 41303 to be clamped by and in-between the third section and the screw. In some instances, the housing and the first and second structures may be in a fixed position relative to each other and the adjustability is provided by the screw being turned towards or away from the third structure. This is also illustrated in FIG. 42 which is a side view of FIG. 41.

In some embodiments, two or more surfaces of the second adjustable connection mechanism are in direct contact with the flanged joint. In some such embodiments, the second adjustable connection mechanism is configured to be moveable so that these two or more surfaces can contact the flanged joint. For example, this configuration includes a sliding or ratcheting system that allows the first and second structures to move towards the third structure so that the flanged joint is clamped by these structures.

In some embodiments, the flanged joint to which this detection device is configured to connect with may be that of a fire hydrant. Many fire hydrants are connected to a water pipe at a flanged joint. In some instances, this flanged joint may be above ground, while in some other embodiments this may be underground or within a sub-structure.

In some instances, when connecting to a fire hydrant, the hydrant may have raised characters, damage, or some obstruction that may prevent the baseplate from having the desirable contact with the hydrant; this desired contact may be a flush contact with the hydrant barrel. However, if the detection device is positioned on raised characters, a label, damage or corrosion, or some obstruction on the hydrant barrel, then the baseplate may not have direct, flush contact with the hydrant barrel. In some such instances, the adjustability of the adjustable positioning mechanism allows the housing of the detection device to be moved along the center axis of the hydrant barrel, e.g., up or down relative to the ground, so that the baseplate is not positioned on the obstruction and the baseplate can have desirable contact with the hydrant barrel.

Referring back to FIG. 33, the housing 3301 includes a baseplate 3336 (i.e., faceplate or back plate) that is configured to contact the fluid conduit. This baseplate may be configured like any of the other baseplates described herein. For instance, it may include orifices like described herein in which sensors may be positioned, through which sensors may pass, or through which electrical connections for sensors may pass. For example, this detection device may include any of the sensors described above, such as one or more acoustic sensors (e.g., transducers or microphones) and one or more acoustic emitters, like a solenoid or speaker. This baseplate 3336 may include holes like described above, such as holes 3335 in which acoustic sensors 3338 may be positioned. The detection device may also have a hoop-stress sensor 3340 as described herein. This hoop-stress sensor may be positioned directly on the hydrant, similar to described above, and it may also be positioned inside the detection device housing on the baseplate.

As stated herein, it may be desirable to position the baseplate in direct contact with the hydrant or pipe. In some embodiments, this positioning may be enabled by a curved positioning feature 3331 that allows the housing to be positioned against the pipe, or hydrant, so that the base plate is in direct contact with the pipe or hydrant.

In some embodiments, the detection device may include a magnet configured to magnetically engage with the fluid conduit. This magnet may be placed inside the housing, internally to the housing on the baseplate 3336, or on the baseplate 3336, for example. This magnet may assist in causing the baseplate to physically contact the fluid conduit.

The second adjustable connection mechanism enables the detection device to connect to a flanged joint or a pipe protrusion of variously shaped and sized pipes. For example, many fire hydrants around the United States have flanged joints above ground, but these flanged joints and hydrant barrels have different geometries, such as different thicknesses in the axial direction of the hydrant and in the radial direction, as well as different barrel diameters. The flanged joint thickness may be the overall thickness of the joint itself (e.g., the thicknesses of the flanges plus seals) in the axial direction; the radial flange thickness may be the distance, in the radial direction perpendicular to center axis of the pipe, from the pipe barrel to the flange outer diameter. In some instances, the intersection between the pipe and the flange may be curved. These dimensions are labeled in FIG. 42. Here, the pipe-flange intersection 42306 is at an approximate 90 degree angle or planar surfaces, but in some other embodiments, this intersection may be curved (e.g., as seen in FIG. 40 above). The second adjustable connection mechanism described herein allows for adjustability in the axial direction (i.e., parallel to the pipe's center axis 41305) and in the radial direction 42307 (i.e., perpendicular to the pipe's center axis 41305). This multi-directional adjustability allows the detection device to be positioned on flanged joints, and their corresponding pipes, of different geometries, such as having different axial flange thicknesses 42309, radial thicknesses 42311, flange outer diameters 42313, pipe diameters, and intersections of flanges 42306 to the pipes.

In some embodiments, the detection device may be connected to a fluid conduit with a securement mechanism which may prevent the detection device from being stolen or forcibly removed from conduit. This securement mechanism may be a chain, lanyard, physical bracket, or steel cable. In some embodiments in which the detection device is connected to a fire hydrant, the securement mechanism may be connected to an existing hydrant bolt.

V. Condition Detection Using Multiple Sensors

A. Introduction

In addition to those conditions described herein, one or more sensors described herein may be used alone or in combination with other sensors to identify water in a pipe or a part of plumbing system that is susceptible hazardous legionella contamination. Sensors that may be employed in a legionella risk detection system include pipe or water temperature sensors, water flow sensors, acoustic sensors, water pressure sensors, and/or pipe vibration sensors.

B. Water Conditions that May Produce Legionellosis

Legionnaires' disease (legionellosis) is a severe lung infection caused by legionella bacteria that grows in water and can spread when droplets get into the air and people breathe them in. The bacteria can also cause a less serious illness called Pontiac fever. There are certain conditions under which legionella thrives. These conditions may include (a) depletion of chlorine or other antibacterial agent added to water, and (b) a temperature range in which Legionella thrives.

Chlorine added to a water supply gradually loses its effectiveness, particularly as the chlorine escapes from the water to which it was added. This means that bacteria have an opportunity to reestablish and flourish. Thus, in a public water system that introduces chlorine at its source, water that stands in a pipe or other part of a water system for a long period of time gradually loses its disinfecting properties, and the water becomes more susceptible to bacterial contamination and growth. Non-chlorine disinfectants such as ozone, chlorine dioxide, chloroamine, other halogens (notably bromine and iodine), and radiation, including UV radiation and ionizing radiation, may also suffer from the same problem.

The rate at which chlorine or other disinfectant leaves water is temperature dependent. At higher temperatures, chlorine leaves faster than at lower temperatures. Thus, pipe conditions that promote growth of legionella include high temperature and or long periods of being present in the system. Particularly problematic, are conditions under which the water is stagnant in a pipe for an extended period of time. A related problem results when the water flows but is continually recycled. In other words, in the absence of a fresh supply of chlorinated water legionella may still to flourish even if the water is flowing. This is particularly the case in fountains and cooling towers where water is flowing but loses chlorination.

Independent of disinfectant effectiveness, legionella growth is temperature dependent. A temperature range of between about 25° C. and 42° C. is known to promote legionella growth. Thus, certain embodiments of a legionella risk system flag dangerous situations where water is present in a pipe or region of a pipe network in this temperature range, particularly for an extended period of time.

Legionella is widespread and was thought to be somewhat benign until the Philadelphia outbreak in 1976. Its presence in surface water is common. It is only dangerous when inhaled. Any process that mixes it with air (shower heads, fountains, cooling towers, misters, etc.) can create a hazard. It tends to affect the young and those over 50. The US Center for Disease Control (CDC) estimates there are between 8000 and 18000 cases of legionellosis per year and more than 10% are fatal. Most cases are thought to originate in building water systems.

Even if legionella is present and growing or thriving in a pipe or pipe network, the legionella do not necessarily create a hazardous situation. Under some conditions, legionella can exist and even thrive but not be released in a form where they are distributed throughout a pipe system and potentially hazardous to humans. For example, legionella may be provided in a scum, sludge, or bacterial mat supporting the growth of legionella bacteria, and yet remain localized in a small area; i.e., the legionella bacteria do not distribute throughout a pipe system or move to a location where they can be present in an aerosol or other hazardous state. When a scum or sludge containing legionella is dislodged such as by a way of pipe vibration or a water pressure spike, it may suddenly convert from an innocuous state to a hazardous state.

Legionella supporting conditions are described in various sources such as in standards and guidelines promulgated by the American National Standards Institute (ANSI) and American Society of Heating, Refrigeration, and Air-Conditioning Engineers (ASHRAE). Such standards and guidelines are described in ASHRAE/ANSI Standard188-2015, "Legionellosis: Risk Management for Building Water Systems," and in ASHRAE Guideline 12-2000, "Minimizing the Risk of Legionellosis Associated with Building Water Systems," both of which are incorporated herein by reference in their entireties. These standards and guidelines contain further description of the conditions that support unhealthy legionella conditions and may be consulted for additional details of water and pipe conditions that may be sensed and interpreted as described herein for identifying potentially unhealthy legionella conditions.

C. Components of a Legionellosis Risk Condition System

In certain embodiments, the water system includes sensors at one or more locations and those sensors and a supporting data communications and computational infrastructure process sensor data to assess a risk of legionellosis. The collective legionellosis risk condition system provides a local or system-wide monitoring to identify conditions favorable for legionella growth.

The legionellosis risk condition system may also generate alerts for appropriate hazard management systems or administrators such as building managers, municipal water supply managers, and the like. Such alerts may take the form of messages to software that can display or announce warnings to occupants or potential users of water that might be contaminated. Such alerts can also be provided to software used by water system administrators (e.g., building, property, and facilities managers). The alerts may be provided by the software as textual content, graphical displays of warnings (e.g., color coded risk assessment levels, etc.). In some embodiments, the legionellosis risk condition system provides information or instructions communicated to systems that automatically shut off water dispensers or other system components that could introduce potentially hazardous water to locations where users might contract legionellosis; e.g., the system can prevent operation of a shower or faucet. Some embodiments focus on risk mitigation by preventing legionella-containing water from becoming airborne.

Examples of water system components that can be controlled to reduce the risk of legionellosis include the following: showerheads and sink faucets, cooling towers (structures that contain water and a fan as part of centralized air cooling systems for building or industrial processes), hot tubs that aren't drained after each use, decorative fountains and water features, hot water tanks and heaters, and large plumbing systems.

Examples of buildings and vessels that may benefit from a legionellosis risk condition system include hospitals, schools, cruise liners, hotels, retirement homes, residences, dormitories, government buildings, amusement parks, and emergency shelters.

Figure 43:
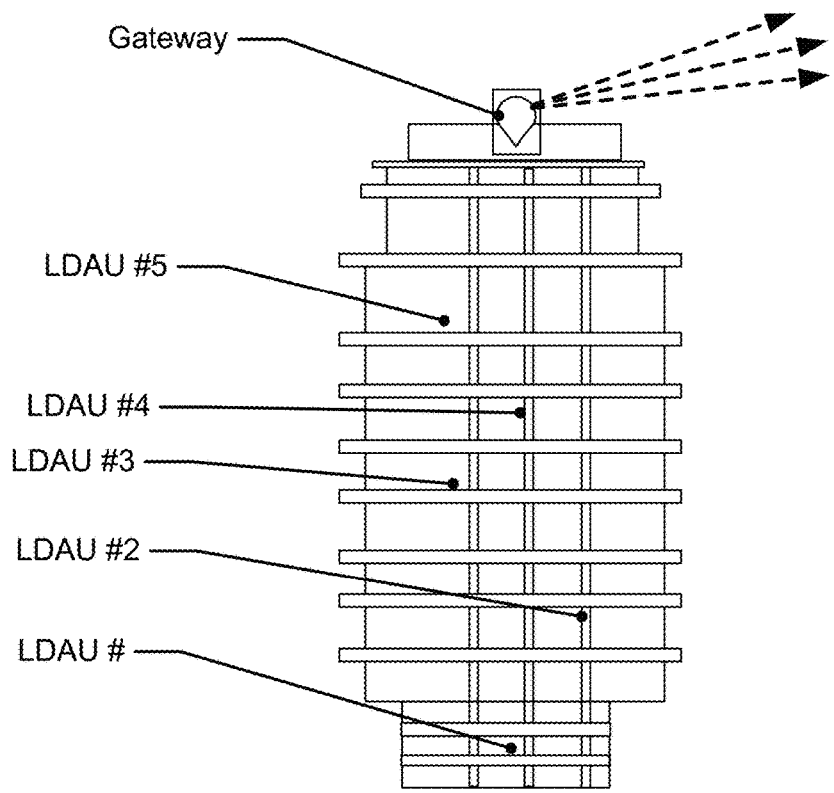
FIG. 43 depicts an example Plumbing/Architectural System for Legionellosis Risk Detection.

D. Example Figure of Plumbing/Architectural System for Legionellosis Risk Detection In some embodiments, a Legionellosis Risk Detection system may include multiple detection units, which may be referred to herein as a "Legionella Data Acquisition Unit" or "LDAU", at various points of a water system. Example features and components of a Legionellosis Risk Condition Detection System for a building may include LoRaWAN, LTE CAT M1, or other communications protocol acceptable for use in buildings, ships, etc., a backbone for all sensors, effective unit cost and data rates, and the ability to provide alert notifications. Example points or positions for legionella monitoring may include multiple floors, end points on system, hot side (near water heater), and sensors strategically located to monitor conditions associated with legionella growth. FIG. 43 depicts an example Plumbing/Architectural System for Legionellosis Risk Detection. As can be seen, multiple LDAUs are positioned on multiple floors of the building at various end points. The LDAUs are communicatively connected (wired or wirelessly) to a backbone which is communicatively connected to a gateway which is configured to communicate with other communications points (e.g., a cell tower, fiber optic cable) and in turn communicate with a remote server (as indicated by the dashed lines).

Figure 44:
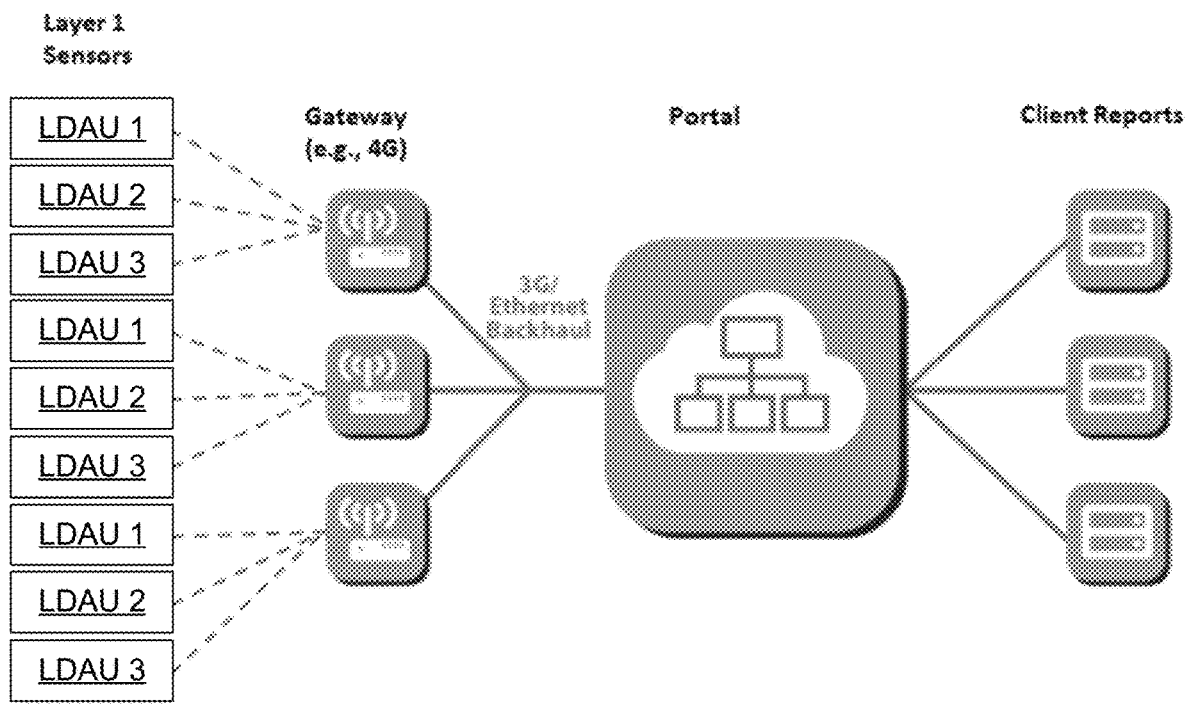
FIG. 44 depicts another Legionellosis Risk Condition Detection System.

FIG. 44 depicts another Legionellosis Risk Condition Detection System. Here, the system includes a first layer of multiple LDAUs, with three LDAUs each connected to a separate gateway (there are three gateways). These LDAUs are communicatively connected through a backbone (e.g., a wireless connection or a wired cable like a fiber optic cable) to a single gateway, or in some embodiments multiple gateways, which are in turn communicatively connected to a portal which may be a remote server like described above (e.g., contains one or more processors and memories for storing the data received by each of the LDAUs). The remote server is configured to transmit client reports and alerts based on the data generated by the LDAUs. As described, each of the LDAUs is positioned on and inline with pipes, or a combination thereof, each sensor transmits signals to a gateway, the gateway relays the data to the portal, the portal and associated logic assesses risk and provides alerts and reports. In some instances, the reports may be a traffic light alert-type system that may include, for instance, red, green, and yellow indications which mean, respectively, likely legionella active, no legionella, or investigate.

E. Legionellosis Condition Determination Examples

Various approaches may be employed to determine a potentially hazardous legionella conditions in a water system. Such approaches may employ software or other logic programmed or configured to receive data taken from one or more pipe and/or flow condition sensors as described herein and analyze such data to determine whether or to what level a risk of hazardous legionella condition exists in the water system. Such sensors may include any or more of water pressure sensors, water temperature sensors, water flow sensors, pipe condition sensors (detecting scum or other occlusion in a pipe), and pipe vibration sensors. The logic for interpreting data from such sensors may be located on a server or other computing system associated with the water system (located either at the water system or remote therefrom) or the logic may be located on a leased or shared computational system such as a cloud-based system available over the internet or other network.

Figure 45:
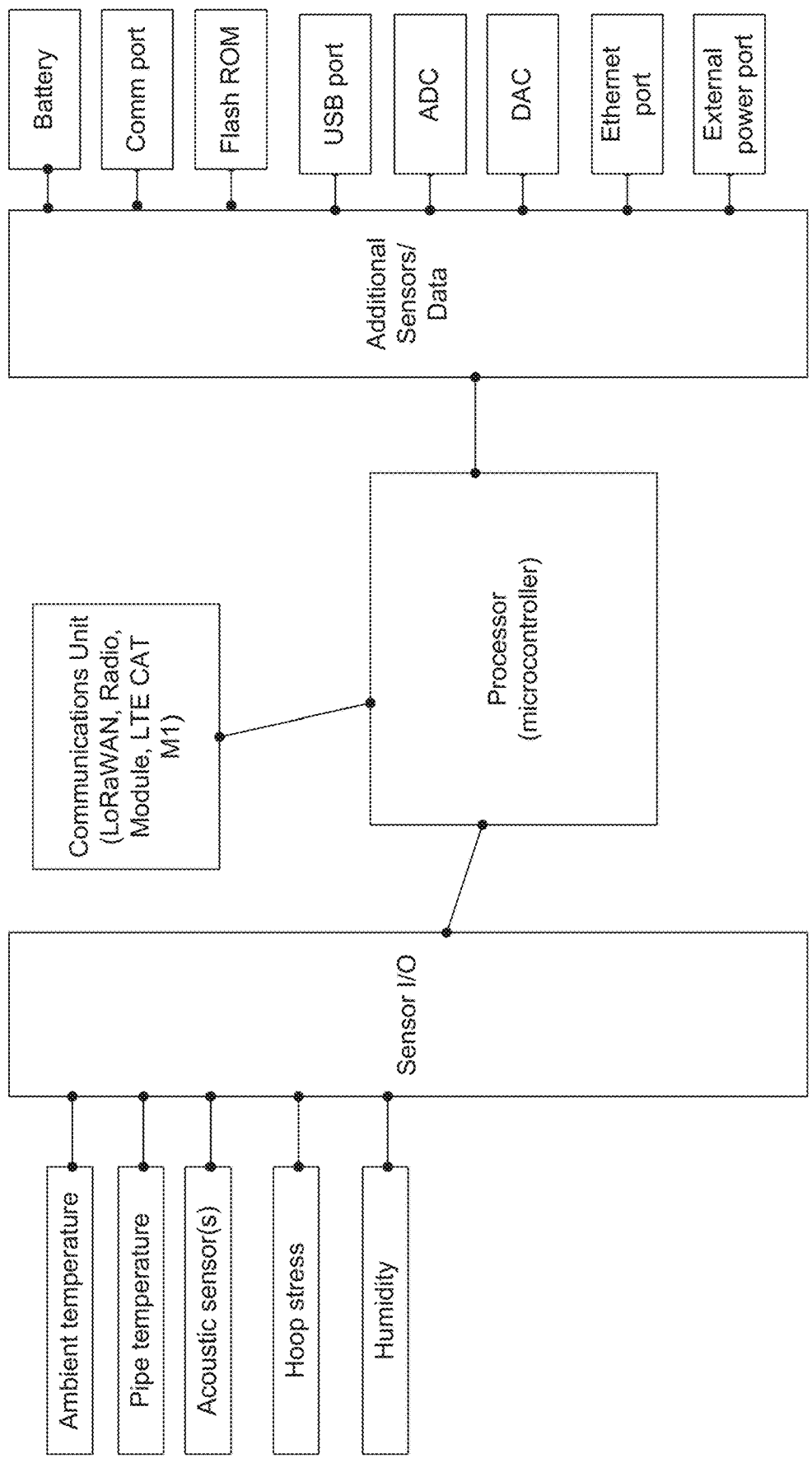
FIG. 45 depicts an example legionella detection device.

FIG. 45 depicts an example legionella detection device. This unit may be similar to those described hereinabove, such as in FIG. 31. Here, the legionella detection unit includes a "sensor I/O" like above and is connected to multiple sensors, such as ambient temperature sensor configured to detect the temperature of the environment where the detection device is positioned, a pipe temperature sensor configured to detect the temperature of the pipe on which the detection device is positioned, one or more acoustic sensors (e.g., a microphone) configured to detect the presence of flow, a shock sensor (e.g., an accelerometer or other motion sensor configured to detect motion of the pipe), a hoop stress sensor (e.g., strain gauge sensor), and a humidity sensor configured to detect the humidity of the environment where the detection device is positioned. These sensors generate data which is received by the microcontroller (e.g., processor 3132 of FIG. 31) which may be transmitted via a communications unit (e.g., unit 3146 of FIG. 31) which may include over LsRaWAN, radio, hardwired, or LTE CAT M1, for instance. The microcontroller, which may be the same as processor 3132 of FIG. 31, may also receive data from other aspects of the device such as, battery status, level, and health, communications status (e.g., whether connected, signal strength), flash memory status (Flash ROM), USB port status, status of the analog to digital converter (ADC), status of the digital to analog converter (DAC), ethernet port status, and external power status, etc.

An example of an approach to interpreting sensor data and providing a legionellosis risk assessment involves a level-based analysis. In one example, the levels include the following.

Level 1—water reaches temperature where legionella flourish. As example, this temperature range is between about 20 and 60° C., with about 25 to 43° C. being most likely to produce issues. In certain embodiments, the water temperature is determined using a thermal flow condition sensor such as described elsewhere herein. In other embodiments, a thermocouple, a thermometer, or other temperature measurement device is used. Of course, the temperature measuring device is typically located on a pipe or other part of the water system where legionella proliferation is a concern. However, in some embodiments, the temperature measuring device is located upstream or even downstream from the region of concern. In such cases, it may be necessary to account for a possible change in temperature between the location where temperature is measured and the location of concern.

Level 2—a volume of water holds at a temperature within this range for a period of time giving legionella an opportunity to proliferate. The level of concern is a function of both the length of time and the temperature. A relatively short time in the temperature range where legionella is most prolific (e.g. about 25 to 43° C.) is more concerning than a relatively short time outside this range (e.g., about 20 to 24° C. or about 44 to 60° C.). Recognizing that depletion of chlorine or other disinfectant may be a condition precedent for legionella to flourish, in certain embodiments, the minimum duration for flagging a concern may be set to at least a duration required for water to lose a significant fraction of its disinfecting power. In certain embodiments, a minimum duration for water to be present in pipes is about 24 hours.

Level 3—water is quiescent (or flowing at a very low rate) during a period of time at which the water is at a temperature susceptible to legionella proliferation. As mentioned, freshly flowing water may come from a source that provides chlorine or other disinfectant in the water supply. As such, any legionella in the vicinity might not have an opportunity to establish or grow in the water system. Further, flowing water can flush nascent legionella colonies out of the system. In view of these considerations, the legionellosis risk detection system may determine water flow conditions in the vicinity where levels 1 and 2 are met (i.e., portions of the water system where water is held at a susceptible temperature for defined period of time). If the system determines that the water has been quiescent or not replenished with freshly chlorinated water, it may further flag the pipe or portion of the water system for increased risk of legionellosis. Sensor that can be used to determine water flow conditions include a thermal flow condition sensor, a hoop stress sensor, and/or an acoustic pipe condition sensor, any of which may have structures and attributes as described elsewhere herein.

Level 4—a vibration on the pipe or pressure spike in the water is observed. Legionella can flourish without being releasing in a form that is potentially hazardous. For example, legionella can reside in a scum or deposit (e.g., a bacterial mat) that tightly adheres to the inner wall of a pipe or other component of a water system and hence the bacteria are not available to be dispensed via a shower, faucet, or other water dispensing fixture. However, when the otherwise adherent legionella colony is mechanically disturbed—such as by a pressure spike or pipe vibration—the bacteria may be released into the wider pipe system. In such cases, what had been a relatively safe condition suddenly becomes hazardous. Therefore, in certain embodiments, a legionellosis risk system determines when a pipe vibration, water pressure spike, or other legionella disturbing event occurs, and then raises the risk of legionellosis. Such event may be detected by an accelerometer or other vibration sensing device on a pipe in the vicinity of the legionellosis risk source or it may be detected by a pressure sensor such as a hoop stress sensor that can detect a pressure spike upstream, downstream, or at the location of interest.

In certain embodiments, a legionellosis danger alert system is employed that accounts for any one or more of the above criteria or levels. The alerts may be generated based on the presence of any of these and/or the severity of the conditions. The severity of the danger (e.g., level 1, level 2, etc.) may be specified using any of various algorithms or other methods. For example, values of any one or more of the above the criteria may be provided in a look up table that specifies alert levels. In another approach, a polynomial, a classification tree (e.g., a CART), a regression model, or other model of legionellosis health risk may employ variables representing any one or more of the above criteria. In such models, the criteria may be represented by a binary values (either they are present or not) or more precise numerical values (e.g., temperature values, time duration values, etc.).

In one implementation of a legionellosis hazardous condition detection system, the system simply detects that fluid has moved little or not at all for X hours and temperature is between about Y and Z.

Figure 46:
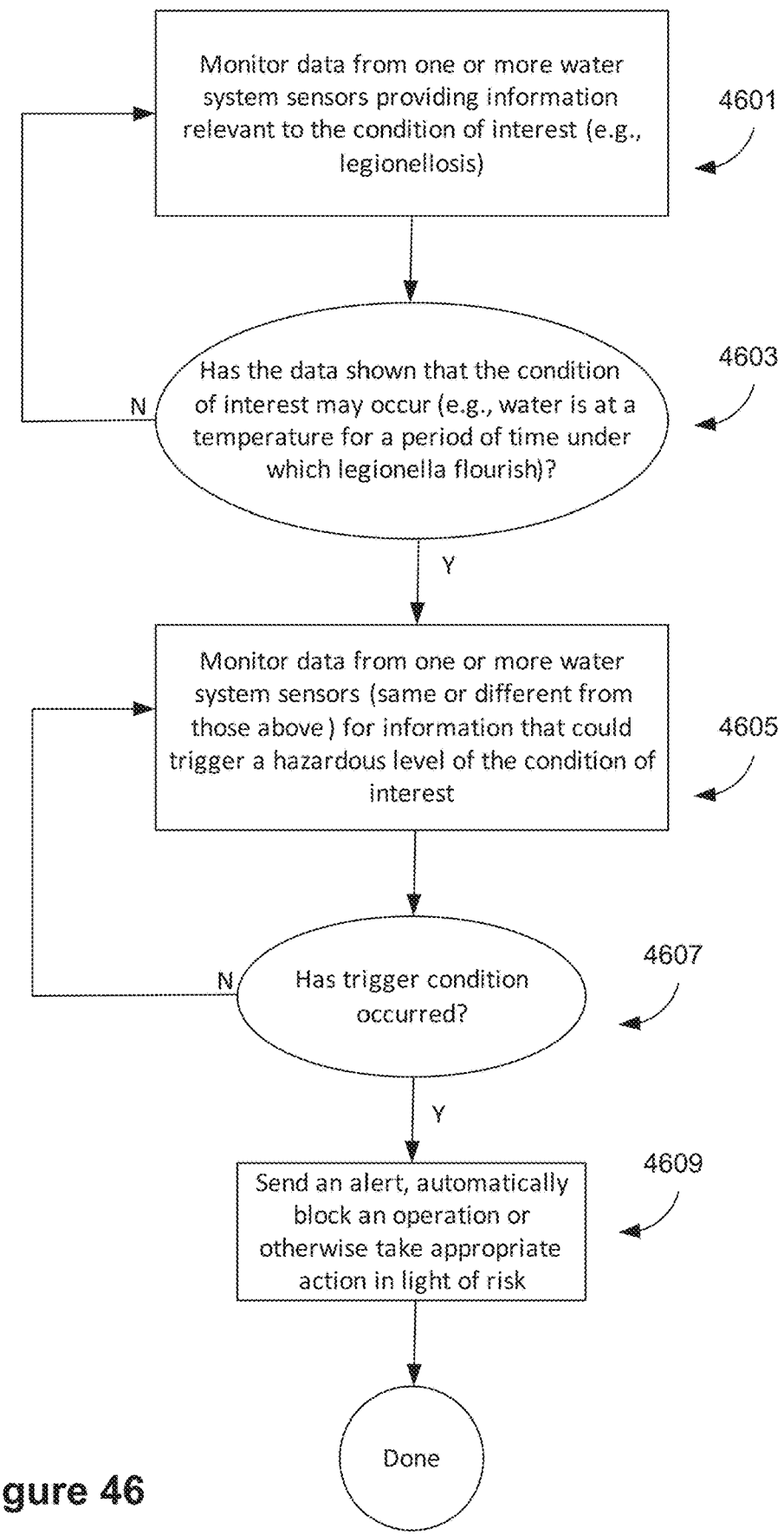
FIG. 46 depicts an example flow chart representing a legionella detection implementation.

FIG. 46 depicts an example flow chart representing a legionella detection implementation. In the depicted flow chart, sensed conditions are monitored (blocks 4501 and 4505) over time and the sensed conditions are of two types: in block 4503, one related to general conditions under which it is possible for a preliminary situation to occur (e.g., a type of pathogen can grow or flourish) and in block 4507 one related to triggering a release of the pathogen into the wider fluid system where it can produce a hazardous result (e.g., a pipe vibration and/or pressure spike greater than a threshold). In terms of the above sensed data, sensors that can detect the first type of condition include flow sensors (for determining whether and to what degree water has flowed through a pipe over the period of time and/or the temperature of water in the pipe, e.g., the ultrasonic transducers, acoustic sensors, or thermal flow condition sensors), hoop stress sensors (for determining whether and to what degree water has flowed through a pipe over the period of time and/or whether a pressure spike has occurred), acoustic pipe condition sensors (for determining whether an film or deposit potentially housing bacteria has formed inside a pipe and/or determining that a vibration has occurred that will potentially dislodge parts of the film or deposit), and an accelerometer (for determining whether a vibration that will potentially dislodge parts of a film or deposit will occur).

Once both the preliminary situation and the triggering event are detected, the system can take steps to alert appropriate persons and/or modify operation of the water system (block 4509). The alert may also indicate to service personnel to verify adequate disinfectant levels for water features or cooling towers.

F. Example Flow Determination

As described above, one or more detection devices described herein may be used alone or in combination with other detection devices to determine flow through a fluid conduit or through various sections of a fluid conduit network, such as a drinking water system or a fire suppression system, and this flow detection may then be used to determine the presence of blockages or restrictions within the fluid conduit network. The detection device may detect flow in any way discussed herein, including using one or more of a hoop stress sensor, one or more thermal flow condition sensors, and an acoustic condition sensor (e.g., microphones or ultrasonic transducers).

For example, flow detection by two detection devices positioned along a section of fluid conduit may together be able to determine a blockage in or around that section of fluid conduit. If flow is intended to pass through this section of fluid conduit and be detected by both detection devices, then example indications related to a blockage or restriction may include: (i) if one detection device detects flow while the other does not, then a blockage may exist between the detection devices, (ii) if both detection devices do not detect flow, then a blockage may exist upstream or downstream of the detection devices, (iii) if both detection devices detect flow, then a blockage may not exist upstream or downstream of the detection devices, and (iv) if both detection devices detect flow, but the magnitude of flow detected by each detection device is different, then a flow restriction may exist between the two detection devices.

To illustrate, referring to FIG. 18, detection devices 1800B and 1800C are positioned along a section of pipe that includes a single sprinkler 18108 between the two detection devices. If the sink 18110 or toilet 18112 is actuated in order to draw water through this section of pipe from the main and detection device 1800B detects flow, but detection device 1800C does not, then a blockage may be present between these two detection devices.

In addition to normal, consistently-used plumbing such pipes for sinks and toilets, infrequently used fluid flow systems may also benefit from multi-position flow detection and/or monitoring. Examples of such infrequently used system are fire suppression systems in buildings, ships, and other structures. Many fire suppression systems, or sprinkler systems, sit idle such that the water or suppression fluid within the pipes or conduits sits stagnant for the majority of the time. This stagnation tends to allow for the development of bore loss which, as described herein, may include the reduction of a pipe's internal diameter, which may be caused by buildup of material within the pipe, such as biological sludge, grease, oxidation products (including corrosion products), tuberculation, and blockages from material originating upstream. Bore loss resulting in flow restriction and blockage is particularly relevant to fire suppression systems because reduced flow or no flow throughout some parts of the system may prevent the system from extinguishing a fire and thus be dangerous to life and property. Due to this, various governmental and private regulations require periodic flushing and/or testing of fire suppression systems, but this flushing does not fully alleviate the development of blockages and buildup within the pipes. This flushing also does not reveal or detect the existence of some flow blockages and restrictions within the fire suppression system.

Accordingly, any one or combination of the various sensors described herein may be useful to assess pipe or flow conditions during such testing. For example, using a plurality of detection devices positioned throughout a fire suppression system may enable the detection of blockages and restrictions within the fire suppression system, thus allowing for the remediation of these potentially dangerous conditions. Such detection may occur during a flushing event of the fire suppression system in which water is intended to flow through all sections of the system. As described above, since flow is intended to pass through all sections of fluid conduit, detection devices positioned at different positions within the system may be able to detect blockages and restrictions within the system. Example indications related to a flow blockage or restriction may include: (i) if one or more detection devices do not detect any flow, then a blockage may exist around or upstream of these detection devices, (ii) if two detection devices are positioned along a section of the system through which the same fluid should flow, and one detection device detects flow while the other detection device does not, then a blockage may exist between these two detection devices along the section of the system, (iii) if two detection devices are positioned along a section of the system through which the same fluid should flow, and both detection devices do not detect flow, then a blockage may exist upstream of the detection devices, (iv) if two detection devices are positioned along a section of the system through which the same fluid should flow, and they detect flow, then a blockage may not exist upstream of the detection devices, and (v) if two detection devices are positioned along a section of the system through which the same fluid should flow, and they detect flow, but the magnitude of flow is different between the two units, then a flow restriction may exist between the two detection devices.

Detection devices positioned along a fluid conduit network may also be used to detect leaks within the network. As discussed herein, the detection devices may detect leaks within a pipe or the flow network using one or more sensors, such as the thermal flow condition sensors and acoustic pipe condition sensors. For example, a detection device may detect a leak within a system if it detects flow when there should be no flow through the section of conduit on which the detection device is positioned or if it detects acoustic signals indicative of a leak in a section of fluid conduit. This leak detection may again be advantageous for numerous uses and applications, such as fire suppression systems in buildings, ships, and other structures as well as municipalities and building fluid conduit systems so that these leaks may be identified and remediated in order to prevent damage to property or life and ensure proper functioning of the fluid conduit networks.

G. Additional Embodiments

While the above description has focused on detecting conditions in which legionella may flourish and present a health risk, the disclosed concepts can be readily extended to non-legionella conditions. Examples of such other conditions include pathogenic contaminations such as contamination by coliform bacteria, cryptosporidium, giardia, enteric viruses, metazoan and protozoa and similar parasites, and any of a host of other waterborne organisms that cause diseases such as cholera, dysentery, typhoid, and the like.

In certain embodiments, the condition being monitored or detected is not the presence of conditions that support hazardous levels of a pathogen, but rather some other condition associated with use of the water system by building occupants or other individuals. In some implementations, the condition detecting system may monitor water usage in a room, building, or geographic region. For example, the system may monitor water consumption and where it occurs and/or in what type of appliance (toilet v. shower v. faucet v. landscaping, etc.) it occurs. Such monitoring may be used for conservation, auditing, etc. In certain embodiments, the system flags a water usage sequence that indicates a problem or need for corrective action; e.g., toilet flush not followed by faucet indicates a hygiene issue for restaurant employees.

The condition to be detected may be present in various contexts such as utilities, municipalities, plants, large buildings, compounds, complexes, and residences. In other words, the sensors used to detect the condition are present on pipes employed in any such location. Of course, the software or other logic used to determine that a potentially hazardous condition exists need not be present at the location of the sensors, although it may be. The logic simply needs to receive input from the sensors and then analyze the sensor data to determine whether condition exists or should be flagged.

Conditions to be detected need not occur in water or piping for water. More generally, certain conditions may be detected in pipes of portions of a pipe system for any type of liquid (e.g., petroleum, chemical feedstocks in chemical plants, and the like). In certain embodiments, the conditions being detected may even apply to gases (e.g., gas pipelines in residences, chemical plants, etc.) or other fluids such as supercritical fluids. Such conditions to be detected may be unrelated to pathogenic contamination. For example, such conditions may relate to overheating, explosive conditions, toxic chemical generation or release conditions, and the like.

In some cases, the conditions to be detected are not limited to systems that contain only fluid carrying pipes. Other conduits such as channels and reservoirs may be monitored. These may be monitored in municipal, residential, or industrial settings; and possibly even human body arteries (e.g. capillary bed).

Lead (Pb) and other chemicals in water lines leache into water depending on time, temperature, and water chemistry. Water that is not flowing tends to have higher concentrations of lead because it has been in contact with lead sources longer than flowing water. Lead monitoring protocols specify allowing water to stand in the pipe for a given amount of time. In certain embodiments, a lead or other chemical hazard condition detection system can indicate that water should be flushed from the line before drinking from it, or that there has been little flow at a given temperature and water in the line is ready to be sampled for chemical content. Sampling water in buildings on a regular basis is on legislative dockets in various jurisdictions.

VI. Context for Disclosed Computational Embodiments

Certain embodiments disclosed herein relate to systems for analyzing sensor data and determining whether the data indicate that conditions exist that might be hazardous and/or require a particular action. Certain embodiments disclosed herein, the conditions under consideration pertain to a water system. A system for analyzing sensor data and determine whether a particular condition exists may be configured to analyze data for calibrating or optimizing sensors on a water system.

Many types of computing systems having any of various computer architectures may be employed as the disclosed systems. For example, the systems may include software components executing on one or more general purpose processors or specially designed processors such as programmable logic devices (e.g., Field Programmable Gate Arrays (FPGAs)). Further, the systems may be implemented on a single device or distributed across multiple devices. The functions of the computational elements may be merged into one another or further split into multiple sub-modules.

In some embodiments, code executed during generation or execution of a model on an appropriately programmed system can be embodied in the form of software elements which can be stored in a nonvolatile storage medium (such as optical disk, flash storage device, mobile hard disk, etc.), including a number of instructions for making a computer device (such as personal computers, servers, network equipment, etc.).

At one level, a software element is implemented as a set of commands prepared by the programmer/developer. However, the module software that can be executed by the computer hardware is executable code committed to memory using "machine codes" selected from the specific machine language instruction set, or "native instructions," designed into the hardware processor. The machine language instruction set, or native instruction set, is known to, and essentially built into, the hardware processor(s). This is the "language" by which the system and application software communicates with the hardware processors. Each native instruction is a discrete code that is recognized by the processing architecture and that can specify particular registers for arithmetic, addressing, or control functions; particular memory locations or offsets; and particular addressing modes used to interpret operands. More complex operations are built up by combining these simple native instructions, which are executed sequentially, or as otherwise directed by control flow instructions.

The inter-relationship between the executable software instructions and the hardware processor is structural. In other words, the instructions per se are a series of symbols or numeric values. They do not intrinsically convey any information. It is the processor, which by design was pre-configured to interpret the symbols/numeric values, which imparts meaning to the instructions.

The condition determining models or algorithms used herein may be configured to execute on a single machine at a single location, on multiple machines at a single location, or on multiple machines at multiple locations. When multiple machines are employed, the individual machines may be tailored for their particular tasks. For example, operations requiring large blocks of code and/or significant processing capacity may be implemented on large and/or stationary machines.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, phase-change devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include design layouts, fixed parameter values, floated parameter values, feature profiles, metrology results, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

In certain embodiments, a model or algorithm for determining whether a condition exists (or is likely to exist) can be viewed as a form of application software that interfaces with a user and with system software. System software typically interfaces with computer hardware and associated memory. In certain embodiments, the system software includes operating system software and/or firmware, as well as any middleware and drivers installed in the system. The system software provides basic non-task-specific functions of the computer. In contrast, the modules and other application software are used to accomplish specific tasks. Each native instruction for a module is stored in a memory device and is represented by a numeric value.

VII. Example Displays

The data representative of the determinations and detections described herein may be displayed on one or more portals, dashboards, or maps. This data includes any data described above, such as the fluid flow data, pipe condition data, and location data.

This data may be sent over an external network and may ultimately be transmitted to a computer or server and stored on a memory device of that computer or server. Such data can be stored in the format of a record as described above or any other suitable format. This data can also be displayed in various manners.

Figure 47:
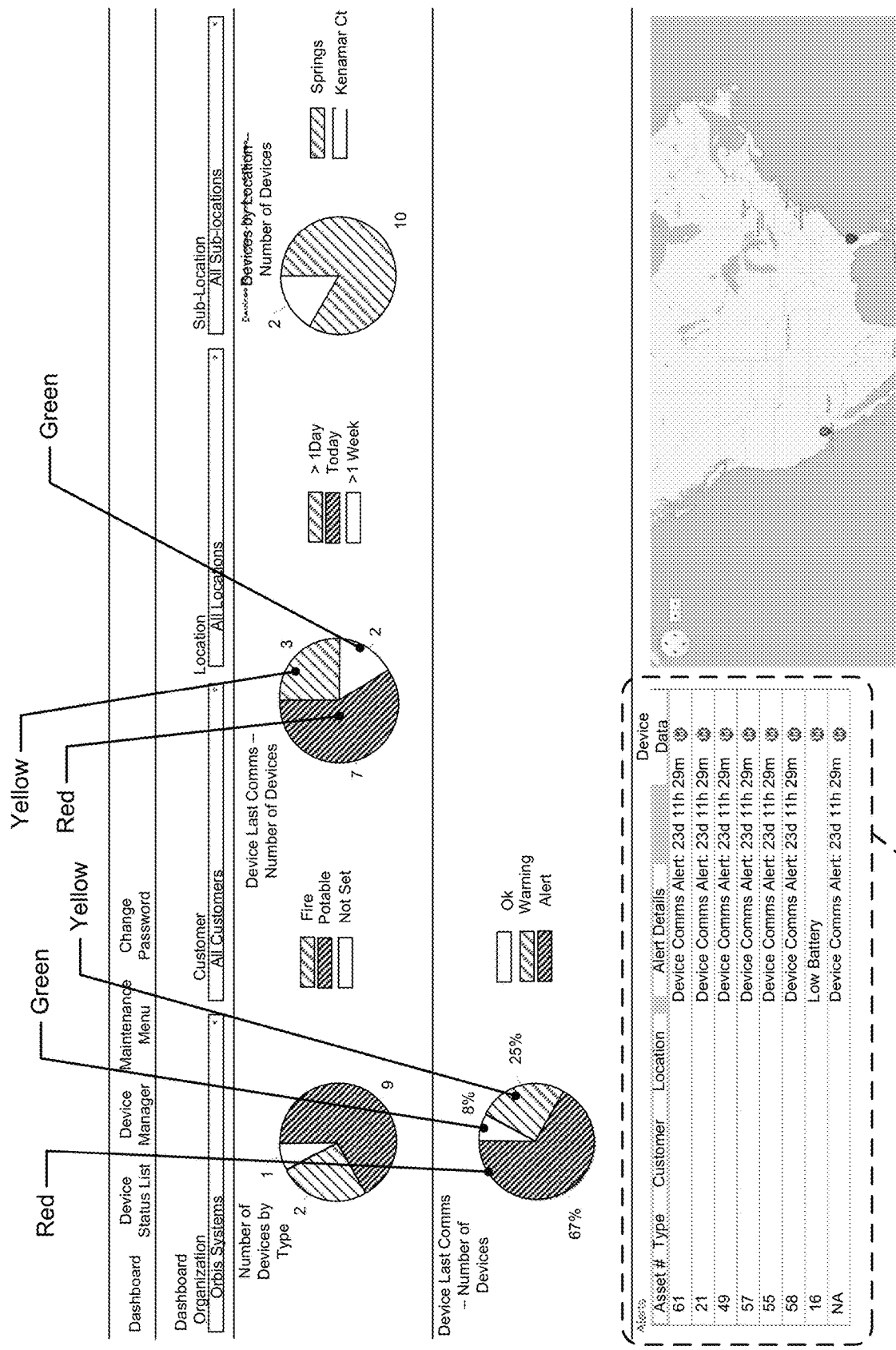
FIG. 47 depicts an example display.

In some cases, a device summary by client, location, or device type, for instance, may be provided as seen in FIG. 47 which depicts an example display. This "Dashboard" includes information related to a number of devices by type, device status (within a certain time period, e.g., 24 hours), device last communicated (within various time periods, e.g., less than 1 day, the present day, and within 1 week), and devices by location. This data may be displayed in various graphical representations, such as pie charts as seen in FIG. 47, or in other chart or graph form. This dashboard may also include a map which shows the geographic location of one or more detection devices. The region of this map may be changeable such that a user may zoom in or out of the location to see a more/less detailed map. This dashboard may also include an alerts section, seen individually in FIG. 48 which depicts an alerts section of a display, which shows information related to any alert for any device. These alerts, detections above/below particular levels, or notifications may be any of those described herein, including low battery, flow data above or below a particular level, a detection of a harmful pipe condition, etc. The alerts may be color coded, for example, with red meaning an alert level (see dark cross-hatching indicating red), yellow meaning a potential alert (see light cross-hatching indicating yellow), and green meaning no alert (shading, as labeled). These alerts may also be sent to a user or device via email, text, call, or other electronic means.

Figure 49:
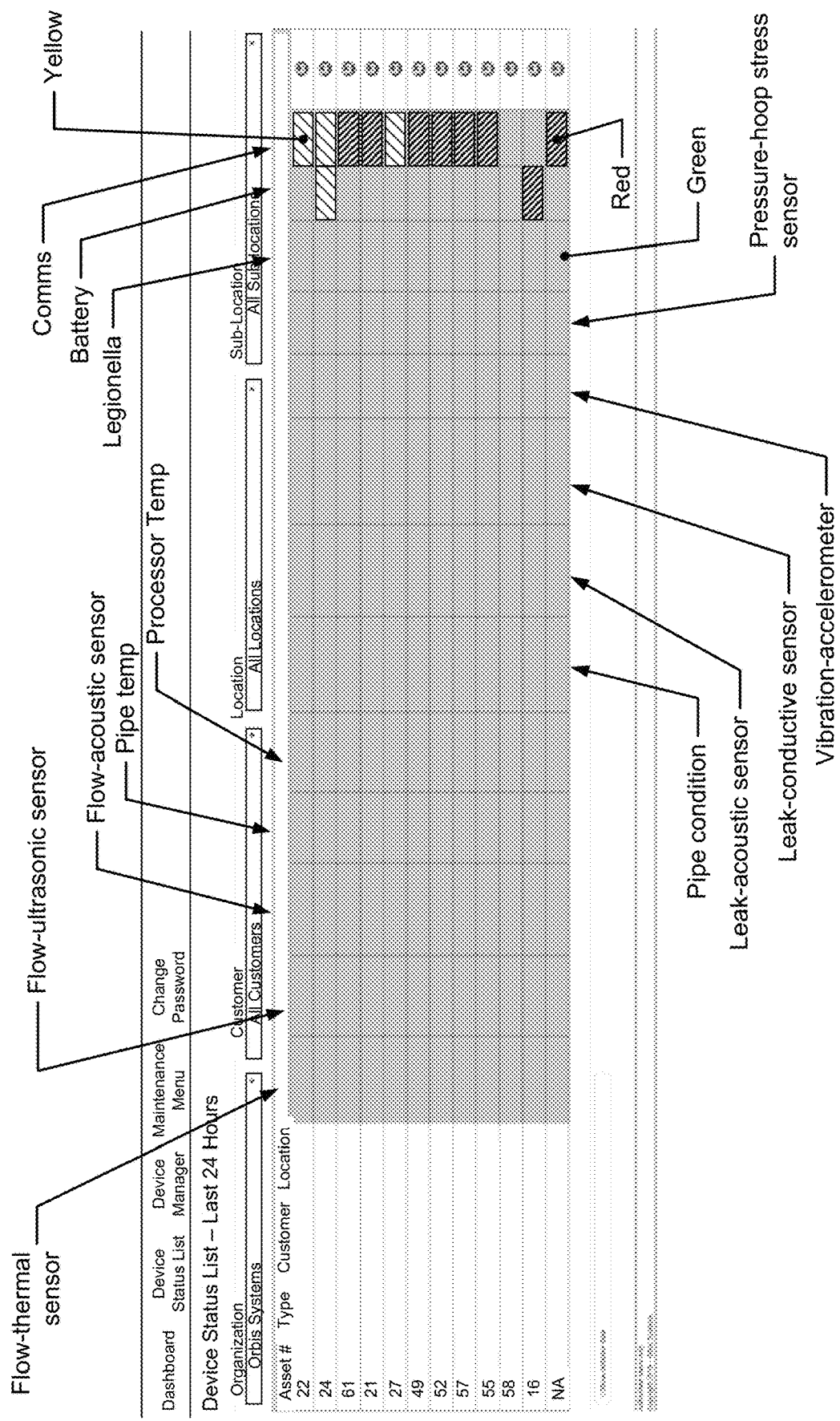
FIG. 49 depicts another example display.

Data may also be provided in a matrix or graph form, an example of which is illustrated in FIG. 49 which depicts another example display. Here in FIG. 49, the matrix can display a listing of the device, the customer or user, the location and type of device (e.g., fire, potable, flow, pipe condition, and any of those listed herein). The matrix can also display any of the detections and determinations provided by each device, such as thermal, ultrasonic, acoustic, temperature, board temperature (e.g., of the board in the device), leak based on acoustic detection, leak based on a conductive sensor, vibration (based on an accelerometer or gyroscope, for example), a pressure, legionella, battery and communications status. These items are the listed columns and identified in FIG. 49. Different embodiments may only have some of these items while others may have different or more items. The status of these detections/determinations may be provided in the chart in various ways, such as with text or be color coded like above, with green being status OK (e.g., not above or below a particular threshold; see shading), yellow being a potential issue which may require attention or investigation (see light cross-hatching), and red being an alert in which the detection/determination is at an alert level (see dark cross-hatching).

For example, each of the features/determinations/detections by each device are listed on the top of the matrix and for each feature if an event or alert is detected then it may change the color. For instance, if legionella was considered a high risk then this particular color would change red (or dark cross-hatching). Ideally, this page should all be green. In another example, red on the battery means dead and yellow means running low. Additionally, if one of these boxes is checked, then the generated data may be displayed (see FIG. 51). For instance, if pressure is selected for one of the devices, then the actual or last measured pressure may be displayed.

Figure 50:
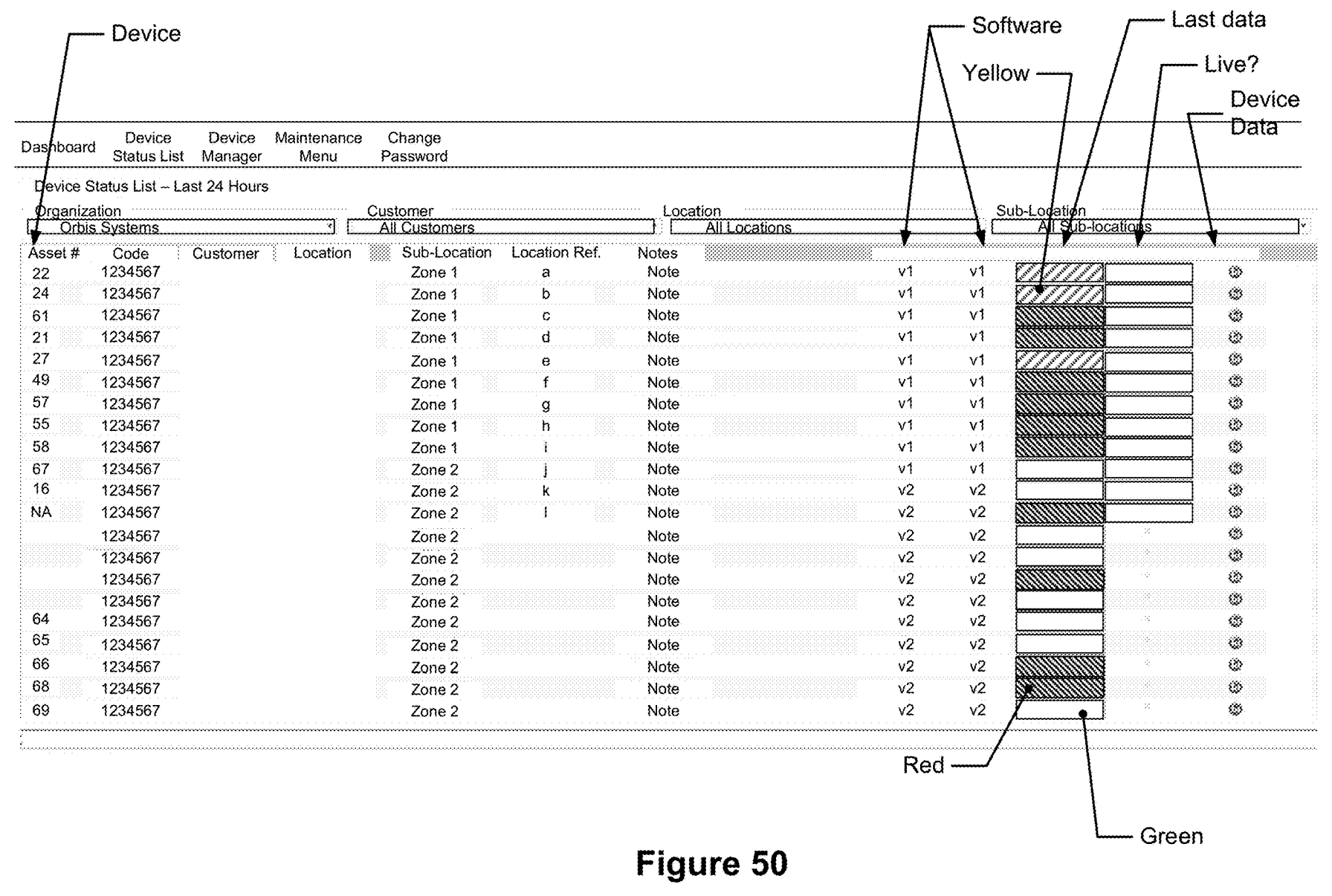

Additional data about each device may also be provided. This may include device specific details, such as type of device, sensors included, software version, last time data was sent, whether the data is being transmitted live; this data may also include other information about the device such as location, notes, customer, size and type of pipe on which the device is installed. FIG. 50 depicts an example display showing various details and data of numerous devices. This data includes, in the columns from left to right, device or asset number, code, customer, location, sub-location (e.g., specific location at the general location; in one example location may be Building, and sub location may be boiler room of the Building), location reference, notes, software versions, last time data was sent, whether the device is live, and a column to see more specific device data (see FIG. 51). As also seen in this Figure, some boxes may be color coded like described above, e.g., red (dark cross-hatching) indicating an issue (e.g., device not working, data not sent, data sent outside of a specific period to time), yellow (light cross-hatching, investigate an issue), and green (OK status).

Figure 51:
FIG. 51 depicts additional data of a detection device.

FIG. 51 depicts additional data of a detection device. In some instance, the data and information displayed in FIG. 50 may be input and edited in FIG. 51. As can be seen, various information about each device may be input into the display; this input may be manually by a user or installer, automatically, or a combination of the two. This may include asset/device number, device model, the type, the organization, location, sub-location, location reference, orientation and diameter of the pipe on which the device is connected, number, whether the device is live, additional notes, and GPS location data (which may be generated by the device itself or input manually).

Figure 52A:
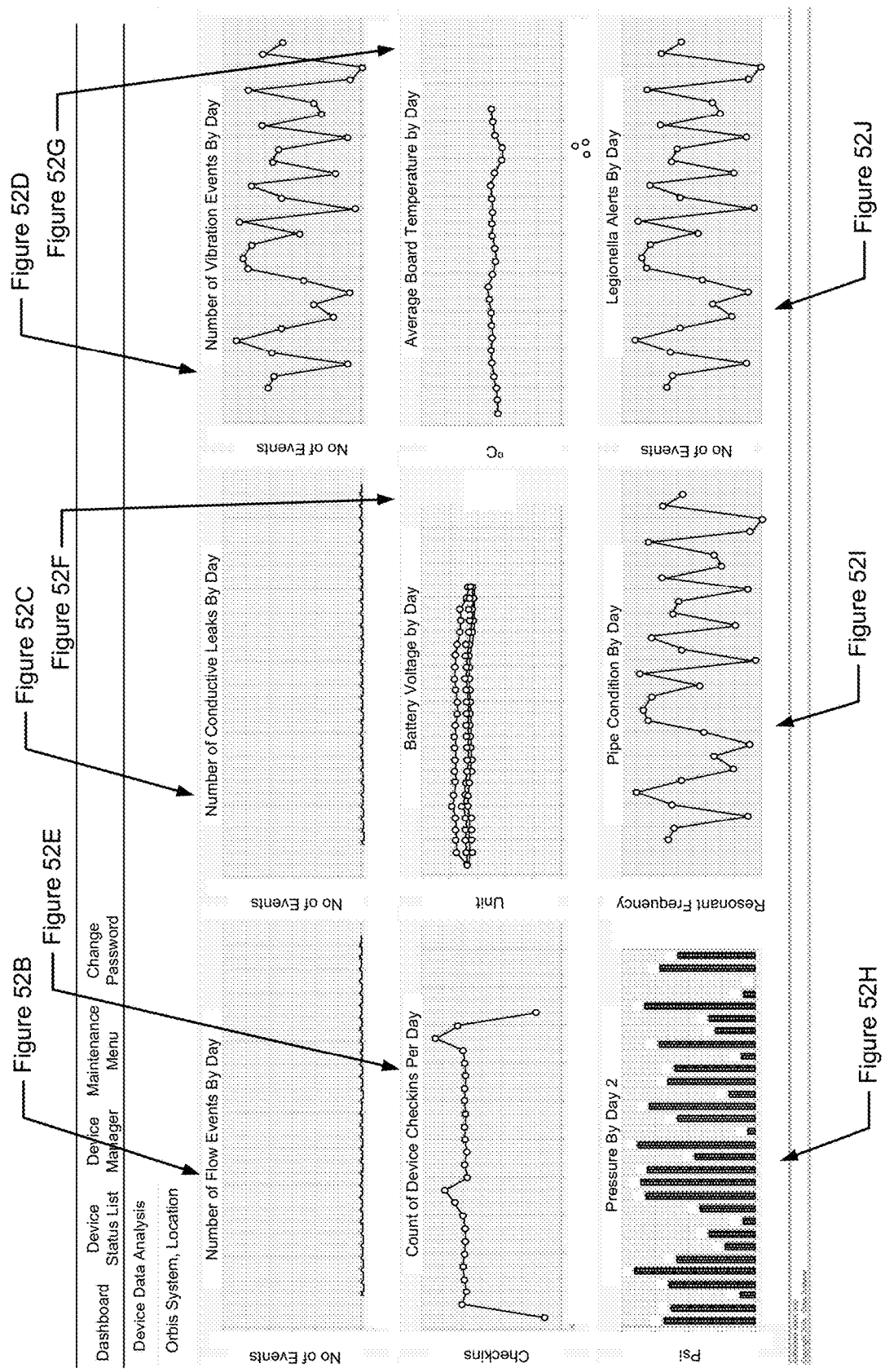
FIG. 52A depicts a display with 9 graphs of determinations, detections, and data generated by one detection device.
Figure 52B:
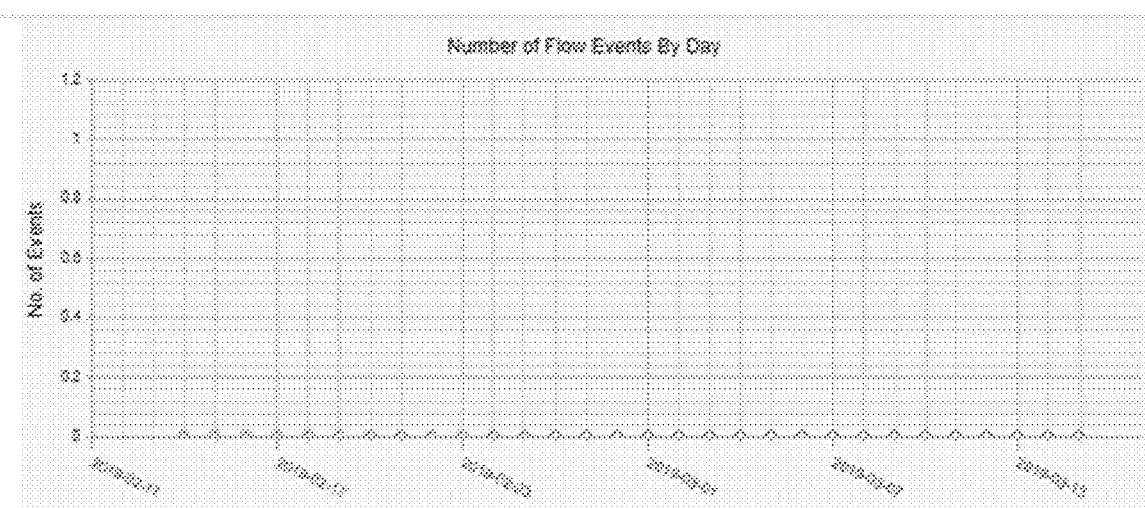
FIGS. 52B through 52J depict magnified images of each individual graph of FIG. 52A.
Figure 52C:
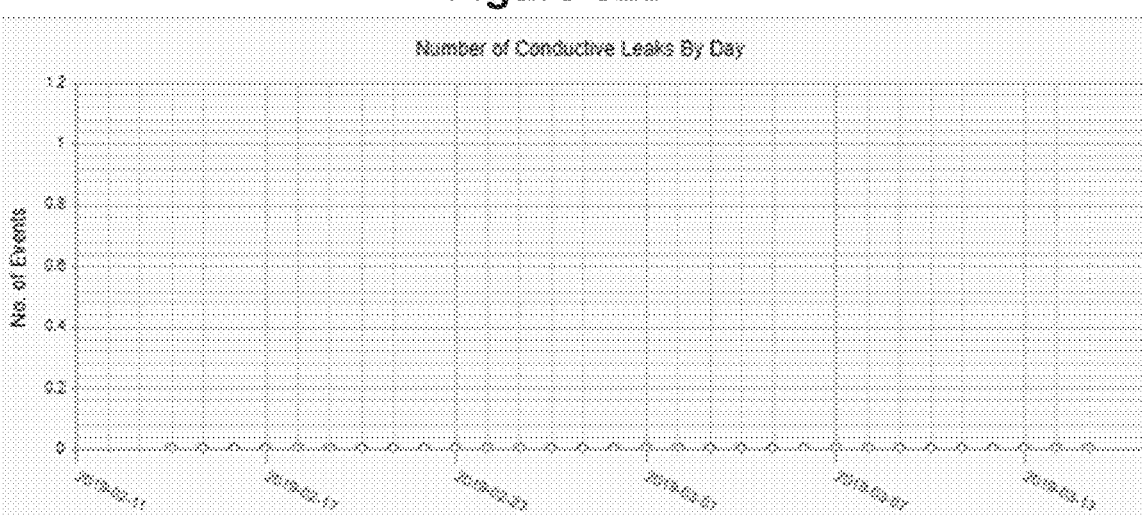
Figure 52D:
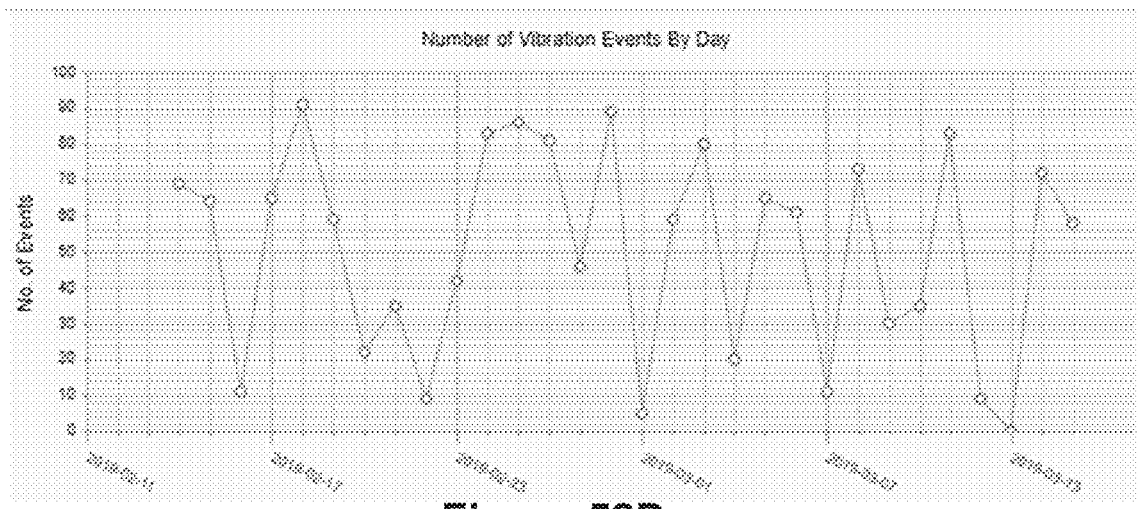
Figure 52E:
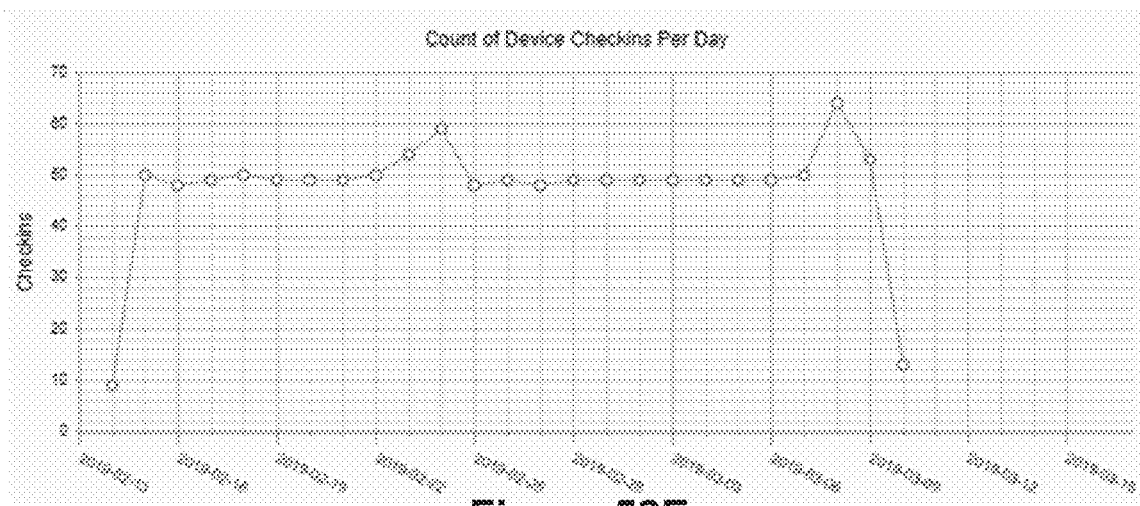
Figure 52F:
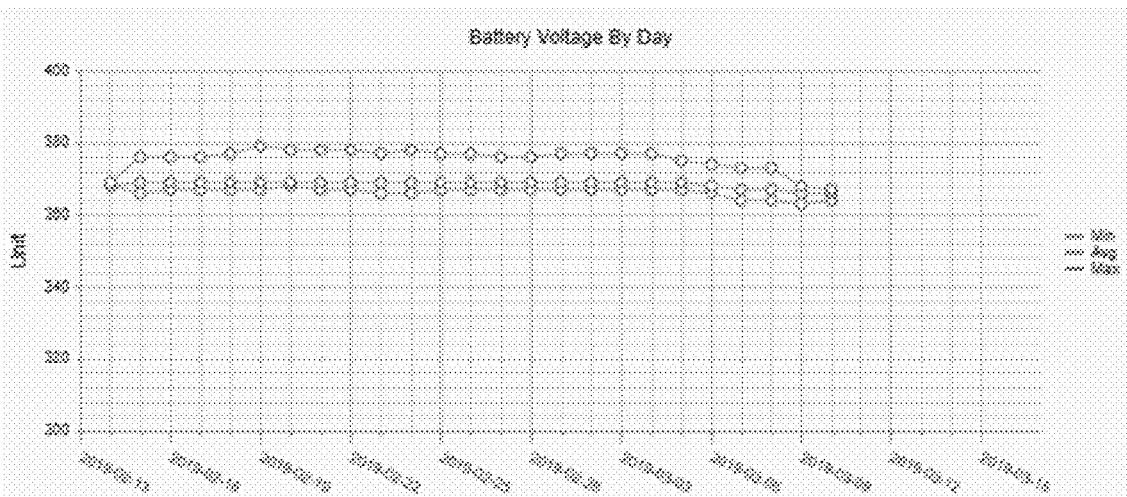
Figure 52G:
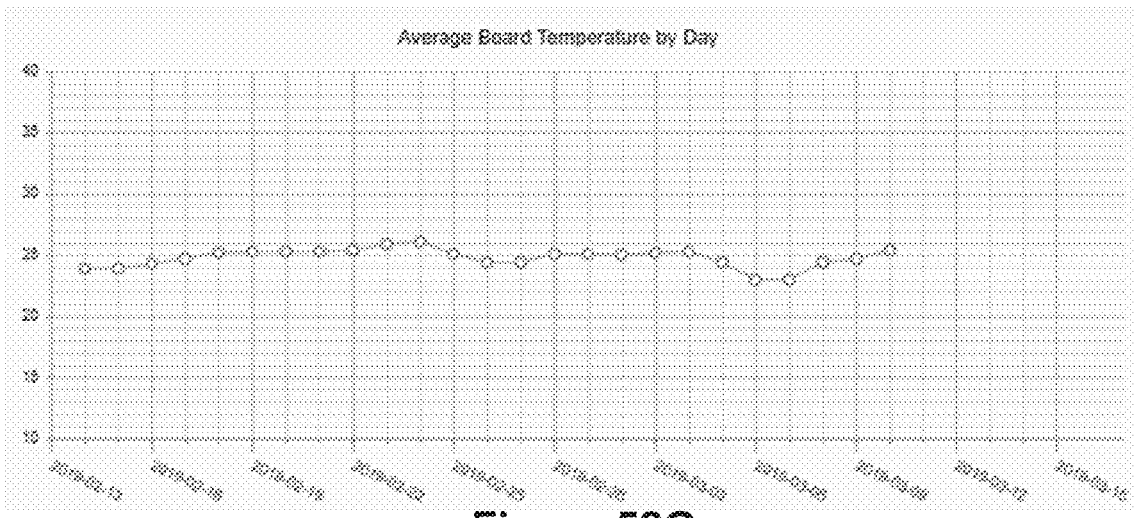
Figure 52H:
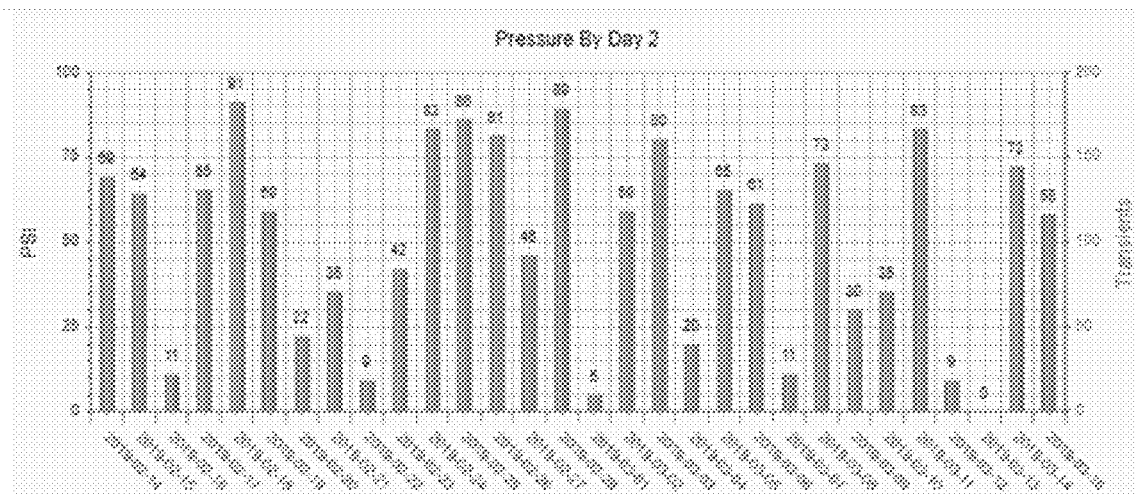
Figure 52I:
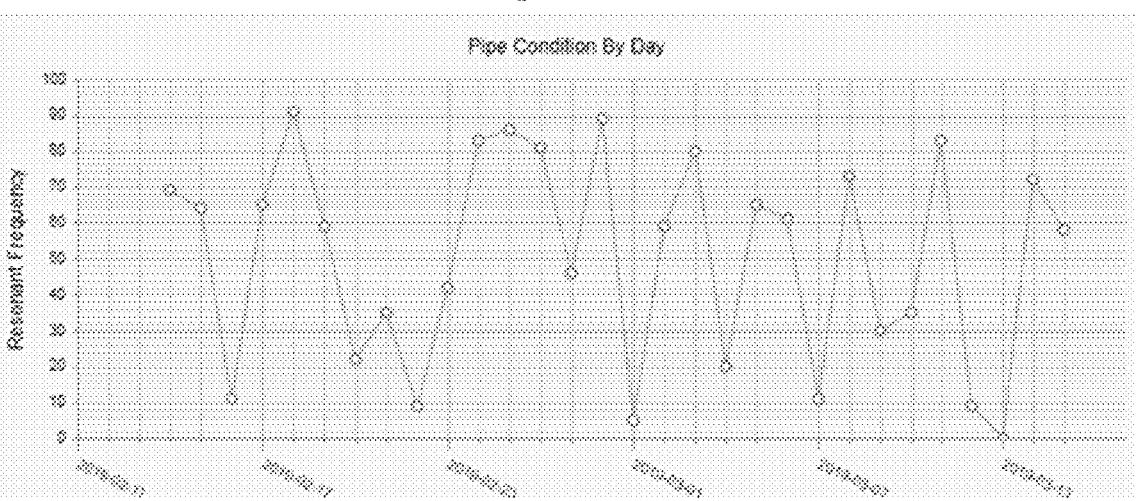
Figure 52J:
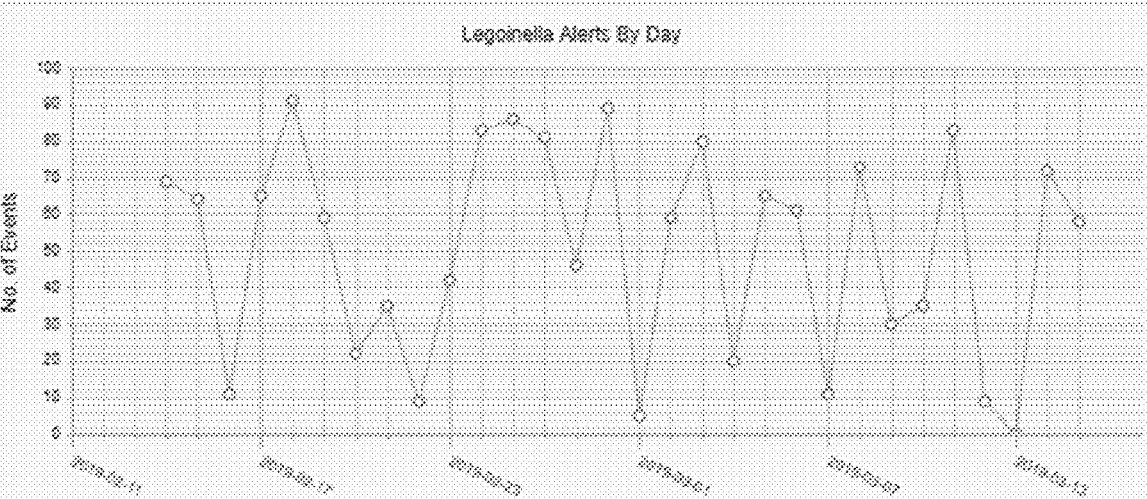

As stated above, the determinations, detections, and data generated by each device may be displayed in the portal/display. This may include a graph of each feature/detection/determination listed in any of the other displays, such as FIG. 49. Each graph may also be individually selected and displayed. FIG. 52A depicts a display with 9 graphs of determinations, detections, and data generated by one detection device. FIGS. 52B through 52J depict magnified images of each individual graph of FIG. 52A. These individual graphs include data, determinations, and detections about number of flow events (e.g., detected flow within a pipe), number of leaks detected by a conductive sensors, number of vibration events detected (e.g., with an accelerometer or gyroscope), number of time a device transmits data, battery voltage per day, average temperature of the circuit board of the device, detected pressure (e.g., by a hoop stress sensor), pipe condition (e.g., detected and determined using the acoustic sensors), and alerts related to legionella. Although these 9 items are displayed in FIGS. 52A through 52J, any other feature, detection, determination described herein may be displayed.

In some embodiments, location determination coupled with fluid transport (volume, mass, rate, etc.) and other pipe condition data is useful not only for identifying where fluid is consumed but also for providing performance indicators based on the functionality and behavior of the pipes, valves, and other infrastructure, as well as services used by the infrastructure.

For example, in some embodiments, this data may be used to provide real-time use of one or more pipes or hydrants. This may be in the form of a chart or a map that is correlated with the geographic location of each pipe or hydrant. The map may include other information, such as historical use data of the geographic locations of all pipes or hydrants that were used to draw fluid from a fluid delivery system in a particular region over a certain amount of time. For example, the map may be of sub-region of a water utility district that includes geographic icons which indicate use within the past 24 hours. The geographic icons may provide any of the data included in the record as well as other flow related information, such as the total amount of water drawn or the number of events at the location.

Figure 53:
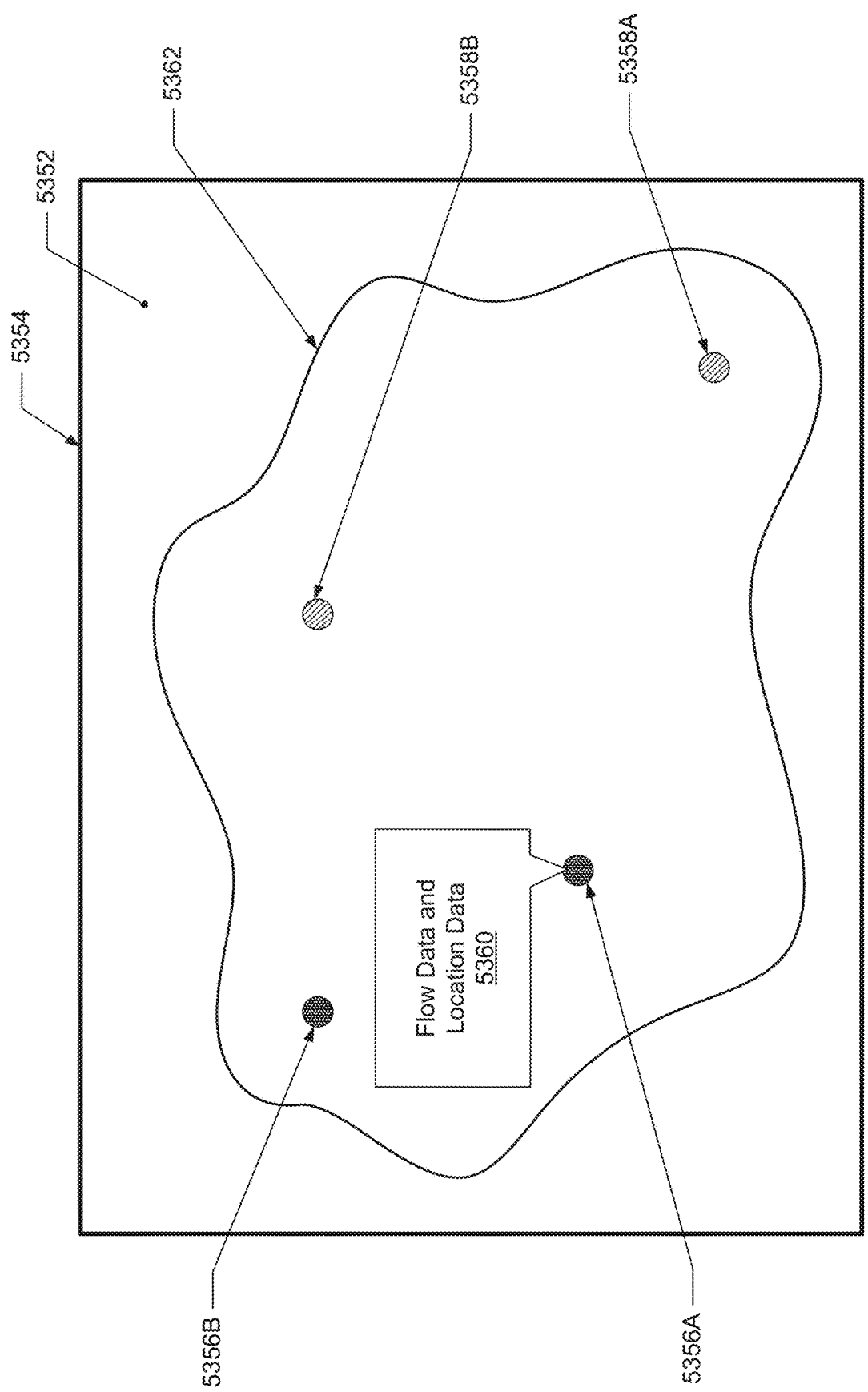
FIG. 53 depicts another example map showing multiple detection devices.

FIG. 53 depicts another example map showing multiple detection devices. The map 5352 is depicted on a screen 5354 of a device, such as a computer, and includes a region 5362 that represents a geographical region, such as the boundary or a city or utility district. The map 5352 includes first geographic icons 5356A and 5356B that each may represent the real-time use of a single detection device, such as any device described herein. The first geographic icons 5356A and 5356B may provide information about the real-time use, such as the flow rate and total volume drawn during an event, as indicated by the pop-up bubble 5360 over the first geographic icon 5356A that may be generated when the first geographic icon 5356A is selected. Second geographic icons 5358A and 5358B may indicate past historical use at a particular location and similar pop-up bubbles may be generated to provide the past use at each of those icons. In some embodiments, the real-time and historical detection device data or geographic location may be displayed in a chart adjacent to the map 5352 on the screen 5354.

In some embodiments, the dashboard or other data described herein may be presented in a "command center" where a municipality, a building manager, a water sensor monitoring company, or other entity monitors and optionally plans actions to address water consumption or other water use issues. The "command center" may be in or remote from any location where the detection devices are deployed.

Unless the context of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein. In certain embodiments, numerical or mathematical values, including end points of numerical ranges, are not to be interpreted with more significant digits than presented and may be understood to include some variation, such as within 5% of the referenced value or within 1% of the referenced value. For example, perpendicular may, in certain embodiments, mean within +/−5% of 90 degrees.

What is claimed is:

1. A method of assessing legionellosis risk in a water system, the method comprising:

receiving sensed data from one or more sensors on pipes in the water system, wherein the data comprises information about (i) temperature of a pipe or water in the water system, (ii) flow of water in the pipe or other component of the water system, (iii) a pressure change in the pipe or other component of the water system, and/or (iv) a vibration of the pipe or other component of the water system;

analyzing the received data to determine a risk of legionellosis resulting from water in the pipe or other component of the water system;

outputting a risk data containing data about the determined risk of legionellosis in the pipe or other component of the water system; and issuing an alert based on the risk data, the temperature of the pipe or water in the water system, and the flow of water in the pipe or other component of the water system.

2. The method of claim 1, wherein:

the one or more sensors comprise one or more acoustic sensors, a temperature sensor, and an accelerometer, and the analyzing the received data includes analyzing data from the one or more acoustic sensors, the temperature sensor, and the accelerometer.

3. The method of claim 2, wherein:

the one or more sensors further comprise a humidity sensor and a pressure sensor, and the analyzing the received data further includes analyzing data from the humidity sensor and the pressure sensor.

4. The method of claim 1, wherein the receiving the sensed data comprises receiving the sensed data at multiple times over a period of time.

5. The method of claim 4, wherein the analyzing further includes analyzing the flow of water in the pipe or other component of the water system over the period of time.

6. The method of claim 1, wherein the temperature of a pipe or water in the water system is in a range between about 25° C. and about 43° C.

7. The method of claim 1, further comprising adjusting, based on the risk data, operation of the water system.

8. A method of assessing legionellosis risk in a water system, the method comprising:

receiving sensed data from one or more sensors on pipes in the water system, wherein the data comprises information about (i) temperature of a pipe or water in the water system, (ii) flow of water in the pipe or other component of the water system, (iii) a pressure change in the pipe or other component of the water system, and/or (iv) a vibration of the pipe or other component of the water system, wherein the temperature of a pipe or water in the water system is in a range between about 25° C. and about 43° C.;

analyzing the received data to determine a risk of legionellosis resulting from water in the pipe or other component of the water system and to determine, in response to determining that the temperature of the pipe or water in the water system is in the range between about 25° C. and about 43° C., fluid flow within the pipe; and outputting a risk data containing data about the determined risk of legionellosis in the pipe or other component of the water system.

9. A method of assessing legionellosis risk in a water system, the method comprising:
receiving sensed data from one or more sensors on pipes in the water system, wherein the data comprises information about (i) temperature of a pipe or water in the water system, (ii) flow of water in the pipe or other component of the water system, (iii) a pressure change in the pipe or other component of the water system, and/or (iv) a vibration of the pipe or other component of the water system;
analyzing the received data to determine a risk of legionellosis resulting from water in the pipe or other component of the water system;
outputting a risk data containing data about the determined risk of legionellosis in the pipe or other component of the water system; and
issuing an alert based on the risk data and accelerometer data indicative of the vibration of the pipe or other component of the water system.

10. A method of assessing legionellosis risk in a water system, the method comprising:
receiving sensed data from one or more sensors on pipes in the water system, wherein the data comprises information about (i) temperature of a pipe or water in the water system, (ii) flow of water in the pipe or other component of the water system, and (iii) at least one other parameter, wherein the at least one other parameter comprises (a) a pressure change in the pipe or other component of the water system and/or (b) a vibration of the pipe or other component of the water system;
analyzing the received data to determine a risk of legionellosis resulting from water in the pipe or other component of the water system;
outputting a risk data containing data about the determined risk of legionellosis in the pipe or other component of the water system; and
adjusting, based on the risk data, operation of the water system, wherein the adjusting comprises shutting off one or more components.

11. The method of claim 10, wherein the one or more components comprises one or more of a showerhead, a faucet, a water dispenser, a cool tower, a hot tub, a sprinkler system, a fountain, a water feature, a water tank, a hot water tank, a heater, or a plumbing system.

12. A detection device comprising:
a temperature sensor;
an accelerometer;
a plurality of acoustic sensors; and
a controller with a communications unit, wherein the controller is communicatively connected to the temperature sensor, the accelerometer, and the plurality of acoustic sensors, and configured to:
receive sensed data from the temperature sensor, the accelerometer, and the plurality of acoustic sensors, wherein the data comprises information about (i) temperature of a pipe or water in a water system, (ii) flow of water in the pipe or other component of the water system, (iii) a pressure change in the pipe or other component of the water system, and/or (iv) a vibration of the pipe or other component of the water system,
analyze the received data to determine a risk of legionellosis resulting from water in the pipe or other component of the water system, and
output a risk data containing data about the determined risk of legionellosis in the pipe or other component of the water system.

13. The detection device of claim 12, further comprising a pressure sensor, wherein the analyzing further includes analyzing data from the pressure sensor.

14. The detection device of claim 12, further comprising a humidity sensor, wherein the analyzing further includes analyzing data from the humidity sensor.

15. The detection device of claim 12, wherein the controller is further configured to issue an alert based on the risk data.

16. The detection device of claim 15, wherein issuing the alert is further based on:
the temperature of the pipe or water in the water system,
the flow of water in the pipe or other component of the water system, and
the vibration of the pipe or other component of the water system.

17. A system comprising:
a plurality of detection devices, wherein each detection device includes:
a temperature sensor,
an accelerometer,
a plurality of acoustic sensors, and
a first controller with a first communications unit, wherein the first controller is communicatively connected to the temperature sensor, the accelerometer, and the plurality of acoustic sensors, and configured to:
receive sensed data from the temperature sensor, the accelerometer, and the plurality of acoustic sensors, wherein the data comprises information about (i) temperature of a pipe or water in a water system, (ii) flow of water in the pipe or other component of the water system, (iii) a pressure change in the pipe or other component of the water system, and/or (iv) a vibration of the pipe or other component of the water system, and
transmit, using the first communications unit, the sensed data to a second controller; and
the second controller with a second communications unit, wherein the second controller is configured to:
receive the sensed data from each first communications unit from the plurality of detection devices,
analyze the received data to determine a risk of legionellosis resulting from water in the pipe or other component of the water system, and
output a risk data containing data about the determined risk of legionellosis in the pipe or other component of the water system.

18. The system of claim 17, wherein:
each detection device further includes a pressure sensor, the sensed data includes data from the pressure sensor, and the analyzing further includes analyzing data from the pressure sensor.

19. A method of assessing legionellosis risk in a water system, the method comprising:

receiving sensed data from one or more sensors on pipes in the water system, wherein the data comprises information about (i) temperature of a pipe or water in the water system, (ii) flow of water in the pipe or other component of the water system, (iii) a pressure change in the pipe or other component of the water system, and/or (iv) a vibration of the pipe or other component of the water system;

analyzing the received data to determine a risk of legionellosis resulting from water in the pipe or other component of the water system; and outputting a risk data containing data about the determined risk of legionellosis in the pipe or other component of the water system, wherein:

the one or more sensors comprise one or more acoustic sensors, a temperature sensor, and an accelerometer, and the analyzing the received data includes analyzing data from the one or more acoustic sensors, the temperature sensor, and the accelerometer.

20. The method of claim 19, wherein:

the one or more sensors further comprise a humidity sensor and a pressure sensor, and the analyzing the received data further includes analyzing data from the humidity sensor and the pressure sensor.

\* \* \* \* \*